US007345049B2

(12) United States Patent
Sagi et al.

(10) Patent No.: US 7,345,049 B2
(45) Date of Patent: Mar. 18, 2008

(54) PHENYLALANINE DERIVATIVES

(75) Inventors: Kazuyuki Sagi, Kawasaki (JP); Tatsuya Okuzumi, Kawasaki (JP); Tatsuhiro Yamada, Kawasaki (JP); Shunsuke Kageyama, Kawasaki (JP); Yoichiro Shima, Kawasaki (JP); Tadakiyo Nakagawa, Kawasaki (JP); Munetaka Tokumasu, Kawasaki (JP); Masayuki Sugiki, Kawasaki (JP); Hajime Ito, Kawasaki (JP); Itsuya Tanabe, Kawasaki (JP); Tamotsu Suzuki, Kawasaki (JP); Akira Nakayama, Kawasaki (JP); Kazuyuki Ubukata, Kawasaki (JP); Kenji Shinkai, Kawasaki (JP); Yasuhiro Tanaka, Kawasaki (JP); Misato Noguchi, Kawasaki (JP); Ayatoshi Andou, Kawasaki (JP); Yoriko Yamamoto, Kawasaki (JP); Noriyasu Kataoka, Kawasaki (JP); Koichi Fujita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/018,226

(22) Filed: Dec. 22, 2004

(65) Prior Publication Data

US 2005/0222141 A1    Oct. 6, 2005

Related U.S. Application Data

(60) Provisional application No. 60/617,026, filed on Oct. 12, 2004, provisional application No. 60/539,108, filed on Jan. 27, 2004.

(30) Foreign Application Priority Data

| Dec. 22, 2003 | (JP) | ............................. 2003-425347 |
| Mar. 16, 2004 | (JP) | ............................. 2004-074943 |
| May 28, 2004 | (JP) | ............................. 2004-159919 |
| Sep. 7, 2004 | (JP) | ............................. 2004-260319 |

(51) Int. Cl.
*A61K 31/517* (2006.01)
*A61K 31/519* (2006.01)
*C07D 239/70* (2006.01)
*C07D 239/95* (2006.01)

(52) U.S. Cl. ............................. 514/266.2; 514/266.22; 514/266.3; 514/267; 544/249; 544/250; 544/285

(58) Field of Classification Search ............. 514/227.8, 514/234.2, 266.22, 266.31, 267, 262.1, 264.1, 514/266.2, 266.3, 256.22; 544/60, 114, 249, 544/267, 284, 285, 262, 279, 250

See application file for complete search history.

(56) References Cited

U.S. PATENT DOCUMENTS

| 5,274,098 | A | 12/1993 | Stueber et al. ............... 540/200 |
| 6,171,578 | B1 * | 1/2001 | Dean et al. ................. 424/1.69 |
| 6,172,072 | B1 * | 1/2001 | Lubisch et al. ............. 514/274 |
| 6,436,925 | B1 * | 8/2002 | Lubisch et al. .......... 514/217.12 |
| 6,436,949 | B1 * | 8/2002 | Lubisch et al. ............. 514/274 |
| 6,448,254 | B1 * | 9/2002 | Lubisch et al. ............. 514/267 |
| 6,610,710 | B2 | 8/2003 | Tanaka et al. ............... 514/330 |
| 6,855,706 | B2 | 2/2005 | Tanaka et al. ............ 514/210.7 |
| 7,105,520 | B2 | 9/2006 | Suzuki et al. ................ 514/330 |
| 7,153,963 | B2 * | 12/2006 | Makino et al. .............. 544/284 |
| 2003/0220268 | A1 | 11/2003 | Makino et al. ................ 514/19 |
| 2003/0220318 | A1 | 11/2003 | Suzuki et al. ........... 514/211.03 |
| 2004/0235848 | A1 | 11/2004 | Okuzumi et al. ........... 514/248 |
| 2005/0101779 | A1 | 5/2005 | Sagi et al. .................. 544/285 |
| 2005/0107357 | A1 * | 5/2005 | Scarborough et al. . 514/210.21 |
| 2006/0009476 | A1 | 1/2006 | Kataoka et al. ........ 514/266.31 |

FOREIGN PATENT DOCUMENTS

| CN | 1067431 A | 12/1992 |
| GB | 2 354 440 A | 3/2001 |
| HU | P0000914 | 4/2001 |
| JP | 2001-89368 | 4/2001 |
| WO | WO 98/38173 | 9/1998 |
| WO | WO 99/06431 | 2/1999 |
| WO | WO 99/10312 | 3/1999 |
| WO | WO 99/10313 | 3/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 01/36376 A1 | 5/2001 |
| WO | WO 01/42215 A1 | 6/2001 |
| WO | WO 01/42225 A2 | 6/2001 |
| WO | WO 01/47868 A1 | 7/2001 |
| WO | WO 01/70670 A1 | 9/2001 |
| WO | WO 02/02556 A2 | 1/2002 |
| WO | WO 02/16329 A1 | 2/2002 |
| WO | WO 02/18320 A2 | 3/2002 |
| WO | WO 02/28830 A1 | 4/2002 |
| WO | WO 03/070709 A1 | 8/2003 |
| WO | WO 2004/074264 A1 | 9/2004 |

OTHER PUBLICATIONS

Angela Zeidler et al, "Therapeutic Effects of Antibodies Against Adhesion Molecules in Murine Collagen Type II-Induced Arthritis", *Autoimmunity*, 1995, vol. 21, pp. 245-252.
Daniel K. Podolsky et al, "Attenuation of Colitis in the Cotton-top Tamarin by Anti-α4 integrin Monoclonal Antibody", *J. Clin. Invest.*, Jul. 1993, vol. 92, pp. 372-380.

(Continued)

*Primary Examiner*—James O. Wilson
*Assistant Examiner*—Tamthom N Truong
(74) *Attorney, Agent, or Firm*—Oblon, Spivak, McClelland, Maier & Neustadt, P.C.

(57) ABSTRACT

Specific phenylalanine derivatives and analogues thereof have an antagonistic activity to α4 integrin. They are used as therapeutic agents for various diseases concerning α4 integrin.

71 Claims, No Drawings

OTHER PUBLICATIONS

Tsutomu Takeuchi et al, "Upregulated Expression and Function of Integrin Adhesive Receptors in Systemic Lupus Erythematosus Patients with Vasculitis", *J. Clin. Invest.*, Dec. 1993, vol. 93, pp. 3008-3016.

S. M. Wellicome et al, "Detection of a circulating form of vascular cell adhesion molecule-1:raised levels in rheumatoid arthritis and systemic lupus erythematosus", *Clin. Exp. Immunol.*, 1993, vol. 92, pp. 412-418.

Ted A. Yednock et al, "Prevention of experimental autoimmune encephalomyelitis by antibodies against α4β1 integrin", *Nature*, Mar. 5, 1992, vol. 356, pp. 63-66.

Jody L. Baron et al, "Surface Expression of α4 Integrin by CD4 T Cells Is Required for Their Entry into Brain Parenchyma", *J. Exp. Med.*, Jan. 1993, vol. 177, pp. 57-68.

Ichiro Saito et al, "Expression of Cell Adhesion Molecules in the Salivary and Lacrimal Glands of Sjogren's Syndrome", *Journal of Clinical Laboratory Analysis*, 1993, vol. 7, pp. 180-187.

William M. Abraham et al, "$\alpha_4$-Integrins Mediate Antigen-induced late Bronchial Responses and Prolonged Airway Hyperresponsiveness in Sheep", *J. Clin. Invest.*, Feb. 1994, vol. 93, pp. 776-787.

Hironori Sagara et al, "A Monoclonal Antibody against Very Late Activation Antigen-4 Inhibits Eosinophil Accumulation and Late Asthmatic Response in a Guinea Pig Model of Asthma", *Int. Arch. Allergy Immunol.*, 1997, vol. 112, pp. 287-294.

Sumi Onuma, "Immunohistochemical Studies of Infiltrating Cells in Early and Chronic Lesions of Psoriasis", *The Journal of Dermatology*, 1994, vol. 21, pp. 223-232.

Toshinori Matsui et al, "Effects of anti-VLA-4 Monoclonal Antibody Treatment in Murine Model of Allergic Rhinitis", *Acta Ololaryngol.*, 2000, vol. 120, pp. 761-765.

Nobuyuki Ebihara et al, "Anti VLA-4 monoclonal antibody inhibits eosinophil infiltration in allergic conjunctivitis model of guinea pig", *Current Eye Research*, 1999, vol. 19, No. 1, pp. 20-25.

Jody L. Baron et al, "The Pathogenesis of Adoptive Murine Autoimmune Diabetes Requires an Interaction between α4-Integrins and Vascular Cell Adhesion Molecule-1", *J. Clin. Invest.*, Apr. 1994, vol. 93, pp. 1700-1708.

Simcha R. Meisel et al, "Increased Expression of Neutrophil and Monocyte Adhesion Molecules LFA-1 and Mac-1 and Their Ligand ICAM-1 and VLA-4 Throughout the Acute Phase of Myocardial Infarction", *JACC*, Jan. 1998, vol. 31, No. 1, pp. 120-125.

Peggy T. Shih et al, "Blocking Very Late Antigen-4 Integrin Decreases Leukocyte Entry and Fatty Streak Formation in Mice Fed an Atherogenic Diet", *Circ. Res.*, Feb. 19, 1999, vol. 84, pp. 345-351.

Alan B. Lumsden et al, "Anti-VLA-4 antibody reduces intimal hyperplasia in the endarterectomized cartoid artery in nonhuman primates", *Journal of Vascular Surgery*, Jul. 1997, vol. 26, No. 1, pp. 87-93.

Yoshihisa Mori et al, "Anti-α4 integrin antibody suppresses the development of multiple myeloma and associated osteoclastic osteolysis", *Blood*, Oct. 1, 2004, vol. 104, No. 7, pp. 2149-2154.

Hitoshi Okahara et al, "Involvement of Very Late Activation Antigen 4 (VLA-4) and Vascular Cell Adhesion Molecule 1 (VCAM-1) in Tumor Necrosis Factor α Enhancement of Experimental Metastasis", *Cancer Research*, Jun. 15, 1994, vol. 54, pp. 3233-3236.

Mitsuaki Isobe et al, "Immunosuppression to Cardiac Allografts and Soluble Antigens by Anti-Vascular Cellular Adhesion Molecule-1 and Anti-Very Late Antigen-4 Monoclonal Antibodies", *The Journal of Immunology*, 1994, vol. 153, pp. 5810-5818.

Yoji Shimizu et al, "Integrins in the Immune System", *Advances in Immunology*, 1999, vol. 72, pp. 325-380.

\* cited by examiner

PHENYLALANINE DERIVATIVES

This application claims the benefit of U.S. Provisional Application No. 60/617,026, filed on Oct. 12, 2004, and U.S. Provisional Application No. 60/539,108, filed on Jan. 27, 2004.

TECHNICAL FIELD OF THE INVENTION

The present invention relates to novel phenylalanine derivatives and the use of the phenylalanine derivatives as medicines. The present invention also relates to the compounds usable as therapeutic agents or preventive agents for inflammatory diseases in which α4 integrin-depending adhesion process participates in the pathology. It was reported that α4 integrins participate in rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplant rejection. The compounds of the present invention having an antagonistic effect on the α4 integrins are usable as therapeutic agents or preventive agents for the above-described diseases.

Further, it was reported that α4 integrins have the potential to participate in preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episcleritis, iritis, uveitides, erythema nodosum, pyoderma gangrenosum and autoimmune hepatitis. The compounds of the present invention are also usable as therapeutic agents or preventive agents for the above-described diseases.

In addition, the compounds of the present invention are usable as therapeutic agents or preventive agents for not only the above diseases but also the diseases in which α4 integrins have the potential to participates in the pathology.

The present invention also relates to the methods for producing the above novel phenylalanine derivatives and the synthesis intermediates thereof.

BACKGROUND OF INVENTION

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β1 through β8 subfamilies) depending on the βchains thereof. Known typical subfamilies are β1 and β3 subfamilies involved in the adhesion of cell ingredients to the extracellular matrix such as collagen and fibronectin; β2 subfamily involved in cell-to-cell adhesion in the immune system; and β7 subfamily which mainly participates in the infiltration of leukocytes into mucosal tissues (Nonpatent Literature 1). As for the above-described α4 integrins, two kinds of molecules thereof are known. They are VLA-4 (very late antigen-4) molecule belonging to the β1 subfamily and comprising α4β1 chain and LPAM-1 (lymphocyte Peyer's patch HEV adhesion molecule-1) molecule belonging to the β7 subfamily and comprising α4β7 chain. Usually most of leukocytes circulating in the blood have only a low adhesion affinity for the vascular-endothelium cells and they cannot move out of the blood vessel. However, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Nonpatent Literature 2). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Nonpatent Literature 1). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Nonpatent Literature 1). The β1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β3 subfamily and β5 subfamily, recognize arginine-glycine-aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine-aspartic acid-valine (LDV) as the core sequence participates (Nonpatent Literature 3). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Nonpatent Literatures 4 to 7). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Nonpatent Literature 8). The above-described facts indicate that all the interactions of α4 integrin and VCAM-1, MAdCAM-1 or fibronectin can be blocked by using a suitable α4 integrin antagonist (the term "α4 integrin antagonist" in the specification indicates a substance antagonistic to α4β1 and/or α4β7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Nonpatent Literatures 9 to 11). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (Nonpatent Literatures 12 and 13), lungs and respiratory tract epithelium in asthma (Nonpatent Literature 14) and allergic diseases (Nonpatent Literature 15), systemic lupus erythematosus (Nonpatent Literature 16), Sjögren's syndrome (Nonpatent Literature 17), multiple sclerosis (Nonpatent Literature 18) and psoriasis (Nonpatent Literature 19); atherosclerotic plagues (Nonpatent Literature 20), intestinal tissues of the patients with inflammatory bowel diseases such as Crohn's disease and ulcerative colitis (Nonpatent Literatures 21 and 22), inflamed tissue of Langerhans islet of patients with diabetes (Nonpatent Literature 23) and implants during the rejection of transplantation of heart or kidney (Nonpatent Literatures 24 and 25). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α4 integrins was effective in controlling the incidence rate or in controlling encephalomyelitis in the experimental autoimmune encephalomyelitis models, i.e. multiple sclerosis models (Nonpatent Literatures 26 and 27). Zeidler et al. reported that in vivo administration of an antibody against α4-integrin was effective in controlling the incidence rate of mouse collagen arthritis (rheumatoid models) (Nonpatent Literature 28). The therapeutic effect of an antibody against a 4-integrin in asthma models was reported by Abraham et al. and Sagara et al. (Nonpatent Literatures 29 and 30). The effect of an antibody against α4-integrin in inflammatory bowel disease models was reported by Podolsky et al. (Nonpatent Literature 31). The effect of an antibody against α4-integrin and that against VCAM antibody in insulin-dependent diabetes models were reported by Baron et al. (Nonpatent Literature 32). It was made apparent with baboon models that the restenosis of a blood vessel after an angioplasty carried out because of arteriosclerosis can be inhibited by the administration of α4 integrin antibody (Nonpatent Literature 33). It was also reported that α4 integrin or VCAM antibody is effective in inhibiting the rejection of an implant or inhibiting metastasis of a cancer (Nonpatent Literatures 34 and 35). The therapeutic effect of an antibody against VCAM-1 in inflammatory bowel disease models was reported by Sans et al. (Nonpatent Literature 44).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Nonpatent Literature 36). Hanninen et al. reported that induction of the expression is observed in an inflamed tissue of Langerhans islet of NOD mouse which is a model of an insulin-dependent diabetes (Nonpatent Literature 37). The fact that LPAM-1/MAdCAM-1 adhesion mechanism participates in the progress of diseases is apparent from the fact that conditions of mouse models with inflammatory bowel disease (Nonpatent Literature 38) and the above-described NOD mouse models are improved by the in vivo administration of antibody to MAdCAM or antibody to β7 integrin (Nonpatent Literatures 39 and 40).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. Regarding the therapeutic effects of the suitable antagonist(s), they can be ensured by the animal models described in the above literatures or the other literatures such as Nonpatent Literature 45 and 46. The use of the antibody against VLA-4 as the VLA-4 antagonist is described in Patent Literatures 1 to 4. Peptide compounds as VLA-4 antagonists are described in Patent Literatures 5 to 8. Amino acid derivatives usable as VLA-4 antagonists are described in Patent Literatures 9 to 13. The low-molecular α4 integrin inhibitor which can be orally administered is described in Patent Literatures 14 and 15.

[Patent Literature 1] WO93/13798
[Patent Literature 2] WO93/15764
[Patent Literature 3] WO94/16094
[Patent Literature 4] WO95/19790
[Patent Literature 5] WO94/15958
[Patent Literature 6] WO95/15973
[Patent Literature 7] WO96/00581
[Patent Literature 8] WO96/06108
[Patent Literature 9] WO99/10312
[Patent Literature 10] WO99/10313
[Patent Literature 11] WO99/36393
[Patent Literature 12] WO99/37618
[Patent Literature 13] WO99/43642
[Patent Literature 14] WO02/16329
[Patent Literature 15] WO03/070709
[Nonpatent Literature 1] Shimizu et al. Adv. Immunol. 72: 325-380, 1999
[Nonpatent Literature 2] Butcher et al. Adv. Immunol. 72: 209-253, 1999
[Nonpatent Literature 3] Pulido et al. J. Biol. Chem. 266: 10241-10245, 1991
[Nonpatent Literature 4] Clements et al. J. Cell Sci. 107: 2127-2135, 1994
[Nonpatent Literature 5] Vonderheide et al. J. Cell Biol. 125: 215-222, 1994
[Nonpatent Literature 6] Renz et al. J. Cell Biol. 125: 1395-1406, 1994
[Nonpatent Literature 7] Kilger et al. Int. Immunol. 9: 219-226, 1997

[Nonpatent Literature 8] Vanderslice et al. J. Immunol. 158: 1710-1718, 1997

[Nonpatent Literature 9] Elices, Cell 60: 577-584, 1990

[Nonpatent Literature 10] Osborn et al. Cell 59: 1203-1211, 1989

[Nonpatent Literature 11] Issekutz et al. J. Eex. Med. 183: 2175-2184, 1996

[Nonpatent Literature 12] van Dinther-Janssen, J. Immunol. 147: 4207-4210, 1991

[Nonpatent Literature 13] Morales-Ducret et al. J. Immunol. 149: 1424-1431, 1992

[Nonpatent Literature 14] ten Hacken et al. Clin. Exp. Allergy 12: 1518-1525, 1998

[Nonpatent Ligerature 15] Randolph et al. J. Clin. Invest. 104: 1021-1029, 1999

[Nonpatent Ligerature 16] Takeuchi et al. J. Clin. Invest. 92: 3008-3016, 1993

[Nonpatent Literature 17] Edwards et al. Ann. Rheum. Dis. 52: 806-811, 1993

[Nonpatent Literature 18] Steffen et al. Am. J. Pathol. 145: 189-201, 1994

[Nonpatent Ligerature 19] Groves et al. J. Am. Acad. Dermatol. 29: 67-72, 1993

[Nonpatent Ligerature 20] O'Brien et al. J. Clin. Invest. 92: 945-951, 1993

[Nonpatent Ligerature 21] Koizumi et al. Gastroenterol. 103: 840-847, 1992

[Nonpatent Ligerature 22] Nakamura et al. Lab. Invest. 69: 77-85, 1993

[Nonpatent Ligerature 23] Martin et al. J. Autoimmun. 9: 637-643, 1996

[Nonpatent Ligerature 24] Herskowitz et al. Am. J. Pathol. 145: 1082-1094, 1994

[Nonpatent Ligerature 25] Hill et al. Kidney Int. 47: 1383-1391, 1995

[Nonpatent Ligerature 26] Yednock et al. Nature 356: 63-66, 1992

[Nonpatent Ligerature 27] Baron et al. J. Exp. Med. 177: 57-68, 1993

[Nonpatent Ligerature 28] Zeidler et al. Autoimmunity 21: 245-252, 1995

[Nonpatent Ligerature 29] Abraham et al. J. Clin. Invest. 93: 776-787, 1994

[Nonpatent Ligerature 30] Sagara et al. Int. Arch. Allergy Immunol. 112: 287-294, 1997

[Nonpatent Ligerature 31] Podolsky et al. J. Clin. Invest. 92: 372-380, 1993

[Nonpatent Ligerature 32] Baron et al. J. Clin. Invest. 93: 1700-1708, 1994

[Nonpatent Ligerature 33] Lumsden et al. J. Vasc. Surg. 26: 87-93, 1997

[Nonpatent Ligerature 34] Isobe et al. J. Immunol. 153: 5810-5818, 1994

[Nonpatent Ligerature 35] Okahara et al. Canser Res. 54: 3233-3236, 1994

[Nonpatent Ligerature 36] Briskin et al. Am. J. Pathol. 151: 97-110, 1997

[Nonpatent Ligerature 37] Hanninen et al. J. Immunol. 160: 6018-6025, 1998

[Nonpatent Ligerature 38] Picarella et al. J. Immunol. 158: 2099-2106, 1997

[Nonpatent Ligerature 39] Hanninen et al. J. Immunol. 160: 6018-6025, 1998

[Nonpatent Ligerature 40] Yang et al. Diabetes 46: 1542-1547, 1997

[Nonpatent Ligerature 41] Prog. Med. 5: 2157-2161, 1985

[Nonpatent Ligerature 42] Iyakuhin no kaihatsu (Hirokawa Shoten) vol. 7: 163-198, 1990

[Nonpatent Ligerature 43] Saishin Soyakkagaku (Technomics, Inc.) Gekan: 271-298, 1999

[Nonpatent Ligerature 44] Sans, M. et al. Gastroenterology 116: 874-883, 1999

[Nonpatent Ligerature 45] Leone, D. R. et al. J. Pharmacol. Exp. Ther 305: 1150-1162, 2003

[Nonpatent Ligerature 46] Kudlacz E. et al. J. Pharmacol. Exp. Ther 301: 747-752, 2002

[Nonpatent Ligerature 47] Gordon, F. H. et al. Gastroenterology 121: 268-274, 2001

DISCLOSURE OF THE INVENTION

An object of the present invention is to provide novel compounds having $\alpha 4$ integrin antagonistic effect.

Another object of the present invention is to provide the compounds having $\alpha 4$ integrin antagonistic effect, which can be administered orally.

Still another object of the present invention is to provide a pharmaceutical composition comprising such novel compounds and a pharmaceutically acceptable carrier thereof.

A further object of the present invention is to provide a medicament containing such novel compounds.

An additional object of the present invention is to provide $\alpha 4$ integrin antagonists.

A still additional object of the present invention is to provide therapeutic agents or preventive agents for diseases in which $\alpha 4$ integrin-depending adhesion process participates in the pathology, such as inflammatory diseases, rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplant rejection.

A further additional object of the present invention is to provide therapeutic agents or preventive agents for diseases such as preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episcleritis, iritis, uveitides, erythema nodosum, pyoderma gangrenosum and autoimmune hepatitis.

A further additional object of the present invention is to provide therapeutic agents or preventive agents for not only the above diseases but also the diseases in which $\alpha 4$ integrins have the potential to participates in the pathology.

A still additional object of the present invention is to provide the methods for producing the above novel compounds and the synthesis intermediates thereof.

For the purpose of solving the above-described problems, the inventors have synthesized various phenylalanine derivatives and have found that specific, novel phenylalanine derivatives have an excellent $\alpha 4$ integrin antagonistic activity under the existence of serum and that the total body clearance thereof is low. The inventors also have found that specific, novel phenylalanine derivatives show a high area under the blood plasma concentration-time curve(AUC) and a high bioavailability when administered orally. They further have found that such derivatives have an excellent in vivo $\alpha 4$ integrin antagonistic activity when administered orally. The present invention has been completed on the basis of this finding. The completion of the present invention makes it possible to decrease its dosage and number of doses.

Namely, the present invention is describes as follows:

[1] Phenylalanine derivatives of the following formula (1) or pharmaceutically acceptable salts thereof:

(1)

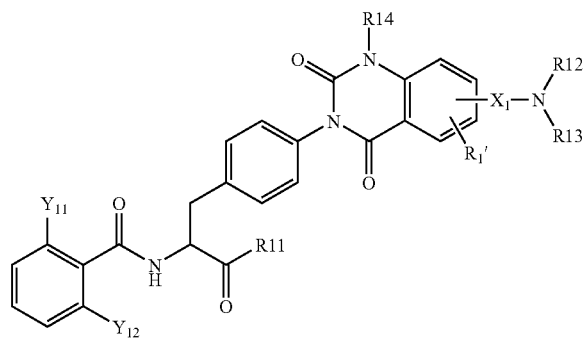

wherein R11 represents a hydroxyl group, an alkoxyl group having 1 to 6 carbon atoms which may have a substitutent(s), a morpholinoethyloxy group or a benzyloxy group which may be substituted with a methyl group(s) or a methoxy group(s), R12 and R13 each independently represent a hydrogen atom, an alkyl group having 1 to 6 carbon atoms, an acetyl group or methyloxycarbonyl group, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, R14 represents a methyl group or an ethyl group, $R_1'$ represents a hydrogen atom, a fluorine atom or a chlorine atom, $X_1$ represents —CH(R1a)-, —CH(R1a)CH(R1b)-, —CH(R1a)CH(R1b)CH(R1c)-, —CH(R1a)CH(R1b)CH(R1c)CH(R1d)-, —N(R1a)CH(R1b)CH(R1c)-, —OCH(R1a)CH(R1b)-, —OCH(R1a)CH(R1b)CH(R1c)- or 1,3-pyrrolidinylene, wherein R1a, R1b, R1c and R1d each independently represent a hydrogen atom or a methyl group, and $Y_{11}$ and $Y_{12}$ represent either one of the combinations, (Cl, Cl), (Cl, Me), (Cl, F), (F, F) and (F, Me).

[20] Phenylalanine derivatives of the following formula (2) or pharmaceutically acceptable salts thereof:

(2)

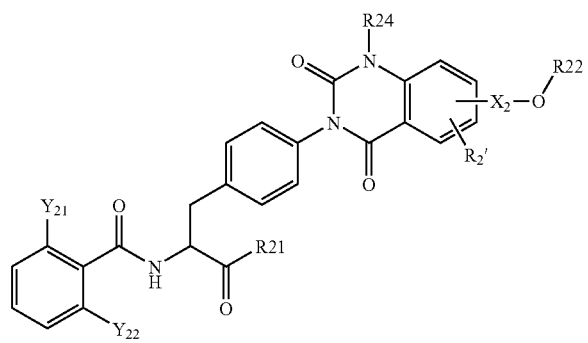

wherein R21 represents a hydroxyl group, an alkoxyl group having 1 to 6 carbon atoms, a morpholinoethyloxy group or a benzyloxy group which may be substituted with a methyl group(s) or a methoxy group(s), R22 represents a hydrogen atom or an alkyl group having 1 to 3 carbon atoms, R24 represents a methyl group or an ethyl group, $R_2'$ represents a hydrogen atom, a fluorine atom or a chlorine atom, $X_2$ represents —CH(R2a)-, —CH$_2$CH$_2$— or —N(R2a)CH$_2$CH$_2$—, wherein R2a represents a hydrogen atom or a methyl group, and $Y_{21}$ and $Y_{22}$ represent either one of the combinations, (Cl, Cl), (Cl, Me), (Cl, F), (F, F) and (F, Me).

[23] Phenylalanine derivatives of the following formula (3) or pharmaceutically acceptable salts thereof:

(3)

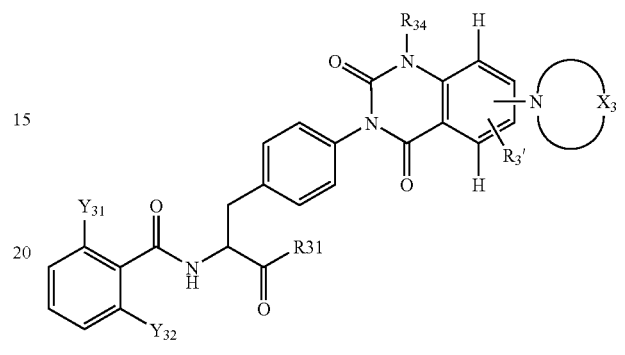

wherein R31 represents a hydroxyl group, an alkoxyl group having 1 to 6 carbon atoms, a morpholinoethyloxy group or a benzyloxy group which may be substituted with a methyl group(s) or a methoxy group(s), R34 represents a methyl group or an ethyl group, $R_3'$ represents a hydrogen atom or a fluorine atom, (3-1)

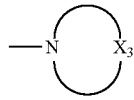

the formula (3-1) represents 4-morpholinyl group, 4-thiomorpholnyl group, 3-tetrahydrothiazolyl group, 1-piperazinyl group of which the fourth position may be substituted with an alkyl group having 1 to 3 carbon atoms, or 1-imidazolyl group which may be substituted with a methyl group, an ethyl group or an amino group, wherein X3 represents an oxygen atom, a nitrogen atom which may be substituted with an alkyl group having 1 to 3 carbon atoms, or a sulfur atom, and $Y_{31}$ and $Y_{32}$ represent either one of the combinations, (Cl, Cl), (Cl, Me), (Cl, F), (F, F) and (F, Me).

[28] Phenylalanine derivatives of the following formula (4) or pharmaceutically acceptable salts thereof:

(4)

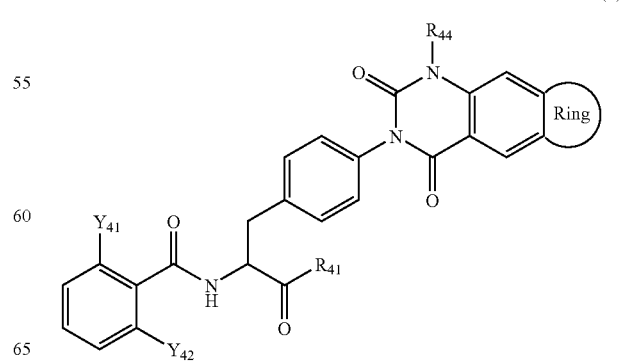

wherein R$_{41}$ represents a hydroxyl group, an alkoxyl group having 1 to 6 carbon atoms, a morpholinoethyloxy group or a benzyloxy group which may be substituted with a methyl group(s) or a methoxy group(s), Ring represents a benzene ring, a pyridine ring, a thiophene ring, a piperidine ring of which the first position may be substituted with an alkyl group having 1 to 3 carbon atoms, a piperazine ring of which the first and/or fourth position may be substituted with an alkyl group having 1 to 3 carbon atoms, or a pyrrolidine ring of which the first position may be substituted with an alkyl group having 1 to 3 carbon atoms, R$_{44}$ represents a methyl group or an ethyl group, and Y$_{41}$ and Y$_{42}$ represent either one of the combinations, (Cl, Cl), (Cl, Me), (Cl, F), (F, F) and (F, Me).

[30] Phenylalanine derivatives of the following formula (5) or pharmaceutically acceptable salts thereof:

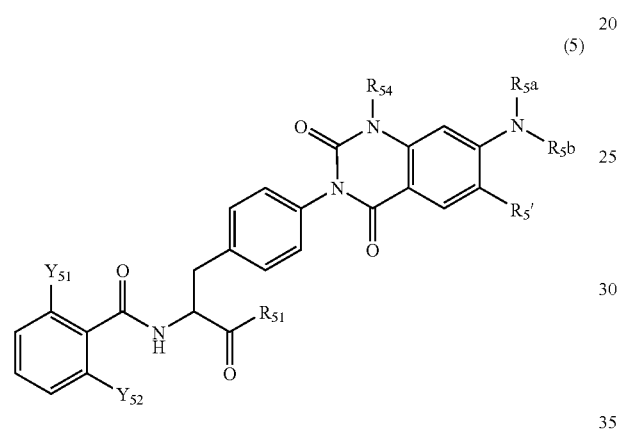

(5)

wherein R$_{51}$ represents a hydroxyl group, an alkoxyl group having 1 to 6 carbon atoms, a morpholinoethyloxy group or a benzyloxy group which may be substituted with a methyl group(s) or a methoxy group(s), R$_{54}$ represents a methyl group or an ethyl group, R$_5$' represents a hydrogen atom or a fluorine atom, R5a and R5b each independently represent a hydrogen atom or an alkyl group having 1 to 3 carbon atoms, or N(R5a)R5b represents 1-pyrrolidinyl group or 1-piperidinyl group, and Y$_{51}$ and Y$_{52}$ represent either one of the combinations, (Cl, Cl), (Cl, Me), (Cl, F), (F, F) and (F, Me).

[32] Phenylalanine derivatives of the following formula (6) or pharmaceutically acceptable salts thereof:

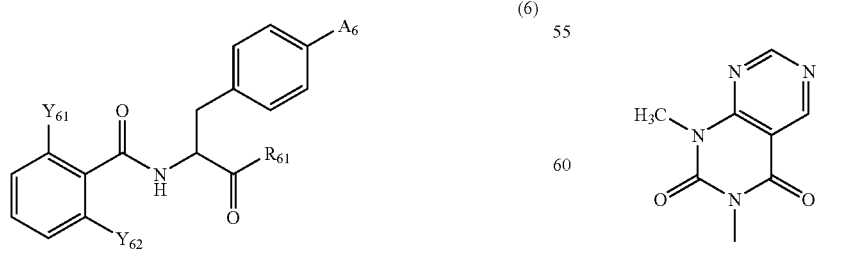

(6)

wherein R$_{61}$ represents a hydroxyl group, an alkoxyl group having 1 to 6 carbon atoms, a morpholinoethyloxy group or a benzyloxy group which may be substituted with a methyl group(s) or a methoxy group(s), A$_6$ represents either one of the following formulae (6-1) to (6-6):

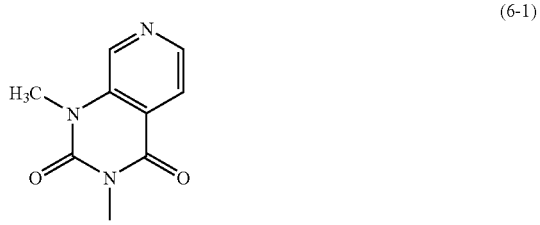

(6-1)

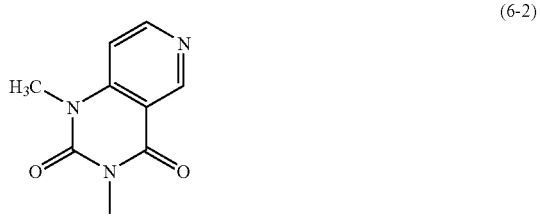

(6-2)

(6-3)

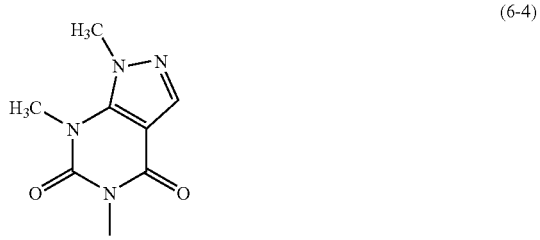

(6-4)

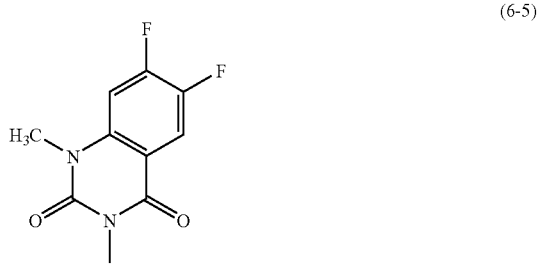

(6-5)

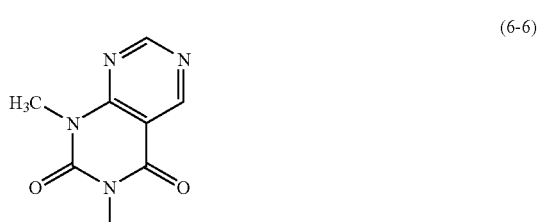

(6-6)

and Y$_{61}$ and Y$_{62}$ represent either one of the combinations, (Cl, Cl), (Cl, Me), (Cl, F), (F, F) and (F, Me).

[35] Phenylalanine derivatives of the following formula (7) or pharmaceutically acceptable salts thereof:

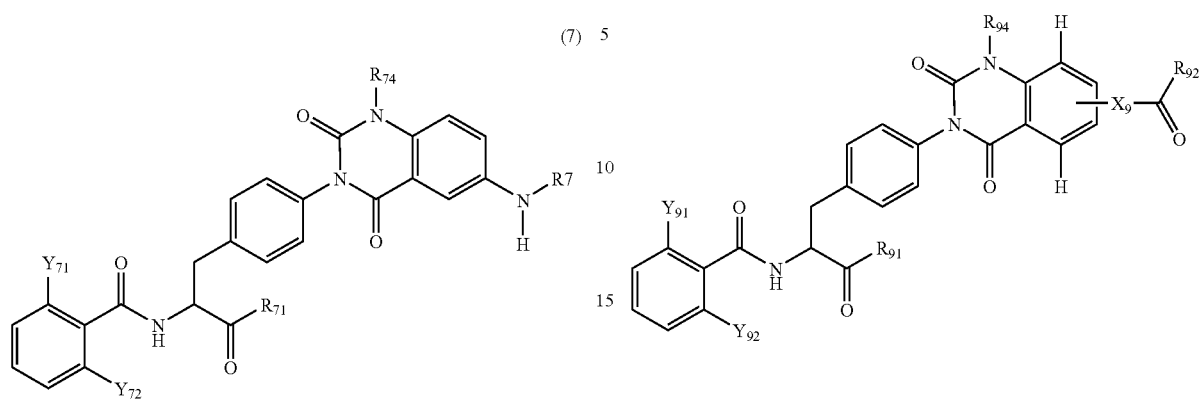

(7)

wherein $R7_1$ represents a hydroxyl group, an alkoxyl group having 1 to 6 carbon atoms, a morpholinoethyloxy group or a benzyloxy group which may be substituted with a methyl group(s) or a methoxy group(s), $R_{74}$ represents a methyl group or an ethyl group, R7 represents an alkynyl group having 3 to 5 carbon atoms, a cycloalkylmethyl group having 4 to 6 carbon atoms, a cycloalkyl group having 3 to 6 carbon atoms, or a propyl group, and $Y_{71}$ and $Y_{72}$ represent either one of the combinations, (Cl, Cl), (Cl, Me), (Cl, F), (F, F) and (F, Me).

[38] Phenylalanine derivatives of the following formula (8) or pharmaceutically acceptable salts thereof:

(8)

wherein $R_{81}$ represents a hydroxyl group, an alkoxyl group having 1 to 6 carbon atoms, a morpholinoethyloxy group, a benzyloxy group which may be substituted with a methyl group(s) or a methoxy group(s), or hydroxyethyl group, $R_{82}$ represents a methyl group or an ethyl group, $R_{84}$ represents a methyl group or an ethyl group, $n_8$ represents an integer from 0 to 2, and $Y_{81}$ and $Y_{82}$ represent either one of the combinations, (Cl, Cl), (Cl, Me), (Cl, F), (F, F) and (F, Me).

[41] Phenylalanine derivatives of the following formula (9) or pharmaceutically acceptable salts thereof:

(9)

wherein $R_{91}$ represents a hydroxyl group, an alkoxyl group having 1 to 6 carbon atoms, a morpholinoethyloxy group or a benzyloxy group which may be substituted with a methyl group(s) or a methoxy group(s), $R_{92}$ represents a hydroxyl group, an alkoxyl group having 1 to 6 carbon atoms, an amino group or a benzyloxy group which may be substituted with a methyl group(s) or a methoxy group(s), $R_{94}$ represents a methyl group or an ethyl group, $X_9$ represents an atomic bond, —$CH_2$—, —$CH_2CH_2$— or —CH=CH—, and $Y_{91}$ and $Y_{92}$ represent either one of the combinations, (Cl, Cl), (Cl, Me), (Cl, F), (F, F) and (F, Me).

[44] Phenylalanine derivatives of the following formula (10) or pharmaceutically acceptable salts thereof:

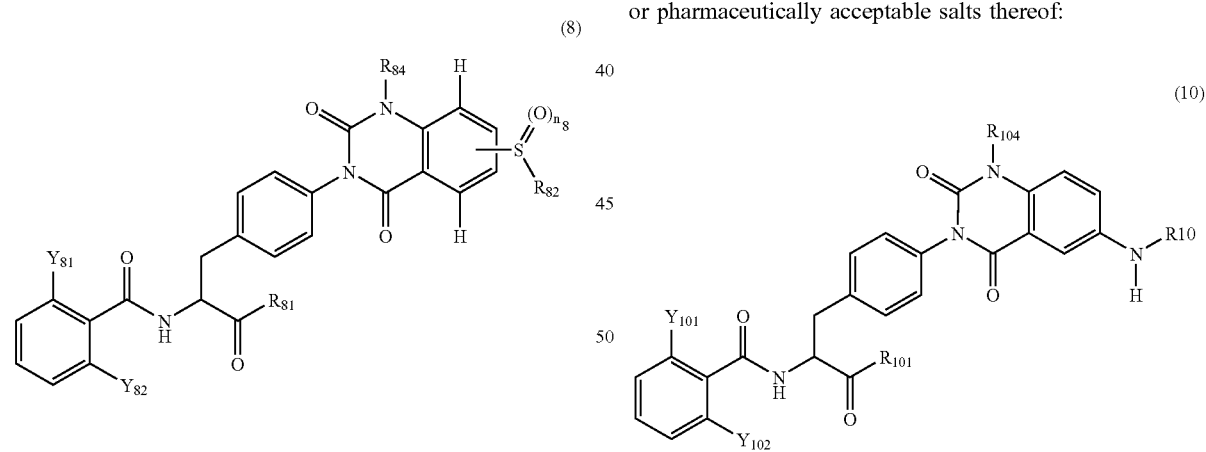

(10)

wherein $R_{101}$ represents an alkoxyl group having 2 to 6 carbon atoms or a morpholinoethyloxy group, R10 represents a methyl group or an ethyl group, $R_{104}$ represents a methyl group or an ethyl group, and $Y_{101}$ and $Y_{102}$ represent either one of the combinations, (Cl, Cl), (Cl, Me), (Cl, F), (F, F) and (F, Me).

[46] Phenylalanine derivatives of the following formula (11) or pharmaceutically acceptable salts thereof:

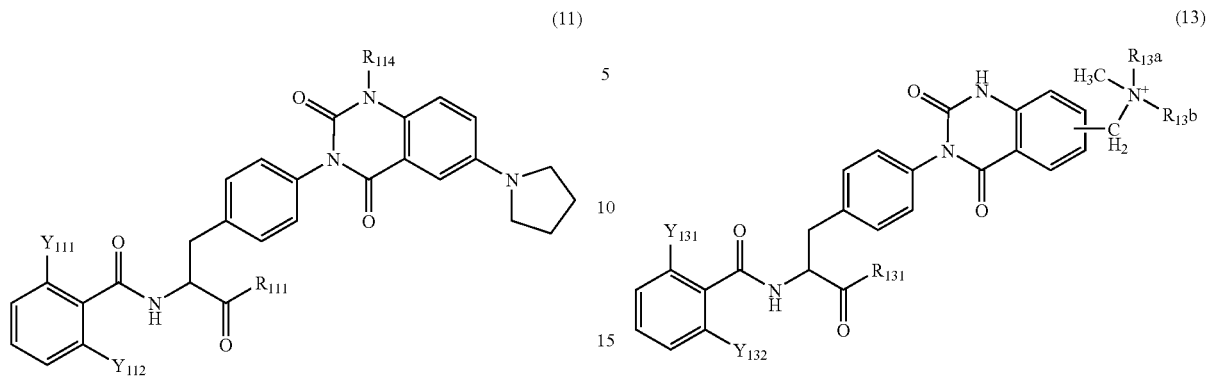

wherein R$_{111}$ represents an alkoxyl group having 1 to 6 carbon atoms or a morpholinoethyloxy group, R$_{114}$ represents a methyl group or an ethyl group, and Y$_{111}$ and Y$_{112}$ represent either one of the combinations, (Cl, Cl), (Cl, Me), (Cl, F), (F, F) and (F, Me).

[47] Phenylalanine derivatives of the following formula (12) or pharmaceutically acceptable salts thereof:

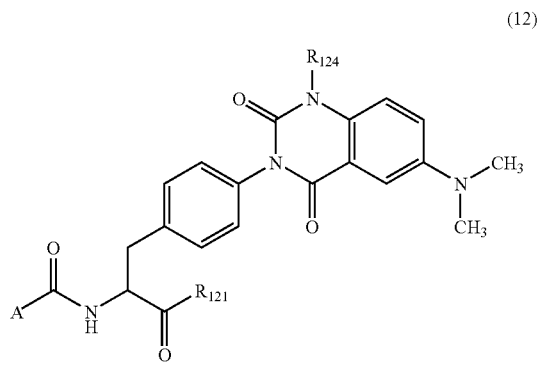

wherein R$_{121}$ represents an alkoxyl group having 1 to 6 carbon atoms or a morpholinoethyloxy group, R$_{124}$ represents a methyl group or an ethyl group, and A represents either one of the following formulae (12-1) and (12-2):

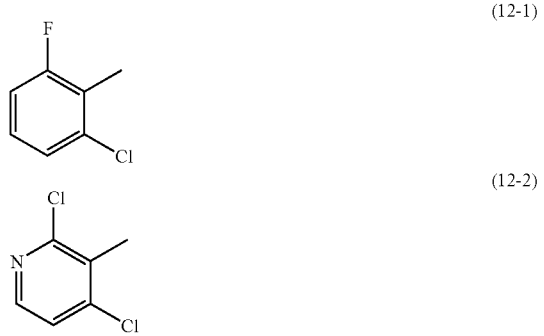

[48] Phenylalanine derivatives of the following formula (13) or pharmaceutically acceptable salts thereof:

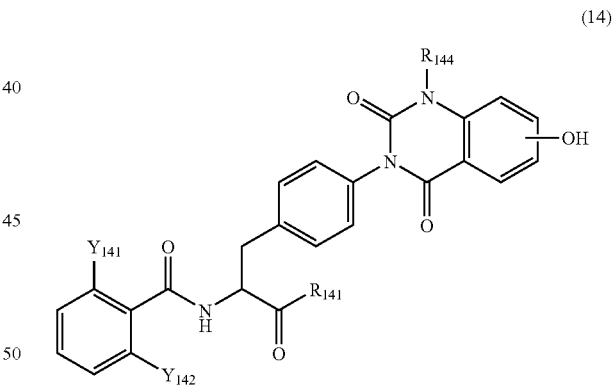

wherein R131 represents a hydroxyl group, an alkoxyl group having 1 to 6 carbon atoms, a morpholinoethyloxy group or a benzyloxy group which may be substituted with a methyl group(s) or a methoxy group(s), R13a and R13b each independently represent a hydrogen atom or an alkyl group having 1 to 3 carbon atoms, or N(R13a)R13b represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, and Y$_{131}$ and Y$_{132}$ represent either one of the combinations, (Cl, Cl), (Cl, Me), (Cl, F), (F, F) and (F, Me).

[49] Phenylalanine derivatives of the following formula (14) or pharmaceutically acceptable salts thereof:

(14)

wherein R141 represents a hydroxyl group, an alkoxyl group having 1 to 6 carbon atoms or a morpholinoethyloxy group, R144 represents a methyl group or an ethyl group, a hydroxyl group on a quinazolinedione ring is located on the sixth or seventh position of the ring, and Y$_{141}$ and Y$_{142}$ represent either one of the combinations, (Cl, Cl), (Cl, Me), (Cl, F), (F, F) and (F, Me).

[51] A pharmaceutical composition comprising a phenylalanine derivative or a pharmaceutically acceptable salt thereof according to any one of the above [1] to [50] as an active ingredient and a pharmaceutically acceptable carrier thereof.

[52] An α4 integrin antagonist comprising a phenylalanine derivative or a pharmaceutically acceptable salt thereof according to any one of the above [1] to [50] as an active ingredient.

[53] A therapeutic agent or preventive agent for inflammatory diseases in which α4 integrin-depending adhesion process participates in the pathology, which comprises a phenylalanine derivative or a pharmaceutically acceptable salt thereof according to any one of the above [1] to [50] as an active ingredient.

[54] A therapeutic agent or preventive agent for rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplant rejection, which contains a phenylalanine derivative or a pharmaceutically acceptable salt thereof according to any one of the above [1] to [50] as an active ingredient.

[55] A therapeutic agent or preventive agent for preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episcleritis, iritis, uveitides, erythema nodosum, pyoderma gangrenosum and autoimmune hepatitis, which comprises a phenylalanine derivative or a pharmaceutically acceptable salt thereof according to any one of the above [1] to [50] as an active ingredient.

[56] A therapeutic agent or preventive agent for the diseases in which α4 integrins have the potential to participates in the pathology, which comprises a phenylalanine derivative or a pharmaceutically acceptable salt thereof according to any one of the above [1] to [50] as an active ingredient.

The present invention also provides the following compounds, which are the synthesis intermediates of the phenylalanine derivatives of the formula (1): isopropyl (S)-2-(2,6-dichlorobenzoylamino)-3-(4-nitrophenyl) propionate, isopropyl (S)-2-(2,6-dichlorobenzoylamino)-3-(4-aminophenyl) propionate, isopropyl (S)-3-[4-(2-amino-5-iodobenzoylamino) phenyl]-2-(2,6-dichlorobenzoylamino)propionate, isopropyl (S)-2-(2,6-dichlorobenzoylamino)-3-[4-(6-iodo-2,4-dioxo-1,2,3,4-tetrahydro-2H-quinazolin-3-yl) phenyl]propionate, isopropyl (S)-2-(2,6-dichlorobenzoylamino)-3-[4-(6-iodo-1-methyl-2,4-dioxo-1,2,3,4-tetrahydro-2H-quinazolin-3-yl)phenyl]propionate, (S)-3-{4-[2-(2,6-dichlorobenzoylamino)-2-isopropoxycarbonylethyl]phenyl}-1-methyl-2,4-dioxo-1,2,3,4-tetrahydroquinazoline-6-carboxylic acid, isopropyl (S)-2-(2,6-dichlorobenzoylamino)-3-[4-(6-hydroxymethyl-1-methyl-2,4-dioxo-1,2,3,4-tetrahydro-2H-quinazolin-3-yl)phenyl] propionate, isopropyl (S)-3-[4-(6-chloromethyl-1-methyl-2,4-dioxo-1,2,3,4-tetrahydro-2H-quinazolin-3-yl)phenyl]-2-(2,6-dichlorobenzoylamino)propionate, and isopropyl (S)-2-(2,6-dichlorobenzoylamino)-3-[4-(6-hydroxy-1-methyl-2,4-dioxo-1,2,3,4-tetrahydro-2H-quinazolin-3-yl)phenyl] propionate.

BEST MODE FOR CARRYING OUT THE INVENTION

An "alkyl group having 1 to 6 carbon atoms" is either straight, branched or cyclic. Its examples are methyl, ethyl, propyl and isopropyl group, butyl group, isobutyl group, sec-butyl group, tertbutyl group, cyclopropylmethyl group, cyclobutyl group, pentyl group, isopentyl group, hexyl group, 1-methyl-butyloxy group, 1,1-dimethyl-propyl group, cyclopropyl group, cyclopentyl group and cyclohexyl group. Further, an "alkyl group having 1 to 3 carbon atoms" is either straight or branched and indicates methyl, ethyl, propyl and isopropyl group.

An "alkoxyl group having 1 to 6 carbon atoms" indicates those of which an alkyl part is either straight, branched or cyclic. Its examples are methoxy, ethoxy, propyloxy, isopropyloxy, butyloxy, isobutyloxy, sec-butyloxy, tert-butyloxy, pentyloxy, isopentyloxy, 1-methyl-butyloxy, 1,1-dimethyl-propyloxy, 2-methyl-butyloxy, neopentyloxy, hexyloxy, isohexyloxy, 1-methyl-pentyloxy, 1,1-dimethyl-butyloxy, cyclopropyloxy, cyclobutyloxy, cyclopentyloxy and cyclohexyloxy group.

An "alkoxyl group having 2 to 6 carbon atoms" indicates those of which an alkyl part is either straight, branched or cyclic. Its examples are ethoxy, propyloxy, isopropyloxy, butyloxy, isobutyloxy, sec-butyloxy, tert-butyloxy, pentyloxy, isopentyloxy, 1-methyl-butyloxy, 1,1-dimethyl-propyloxy, 2-methyl-butyloxy, neopentyloxy, hexyloxy, isohexyloxy, 1-methyl-pentyloxy, 1,1-dimethyl-butyloxy, cyclopropyloxy, cyclobutyloxy, cyclopentyloxy and cyclohexyloxy group.

A "branched alkoxyl group having 3 to 6 carbon atoms" indicates those of which an alkyl part is either branched or cyclic. They may be substituted with a methoxy group or a hydroxyl group. Its examples are isopropyloxy, sec-butyloxy, tert-butyloxy, 1-methyl-butyloxy, 1,1-dimethyl-propyloxy, 2-methyl-butyloxy, neopentyloxy, 1-methyl-pentyloxy, 1,1-dimethyl-butyloxy, cyclopropyloxy, cyclobutyloxy, cyclopentyloxy and cyclohexyloxy group. Among them, an isopropyloxy group, a sec-butyloxy group, a 1-methyl-butyloxy group, a cyclopentyloxy group and a cyclohexyloxy group are preferable, and an isopropyloxy group is particularly preferable.

In an "alkynyl group having 3 to 5 carbon atoms", a carbon atom(s) having a free radical(s) is not limited to a SP atom(s). Its examples are 2-propynyl, 3-butynyl, 2-butynyl, 4-pentynyl, 3-pentynyl and 2-pentynyl groups.

A "cycloalkylmethyl group having 4 to 6 carbon atoms" indicates cyclopropylmethyl, cyclobutylmethyl and cyclopentylmethyl groups.

A "cycloalkyl group having 3 to 6 carbon atoms" indicates cyclopropyl, cyclobutyl, cyclopentyl and cyclohexyl groups.

A "piperazinyl group of which the fourth position may be substituted with an alkyl group having 1 to 3 carbon atoms" indicates piperazinyl, N-methylpiperazinyl, N-ethylpiperazinyl, N-propylpiperazinyl and N-isopropylpiperazinyl groups.

In a "piperazine ring of which the first and/or fourth position may be substituted with an alkyl group having 1 to 3 carbon atoms", a substituent(s) on the nitrogen of the first and/or fourth position thereof may be same or different from each other. Examples of the combination of the substituents are (H, H), (H, Me), (H, Et), (H, Pr), (H, isoPr), (Me, Me), (Me, Et), (Me, Pr), (Me, isoPr), (Et, Et), (Et, Pr), (Et, isoPr), (Pr, Pr), (Pr, isoPr) and (isoPr, isoPr).

The fifth, sixth, seventh and eighth positions of a quinazolinedione ring indicate the following formula:

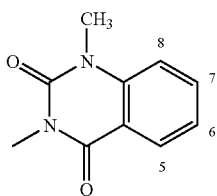

—CO—R11, —CO—R21, —CO—R31, —CO—R41, —CO—R51, —CO—R61, —CO—R71, —CO—R81, —CO—R91, —CO—R101, —CO—R111, —CO—R121, —CO—R131, and —CO—R141 in the formulae (1) to (14) of the present invention indicate a carboxyl group or a carboxyl group in a prodrug modification which is converted into a carboxyl group in vivo. Namely, R11, R21, R31, R41, R51, R61, R71, R81, R91, R101, R11, R121, R131 and R141 (hereinafter referred to as R11 to R141) indicate a hydroxyl group or a group which is substituted with a hydroxyl group in vivo. Concrete examples of a carboxyl group in a prodrug modification are described in, for example, Nonpatent Literatures 41 to 43.

R11 to R141 includes, for example, an alkoxyl group having 1 to 8 carbon atoms which may have a substituent(s), an aryloxyl group which may have a substituent(s), an arylalkyloxy group which may have a substituent(s), a heteroaryloxy group which may have a substituent(s) and a heteroarylalkyloxy group which may have a substituent(s).

An alkoxyl group having 1 to 8 carbon atoms herein indicates those of which an alkyl part is either straight, branched or cyclic. Its examples are methoxy, ethoxy, propyloxy, isopropyloxy, butyloxy, isobutyloxy, sec-butyloxy, tert-butyloxy, pentyloxy, isopentyloxy, 1-methyl-butyloxy, 1,1-dimethyl-propyloxy, 2-methyl-butyloxy, neopentyloxy, hexyloxy, isohexyloxy, 1-methyl-pentyloxy, 1,1-dimethyl-butyloxy heptyloxy, octyloxy, cyclopropyloxy, cyclobutyloxy, cyclopentyloxy, cyclohexyloxy, cycloheptyloxy and cyclooctyloxy group.

An alkoxyl group having 1 to 8 carbon atoms is preferably an alkoxyl group having 1 to 6 carbon atoms. Concretely, they include a methoxy group, O,2-benzoyloxirene group and hydroxy group. A methoxy group having O,2-benzoyloxirene group as a substituent(s) indicates 3-oxo-1,3-dihydro-2-benzofuran-1-yloxy group.

A substituent(s) in "an aryloxy group which may have a substituent(s)" includes a methoxy group and a methyl group.

A substituent(s) in "a heteroaryloxy group which may have a substituent(s)" includes a methoxy group and a methyl group.

It can be considered that the phenylalanine derivatives of the formulae (1) to (14) are optical isomers and the compounds indicated in the present invention include all of the said optical isomers. Further, both the compounds formed by a single optical isomer and the mixture of several optical isomers are included in the compounds of the present invention. Further, regarding stereochemistry of the phenylalanine portion explicitly indicated in the formula (1) to (14), L-form is preferable.

It can be considered that the phenylalanine derivatives of the formulae (1) to (14) are diastereomers, and the diastereomer and the diastereomer mixture are included in the compounds of the present invention. When the phenylalanine derivatives of the formulae (1) to (14) of the present invention include a mobile hydrogen atom, it can be considered that the phenylalanine derivatives of the formulae (1) to (14) of the present invention include a variety of tautomeric forms and the compounds indicated in the present invention include the said tautomeric forms.

<Preferable Examples of Each Sign in the Formula (1)>

R11 is preferably a hydroxyl group, an alkoxyl group having 1 to 6 carbon atoms or a benzyloxy group, and more preferably a hydroxyl group, an isopropyloxy group, a butyloxy group, a pentyloxy group, a benzyloxy group, a sec-butyl group, a tert-butyl group, 1-methyl-butyloxy group, 1,1-dimethyl-propyl group, 1-methyl-pentyloxy group, 1,1-dimethyl-butyloxy group, a cyclopropyl group, a cyclobutyl group, a cyclopentyl group or a cyclohexyl group. A hydroxy group and an isopropyloxy group are group, an ethoxy group, an isopropyloxy group, a butyloxy group, an isobutyloxy group, a sec-butyloxy group, a pentyloxy group and a cyclopentyloxy group. Particularly preferably, they include a methoxy group, an ethoxy group, an isopropyloxy group and a butyloxy group.

An alkoxyl group having 1 to 6 carbon atoms which has a substituent(s) preferably includes a morpholinoethyloxy group, 2-methoxy-ethoxy group and 1-methyl-2-methoxy-ethyloxy group; an arylalkyloxy group which may have a substituent(s) preferably includes a benzyloxy group; an aryloxy group which may have a substituent(s) preferably includes a phenyloxy group and 2-methoxy-phenyloxy group; and a heteroaryloxy group which may have a substituent(s) preferably includes a furanyloxy group.

The term "aryr" in an "aryloxy group" indicates phenyl and naphthyl.

The term "heteroaryl" in a "heteroaryloxy group" indicates a 5-to-8-membered mono-, bi- or tri-cyclic hetero aromatic ring group containing 1, 2, 3 or 4 hetero atoms selected from the group consisting of oxygen, sulfur and nitrogen atoms as a ring atom. For example, they include pyridyl, pyridazinyl, pyrimidyl (=pyrimidinyl), pyrazinyl, furyl, thienyl, pyrrolyl, isoxazolyl, oxazolyl, isothiazolyl, thiazolyl, pyrazolyl, imidazolyl, oxadiazolyl, thiadiazolyl, triazoyl, tetrazolyl, benzofuranyl, benzothienyl, indolyl, isoindolyl, benzoxazolyl, benzothiazolyl, benzimidazolyl, indazolyl, benzisoxazolyl, benzisothiazolyl, benzofurazanyl, benzothiadiazolyl, purinyl, quinolyl (=quinolinyl), isoquinolyl, cinnolinyl, phthalazinyl, quinazolinyl, quinoxalinyl, pteridinyl, imidazoxazolyl, imidazothiazolyl, imidazoimidazolyl, dibenzofuranyl, dibenzothienyl, carbazolyl and acridinyl.

A substituent(s) in "an alkoxyl group which may have a substituent(s)" includes, for example, a morpholinyl group, a piperidinyl group, a pyrrolidinyl group, a dimethylamino group, a diethylamino group, a methoxy group, a pivaloyloxy group, an ethoxycarbonyloxy group, a cyclohexyloxycarbonyloxy group, a (5-methyl-2-oxo-1,3-dioxol-4-yl)methyl particularly preferable among them.

An alkyl group in R12 and R13 is preferably an alkyl group having 1 to 3 carbon atoms.

R12 is preferably a hydrogen atom, a methyl group or an ethyl group, and particularly preferably a methyl group or an ethyl group.

R13 is preferably a hydrogen atom or a methyl group, and particularly preferably a hydrogen atom.

Among the above, N(R12)R13 is preferably a dimethylamino group, an ethylamino group or a methylamino group, or, N(R12)R13 is also preferably 1-pyrrolidinyl group, 1-piperidinyl group or 4-morpholinyl group.

R14 is preferably a methyl group.

$R_1'$ is preferably a hydrogen atom or a fluorine atom and particularly preferably a hydrogen atom.

The substituting position of $R_1'$ is preferably the sixth or seventh position of a quinazolinedione ring.

$X_1$ is preferably —CH(R1a)-, —CH(R1a)CH(R1b)-, —N(R1a)CH(R1b)CH(R1c)-, —OCH(R1a)CH(R1b)- or 1,3-pyrrolidinylene, and particularly preferably —CH$_2$—.

The substituting position of $X_1$ is preferably the sixth, seventh or eighth position of a quinazolinedione ring and more preferably the sixth or seventh position thereof, and particularly preferably the sixth position thereof.

R1a, R1b, R1c and R1d are preferably a hydrogen atom.

Both $Y_{11}$ and $Y_{12}$ are preferably a chlorine atom.

[2] The phenylalanine derivatives or pharmaceutically acceptable salts thereof according to the above [1] are preferred, wherein, in the formula (1), R11 represents a hydroxyl group, an alkoxyl group having 1 to 6 carbon atoms, a morpholinoethyloxy group or a benzyloxy group which may be substituted with a methyl group(s) or a methoxy group(s), an alkyl group in R12 and R13 represents an alkyl group having 1 to 3 carbon atoms, and $X_1$ represents —CH(R1a)-, —CH(R1a)CH(R1b)-, —N(R1a)CH(R1b)CH (R1c)-, —OCH(R1a)CH(R1b)- or 1,3-pyrrolidinylene.

[4] The phenylalanine derivatives or pharmaceutically acceptable salts thereof according to the above [2] are preferred, wherein, in the formula (1), $X_1$ represents —CH (R1a)-, —CH$_2$CH$_2$—, —N(R1a)CH$_2$CH$_2$—, or 1,3-pyrrolidinylene, wherein R1a represents a hydrogen atom or a methyl group.

[4] The phenylalanine derivatives or pharmaceutically acceptable salts thereof according to the above [3] are preferred, wherein, in the formula (1), R12 and R13 each independently represent a hydrogen atom or an alkyl group having 1 to 3 carbon atoms, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms.

[5] The phenylalanine derivatives or pharmaceutically acceptable salts thereof according to the above [3] are preferred, wherein, in the formula (1),
R12 represents a methyl group or an ethyl group,
R13 represents a hydrogen atom, a methyl group or an ethyl group, or
N(R12)R13 represents 1-pyrrolidinyl group, 1-piperidinyl group or 4-morpholinyl group,
R14 represents a methyl group,
$R_1'$ represents a hydrogen atom,
$X_1$ represents —CH$_2$—, which is located on the sixth, seventh or eighth position of quinazolinedione ring, and
$Y_{11}$ and $Y_{12}$ represent either one of the combinations, (Cl, Cl), (Cl, Me), (Cl, F), (F, F) and (F, Me).

Further, the phenylalanine derivatives or pharmaceutically acceptable salts thereof according to the above [5] are preferred, wherein, in the formula (1), both $Y_{11}$ and $Y_{12}$ represent a chlorine atom.

[6] The phenylalanine derivatives or pharmaceutically acceptable salts thereof according to the above [3] are preferred, wherein, in the formula (1),
R13 represents a hydrogen atom, a methyl group or an ethyl group,
$X_1$ represents —CH$_2$—, which is located on the sixth, seventh or eighth position of quinazolinedione ring, and
$Y_{11}$ and $Y_{12}$ represent the combination of (Cl, Cl).

[7] The phenylalanine derivatives or pharmaceutically acceptable salts thereof according to the above [6] are preferred, wherein, in the formula (1),
R13 represents a hydrogen atom, a methyl group or an ethyl group, and
$X_1$ represents —CH$_2$—, which is located on the sixth position of quinazolinedione ring.

[8] The phenylalanine derivatives or pharmaceutically acceptable salts thereof according to the above [6] are preferred, wherein, in the formula (1),
R13 represents a hydrogen atom, a methyl group or an ethyl group, and
$X_1$ represents —CH$_2$—, which is located on the seventh position of quinazolinedione ring.

[9] The phenylalanine derivatives or pharmaceutically acceptable salts thereof according to the above [3] are preferred, wherein, in the formula (1),
R12 and R13 each independently represent a methyl group or an ethyl group,
R14 represents a methyl group,
$R_1'$ represents a hydrogen atom or a fluorine atom, which is located on the sixth or seventh position of quinazolinedione ring,
$X_1$ represents —N(CH$_3$)CH$_2$CH$_2$— or 1,3-pyrrolidinylene, which is located on the sixth or seventh position of quinazolinedione ring, and
$Y_{11}$ and $Y_{12}$ represent the combination of (Cl, Cl).

[10] The phenylalanine derivatives or pharmaceutically acceptable salts thereof according to the above [2] are preferred, wherein, in the formula (1),
R12 and R13 each independently represent a hydrogen atom, a methyl group or an ethyl group, or N(R12)R13 represents 1-pyrrolidinyl, 1-piperidinyl group or 4-morpholinyl group,
R14 represents a methyl group or an ethyl group,
$R_1'$ represents a hydrogen atom,
$X_1$ represents —OCH(R1a)CH(R1b)-, wherein R1a and R1b each independently represent a hydrogen atom or a methyl group, and
$Y_{11}$, and $Y_{12}$ represent either one of the combinations, (Cl, Cl), (Cl, Me), (Cl, F), (F, F) and (F, Me).

[11] The phenylalanine derivatives or pharmaceutically acceptable salts thereof according to the above [10] are preferred, wherein, in the formula (1),
R12 and R13 each independently represent a hydrogen atom, a methyl group or an ethyl group,
R14 represents a methyl group, and
$Y_{11}$ and $Y_{12}$ represent the combination of (Cl, Cl).

[12] The phenylalanine derivatives or pharmaceutically acceptable salts thereof according to the above [1] are preferred, wherein, in the formula (1),
R11 represents a hydroxyl group or an alkoxyl group having 1 to 6 carbon atoms which may have a methoxy group(s) as a substituent(s),
R12 represents a hydrogen atom or an alkyl group having 1 to 6 carbon atoms,
R13 represents a hydrogen atom, a methyl group or an ethyl group, or
N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms,
R14 represents a methyl group, R₁' represents a hydrogen atom,
X₁ represents —CH(R1a)-, —CH(R1a)CH(R1b)-, —CH(R1a)CH(R1b)CH(R1c)- or —OCH(R1a)CH(R1b)-, which is located on the sixth position of quinazolinedione ring, wherein each of R1a, R1b and R1c represents a hydrogen atom, and
Y₁₁ and Y₁₂ represent the combination of (Cl, Cl).

[13] The phenylalanine derivatives or pharmaceutically acceptable salts thereof according to the above [1] are preferred, wherein, in the formula (1),
R11 represents a hydroxyl group or an alkoxyl group having 1 to 6 carbon atoms,
R12 represents an alkyl group having 1 to 6 carbon atoms,
R13 represents a hydrogen atom, a methyl group or an ethyl group,
R14 represents a methyl group,
R₁' represents a hydrogen atom,
X₁ represents —CH(R1a)- or —CH(R1a)CH(R1b)-, which is located on the sixth position of quinazolinedione ring, wherein each of R1a and R1b represents a hydrogen atom, and
Y₁₁ and Y₁₂ represent the combination of (Cl, Cl).

[14] The phenylalanine derivatives or pharmaceutically acceptable salts thereof according to the above [1] are preferred, wherein, in the formula (1),
R11 represents a hydroxyl group or an alkoxyl group having 1 to 6 carbon atoms,
R12 represents an alkyl group having 1 to 5 carbon atoms,
R13 represents a hydrogen atom,
R14 represents a methyl group,
R₁' represents a hydrogen atom,
X₁ represents —CH(R1a)-, —CH(R1a)CH(R1b)- or —CH(R1a)CH(R1b)CH(R1c)-, which is located on the sixth position of quinazolinedione ring, wherein each of R1a, R1b and R1c represents a hydrogen atom, and
Y₁₁ and Y₁₂ represent the combination of (Cl, Cl).

[15] The phenylalanine derivatives or pharmaceutically acceptable salts thereof according to the above [1] are preferred, wherein, in the formula (1),
R11 represents a hydroxyl group or an alkoxyl group having 1 to 6 carbon atoms,
R12 represents a methyl group or an ethyl group,
R13 represents a hydrogen atom,
R14 represents a methyl group,
R₁' represents a hydrogen atom,
X₁ represents —CH(R1a)-, —CH(R1a)CH(R1b)- or —CH(R1a)CH(R1b)CH(R1c)-,
which is located on the sixth position of quinazolinedione ring, wherein each of R1a, R1b and R1c represents a hydrogen atom, and
Y₁₁ and Y₁₂ represent the combination of (Cl, Cl).

[16] The phenylalanine derivatives or pharmaceutically acceptable salts thereof according to the above [1] are preferred, wherein, in the formula (1),
R11 represents a hydroxyl group or an alkoxyl group having 1 to 6 carbon atoms,
R12 represents a methyl group, an ethyl group, an isobutyl group, a cyclopropylmethyl group, a cyclobutyl group, a sec-butyl group or an isopentyl group,
R13 represents a hydrogen atom,
R14 represents a methyl group,
R₁' represents a hydrogen atom,
X₁ represents —CH(R1a)-, which is located on the sixth position of quinazolinedione ring, wherein R1a represents a hydrogen atom, and
Y₁₁ and Y₁₂ represent the combination of (Cl, Cl).

[17] The phenylalanine derivatives or pharmaceutically acceptable salts thereof according to the above [1] are preferred, wherein, in the formula (1),
R11 represents a hydroxyl group or an alkoxyl group having 1 to 6 carbon atoms,
R12 represents a hydrogen atom or an alkyl group having 1 to 3 carbon atoms,
R13 represents a hydrogen atom, a methyl group or an ethyl group, or
N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms,
R14 represents a methyl group,
R₁' represents a hydrogen atom,
X₁ represents —O—CH(R1a)CH(R1b)- or —O—CH(R1a)CH(R1b)CH(R1c)-, which is located on the sixth position of quinazolinedione ring, wherein each of R1a, R1b and R1c independently represents a hydrogen atom or a methyl group, and
Y₁₁ and Y₁₂ represent the combination of (Cl, Cl).

[18] The phenylalanine derivatives or pharmaceutically acceptable salts thereof according to any one of the above [1] to [17] are preferred, wherein, in the formula (1), R11 represents a branched alkoxyl group having 3 to 6 carbon atoms.

[19] The phenylalanine derivatives or pharmaceutically acceptable salts thereof according to the above [1] represented by the following formulae are preferred:

-continued
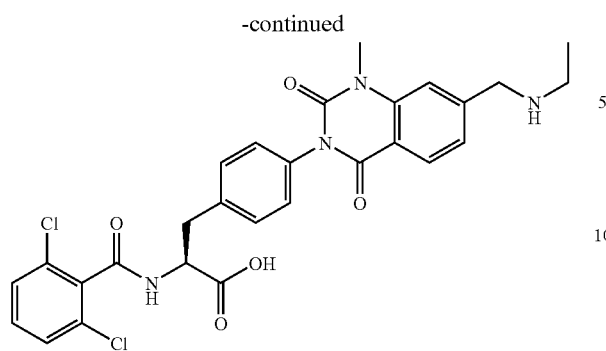
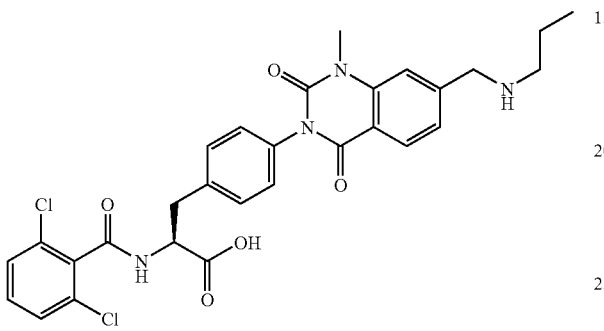
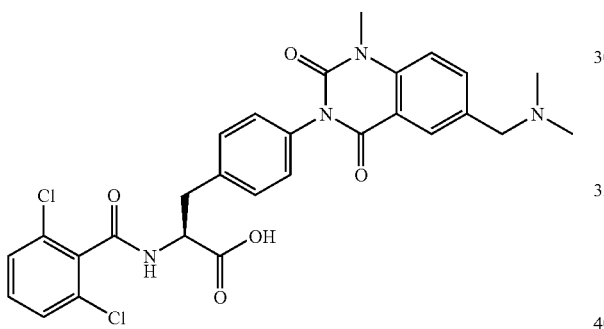
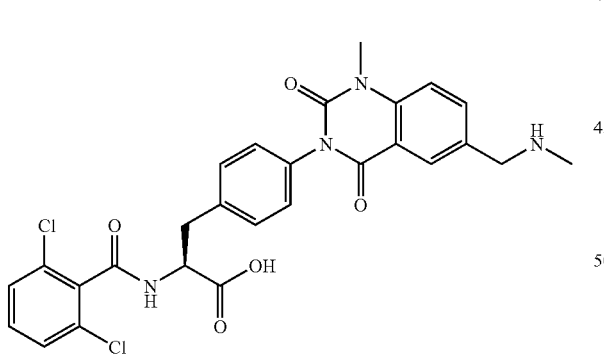
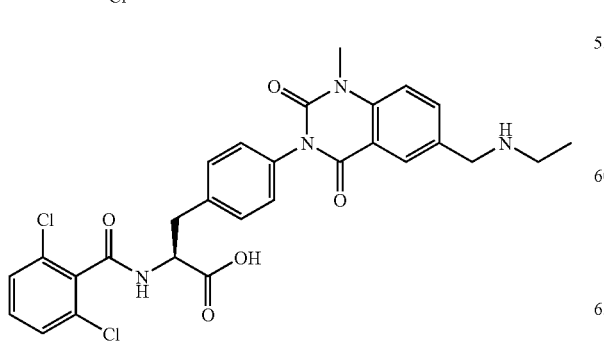
-continued
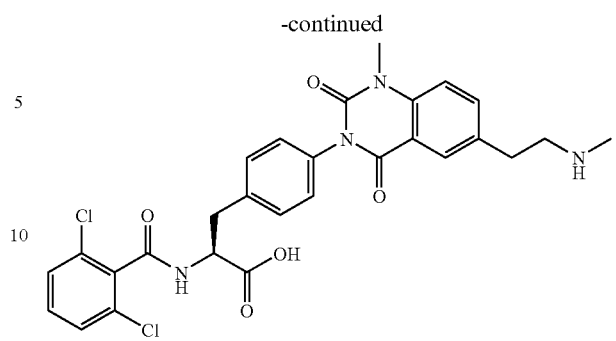
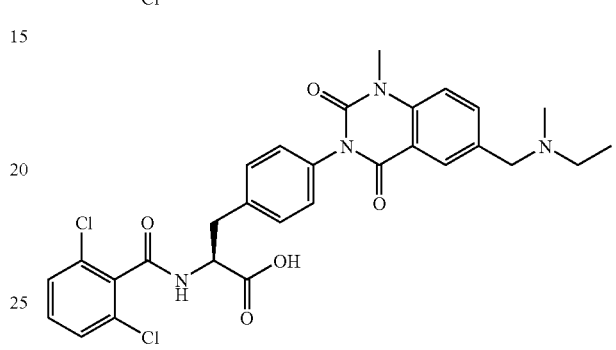
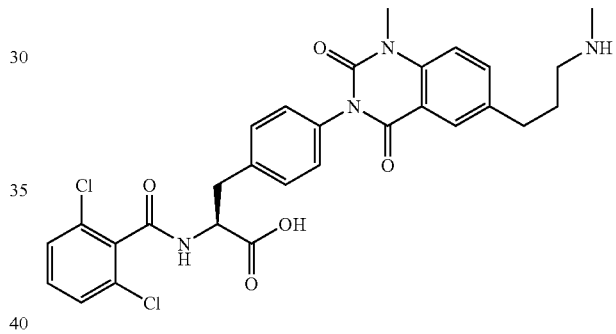
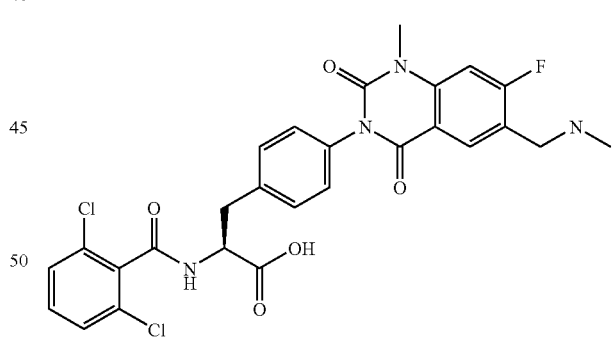
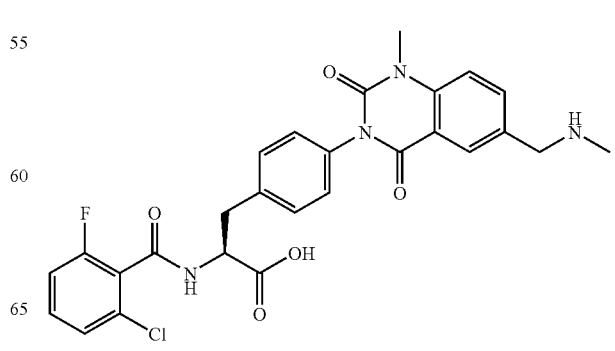

25
-continued
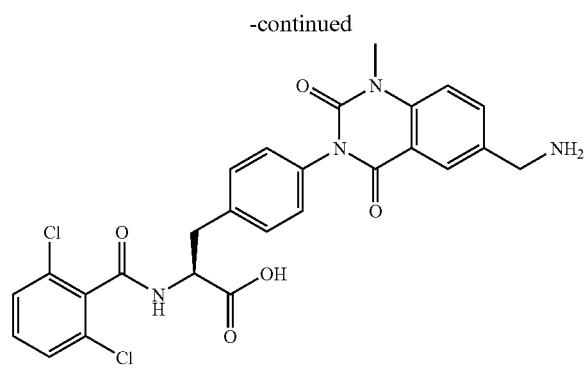
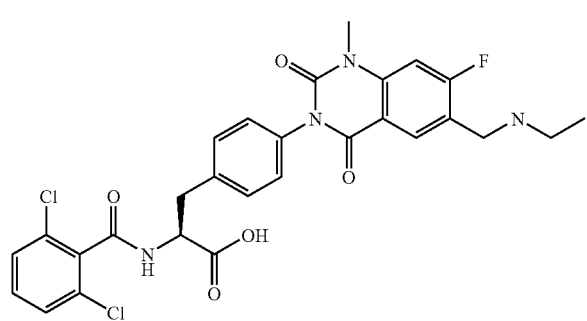
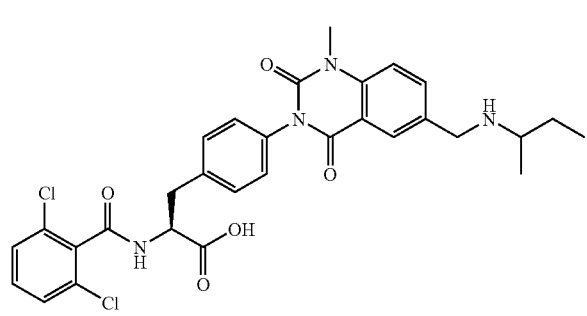
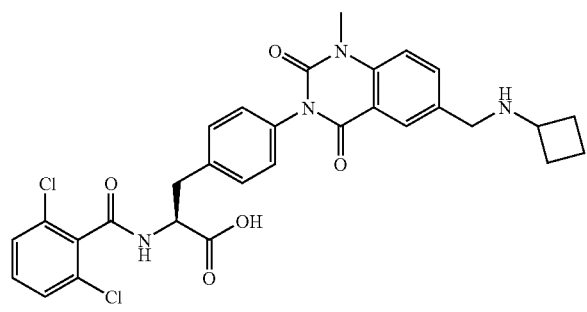
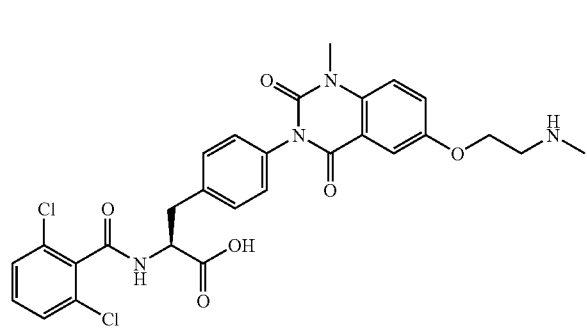
26
-continued
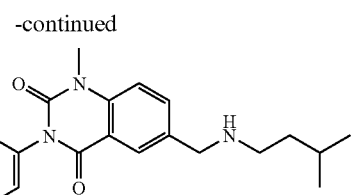
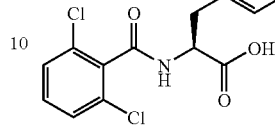
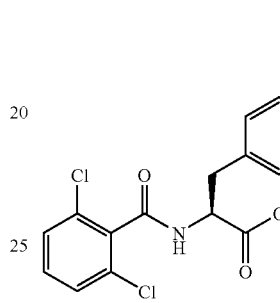
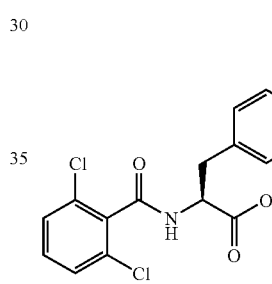
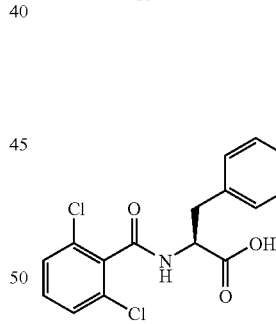
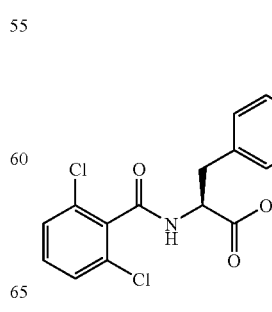

-continued
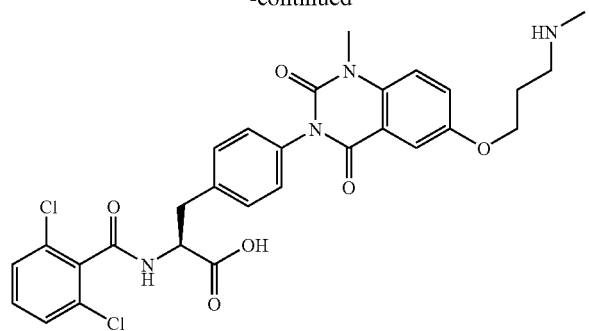
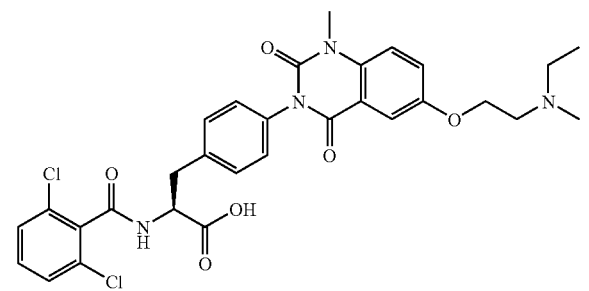
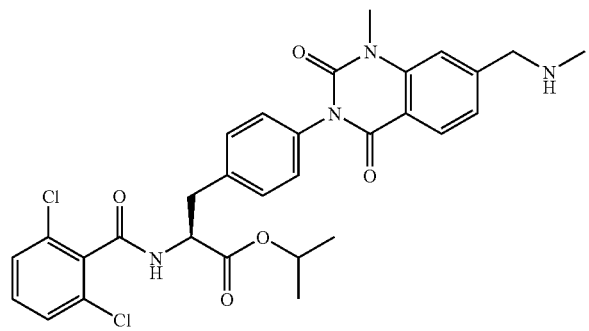
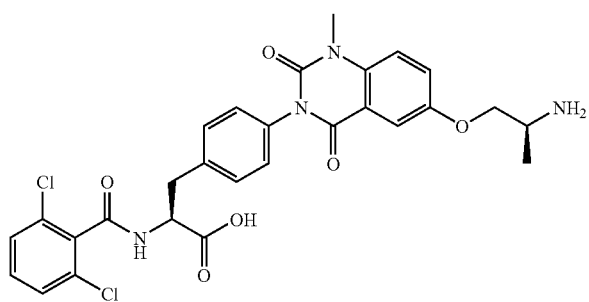
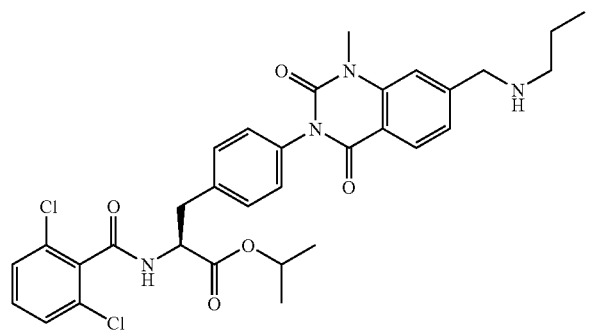
-continued
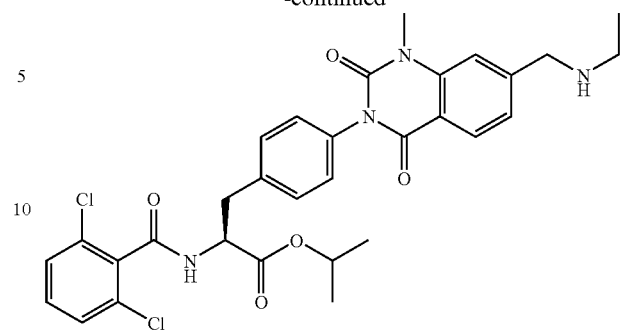
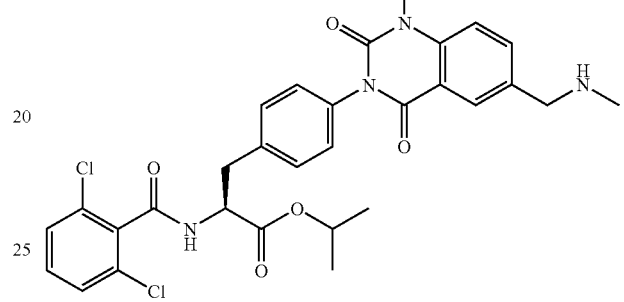
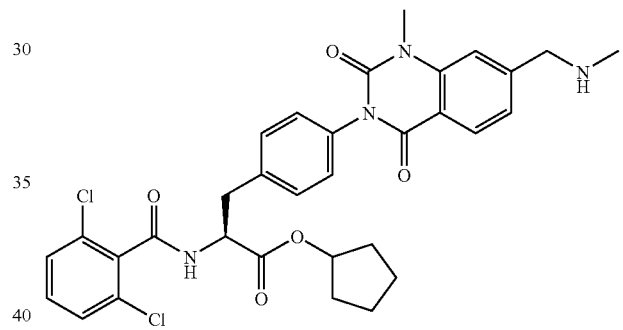
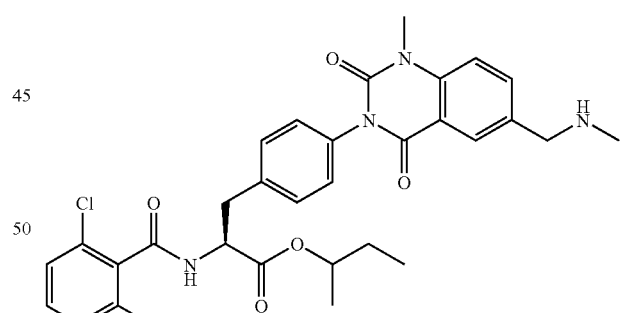
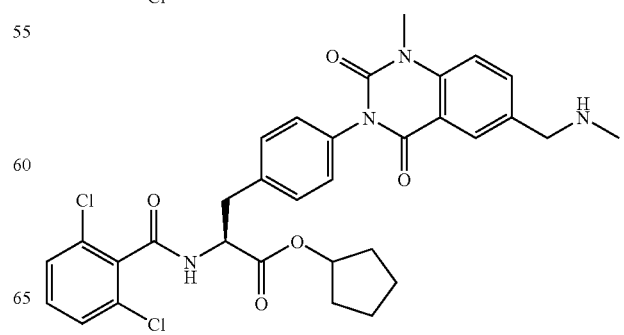

-continued
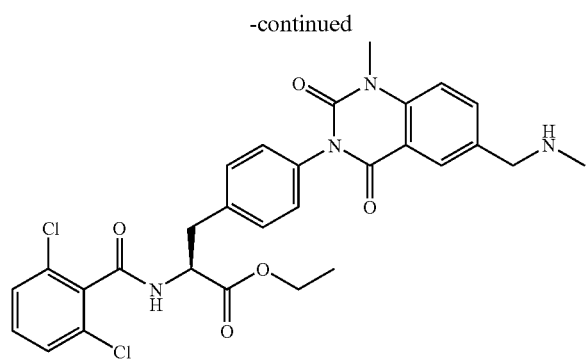
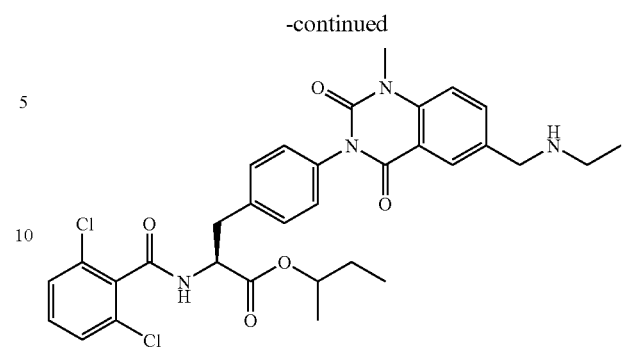
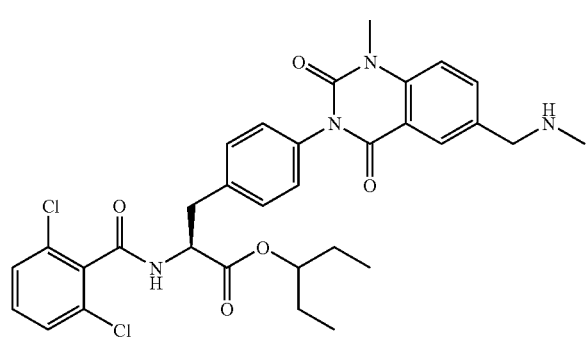
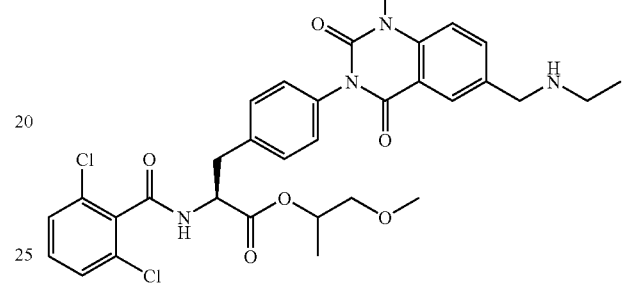
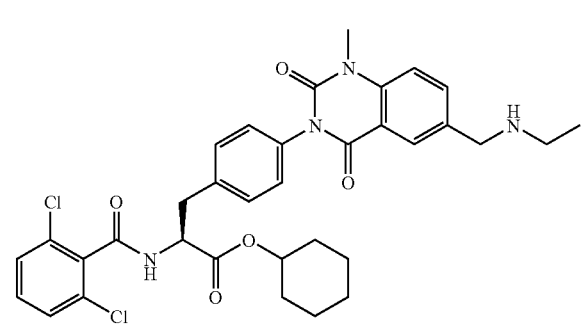
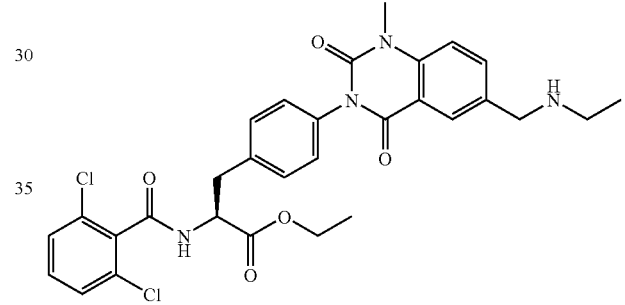
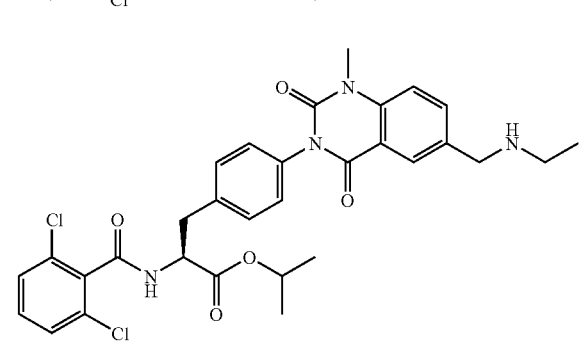
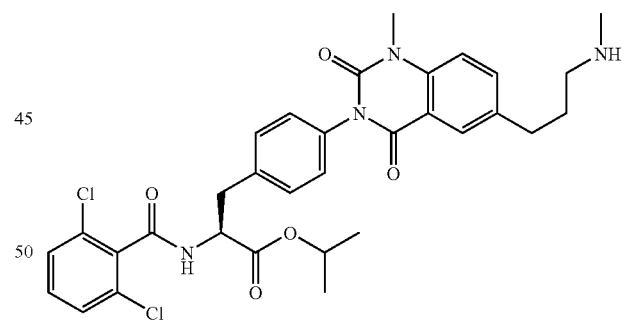
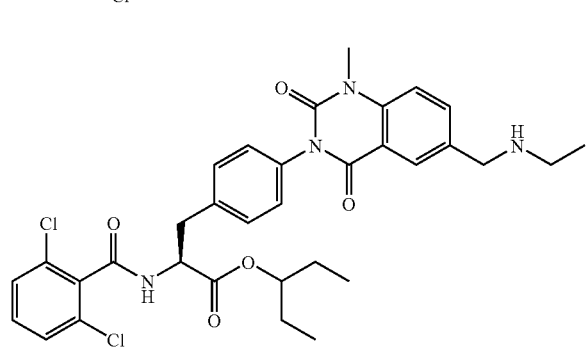
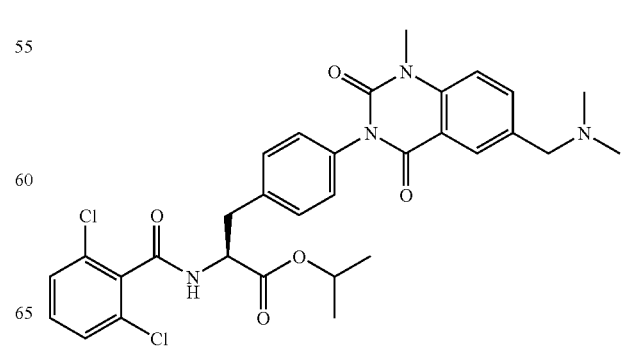

-continued
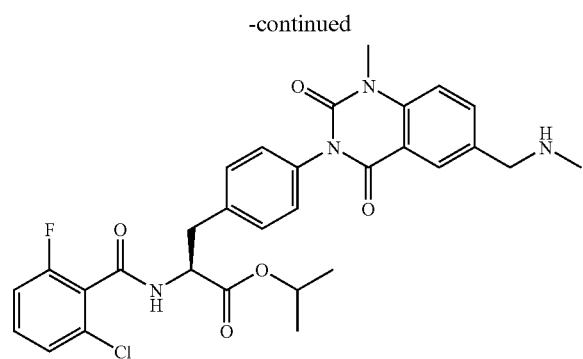
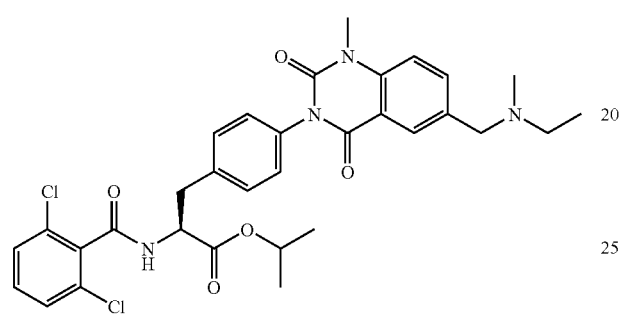
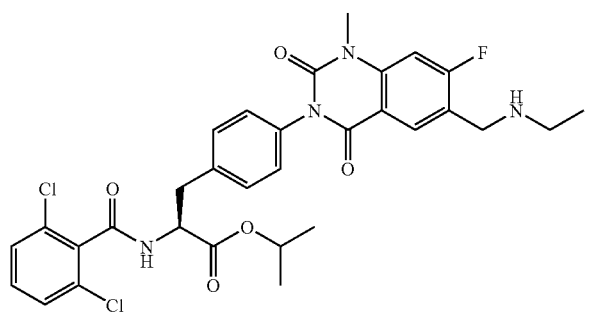
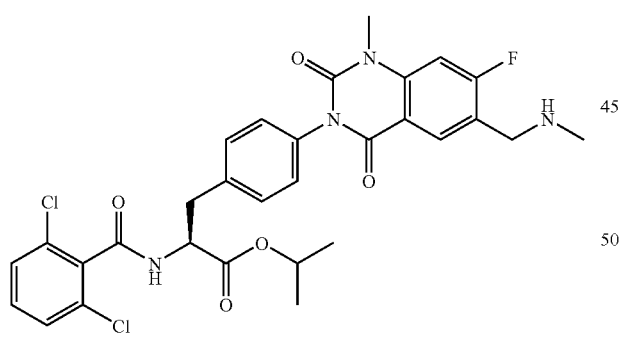
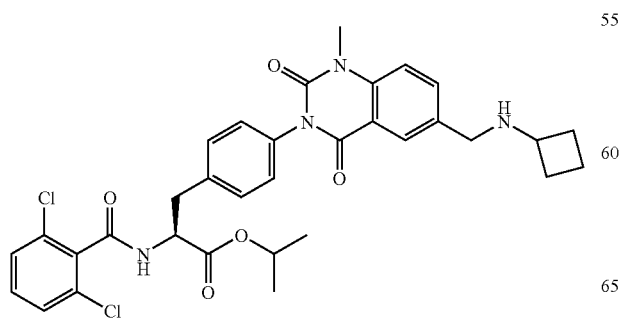
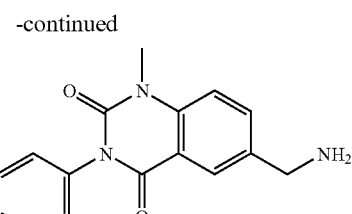
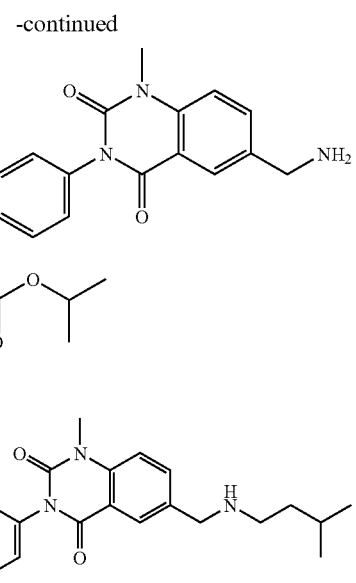

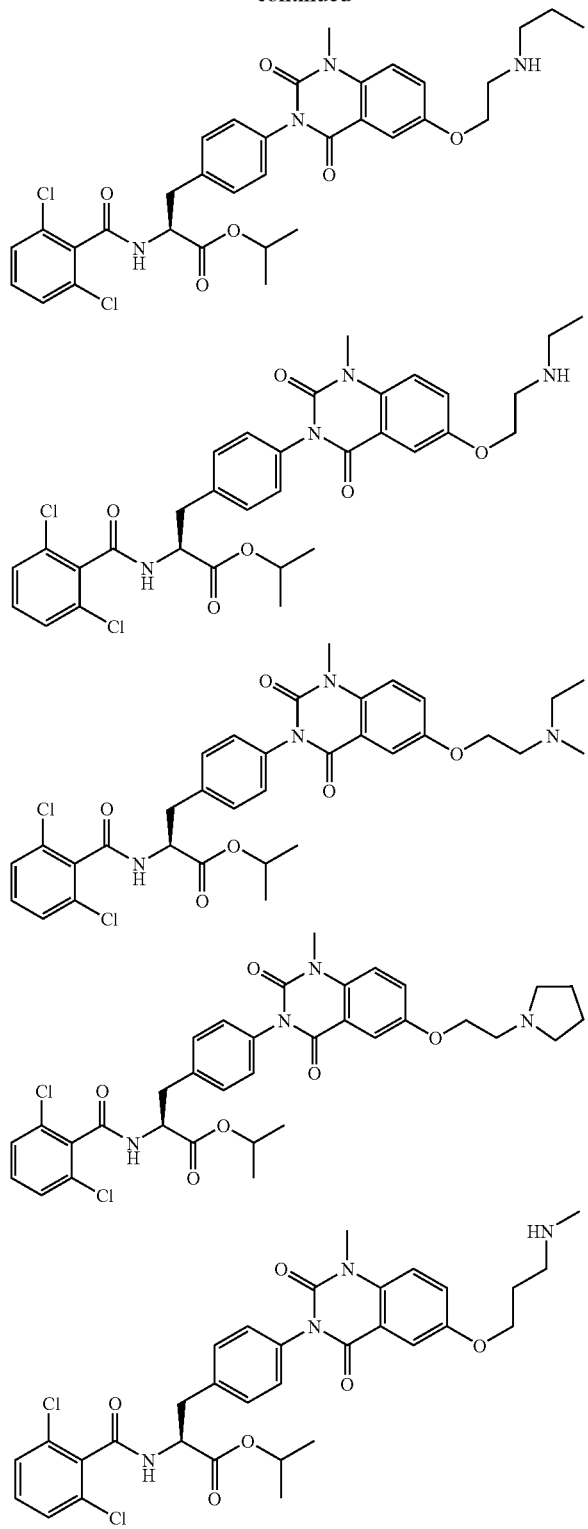

<Preferable Examples of Each Sign in the Formula (2)>

R21 is preferably a hydroxyl group, an alkoxyl group having 1 to 6 carbon atoms or a morpholinoethyloxy group, and particularly preferably a hydroxyl group, a methoxy group, an ethoxy group, an isopropyloxy group, a butyloxy group or a morpholinoethyloxy group.

R22 is preferably a methyl group or an ethyl group.

R24 is preferably a methyl group.

$R_2'$ is preferably a hydrogen atom or a fluorine atom.

The substituting position of $R_2'$ is preferably the sixth or seventh position of a quinazolinedione ring.

$X_2$ is preferably —$CH_2$—, —$NHCH_2CH_2$— or —$N(Me)CH_2CH_2$—.

The substituting position of $X_2$ is preferably the sixth, seventh or eighth position of a quinazolinedione ring and more preferably the seventh or eighth position thereof.

Both $Y_{21}$ and $Y_{22}$ are preferably a chlorine atom.

[21] The phenylalanine derivatives or pharmaceutically acceptable salts thereof according to the above [20] are preferred, wherein, in the formula (2), R22 represents a methyl group or an ethyl group, R24 represents a methyl group, $R_2'$ represents a hydrogen atom, $X_2$ represents —$CH_2$—, which is located on the sixth, seventh or eighth position of quinazolinedione ring, and $Y_{21}$ and $Y_{22}$ represent the combination of (Cl, Cl).

[22] The phenylalanine derivatives or pharmaceutically acceptable salts thereof according to the above [20] are preferred, wherein, in the formula (2), R22 represents a hydrogen atom, a methyl group or an ethyl group, R24 represents a methyl group, $R_2'$ represents a hydrogen atom or a fluorine atom, which is located on the sixth or seventh position of quinazolinedione ring, $X_2$ represents —$N(CH_3)CH_2CH_2$— or —$NHCH_2CH_2$—, which is located on the sixth or seventh position of quinazolinedione ring, and $Y_{21}$ and $Y_{22}$ represent the combination of (Cl, Cl).

<Preferable Examples of Each Sign in the Formula (3)>

R31 is preferably a hydroxyl group, an alkoxyl group having 1 to 6 carbon atoms, a morpholinoethyloxy group or a benzyloxy group, and particularly preferably a hydroxyl group, a methoxy group, an ethoxy group, an isopropyloxy group, a butyloxy group, a pentyloxy group, a morpholinoethyloxy group or a benzyloxy group.

$R_{34}$ is preferably a methyl group.

$R_3'$ is preferably a hydrogen atom.

The above formula (3-1) is preferably 4-morpholinyl group, 1-piperazinyl group of which the fourth position may be substituted with an alkyl group having 1 to 3 carbon atoms, or 1-imidazolyl group which may be substituted with a methyl group, an ethyl group or an amino group. The bonds in the formula (3-1) may be saturated or unsaturated. X3 in the formula (3-1) is preferably an oxygen atom or a nitrogen atom. The above formula (3-1) is particularly preferably 4-morpholinyl group, 4-methyl-1-piperazinyl group or 2-amino-1-imidazolyl group.

Both $Y_{31}$ and $Y_{32}$ are preferably a chlorine atom.

[24] The phenylalanine derivatives or pharmaceutically acceptable salts thereof according to the above [23] are preferred, wherein the formula (3-1) represents 4-morpholinyl group, 4-thiomorpholinyl group, 3-tetrahydrothiazolyl group, 1-piperazinyl group of which the fourth position may be substituted with an alkyl group having 1 to 3 carbon atoms, or 1-imidazolyl group which may be substituted with a methyl group or an amino group, wherein X3 represents an oxygen atom, a nitrogen atom which may be substituted with an alkyl group having 1 to 3 carbon atoms, or a sulfur atom.

[25] The phenylalanine derivatives or pharmaceutically acceptable salts thereof according to the above [24] are preferred, wherein, in the formula (3),
$R_{34}$ represents a methyl group,
$R_3'$ represents a hydrogen atom,
the formula (3-1) represents 4-morpholinyl group or 1-piperazinyl group of which the fourth position may be substituted with an alkyl group having 1 to 3 carbon atoms, and
$Y_{31}$ and $Y_{32}$ represent the combination of (Cl, Cl).

[26] The phenylalanine derivatives or pharmaceutically acceptable salts thereof according to the above [24] are preferred, wherein, in the formula (3),
$R_{34}$ represents a methyl group,
$R_3'$ represents a hydrogen atom,
the formula (3-1) represents 2-amino-1-imidazolyl group, and
$Y_{31}$ and $Y_{32}$ represent the combination of (Cl, Cl).

[27] The phenylalanine derivatives or pharmaceutically acceptable salts thereof according to the above [23] are preferred, wherein, in the formula (3),
$R_{34}$ represents a methyl group,
$R_3'$ represents a hydrogen atom or a fluorine atom, the formula (3-1) represents 1-imidazolyl group of which the second position may be substituted with a methyl group or an ethyl group, and
$Y_{31}$ and $Y_{32}$ represent the combination of (Cl, Cl).

<Preferable Examples of Each Sign in the Formula (4)>

Ring is preferably a benzene ring, a pyridine ring, a thiophene ring, a piperidine ring of which the first position may be substituted with an alkyl group having 1 to 3 carbon atoms or a piperazine ring of which the first and/or fourth position may be substituted with an alkyl group having 1 to 3 carbon atoms.

$R_{41}$ is preferably a hydroxyl group, an alkoxyl group having 1 to 6 carbon atoms, a morpholinoethyloxy group or a benzyloxy group, and particularly preferably a hydroxyl group, a methoxy group, an ethoxy group, an isopropyloxy group, a butyloxy group, a pentyloxy group, a morpholinoethyloxy group or a benzyloxy group.

Ring is preferably a benzene ring, a piperidine ring of which the first position may be substituted with an alkyl group having 1 to 3 carbon atoms, or a piperazine ring of which the first and/or fourth position may be substituted with an alkyl group having 1 to 3 carbon atoms, and particularly preferably a piperazine ring of which the first and/or fourth position may be substituted with a methyl group.

$R_{44}$ is preferably a methyl group.
Both $Y_{41}$ and $Y_{42}$ are preferably a chlorine atom.

[29] The phenylalanine derivatives or pharmaceutically acceptable salts thereof according to the above [28] are preferred, wherein, in the formula (4), Ring represents a piperazine ring of which the first and/or fourth position may be substituted with a methyl group,
$R_{44}$ represents a methyl group, and
$Y_{41}$ and $Y_{42}$ represent the combination of (Cl, Cl).

<Preferable Examples of Each Sign in the Formula (5)<

$R_{51}$ is preferably a hydroxyl group, an alkoxyl group having 1 to 6 carbon atoms or a morpholinoethyloxy group, and particularly preferably a hydroxyl group, a methoxy group, an ethoxy group, an isopropyl group, a butyloxy group or a morpholinoethoxy group.

$R_{54}$ is preferably a methyl group.
$R_5'$ is preferably a hydrogen atom.
N(R5a)R5b is preferably an ethylamino group or 1-pyrrolidinyl group.
Both $Y_{51}$ and $Y_{52}$ are preferably a chlorine atom.

[31] The phenylalanine derivatives or pharmaceutically acceptable salts thereof according to the above [30] are preferred, wherein, in the formula (5),
$R_{54}$ represents a methyl group,
$R_5'$ represents a hydrogen atom,
N(R5a)R5b represents an ethylamino group or 1-pyrrolidinyl group, and
$Y_{51}$ and $Y_{52}$ represent the combination of (Cl, Cl).

<Preferable Examples of Each Sign in the Formula (6)>

$R_{61}$ is preferably a hydroxyl group, an alkoxyl group having 1 to 6 carbon atoms, a morpholinoethyloxy group or a benzyloxy group, and particularly preferably a hydroxyl group, a methoxy group, an ethoxy group, an isopropyloxy group, a butyloxy group, a pentyloxy group, a morpholinoethyloxy group or a benzyloxy group.

A is preferably any one of the formulae (6-1) to (6-6).
Both $Y_{61}$ and $Y_{62}$ are preferably a chlorine atom.

[33] The phenylalanine derivatives or pharmaceutically acceptable salts thereof according to the above [32] are preferred, wherein, in the formula (6), $A_6$ represents either one of the above formulae (6-1) to (6-4).

[34] The phenylalanine derivatives or pharmaceutically acceptable salts thereof according to the above [32] are preferred, wherein, in the formula (6), $R_{61}$ represents a hydroxyl group, and $Y_{61}$ and $Y_{62}$ represent the combination of (Cl, Cl).

<Preferable Examples of Each Sign in the Formula (7)>

$R_{71}$ is preferably a hydroxyl group, an alkoxyl group having 1 to 6 carbon atoms or a morpholinoethyloxy group, and particularly preferably a hydroxyl group, a methoxy group, an ethoxy group, an isopropyl group, a butyloxy group or a morpholinoethyloxy group.

$R_{74}$ is preferably a methyl group.
R7 is preferably 2-propynyl group, a cyclopropylmethyl group, a propyl group or a cyclopentyl group.
Both $Y_{71}$ and $Y_{72}$ are preferably a chlorine atom.

[36] The phenylalanine derivatives or pharmaceutically acceptable salts thereof according to the above [35] are preferred, wherein, in the formula (7),
$R_{74}$ represents a methyl group,
R7 represents 2-propynyl group or a cyclopropylmethyl group, and
$Y_{71}$ and $Y_{72}$ represent the combination of (Cl, Cl).

[37] The phenylalanine derivatives or pharmaceutically acceptable salts thereof according to the above [35] are preferred, wherein, in the formula (7),
$R_{74}$ represents a methyl group,
R7 represents a propyl group, and
$Y_{71}$ and $Y_{72}$ represent the combination of (Cl, Cl).

<Preferable Examples of Each Sign in the Formula (8)>

$R_{81}$ is preferably a hydroxyl group, an alkoxyl group having 1 to 6 carbon atoms or a morpholinoethyloxy group, and particularly preferably a hydroxyl group, a methoxy group, an ethoxy group, an isopropyloxy group, a butyloxy group or a morpholinoethyloxy group.

$R_{82}$ is preferably a methyl group.
$R_{84}$ is preferably a methyl group.

$n_8$ is preferably either one of the integers 0 or 2, and particularly preferably 0.

$S(=O)_{ns}R_{82}$ is preferably a methylthio group or a methanesulfonyl group.

The substituting position of S is preferably the sixth position of a quinazolinedione ring.

Both $Y_{81}$ and $Y_{82}$ are preferably a chlorine atom.

[39] The phenylalanine derivatives or pharmaceutically acceptable salts thereof according to the above [38] are preferred, wherein, in the formula (8), $R_{81}$ represents a hydroxyl group, an alkoxyl group having 1 to 6 carbon atoms, a morpholinoethyloxy group or a benzyloxy group which may be substituted with a methyl group(s) or a methoxy group(s).

[40] The phenylalanine derivatives or pharmaceutically acceptable salts thereof according to the above [38] are preferred, wherein, in the formula (8), $R_{82}$ represents a methyl group, $R_{84}$ represents a methyl group, $n_8$ represents either one of the integers 0 or 2, S is located on the sixth position of quinazolinedione ring, and $Y_{81}$ and $Y_{82}$ represent the combination of (Cl, Cl).

<Preferable Examples of Each Sign in the Formula (9)>

R91 is preferably a hydroxyl group, an alkoxyl group having 1 to 6 carbon atoms, a morpholinoethyloxy group or a benzyloxy group, and particularly preferably a hydroxyl group, a methoxy group, an ethoxy group, an isopropyloxy group, a butyloxy group, a pentyloxy group, a morpholinoethyloxy group or a benzyloxy group.

$R_{92}$ is preferably a hydroxyl group, a benzyloxy group, a methoxy group or an amino group. CO—$R_{92}$ may be a carboxyl group in a prodrug modification which is converted into a carboxyl group in vivo. Namely, $R_{92}$ is preferably a hydroxyl group or a group which is substituted with a hydroxyl group in vivo.

Specific examples of the group(s) which is substituted with a hydroxyl group in vivo are mentioned above.

$R_{94}$ is preferably a methyl group.

$X_9$ is preferably an atomic bond.

The substituting position of $X_9$ is preferably the sixth position of a quinazolinedione ring.

Both $Y_{91}$ and $Y_{92}$ are preferably a chlorine atom.

[42] The phenylalanine derivatives or pharmaceutically acceptable salts thereof according to the above [41] are preferred, wherein, in the formula (9), $X_9$ represents —$CH_2CH_2$— or —CH=CH— and $R_{92}$ represents a hydroxyl group, or $X_9$ represents an atomic bond and $R_{92}$ represents a benzyloxy group, $X_9$ is located on the sixth position of quinazolinedione ring, $R_{94}$ represents a methyl group, and $Y_{91}$ and $Y_{92}$ represent the combination of (Cl, Cl).

[43] The phenylalanine derivatives or pharmaceutically acceptable salts thereof according to the above [41] are preferred, wherein, in the formula (9), $X_9$ represents an atomic bond and $R_{92}$ represents a hydroxyl group, a methoxy group or an amino group, $X_9$ is located on the sixth position of quinazolinedione ring, $R_{94}$ represents a methyl group, and $Y_{91}$ and $Y_{92}$ represent the combination of (Cl, Cl).

<Preferable Examples of Each Sign in the Formula (10)>

$R_{101}$ is preferably an alkoxyl group having 2 to 4 carbon atoms or a morpholinoethyloxy group, and particularly preferably an ethoxy group, an isopropyloxy group, a butyloxy group or a morpholinoethyloxy group.

R10 is preferably a methyl group or an ethyl group, and particularly preferably an ethyl group.

$R_{104}$ is preferably a methyl group.

Both $Y_{101}$ and $Y_{102}$ are preferably a chlorine atom.

[45] The phenylalanine derivatives or pharmaceutically acceptable salts thereof according to the above [44] are preferred, wherein, in the formula (10), R10 represents an ethyl group.

<Preferable Examples of Each Sign in the Formula (11)>

$R_{111}$ is preferably an alkoxyl group having 1 to 4 carbon atoms or a morpholinoethyloxy group, and particularly preferably a methoxy group, an ethoxy group, an isopropyloxy group, a butyloxy group or a morpholinoethyloxy group.

$R_{114}$ is preferably a methyl group.

Both $Y_{111}$ and $Y_{112}$ are preferably a chlorine atom.

<Preferable Examples of Each Sign in the Formula (12)>

$R_{121}$ is preferably an alkoxyl group having 1 to 4 carbon atoms or a morpholinoethyloxy group, and particularly preferably a methoxy group, an ethoxy group, an isopropyloxy group, a butyloxy group or a morpholinoethyloxy group.

$R_{124}$ is preferably a methyl group.

A is preferably the formula (12-1).

<Preferable Examples of Each Sign in the Formula (13)>

$R_{131}$ is preferably an alkoxyl group having 1 to 6 carbon atoms or a benzyloxy group which may be substituted with a methyl group(s) or a methoxy group(s), and particularly preferably an ethoxy group or a benzyloxy group.

The substituting position of an ammonium side chain is preferably the sixth, seventh or eighth position of a quinazolinedione ring and more preferably the eighth position thereof.

R13a and R13b are preferably a methyl group, or N(R13a) R13b is preferably 1-pyrrolidinyl group.

$Y_{131}$ and $Y_{132}$ are preferably (Cl, Cl), (Cl, Me) or (Cl, F).

<Preferable Examples of Each Sign in the Formula (14)>

$R_{141}$ is preferably a hydroxyl group, an alkoxyl group having 1 to 6 carbon atoms or a morpholinoethyloxy group, and particularly preferably an ethoxy group or a benzyloxy group.

$R_{144}$ is preferably a methyl group or an ethyl group. The substituting position of a hydroxyl group on a quinazolinedione ring is preferably the sixth or seventh position of the ring, and more preferably the eighth position thereof.

$Y_{141}$ and $Y_{142}$ are preferably (Cl, Cl), (Cl, Me), (Cl, F), (F, F) or (F, Me), and particularly preferably (Cl, Cl), (Cl, Me) or (Cl, F).

[50] The phenylalanine derivatives or pharmaceutically acceptable salts thereof according to the above [49] are preferred, wherein, in the formula (14), R144 represents a methyl group, a hydroxyl group is located on the sixth position of quinazolinedione ring, and $Y_{141}$ and $Y_{142}$ represent the combination of (Cl, Cl).

The preferable compounds in the formulae (1) to (14) are those described in Examples. The particularly preferable compounds are those in Examples 7, 8, 12, 21, 28, 30, 34, 37, 40, 46, 54, 59, 90, 91, 92, 99, 103, 106, 111, 116, 124, 136, 138, 139, 141, 142, 143, 144, 145, 147, 148, 149, 150, 151, 153, 154, 155, 156, 157, 159, 162, 163, 164, 165, 166, 170, 171, 172, 173, 174, 176, 179, 181, 184, 185, 189, 191, 193, 196, 198, 201, 210, 213, 214, 216, 217, 218, 219, 220, 222, 223, 224, 225, 226, 229, 207, 230, 232, 233, 234 and 235.

Among the compounds of the formulae (1) to (14), the compound of the formula (1) is particularly preferable, and especially those wherein R11 represents a hydroxyl group not only exhibit an excellent antagonistic activity against α4β1 binding but also exhibit an extremely low total body clearance (CLtot). Therefore, the compounds have excellent characteristics as an active form for orally administered α4 integrin antagonist (prodrug) which is effective at lower dosage and less number of doses.

Particularly, the compounds wherein R11 represents a branched alkoxyl group having 3 to 6 carbon atoms exhibit an excellent durability of effect when administered orally.

When the compounds of the formulae (1) to (14) of the present invention can form salts thereof, it is sufficient for the salts to be pharmaceutically acceptable ones. When the compound has an acidic group such as carboxyl group in the formulae, the salts can be ammonium salts, or salts thereof with alkali metals, e.g. sodium and potassium, salts thereof with alkaline earth metals, e.g. calcium and magnesium, salts thereof with aluminum, salts thereof with zinc, salts thereof with organic amines, e.g. triethylamine, ethanolamine, morpholine, piperidine and dicyclohexylamine, and salts thereof with basic amino acids, e.g. arginine and lysine. When the compound has a basic group in the formulae, the salts can be those with inorganic acids, e.g. hydrochloric acid, sulfuric acid, phosphoric acid, nitric acid and hydrobromic acid; those with organic carboxylic acids, e.g. acetic acid, citric acid, benzoic acid, maleic acid, fumaric acid, tartaric acid, succinic acid, tannic acid, butyric acid, hibenzic acid, pamoic acid, enanthic acid, decanoic acid, theoclic acid, salicylic acid, lactic acid, oxalic acid, mandelic acid, and malic acid; and those with organosulfonic acids, e.g. methanesulfonic acid, benzenesulfonic acid and p-toluenesulfonic acid. The salts can be formed by mixing a compound of the formulae (1) to (14) with a necessitated acid or base in a proper ratio in a solvent or dispersant or by the cation exchange or anion exchange reaction with another salt.

The compounds of the present invention include also solvates of the compounds of the formulae (1) to (14) such as hydrates and alcohol adducts thereof.

The compounds of the present invention can be modified into prodrug forms. The prodrug in the present invention means a compound(s) which is converted into the compounds of the present invention in vivo. For example, when an active compound contains a carboxyl group, a phosphoric group and the like, the compounds in a prodrug modification include the esters, amides and the like thereof. When an active compound contains an amino group, the compounds in a prodrug modification include the amides, carbamates and the like thereof. When an active compound contains a hydroxyl group, the compounds in a prodrug modification include the esters, carbonates, carbamates and the like thereof. When the compounds of the present invention are modified into prodrug forms, the compounds may connect with amino acids or saccharides.

The present invention also includes metabolites of the compounds of the present invention. The metabolites of the compounds of the present invention mean compounds into which the compounds of the present invention have been converted by metabolic enzymes and so on in vivo. Their examples are compounds where a hydroxyl group has been introduced on a benzene ring by metabolism; compounds where an alkoxyl group has been converted into a hydroxyl group by metabolism; and compounds where an alkyl group on a nitrogen atom has been dealkylated by metabolism. Further, they include the compounds where a glucuronic acid, glucose, an amino acid or a sulfuric acid has connected with a carboxylic acid moiety of the compounds of the present invention, a hydroxyl group moiety of the compounds of the present invention or a hydroxyl group moiety introduced by metabolism.

The compounds of the present invention have an excellent antagonistic effect against the adhesion of cells via α4 integrins and an excellent bioavailability and durability after administered orally. Further, they have an excellent durability even by parenteral administration. These characteristics reflect an excellent affinity for α4 integrins, plasma protein binding, solubility, hepatic clearance, total body clearance or intestinal tract membrane permeability.

Especially, as the compounds of the present invention have an excellent α4 integrin antagonistic activity even under the existence of plasma protein, a low dosage of the compound of the present invention can be effective when administered in vivo.

Further, the total body clearance of the compounds of the present invention is low and, therefore, they excel in sustained profile in blood plasma. These characteristics make it possible to decrease its dosage and number of doses. Further, the blood plasma level of the compounds of the present invention can be kept and then the adhesion of cells via α4 integrin can be inhibited effectively.

The compounds of the present invention have a high membrane permeability, and a high area under the blood plasma concentration-time curve (AUC) and bioavailability when administered orally.

Further, the compounds of the present invention have an excellent safety.

Particularly, the compound of the formula (1) in the compounds of the formulae (1) to (14) exhibits a high solubility and is useful.

Therefore, novel phenylalanine derivatives of the present invention and the salts thereof provide excellent α4 integrin antagonists and therapeutic agents or preventive agents for diseases in which α4 integrin-depending adhesion process participates in the pathology, such as inflammatory diseases, rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplant rejection.

They also provide therapeutic agents or preventive agents for diseases such as preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episcleritis, iritis, uveitides, erythema nodosum, pyoderma gangrenosum and autoimmune hepatitis.

Further, they provide therapeutic agents or preventive agents for not only the above diseases but also the diseases in which α4 integrins have the potential to participates in the pathology.

The dose of the compounds of the present invention or salt thereof used for the above-described purpose varies depending on the compound used, the intended therapeutic effect, administration method, period of the treatment, and age and body weight of the patient. The dose is usually 1 µg to 5 g a day for adults in the oral administration, and 0.01 µg to 1 g a day for adults in the parenteral administration (for instance, intravenously, subcutaneously, intramuscularly, suppository, barium enema, ointment, adhesive skin patch, sublingually, and eye-drops).

The compounds of the present invention have high stability in acidic or alkaline solution and are useful as it is possible to apply to various dosage forms.

The compounds of the present invention or salts thereof are administered as they are or in the form of various pharmaceutical compositions having a pharmaceutically acceptable carrier to patients.

Pharmaceutically acceptable carriers include, for example, various organic or inorganic carrier materials in common use as drug preparation materials. Their examples are diluents, lubricants, binders, disintegrating agents, water-soluble polymer and basic inorganic salts in solid preparation; and solvents, solubilizing agents, suspending agents, isotonizing agents, buffering agents and soothing agents in liquid solution. Further, additives can be used, if necessary, such as antiseptic agents, antioxidant substance, coloring agents, sweetening agents, souring agents, foaming agents and fragrant materials.

The dosage forms of the pharmaceutical compositions are, for example, tablets, powders, pills, granules, capsules, suppositories, solutions, sugar-coated tablets, depots, syrups, suspending agents, emulsions, trochisci, sublingual agents, adhesive skin patches, oral disintegrating agents (tablets), respiratory agents, barium enema, ointments, adhesive skin patches, adhesives and eye-drops. They can be prepared with ordinary preparation assistants by an ordinary method.

The pharmaceutical compositions of the present invention can be produced by methods in common use in the preparation technical field and, for instance, by the methods described in Japanese Pharmacopoeia. The methods for preparation are described below in detail.

For example, when the compounds of the present invention are prepared as oral preparation, diluents and, if necessary, binders, disintegrating agents, lubricants, coloring agents, flavoring agents are added thereto. Then they are formed as, for instance, tablets, powders, pills, granules, capsules, suppositories, solutions, sugar-coated tablets, depots, syrups, suspending agents, emulsions, trochisci, sublingual agents, oral disintegrating agents (tablets) and respiratory agents by ordinary methods. As the diluents, for example, lactose, corn starch, sucrose, glucose, sorbit and crystalline cellulose are used; as the binders, for example, polyvinyl alcohol, polyvinyl ether, ethylcellulose, methylcellulose, acacia, tragant, gelatin, shellac, hydroxypropylcellulose, hydroxypropylstarch and polyvinyl pyrrolidone are used; used as the disintegrating agents are, for instance, starch, agar, gelatin powder, crystalline cellulose, calcium carbonate, sodium hydrogen carbonate, calcium citrate, dextran and pectin; used as the lubricants are magnesium stearate, tarc, polyethylene glycol, silica, hydrogenated vegetable oil and the like; materials which are permitted to be added to drugs are used as the coloring agents; and as flavoring agents, for example, cocoa powder, menthol, aromatic acid, peppermint oil, borneol and cinnamon powder. These tablets or granules may be coated, if necessary, with sugar, gelatin and the like.

When injectable agents are prepared, pH adjuster, buffering agents, stabilizing agents and preservatives are added thereto, if necessary, and then they are prepared as subcutaneously, intramuscularly and intravenously administered agents by ordinary methods.

The phenylalanine derivatives (1) of the present invention can be produced, for example, by methods described below. The phenylalanines derivatives (2) to (14) can be produced by the same methods as those described below.

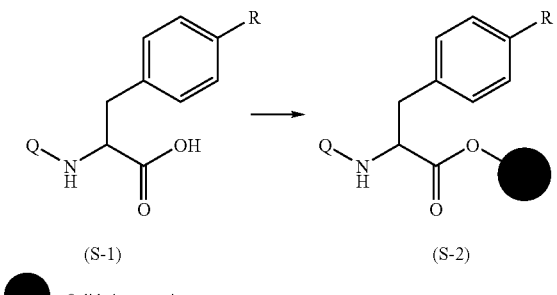

(S-1)   (S-2)

● Solid phase carrier

A suitably protected carboxylic acid (S-1) is loaded into a resin by a usual method. The substituent Q of the carboxylic acid (S-1) has a structure of 2-$Y_{11}$-6-$Y_{12}$-Ph-CO as described above with reference to the formula (1), it is a substituent which can be converted into 2-$Y_{11}$-6-$Y_{12}$-Ph-CO in any stage of the synthesis or it is a protective group of an amino group. The substituent R of the carboxylic acid (S-1) has a structure of a substituent which can be converted into $NH_2$ or suitably protected form of group of $NH_2$.

As for the loading reaction conditions, the reaction can be conducted by using, if necessary, a suitable additive such as HOAt (1-hydroxy-7-azabenzotriazole), HOBt (1-hydroxybenzotriazole) or DMAP (dimethylaminopyridine) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of DIC and DMAP in DMF to obtain an ester (S-2).

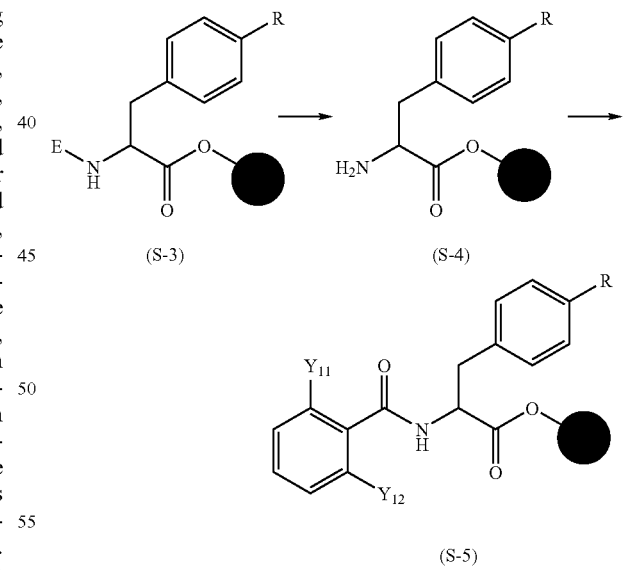

(S-3)   (S-4)

(S-5)

When Q is, for example, a protective group E (S-3) of an amino group, the protective group can be removed depending on the protective group E under proper conditions to obtain the amine (S-4). For instance, in case Fmoc group (9-fluorenylmethoxycarbonyl group) is used as E, the protective group can be removed with a base such as piperidine in a solvent such as DMF. The amide (S-5) can be obtained by reacting the amine (S-4) with a proper carboxylic acid by using a condensing agent such as DIC and, if necessary, a suitable additive such as HOAt or HOBt in an organic solvent such as DMF, NMP or dichloromethane. The amide (S-5) can also be obtained by reacting a proper acid chloride under the presence of a base.

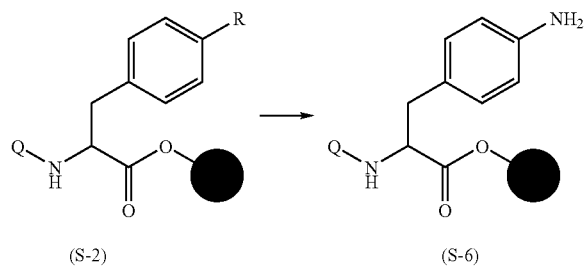

The ester (S-2) can be changed to an amine (S-6) under suitable conditions depending on the substituent R. For example, when a nitro group is used as R, the ester (S-2) can be changed to the amine (S-6) in the presence of a reducing agent such as $SnCl_2$ or hydrates thereof in a solvent such as NMP, DMF or ethanol. In the case of an amine protected with Fmoc group (9-fluorenylmethoxycarbonyl group) (FmocNH), the protective group can be removed with a base such as piperidine in a solvent such as DMF to obtain the amine (S-6).

A quinazolinedione (S-9) can be synthesized by the following method. First, an amide (S-7) can be obtained by reacting the amine (S-6) with a benzoic acid halide having a nitro group in the ortho position under the existence of 2,6-lutidine base in a solvent such as NMP, or by reacting it with a carboxylic acid having a nitro group in the ortho position activated by using a condensing agent such as DIC and, if necessary, a suitable additive such as HOAt or HOBt in an organic solvent such as DMF, NMP or dichloromethane. Then, an amine (S-8) is obtained by reducing the nitro group with $SnCl_2$ or hydrates thereof and cyclized by reagents such as CDI (carbonyldiimidazole), triphosgene or p-nitrophenylchloroformate to obtain the quinazolinedione (S-9).

As the other synthesizing methods, the quinazolinedione (S-9) can also be obtained by the following method. First, an amide (S-8) can be obtained by reacting the amine (S-6) with a carboxylic acid having a amino group in the ortho position activated by using a condensing agent such as DIC and, if necessary, a suitable additive such as HOAt or HOBt in an organic solvent such as DMF, NMP or dichloromethane. Then, an amide (S-8) is cyclized by the same process mentioned above to obtain the quinazolinedione (S-9).

The substituents R' and R''' on the formulae (S-7) to (S-9) are groups which result from benzoic acid derivatives used in the above reaction. They are R1' or —$X_1$—N(R12)R13 described in the formula (1), or groups which can be converted into R1' or —$X_1$—N(R12)R13 in any stage of the synthesis.

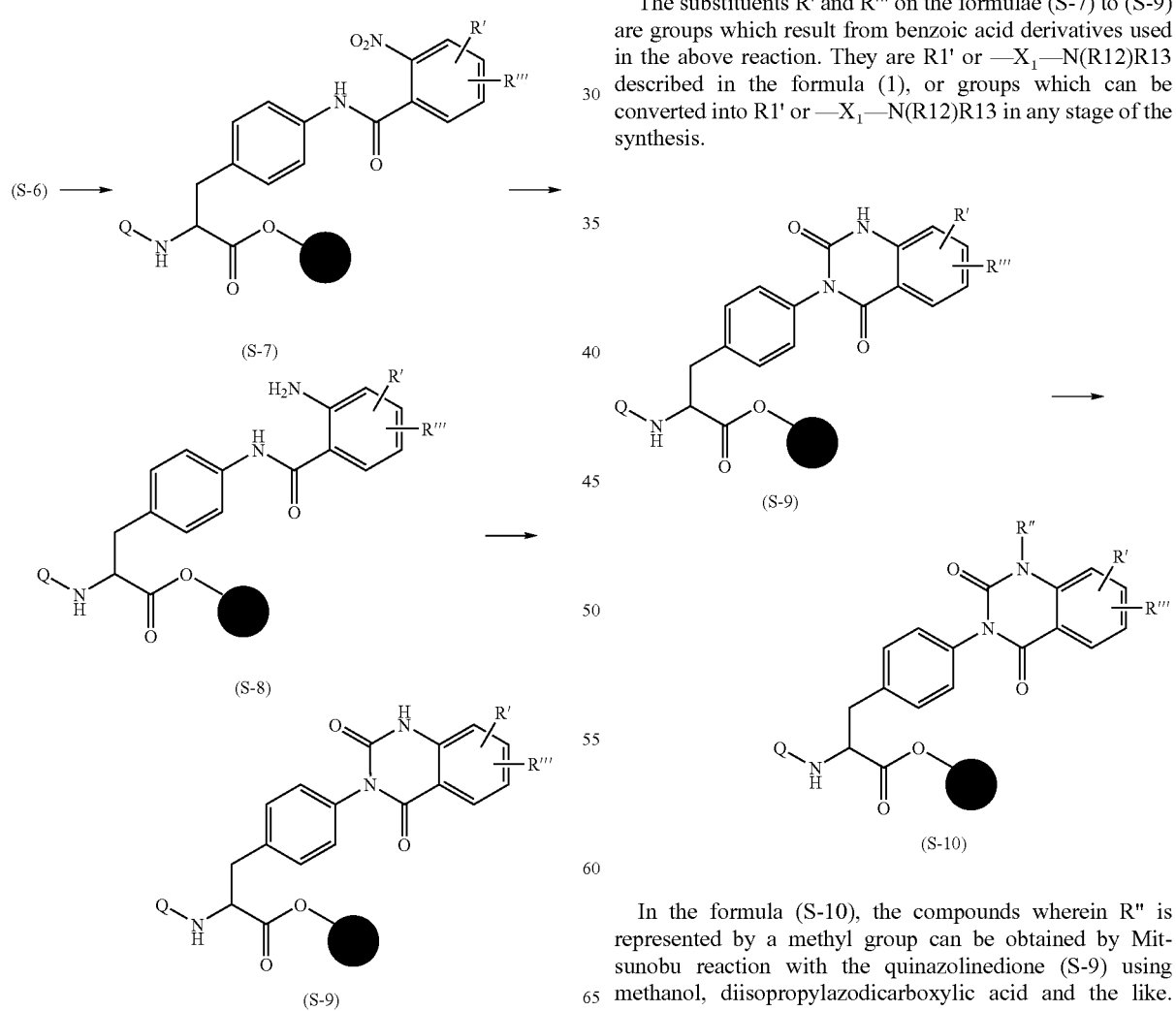

In the formula (S-10), the compounds wherein R'' is represented by a methyl group can be obtained by Mitsunobu reaction with the quinazolinedione (S-9) using methanol, diisopropylazodicarboxylic acid and the like. They can also be obtained by reacting methyl iodide under the existence of a base such as potassium carbonate.

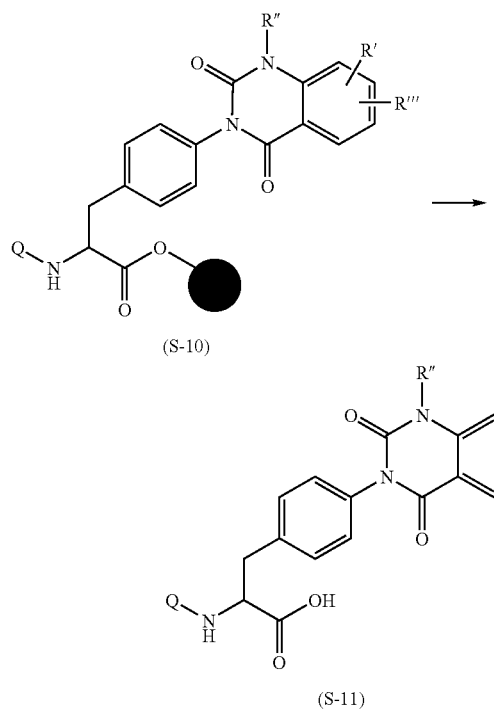

(S-10)

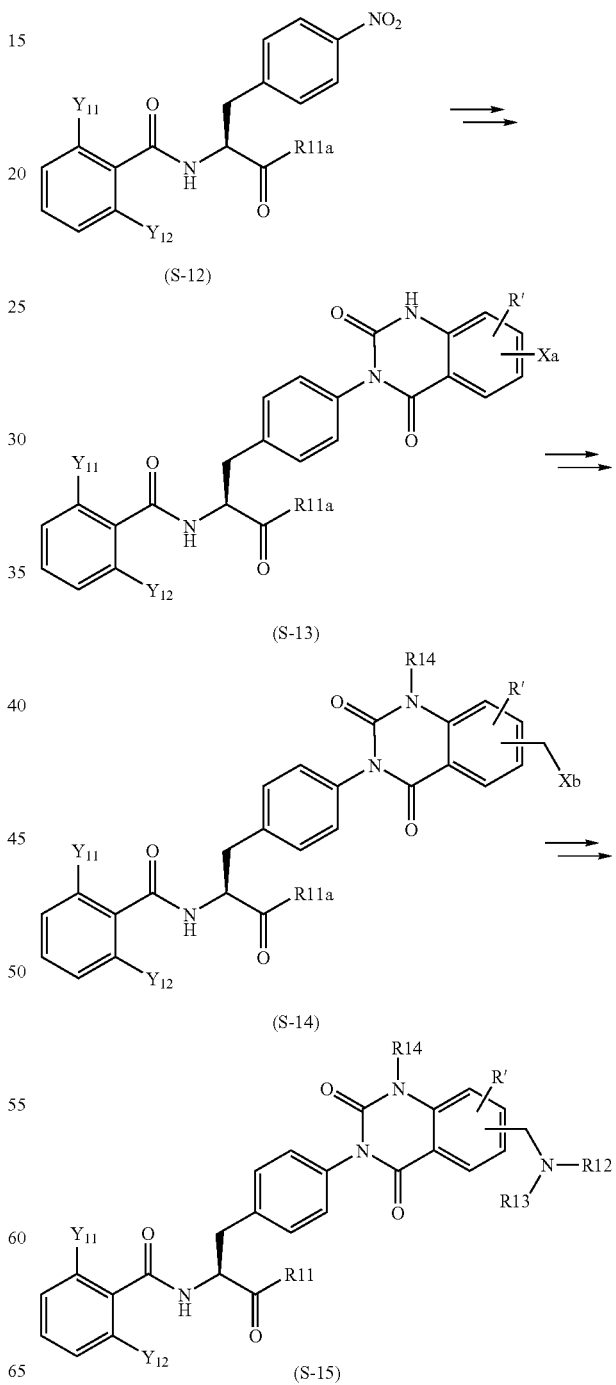

The ester (S-10) thus obtained are cleaved from a resin under suitable conditions to obtain a carboxylic acid (S-11).

For example, when Wang resin is used, in the ester (S-10), each of Q, R', R" and R'" are converted, if necessary, into 2-$Y_{11}$-6-$Y_{12}$-Ph-CO, —$X_1$—N($R_{12}$)$R_{13}$, a methyl group or $R_1$', or groups which are converted into 2-$Y_{11}$-6-$Y_{12}$-Ph-CO, —$X_1$—N($R_{12}$)$R_{13}$, a methyl group or $R_1$' under the conditions of removal of the resin. Then, the ester (S-10) is treated with an acidic solution including such as TFA (trifluoroacetic acid) thereto to obtain a solution of the carboxylic acid (1: R1=OH) wherein, in the formula (1), R1 is represented by a hydroxyl group. Further, the pure carboxylic acid (1: R1=OH) can be obtained by applying well-known isolating and purification methods such as concentration, extraction, crystallization, column chromatography, HPLC and recrystallization to the thus-obtained carboxylic acid (1:R1=OH).

Besides, the carboxylic acid (1:R1=OH) can also be obtained by applying the synthesizing methods on the solid phase to the liquid phase method wherein a suitable protective group is selected and well-known isolating and purification methods are used.

In the carboxylic acid (S-11), each of Q, R', R" and R'" represent 2-$Y_{11}$-6-$Y_{12}$-Ph-CO, —$X_1$—N($R_{12}$)$R_{13}$, a methyl group or $R_1$', or groups which can be converted into 2-$Y_{11}$-6-$Y_{12}$-Ph-CO, —$X_1$—N($R_{12}$)$R_{13}$, a methyl group or $R_1$' in subsequent processes. The carboxyl group in the formula (S-11) can be converted into —CO—R11 group (wherein R11 represents an alkoxyl group) by well-known esterification. More concretely, the methods are as follows. The carboxyl group is treated with suitable alcohol under the dehydration condition under an acidic catalyst; it is treated with O-alkylating agents such as an alkyl halide under the existence of a base or an acid, if necessary; it is treated with suitable alcohol under the existence of a base, if necessary, after converting into acid halide with thionyl chloride and the like; more concretely, it is treated with, for example, ethyl chloroformate under the existence of a base to convert into acid anhydride. Then the reaction substance is treated with suitable alcohol, if necessary, under the existence of a base.; Further it is also treated with suitable alcohol under the existence of a condensing agent such as dicyclohexylcarbodiimide and a catalyst such as dimethylaminopyridine, if necessary.

After these processes, the compounds of the present invention (1:R1 is an alkoxyl group) can be obtained by conversion of Q, R', R" and R'", if necessary.

In the formula (1), for example, a compound of (S-15) wherein $X_1$ represents $CH_2$ can be synthesized as follows. In the formula, R11a represents R11 or functional groups which can be converted into R11 in any stage of the synthesis.

A nitro compound (S-12), which is a starting material, can be obtained, for example, by the synthesizing procedure such as that of isopropylester of (S)-2-(2,6-dichlorobenzoylamino)-3-(4-nitrophenyl)propionic acid in Process 1 of Reference Example 4. The nitro compound (S-12) is reduced to an aniline compound by reacting with $SnCl_2$, the hydrogenation reaction in the presence of metal catalysts, and the like. More concretely, corresponding aniline compounds can be obtained, for example, by the synthesizing procedure such as that of isopropylester of (S)-2-(2,6-dichlorobenzoylamino)-3-(4-aminophenyl)propionic acid in Process 2 of Reference Example 4. After condensing thus obtained aniline compounds and an anthranilic acid substituted with Xa (Xa represents a halogen atom, a triflate group and the like) by using a suitable condensing agent(s), cyclization is conducted by reagents such as CDI (carbonyldiimidazole), ethyl chloroformate and triphosgene to obtain (S-13). Another methods for obtaining (S-13) is as follows: The above aniline compounds are reacted with 2-nitrobenzoic acid chloride substituted with Xa under the existence of a suitable base; and then, a nitro group is reduced by $SnCl_2$, the hydrogenation reaction in metal catalysts, and the like and cyclized by reagents such as CDI, ethyl chloroformate and triphosgene. The additional other method for obtaining (S-13) is as follows: The urea linkage is formed between the above aniline compounds and ester of an anthranilic acid substituted with Xa by using CDI, ethyl chloroformate, triphosgene and the like; and then the reaction mixture is cyclized by reacting with a suitable base, if necessary. Next, R14 is introduced by the methods such as reacting the compound (S-13) with alkylhalide under the existence of a suitable base, and Mitsunobu reaction using alcohol. Then, Xa is converted into a carboxylic acid by, for example, a conversion reaction using a palladium catalyst and carbon monoxide. The carboxylic acid is converted into an alcohol compound (S-14, Xb=OH) by the method such as the reductive reaction via mixed acid anhydride. Further, Xb is converted into a leaving group (Xb=a halogen group, a triflate group, a mesylate group, a tosylate group, etc) using a suitable acid halide, sulfonyl halide, thionyl halide, phosphoryl halide and the like. Then, the substitution reaction is conducted thereto using a suitably substituted amine to obtain the object compound (S-15).

The present invention provides compounds having an α4 integrin antagonistic activity or a pharmaceutically acceptable salt thereof. The present compounds are useful for treating or preventing diseases in which α4 integrin-depending adhesion process participates in the pathology, such as inflammatory diseases, rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplantation rejection.

The present compounds are also useful for treating or preventing preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episcleritis, iritis, uveitides, erythema nodosum, pyoderma gangrenosum and autoimmune hepatitis. Further, the present compounds are useful for treating or preventing not only the above diseases but also the diseases in which α4 integrins have the potential to participates in the pathology.

EXAMPLES

The following Examples will further illustrate the present invention, which are only preferred embodiments of the invention and which by no means limit the invention. In the following Examples, though salts of the intended compounds may not be described, they were obtained as trifluoroacetic acid (TFA) salts in case of the compounds being able to form TFA salts thereof. This is because the intended compounds were obtained by being purified by a solvent containing 0.1% TFA and freeze-dried in the final process.

Example 1

Synthesis of the Compound of the Following Formula (E-1) which has a Substituent(s) of Example 1 of Table 1

Process 1 Loading to Resin

Fmoc-Phe(4-nitro)-OH (25 g), DIC (8.9 mL), DMAP (281 mg) and DMF (193 mL) were added to Wang resin (1.2 mmol/g, 19.3 g) and stirred at room temperature for 3 hours. After removing the excess solvent, the resin was washed with DMF, methanol, dichloromethane and DMF three times each. In order to conduct capping of an unreacted hydroxyl group on the resin, the resin was treated with acetic anhydride (19.6 mL), pyridine (16.8 mL) and DMF (193 mL) for 2 hours. After removing the excess solvent, the resin was washed with DMF, methanol and dichloromethane three times each, and dried under reduced pressure.

Process 2 Removal of Fmoc Group

A DMF solution of 20% piperidine (200 mL) was added to the resin obtained in Process 1 and reacted for 15 minutes. The reaction mixture was further reacted with a DMF solution of 20% piperidine (200 mL) for 15 minutes. After removing the solvent, the resin was washed with NMP, methanol and dichloromethane three times each, and dried under reduced pressure.

Process 3 Acylation Reaction 2,6-dichlorobenzoyl chloride (10.3 mL), 2,6-lutidine (13.7 mL) and NMP (120 mL) were added to the resin obtained in Process 2 and reacted for 14 hours. After removing the excess solvent, the resin was washed with NMP, methanol and dichloromethane three times each, and dried under reduced pressure.

Process 4 Reduction of Nitro Group $SnCl_2 \cdot 2H_2O$ (150 g), NMP (300 mL) and EtOH (15 mL) were added to the resin obtained in Process 3 and reacted for 14 hours. After removing the solvent, the resin was washed with NMP, methanol and dichloromethane three times each, and dried under reduced pressure.

Process 5 Acylation Reaction

5-Fluoro-2-nitrobenzoic acid (1.63 g), DIC (675 μL), HOAt (1.2 g) and NMP (25 mL) were mixed and stirred for 1 hour, and then added to 1 g of the resin obtained in Process 4 and reacted for 14 hours. After removing the excess solvent, the resin was washed with NMP, methanol and dichloromethane three times each, and dried under reduced pressure.

Process 6 Substitution of Fluoro Group with Amine

Morpholine (400 μL) and NMP (2 mL) were added to 200 mg of the resin obtained in Process 5 and reacted for 14 hours. After removing the excess solvent, the resin was washed with NMP, methanol and dichloromethane three times each, and dried under reduced pressure.

Process 7 Reduction of Nitro Group

The reduction of nitro group was conducted to the resin obtained in Process 6 by the same procedure as that of Process 4 in Example 1.

Process 8 Construction of Quinazolinedione Ring by Carbonyldiimidazole

Carbonyldiimidazole (400 mg) and NMP (2 mL) were added to the resin obtained in Process 7 and stirred at 95° C. for 14 hours. After removing the excess solvent, the resin was washed with NMP, methanol and dichloromethane three times each, and dried under reduced pressure.

Process 9 Alkylation

Triphenylphosphine (520 mg), methanol (80 μL), 40% toluene solution (1 mL) of diisopropylazodicarboxylic acid and dichloromethane (2 mL) were added to the resin obtained in Process 8 and stirred for 14 hours. After removing the excess solvent, the resin was washed with NMP, methanol and dichloromethane three times each, and dried under reduced pressure.

Process 10 Cleavage from Resin

The resin obtained in Process 9 was treated with trifluoroacetic acid containing 5% of water for 1 hour. After filtration, the filtrate was concentrated under reduced pressure. The residue was purified with high performance liquid chromatography (water/acetonitrile, each containing 0.1% TFA) to obtain 61 mg of the intended compound.

MS(ESI MH+): 597

Examples 2 to 6

Synthesis of the Compounds of the Following Formula (E-1) which has a Substituent(s) of Examples 2 to 6 of Table 1

The compounds of the following formula (E-1) which has a substituent(s) of Examples 2 to 6 of Table 1 were synthesized by the same procedure as that of Example 1 except that corresponding amines were used in Process 6 of Example 1.

Example 7

Synthesis of the Compound of the Following Formula (E-2) which has a Substituent(s) of Example 7 of Table 2

Process 1 Acylation Reaction 1 g of the resin obtained in Process 4 of Example 1 was acylated by the same procedure as that of Process 5 in Example 1 except that 2-amino-5-nitrobenzoic acid was used in the process.

Process 2 Construction of Quinazolinedione Ring

The construction of quinazolinedione ring was conducted to the resin obtained in Process 1 by the same procedure as that of Process 8 in Example 1.

Process 3 Alkylation

Methyl iodide (1 mL), diisopropylethylamine (1 mL) and NMP (5 mL) were added to the resin obtained in Process 2 and stirred for 14 hours. After removing the solvent, the resin was washed with NMP, methanol and dichloromethane three times each, and dried under reduced pressure.

Process 4 Reduction of Nitro Group

The reduction of nitro group was conducted to the resin obtained in Process 1 by the same procedure as that of Process 4 in Example 1.

Process 5 2-nitrosulfonylation 2-nitrosulfonylchloride (1 g), 2,6-di-t-butyl-4-methylpyridine (1 mL) and dichloromethane (15 mL) were added to the resin obtained in Process 4 and stirred at 4° C. for 24 hours. After removing the solvent, the resin was washed with NMP, methanol and dichloromethane three times each, and dried under reduced pressure.

Process 6 Alkylation

Propyl-iodide (400 μL), diisopropylethylamine (400 μL) and NMP (2 mL) were added to 200 mg of the resin obtained in Process 5 and stirred for 14 hours. After removing the solvent, the resin was washed with NMP, methanol and dichloromethane three times each, and dried under reduced pressure.

Process 7 Removal of 2-nitrosulfonyl Group 2-mercaptoethanol (200 μL), 1,8-diazabicyclo[5.4.0]undec-7-ene (100 μL) and NMP (2 mL) were added to the resin obtained in Process 6 and stirred for 1 hour. After removing the solvent, the resin was washed with NMP, methanol and dichloromethane three times each, and dried under reduced pressure.

Process 8 Cleavage from Resin, Purification

The cleavage from resin and purification thereof were conducted to the resin obtained in Process 7 by the same procedure as that of Process 10 in Example 1 to obtain 38 mg of the intended compound.

MS(ESI MH+): 569

Examples 8 to 12

Synthesis of the Compounds of the Following Formula (E-2) which has a Substituent(s) of Examples 8 to 12 of Table 2

The compounds of the following formula (E-2) which has a substituent(s) of Examples 8 to 12 of Table 2 were synthesized by the same procedure as that of Example 7 except that corresponding halides were used in Process 6 of Example 7.

Example 13

Synthesis of the Compound of the Following Formula (E-3) which has a Substituent(s) of Example 13 of Table 3

Process 1 Acylation Reaction 1 g of the resin obtained in Process 4 of Example 1 was acylated by the same procedure as that of Process 5 in Example 1 except that 2-amino-4,5-difluorobenzoic acid was used in the process.

Process 2 Construction of Quinazolinedione Ring

Carbonyldiimidazole (3 g) and NMP (15 mL) were added to the resin obtained in Process 1 and stirred for 14 hours. After removing the excess solvent, the resin was washed with NMP, methanol and dichloromethane three times each, and dried under reduced pressure.

Process 3 Substitution of Fluoro Group with Amine

N,N,N'-trimethylethylenediamine (400 μL) and NMP (2 mL) were added to 200 mg of the resin obtained in Process 2 and stirred at 90° C. for 14 hours. After removing the excess solvent, the resin was washed with NMP, methanol and dichloromethane three times each, and dried under reduced pressure.

Process 4 Alkylation

The resin obtained in Process 3 was alkylated by the same procedure as that of Process 9 in Example 1.

Process 5 Cleavage from Resin, Purification

The cleavage from resin and purification thereof were conducted to the resin obtained in Process 4 by the same procedure as that of Process 10 in Example 1 to obtain 39 mg of the intended compound.

MS(ESI MH+): 630

Examples 14 to 15

Synthesis of the Compounds of the Following Formula (E-3) which has a Substituent(s) of Examples 14 to 15 of Table 3

The compounds of the following formula (E-3) which has a substituent(s) of Examples 14 to 15 of Table 3 were synthesized by the same procedure as that of Example 13 except that corresponding amines were used in Process 3 of Example 13.

Example 16

Synthesis of the Compound of the following formula (E-4)

Process 1 Acylation Reaction 200 mg of the resin obtained in Process 4 of Example 1 was acylated by the same procedure as that of Process 5 in Example 1 except that 2-nitro-4,5-difluorobenzoic acid was used in the process.

Process 2 Substitution of Fluoro Group with Amine

The substitution of fluoro group with amine was conducted to the resin obtained in Process 1 by the same procedure as that of Process 6 in Example 1 except that 2-methoxy-N-methylethylamine was used in the process.

Process 3 Reduction of Nitro Group, Construction of Quinazolinedione Ring, Alkylation, Cleavage from Resin, Purification The reduction of nitro group was conducted to the resin obtained in Process 2 by the same procedure as that of Process 4 in Example 1; the construction of quinazolinedione ring was conducted to the resin by the same procedure as that of Process 8 in Example 1; the alkylation was conducted to the resin by the same procedure as that of Process 9 in Example 1; and then the cleavage from resin and purification thereof were conducted to the resin by the same procedure as that of Process 10 in Example 1 to obtain 59 mg of the intended compound.

MS(ESI MH+): 617

Example 17

Synthesis of the Compound of the Following Formula (E-5)

Process 1 Substitution of Fluoro Group with Amine

The substitution of two fluoro groups with amines was conducted to 200 mg of the resin obtained in Process 1 of Example 16 by the same procedure as that of Process 3 in Example 13 except that N,N'-dimethylethylenediamine was used in the process.

Process 2 Reduction of Nitro Group, Construction of Quinazolinedione Ring, Alkylation, Cleavage from Resin, Purification The reduction of nitro group was conducted to the resin obtained in Process 1 by the same procedure as that of Process 4 in Example 1; the construction of quinazolinedione ring was conducted to the resin by the same procedure as that of Process 8 in Example 1; the alkylation was conducted to the resin by the same procedure as that of Process 9 in Example 1; and then the cleavage from resin and purification thereof were conducted to the resin by the same procedure as that of Process 10 in Example 1 to obtain 16 mg of the intended compound.

MS(ESI MH+): 596

Example 18

Synthesis of the Compound of the Following Formula (E-6)

Process 1 Acylation Reaction 200 mg of the resin obtained in Process 4 of Example 1 was acylated by the same procedure as that of Process 5 in Example 1 except that 1-methyl-5-nitro-1H-pyrazole-4-carboxylic acid was used in the process.

Process 2 Reduction of Nitro Group, Construction of Quinazolinedione Ring, Alkylation, Cleavage from Resin, Purification The reduction of nitro group was conducted to the resin obtained in Process 1 by the same procedure as that of Process 4 in Example 1; the construction of quinazolinedione ring was conducted to the resin by the same procedure as that of Process 8 in Example 1; the alkylation was conducted to the resin by the same procedure as that of Process 9 in Example 1; and then the cleavage from resin and purification thereof were conducted to the resin by the same procedure as that of Process 10 in Example 1 to obtain 15 mg of the intended compound.

MS(ESI MH+): 516

Example 19

Synthesis of the Compound of the Following Formula (E-7)

Process 1 Acylation Reaction 1 g of the resin obtained in Process 4 of Example 1 was acylated by the same procedure as that of Process 5 in Example 1 except that 2-amino-4-nitrobenzoic acid was used in the process.

Process 2 Construction of Quinazolinedione Ring, Alkylation, Reduction of Nitro Group The construction of quinazolinedione ring was conducted to the resin obtained in Process 1 by the same procedure as that of Process 8 in Example 1; the alkylation was conducted to the resin by the same procedure as that of Process 3 in Example 7; and then the reduction of nitro group was conducted to the resin by the same procedure as that of Process 4 in Example 1

Process 3 Alkylation

Ethyl iodide (200 µL), potassium carbonate (200 mg) and NMP (4 mL) were added to 400 mg of the resin obtained in Process 2 and stirred at 80° C. for 9 hours. After removing the solvent, the resin was washed with NMP, methanol and dichloromethane three times each, and dried under reduced pressure.

Process 4 Cleavage from Resin, Purification

The cleavage from resin and purification thereof were conducted to the resin obtained in Process 3 by the same procedure as that of Process 10 in Example 1 to obtain 43 mg of the intended compound.

MS(ESI MH+): 555

Example 20

Synthesis of the Compound of the Following Formula (E-8)

Process 1 Substitution of Fluoro Group with Amine

The substitution of fluoro group with amine was conducted to 200 mg of the resin obtained in Process 5 of Example 1 by the same procedure as that of Process 6 in Example 1 except that 2-(methylamino)ethanol was used in the process.

Process 2 Protection of Hydroxyl Group with Acetyl Group

Acetic anhydride (200 μL), pyridine (200 μL) and NMP (2 mL) were added to the resin obtained in Process 1 and stirred for 14 hours. After removing the solvent, the resin was washed with NMP, methanol and dichloromethane three times each, and dried under reduced pressure.

Process 3 Reduction of Nitro Group, Construction of Quinazolinedione Ring, Alkylation The reduction of nitro group was conducted to the resin obtained in Process 2 by the same procedure as that of Process 4 in Example 1; the construction of quinazolinedione ring was conducted to the resin by the same procedure as that of Process 8 in Example 1; and then the alkylation was conducted to the resin by the same procedure as that of Process 9 in Example 1.

Process 4 Cleavage from Resin, Cleavage of Acetyl Group from Protecting Group

The resin obtained in Process 3 was treated with trifluoroacetic acid containing 5% of water for 1 hour. After filtration, the filtrate was concentrated under reduced pressure. 4M hydrogen chloride dioxane solution (3 mL) and water (600 μL) were added to the obtained residue and stirred at 90° C. for 1.5 hours. Then the residue was purified with high performance liquid chromatography (water/acetonitrile, each containing 0.1% TFA) to obtain 42 mg of the intended compound.

MS(ESI MH+): 585

Example 21

Synthesis of the Compound of the Following Formula (E-9) which has a Substituent(s) of Example 21 of Table 4

Process 1 Methylesterification 2M hexane solution (4.5 mL) of trimethylsilyldiazomethane was added to the mixture of 2-Nitro-3-methylbenzoic acid (1.6 g) and acetone (15 mL) and stirred for 3 hours. After removing the solvent, the residue was diluted with ethyl acetate and washed with 1M sodium hydrate aqueous solution, water and saturated aqueous solution of sodium chloride respectively. Then the obtained substance was concentrated and dried to obtain methyl 2-nitro-3-methylbenzoate.

Process 2 Bromination

Benzoyl peroxide was added to the mixture of methyl 2-nitro-3-methylbenzoate (1.6 g), N-bromosucciimide (2.0 g) and benzene (15 mL) and stirred at 90° C. overnight. After removing the solvent, the residue was diluted with ethyl acetate and washed with sodium thiosulfate aqueous solution, 1M sodium hydrate aqueous solution, water and saturated aqueous solution of sodium chloride respectively. Then the obtained substance was concentrated and dried, and the obtained crude material was purified with silica gel column chromatography to obtain methyl 3-bromomethyl-2-nitrobenzoate.

Process 3 Amination

Methyl 3-bromomethyl-2-nitrobenzoate (1.6 g) was dissolved in methanol (5 mL). Methanol solution (6 mL) of 2M dimethylamine was added thereto and stirred overnight. After removing the solvent, the residue was diluted with 1M hydrochloric acid and washed with ethyl acetate. The water layer was alkalized with sodium hydrate aqueous solution and extracted with ethyl acetate. The usual workup procedure was conducted to obtain methyl 3-dimethylaminomethyl-2-nitrobenzoate.

Process 4 Hydrolysis of Ester

The mixture of methyl 3-dimethylaminomethyl-2-nitrobenzoate (0.72 g) and 6M hydrochloric acid was stirred at 100° C. overnight. After cooling the mixture to room temperature, the precipitated crystals were filtered out, washed with diethylether and dried under reduced pressure to obtain 3-dimethylaminomethyl-2-nitrobenzoic acid hydrochloride.

H-NMR(DMSO) δ2.70(s, 6H), 4.31(s, 2H), 7.84(m, 1H), 8.07(1H, d, J=7.8 Hz), 8.32(1H, d, J=7.5 Hz)

Process 5 Acid Chloride Formation

The mixture of 3-dimethylaminomethyl-2-nitrobenzoic acid hydrochloride (0.1 g) and thionylchloride (5 mL) was stirred at 80° C. for 3 hours. The solvent was removed and the residue was dried to obtain 3-dimethylamino methyl-2-nitrobenzoyl chloride.

Process 6 Acylation Reaction 3-dimethylaminomethyl-2-nitrobenzoyl chloride (0.69 g), 0.11 g of the resin obtained in Process 4 of Example 1,2,6-lutidine (0.04 mL) and NMP (1.5 mL) were mixed and reacted overnight. After removing the excess solvent, the residue was washed with NMP, methanol and dichloromethane three times each, and dried under reduced pressure.

Process 7 Reduction of Nitro Group

The reduction of nitro group was conducted to the resin obtained in Process 6 by the same procedure as that of Process 7 in Example 1.

Process 8 Construction of Quinazolinedione Ring by Carbonyldiimidazole

The construction of quinazolinedione ring was conducted to the resin obtained in Process 7 by the same procedure as that of Process 8 in Example 1.

Process 9 Alkylation

The resin obtained in Process 8 was alkylated by the same procedure as that of Process 9 in Example 1.

Process 10 Cleavage from Resin

The cleavage from resin was conducted to the resin obtained in Process 9 by the same procedure as that of Process 10 in Example 1 to obtain 12 mg of the intended compound.

MS(ESI MH+): 569

Example 22

Synthesis of the Compound of the Following Formula (E-9) which has a Substituent(s) of Example 22 of Table 4

Methyl 3-(1-pyrrolidinylmethyl)-2-nitrobenzoate was obtained by using pyrrolidine instead of dimethylamine in Process 3 of Example 21. Then, the intended compound was obtained by the same procedures as those of Processes 4 to 10 in Example 21.

MS(ESI MH+): 595

Example 23

Synthesis of the Compound of the Following Formula (E-9) which has a Substituent(s) of Example 23 of Table 4

The mixture of 4 mg of the compound of Example 21, ethanol (3 mL) and 4M hydrogen chloride/dioxane solution (2 mL) was stirred at 85° C. for 5 hours. After removing the solvent, the residue was purified with high performance liquid chromatography (water/acetonitrile, each containing 0.1% TFA) to obtain 3.6 mg of the intended compound.

MS(ESI MH+): 597

Example 24

Synthesis of the Compound of the Following Formula (E-9) which has a Substituent(s) of Example 24 of Table 4

The mixture of 4 mg of the compound of Example 21, dichloromethane (2 mL), triethylamine (10 µL), isopropanol (1 mL), HOBt (15 mg) and EDC hydrochloride (20 mg) was stirred overnight. After removing the solvent, the residue was purified with high performance liquid chromatography (water/acetonitrile, each containing 0.1% TFA) to obtain 3.6 mg of the intended compound.

MS(ESI MH+): 611

Examples 25 to 27

Synthesis of the Compounds of the Following Formula (E-9) which has a Substituent(s) of Examples 25 to 27 of Table 4

The compounds were synthesized by the same procedure as that of Example 24 except that corresponding alcohols were used instead of isopropanol.

Example 28

Synthesis of the Compound of the Following Formula (E-10) which has a Substituent(s) of Example 28 of Table 5

The intended compound was obtained by the same procedure as that of Example 21 except that 2-nitro-5-methyl-benzoic acid was used as a starting material.

MS(ESI MH+): 569

Examples 29 to 33

Synthesis of the Compounds of the Following Formula (E-10) which has a Substituent(s) of Examples 29 to 33 of Table 5

The intended compounds were obtained by the same procedure as that of Example 23 or 24 except that the compound of Example 28 was used as a starting material.

Example 34

Synthesis of the Compound of the Following Formula (E-11) which has a Substituent(s) of Example 34 of Table 6: Synthesis of N-(2,6-dichlorobenzoyl)-4-[7-[(dimethylamino)methyl]-1-methyl-2,4-quinazoline-dione-3-yl]-L-phenylalanine Trifluoroacetate Process 1 Synthesis of Methyl ester 4-(hydroxymethyl)-2-nitrobenzoic Acid 0.51 ml (5.36 mmol) of ethyl chloroformate was added to the mixture of 11.0 g (4.46 mmol) of 4-methoxycarbonyl-3-nitrobenzoic acid, 15 mL of tetrahydrofuran and 1.55 mL (11.2 mmol) of triethylamine under cooling with ice. After stirring it for 30 minutes, the precipitated salts were filtered out and 0.17 g (4.46 mmol) of sodium borohydride and 2 g of ice were added to the filtrate. After stirring it at room temperature overnight, the solvent was removed and the usual workup procedure was conducted to the residue. Then the obtained material was purified with silica gel column chromatography (30% ethyl acetate/hexane) to obtain the title compound.

Yield: 0.64 g (3.04 mmol) 68%

Process 2 Synthesis of 4-[(dimethylamino)methyl]-2-nitrobenzoylchloride hydrochloride 0.64 g (3.04 mmol) of the compound obtained in Process 1 was dissolved in 10 mL of methylene chloride and 0.635 mL (4.56 mmol) of triethylamine, and 0.282 mL (3.64 mmol) of methanesulfonyl chloride was added thereto drop-wise under cooling with ice. After stirring it for 2 hours, the usual workup procedure was conducted to the mixture in accordance with the ordinary method to obtain a crude material. The obtained crude material was treated by the same procedures as those of Processes 3, 4 and 5 in Example 21 to obtain the title compound.

Yield: 0.64 g (2.20 mmol) 75%

Process 3

The same procedures as those of Process 6 in Example 21 and Processes 7, 8, 9 and 10 in Example 1 were sequentially conducted using the acid chloride obtained in Process 2 and the resin obtained in Process 4 of Example 1 to obtain the title compound.

MS(ESI MH+): 569

Example 35

Synthesis of the Compound of the Following Formula (E-11) which has a Substituent(s) of Example 35 of Table 6: Synthesis of N-(2,6-dichlorobenzoyl)-4-[1-methyl-7-(pyrrolidine-1-ylmethyl)-2,4-quinazoline-dione-3-yl]-L-phenylalanine trifluoroacetate Process 1 Synthesis of 2-nitro-4-(pyrrolidine-1-ylmethyl) benzoylchloride hydrochloride The title compound was obtained by the same procedure as that of Example 34 except that pyrrolidine was used as amine instead of dimethylamine in Process 2 of Example 34.

Process 2 Synthesis of N-(2,6-dichlorobenzoyl)-4-[1-methyl-7-(pyrrolidine-1-ylmethyl)-2,4-quinazoline-dione-3-yl]-L-phenylalanine trifluoroacetate The same procedures as those of Process 6 in Example 21 and Processes 7, 8, 9 and 10 in Example 1 were sequentially conducted using the acid chloride obtained in Process 1 and the resin obtained in Process 4 of Example 1 to obtain the title compound.

MS(ESI MH+): 595

Example 36

Synthesis of the Compound of the Following Formula (E-12): Synthesis of N-(2,6-dichlorobenzoyl)-4-(1-methyl-2,4-dioxo-1,2,3,4-tetrahydrobenzo[g]quinazoline-3(2H)-yl)-L-phenylalanine The title compound was obtained by the same procedures as those of Processes 5, 8, 9 and 10 in Example 1 except that 3-amino-2-naphthalenecarboxylic acid and the resin obtained in Process 4 of Example 1 were used as starting materials.

MS(ESI MH+): 562

Example 37

Synthesis of the Compound of the Following Formula (E-13) which has a Substituent(s) of Example 37 of Table 7: Synthesis of N-(2,6-dichlorobenzoyl)-4-[1-methyl-6-(methylthio)-2,4-quinazoline-dione-3-yl]-L-phenylalanine Process 1 Synthesis of 5-methylthio-2-nitrobenzoylchloride 2.5 mL of 15% sodium methylmercaptan aqueous solution was added to the mixture of 11.0 g (5.40 mmol) of 5-fluoro-2-nitrobenzoic acid and 5 mL of ethanol and stirred for 2 days. Then, 10 mL of water was added and pH thereof was adjusted to become 1 by concentrated hydrochloric acid. After filtering out the precipitated compound, it was washed with water, ether and hexane and dried to obtain a crude material of 5-methylthio-2-nitrobenzoic acid. 3 mL of thionyl chloride was added to the obtained crude material and stirred for 5 hours. The thionyl chloride was removed to obtain the title compound.

Process 2 Synthesis of N-(2,6-dichlorobenzoyl)-4-[1-methyl-6-(methylthio)-2,4-quinazoline-dione-3-yl]-L-phenylalanine The title compound was obtained by the same procedures as those of Process 6 in Example 21 and Processes 7, 8, 9 and 10 in Example 1 except that the acid chloride obtained in Process 1 and the resin obtained in Process 4 of Example 1 were used as starting materials.

MS(ESI MH+): 558

Example 38

Synthesis of the Compound of the Following Formula (E-13) which has a Substituent(s) of Example 38 of Table 7: Synthesis of N-(2,6-dichlorobenzoyl)-4-[1-methyl-6-(methylsulfonyl)-2,4-quinazoline-dione-3-yl]-L-phenylalanine Process 1 Oxidation The mixture of 130 mg of the resin in Process 2 of Example 37 before conducting the same procedure as that of Process 10 in Example 1 (cleavage from resin), 1.5 mL of methylene chloride and 0.20 g of meta-chloro perbenzoic acid was reacted for 24 hours. The obtained resin was washed with NMP, the mixed aqueous solution of sodium hydrogen carbonate and sodium thiosulfate, methanol and methylene chloride three times each and dried under reduced pressure.

Process 2 Synthesis of N-(2,6-dichlorobenzoyl)-4-[1-methyl-6-(methylsulfonyl)-2,4-quinazoline-dione-3-yl]-L-phenylalanine The resin obtained in Process 1 was treated by the same procedure as that of Process 10 in Example 1 to obtain the title compound.

MS(ESI MH+): 590

Example 39

Synthesis of the Compound of the Following Formula (E-14) which has a Substituent(s) of Example 39 of Table 8: Synthesis of N-(2,6-dichlorobenzoyl)-4-[1-methyl-7-(morpholine-4-yl)-2,4-quinazoline-dione-3-yl]-L-phenylalanine trifluoroacetate Process 1 Synthesis of 4-fluoro-2-nitrobenzoylchloride 5 mL of thionyl chloride was added to 0.5 g of 4-fluoro-2-nitrobenzoic acid and stirred overnight. The thionyl chloride was removed to obtain the title compound.

Process 2 Synthesis of N-(2,6-dichlorobenzoyl)-4-[1-methyl-7-(morpholine-4-yl)-2,4-quinazoline-dione-3-yl]-L-phenylalanine trifluoroacetate The title compound was obtained by the same procedures as those of Process 6 in Example 21 and Processes 6, 7, 8, 9 and 10 in Example 1 using the acid chloride obtained in Process 1 and the resin obtained in Process 4 of Example 1 as starting materials.

MS(ESI MH+): 596

Example 40

Synthesis of the compound of the Following Formula (E-14) which has a Substituent(s) of Example 40 of Table 8: Synthesis of N-(2,6-dichlorobenzoyl)-4-[1-methyl-7-(pyrrolidine-1-yl)-2,4-quinazoline-dione-3-yl]-L-phenylalanine trifluoroacetate The title compound was obtained by the same procedure as that of Example 39 except that pyrrolidine was used instead of morpholine in conducting the same procedure as that of Process 6 in Example 1 in Process 2 of Example 39.

MS(ESI MH+): 581

Examples 41 to 42

Synthesis of the Compounds of the Following Formula (E-15) which has a Substituent(s) of Examples 41 to 42 of Table 9

The compounds of the following formula (E-15) which has a substituent(s) of Examples 41 to 42 of Table 9 were synthesized by the same procedure as that of Example 1 except that corresponding amines were used in Process 6 of Example 1.

Example 43

Synthesis of the Compound of the Following Formula (E-16) which has a Substituent(s) of Example 43 of Table 10

Process 1 N-(2,6-dichlorobenzoyl)-4-[(2-amino-5-iodobenzoyl) amino]-L-phenylalanine methylester The mixture of N-(2,6-dichlorobenzoyl)-4-amino-L-phenylalanine methylester(2.22 g), EDC/HCl (960 mg), HOBT (675 mg), triethylamine (834 µL), 2-amino-5-iodobenzoic acid (1.3 g) and dichloromethane (100 mL) was stirred overnight. The mixture was extracted with ethyl acetate and treated in accordance with the ordinary method to obtain a crude material of the intended compound.

Process 2 N-(2,6-dichlorobenzoyl)-4-[6-iodo-2,4-quinazoline-dione-3-yl]-L-phenylalanine Methylester The mixture of the crude material obtained in Process 1, DMF (120 mL) and carbonyldiimidazole (4.5 g) was stirred at 80° C. for 4 hours. The mixture was extracted with ethyl acetate and treated in accordance with the ordinary method to obtain the title compound.

Process 3 N-(2,6-dichlorobenzoyl)-4-[1-methyl-6-iodo-2,4-quinazoline-dione-3-yl]-L-phenylalanine methylester DMF (20 mL), potassium carbonate (648 mg) and methyl iodide (176 µL) were added to the crude material obtained in Process 2 and stirred at room temperature overnight. The mixture was extracted with ethyl acetate and treated in accordance with the ordinary method.

Process 4 N-(2,6-dichlorobenzoyl)-4-[1-methyl-6-iodo-2,4-quinazoline-dione-3-yl]-L-phenylalanine The mixture of the crude material obtained in Process 3 (20 mg), 4M hydrogen chloride dioxane solution (1 mL) and water (100 µL) was stirred at 90° C. for 4 hours. After removing the solvent, the residue was purified with high performance liquid chromatography (water/acetonitrile, each containing 0.1% TFA) to obtain 3 mg of the intended compound.

MS(ESI MH+): 638

Example 44

Synthesis of the Compound of the Following Formula (E-16) which has a Substituent(s) of Example 44 of Table 10

Process 1 N-(2,6-dichlorobenzoyl)-4-[1-methyl-6-cyano-2,4-quinazoline-dione-3-yl]-L-phenylalanine methylester The mixture of the crude material obtained in Process 3 of Example 43 (220 mg), DMF (2 mL), tetrakis(triphenylphosphine)palladium (5 mg) and zinc cyanide (79 mg) was stirred at 90° C. for 4 hours. The mixture was extracted with ethyl acetate and treated in accordance with the ordinary method to obtain the title compound.

Process 2 N-(2,6-dichlorobenzoyl)-4-[1-methyl-6-cyano-2,4-quinazoline-dione-3-yl]-L-phenylalanine The crude material obtained in Process 1 (60 mg) was treated by the same procedure as that of Process 4 in Example 43 to obtain the title compound.

MS(ESI MH+): 537

Examples 45 and 46

Synthesis of the Compounds of the Following Formula (E-16) which has a Substituent(s) of Examples 45 to 46 of Table 10

Process 1 N-(2,6-dichlorobenzoyl)-4-[1-methyl-6-benzyloxycarbonyl-2,4-quinazoline-dione-3-yl]-L-phenylalanine methylester The mixture of the crude material obtained in Process 3 of Example 43 (311 mg), DMF (5 mL), palladium acetate (10 mg), benzyl alcohol (99 µL) and triethylamine (134 µL) was stirred under the existence of carbon monoxide at 100° C. for 3 hours. The mixture was extracted with ethyl acetate and treated in accordance with the ordinary method to obtain a crude material of the title compound.

Process 2 N-(2,6-dichlorobenzoyl)-4-[1-methyl-6-benzyloxycarbonyl-2,4-quinazoline-dione-3-yl]-L-phenylalanine and N-(2,6-dichlorobenzoyl)-4-[1-methyl-6-carboxyl-2,4-quinazoline-dione-3-yl]-L-phenylalanine The mixture of the crude material obtained in Process 1 (60 mg), 4M hydrogen chloride dioxane solution (1 mL) and water (100 µL) was stirred at 90° C. for 4 hours. After removing the solvent, the residue was purified with high performance liquid chromatography (water/acetonitrile, each containing 0.1% TFA) to obtain the intended compound, 6-carboxyl compound (5 mg) and 6-benzyloxycarbonyl compound (1 mg).

MS(ESI MH+): 556 (6-carboxyl compound)
MS(ESI MH+): 646 (6-benzyloxycarbonyl compound)

Example 47

Synthesis of the Compound of the Following Formula (E-17)

Process 1 N-(2,6-dichlorobenzoyl)-4-[2,4-dioxo-1,2,3,4-tetrahydro-3-(2H)pyrido[3,2-d]pyrimidinyl]-L-phenylalanine methylester The title compound was obtained by the same procedures as those of Process 1 in Example 43 except that 2-carboxy-3-aminopyridine was used instead of 2-amino-5-iodobenzoic acid, and then Process 2 in Example 43.

Process 2 N-(2,6-dichlorobenzoyl)-4-[1-methyl-2,4-dioxo-1,2,3,4-tetrahydro-3-(2H)pyrido[3,2-d]pyrimidinyl]-L-phenylalanine methylester The mixture of the crude material obtained in Process 1, triphenylphosphine (61 mg), methanol (15 µL), 40% toluene solution (118 mg) of diisopropylazodicarboxylic acid and dichloromethane (2 mL) was stirred overnight. The mixture was extracted with ethyl acetate and treated in accordance with the ordinary method to obtain the title compound.

Process 3 N-(2,6-dichlorobenzoyl)-4-[1-methyl-2,4-dioxo-1,2,3,4-tetrahydro-3-(2H)pyrido[3,2-d]pyrimidinyl]-L-phenylalanine The crude material obtained in Process 2 (20 mg) was treated by the same procedure as that of Process 4 in Example 43 to obtain the title compound.

MS(ESI MH+): 513

Example 48

Synthesis of the Compound of the Following Formula (E-18)

The compound was obtained by the same procedure as that of Example 47 except that 3-amino-4-carboxypyridine was used instead of 2-carboxy-3-aminopyridine in Process 1 of Example 47.

Example 49

Synthesis of the Compound of the Following Formula (E-19) which has a Substituent(s) of Example 49 of Table 11

Process 1 N-(2,6-dichlorobenzoyl)-4-[1-methyl-6-(2-t-butoxycarbonylethenyl)-2,4-quinazoline-dione-3-yl]-L-phenylalanine methylester The mixture of the crude material obtained in Process 3 of Example 43 (630 mg), DMF (5 mL), palladium acetate (22 mg), t-butyl acrylate (283 µL) and triethylamine (270 µL) was stirred at 70° C. for 3 hours. The mixture was extracted with ethyl acetate and treated in accordance with the ordinary method to obtain the title compound.

Process 2

The mixture of the crude material obtained in Process 1, dichloromethane and TFA was stirred at room temperature for 1 hour. After removing the solvent, the mixture of the obtained crude material, 4M hydrogen chloride dioxane solution and water was stirred at 90° C. for 4 hours. After removing the solvent, the residue was purified with high performance liquid chromatography(water/acetonitrile, each containing 0.1% TFA) to obtain 10 mg of the intended compound.

MS(ESI MH+): 582

Example 50

Synthesis of the Compound of the Following Formula (E-19) which has a Substituent(s) of Example 50 of Table 11

Process 1 N-(2,6-dichlorobenzoyl)-4-[1-methyl-6-(trimethylsilylethyloxycarbonyl)-2,4-quinazoline-dione-3-yl]-L-phenylalanine methylester The mixture of the crude material obtained in Process 3 of Example 43 (6.58 mg), DMF (5 mL), palladium acetate (226 mg), trimethylsilyl ethanol (2.9 mL) and triethylamine (2.8 mL) was stirred under the existence of carbon monoxide at 50° C. overnight. The mixture was extracted with ethyl acetate and treated in accordance with the ordinary method to obtain the title compound.

Process 2 N-(2,6-dichlorobenzoyl)-4-[1-methyl-6-carboxy-2,4-quinazoline-dione-3-yl]-L-phenylalanine methylester The mixture of the crude material obtained in Process 1 (4.2 g), tetrahydrofuran (100 mL) and tetrabutylammonium fluoride (3.3 g) was stirred at room temperature for 2 hours. The mixture was extracted with ethyl acetate and treated in accordance with the ordinary method to obtain the title compound.

Process 3

Triethylamine (70 μL) and ethyl chloroformate (28 μL) were added to the mixture of the crude material obtained in Process 2 (142 mg) and tetrahydrofuran (50 mL) under cooling with ice and stirred for 30 minutes. After adding ammonia water (1 mL) to the reaction solvent and warming it to room temperature, the reaction mixture was stirred for 2 hours. Then, the mixture was extracted with ethyl acetate and treated in accordance with the ordinary method. The mixture of the obtained crude material, 4M hydrogen chloride dioxane solution (2 mL) and water (200 μL) was stirred at 90° C. for 4 hours. After removing the solvent, the residue was purified with high performance liquid chromatography (water/acetonitrile, each containing 0.1% TFA) to obtain 7 mg of the intended compound.

MS(ESI MH+): 555

Example 51

Synthesis of the Compound of the Following Formula (E-19) which has a Substituent(s) of Example 51 of Table 11

Process 1 N-(2,6-dichlorobenzoyl)-4-[1-methyl-6-(2-t-butoxycarbonylethyl)-2,4-quinazoline-dione-3-yl]-L-phenylalanine methylester The mixture of the amount of five sixths of the crude material obtained in Process 1 of Example 49, methanol (10 mL), nickel-chloride 6-hydrate (191 mg) and sodium borohydride (62 mg) was stirred at room temperature for 6 hours. The mixture was extracted with ethyl acetate and treated in accordance with the ordinary method to obtain the intended compound.

Process 2 N-(2,6-dichlorobenzoyl)-4-[1-methyl-6-(2-carbonylethyl)-2,4-quinazoline-dione-3-yl]-L-phenylalanine methylester The mixture of the crude material obtained in Process 1, dichloromethane (2 mL) and TFA (2 mL) was stirred at room temperature for 1 hour. The solvent was removed to obtain a crude material of the intended compound.

Process 3

The mixture of the crude material obtained in Process 2, 4M hydrogen chloride dioxane solution and water was stirred at 90° C. for 4 hours. After removing the solvent, the residue was purified with high performance liquid chromatography (water/acetonitrile, each containing 0.1% TFA) to obtain the intended compound.

MS(ESI MH+): 584

Example 52

Synthesis of the Compound of the Following Formula (E-19) which has a Substituent(s) of Example 52 of Table 11

Triethylamine (190 μL) and ethyl chloroformate (80 μL) were added to the mixture of the amount of five sixths of the crude material obtained in Process 2 of Example 51 and tetrahydrofuran (20 mL) under cooling with ice and stirred for 30 minutes. After adding two or three pieces of ice and sodium borohydride (20 mg) to the reaction solvent and warming it to room temperature, the reaction mixture was stirred for 2 hours. Then, the mixture was extracted with ethyl acetate and treated in accordance with the ordinary method. The obtained crude material was dissolved into 4M hydrogen chloride dioxane solution (2 mL) and water (200 μL) and stirred at 90° C. for 4 hours. After removing the solvent, the residue was purified with high performance liquid chromatography (water/acetonitrile, each containing 0.1% TFA) to obtain 7 mg of the intended compound.

MS(ESI MH+): 570

Example 53

Synthesis of the Compound of the Following Formula (E-20) which has a Substituent(s) of Example 53 of Table 12

Process 1 N-(2,6-dichlorobenzoyl)-4-[1-methyl-6-hydroxymethyl-2,4-quinazoline-dione-3-yl]-L-phenylalanine methylester Triethylamine (970 μL) and ethyl chloroformate (4001 μL) were added to the mixture of the crude material obtained in Process 2 of Example 50 (142 mg) and tetrahydrofuran (100 mL) under cooling with ice and stirred for 30 minutes. After filtration, two or three pieces of ice and sodium borohydride (160 mg) were added to the filtrate. After warming it to room temperature, the reaction mixture was stirred for 2 hours. Then, the mixture was extracted with ethyl acetate and treated in accordance with the ordinary method to obtain the intended compound.

Process 2 N-(2,6-dichlorobenzoyl)-4-[1-methyl-6-chloromethyl-2,4-quinazoline-dione-3-yl]-L-phenylalanine The mixture of the crude material obtained in Process 1, 4M hydrogen chloride dioxane solution (4 mL) and water (400 μL) was stirred at 80° C. for 2 hours. After removing the solvent, the residue was purified with high performance liquid chromatography (water/acetonitrile, each containing 0.1% TFA) to obtain the intended compound.

Process 3

The mixture of the substance obtained in Process 2 (20 mg), acetonitrile (1 mL) and morpholine (6 μL) was stirred at room temperature for 2 hours. After removing the solvent, the residue was purified with high performance liquid chromatography (water/acetonitrile, each containing 0.1% TFA) to obtain 3 mg of the intended compound.

MS(ESI MH+): 611

Examples 54 to 58

Synthesis of the compounds of the following formula (E-20) which has a Substituent(s) of Examples 54 to 58 of Table 12

The compounds were synthesized by the same procedure as that of Process 3 in Example 53 except that corresponding amines were used instead of morpholine in the process.

NMR data of the compound of Example 54: $^1$H-NMR (DMSO-$d_6$) 9.13 (d, 1H, J=8.4 Hz), 8.69-8.97(br, 2H), 8.23 (d, 1H, J=2.1 Hz), 7.86 (dd, 1H, J=8.6, 2.1 Hz), 7.57 (d, 1H, J=8.7 Hz), 7.34-7.43 (m, 6H), 7.18 (d, 2H, J=8.4 Hz), 4.70-4.78 (m, 1H), 4.22-4.26 (m, 2H), 3.53(s, 3H), 3.22 (dd, 1H, J=14.2, 4.3 Hz), 2.91-3.00 (m, 3H), 1.19 (t, 3H, J=7.3 Hz).

Example 59

Synthesis of the Compound of the Following Formula (E-21)

Process 1

The mixture of the crude material obtained in Process 3 of Example 43, DMSO (2 mL), copper iodide (11 mg), potassium carbonate (273 mg) and aminoimidazole (273 mg) was stirred at 130° C. for 2 days. The mixture was extracted with ethyl acetate and treated in accordance with the ordinary method. After removing the solvent, the residue was purified with high performance liquid chromatography (water/acetonitrile, each containing 0.1% TFA) and ester hydrolysis was conducted by the same procedure as that of Process 4 in Example 43 to obtain the title compound.

MS(ESI MH+): 593

Example 60

Synthesis of the Compound of the Following Formula (E-22) which has a Substituent(s) of Example 60 of Table 13

The mixture of N-(2,6-dichlorobenzoyl)-4-[1-methyl-6-hydroxymethyl-2,4-quinazoline-dione-3-yl]-L-phenylalanine methylester(7 mg) which was obtained by the same procedure as that of Process 1 in Example 53 and then purification with high performance liquid chromatography, tetrahydrofuran (1 mL), water (1 mL) and lithium hydroxide (1.2 mg) was stirred at room temperature for 2 hours. The mixture was extracted with ethyl acetate, treated in accordance with the ordinary method and purified with high performance liquid chromatography (water/acetonitrile, each containing 0.1% TFA) to obtain 1 mg of the intended compound.

MS(ESI MH+): 542

Example 61

Synthesis of the Compound of the Following Formula (E-22) which has a Substituent(s) of Example 61 of Table 13

The mixture of the substance obtained in Process 2 of Example 53 (40 mg), methanol (1 mL) and 40% methanol solution (1 mL) of sodium methoxide was stirred at room temperature for 2 hours. The mixture was treated in accordance with the ordinary method and purified with high performance liquid chromatography (water/acetonitrile, each containing 0.1% TFA) to obtain 4 mg of the intended compound.

MS(ESI MH+): 556

Example 62

Synthesis of the Compound of the Following Formula (E-23) which has a Substituent(s) of Example 62 of Table 14

Process 1 Acylation Reaction

3-Methoxymethyl-2-nitrobenzoic acid (160 mg), DIC (58 μL), HOAt (101 mg) and NMP (1.5 mL) were mixed and stirred for 3 hours. Then, the mixture was added to 200 mg of the resin obtained in Process 4 in Example 1 and reacted for 17 hours. After removing the excess solvent, the resin was washed with NMP, methanol and dichloromethane three times each, and dried under reduced pressure.

Process 2 Reduction of Nitro Group $SnCl_2.2H_2O$ (1.5 g), NMP (3 mL) and EtOH (150 μL) were added to the resin obtained in Process 1 and reacted at room temperature for 16 hours. After removing the solvent, the resin was washed with NMP, methanol and dichloromethane three times each, and dried under reduced pressure.

Process 3 Construction of Quinazolinedione Ring with Carbonyldiimidazole

Carbonyldiimidazole (400 mg) and NMP (2 mL) were added to the resin obtained in Process 2 and stirred at 90° C. for 21 hours. After removing the excess solvent, the resin was washed with NMP, methanol and dichloromethane three times each, and dried under reduced pressure.

Process 4 Alkylation

Methyl iodide (200 μL), tetramethyl guanidine (200 μL) and NMP (2.5 mL) were added to the resin obtained in Process 3, stirred for 1 hour, and washed with methanol and NMP three times each after removing the excess solvent. After repeating these processes three times, the resin was washed with methanol and dichloromethane three times each, and dried under reduced pressure.

Process 5 Cleavage from Resin

The resin obtained in Process 4 was treated with trifluoroacetic acid containing 5% of water for 1 hour. After filtration, the filtrate was concentrated under reduced pressure. The residue was purified with high performance liquid chromatography (water/acetonitrile, each containing 0.1% TFA) to obtain 16 mg of the intended compound.
MS(ESI MH+): 556

Example 63

Synthesis of the Compound of the Following Formula (E-23) which has a Substituent(s) of Example 63 of Table 14

The intended compound was obtained by the same procedure as that of Example 62 except that 4-methoxymethyl-2-nitrobenzoic acid was used instead of 3-methoxymethyl-2-nitrobenzoic acid.
MS(ESI MH+): 556

Example 64

Synthesis of the Compound of the following formula (E-24)

Process 1 Nitration

β-Picoline-N-oxide (10 g) was slowly added to the mixed acid of concentrated sulfuric acid (35 mL) and concentrated nitric acid (27.5 mL) at 0° C., gradually warmed up to 105° C. and stirred for 4 hours. The reaction solvent which was cooled down to room temperature was poured into ice (100 g) and sodium carbonate (60 g) was added thereto. After filtering out the precipitate, the reaction mixture was washed with water and dried under reduced pressure to obtain 5.83 g of 3-methyl-4-nitropyridine-N-oxide.

Process 2 Oxidation

The substance obtained in Process 1 (5.83 g) and sodium dichromate dehydrate (11.4 g) were slowly added to the concentrated sulfuric acid (39.5 mL) at 0° C. and reacted at room temperature for 4 hours. The reaction solvent was poured into ice (80 g) and water (100 mL) was slowly added thereto. Sodium hydrogen sulfite was further added thereto until the orange color of hexavalent chromium faded and the precipitate was filtered out. Ethyl acetated and 1N hydrochloric acid were added to the filtered out solid substance, extracted and washed. The layer of ethyl acetate was concentrated under reduced pressure to obtain the powder of 4-nitronicotinic acid-N-oxide (3.23 g).

Process 3 Catalytic Reduction

Water (75 mL), 28% ammonia water (1.2 mL) and 10% Pd/C (0.8 g) were added to the substance obtained Process 2 (1.5 g) and stirred in hydrogen atmosphere (3.8 kg/cm$^2$) for 8 hours. The reaction solvent was filtered and the filtrate was concentrated under reduced pressure so that the liquid measure thereof became 15 mL. 1N hydrochloric acid was added to adjust the solvent to become slightly acidic and the precipitated insoluble materials were filtered out. The residue was washed with water and dried under reduced pressure to obtain the powder of 4-aminonicotinic acid (620 mg).

Process 4 Acylation Reaction

The substance obtained in Process 3 (207 mg), DIC (116 μL), HOAt (204 mg), DIEA (131 μL) and NMP (3 mL) were mixed and stirred for 10 hours. Then, the mixture was added to 200 mg of the resin obtained in Process 4 in Example 1 and reacted for 14 hours. After removing the excess solvent, the resin was washed with NMP, methanol and dichloromethane three times each, and dried under reduced pressure.

Process 5 Construction of Quinazolinedione Ring with Carbonyldiimidazole

Carbonyldiimidazole (400 mg) and NMP (2 mL) were added to the resin obtained in Process 4 and stirred at 90° C. for 18 hours. After removing the excess solvent, the resin was washed with NMP, methanol and dichloromethane three times each, and dried under reduced pressure.

Process 6 Alkylation

Triphenylphosphine (520 mg), methanol (80 μL), 40% toluene solution (1 mL) of diisopropylazodicarboxylic acid and dichloromethane (2 mL) were added to the resin obtained in Process 5 and stirred for 19 hours. After removing the excess solvent, the resin was washed with NMP, methanol and dichloromethane three times each, and dried under reduced pressure.

Process 7 Cleavage from Resin

The resin obtained in Process 6 was treated with trifluoroacetic acid containing 5% of water for 1 hour. After filtration, the filtrate was concentrated under reduced pressure. The residue was purified with high performance liquid chromatography (water/acetonitrile, each containing 0.1% TFA) to obtain 28 mg of the intended compound. MS(ESI MH+): 513

Examples 65 to 81

Synthesis of the Compounds of the Following Formula (E-25) which has a Substituent(s) of Examples 65 to 81 of Tables 15-1 and 15-2

The intended compounds were obtained by the following methods, A to C:

A (Methylesterification)

The corresponding carboxylic acids were added to the mixture of methanol and thionyl chloride and stirred overnight. After removing the solvent, the residue was purified with high performance liquid chromatography (water/acetonitrile, each containing 0.1% TFA) to obtain the intended compound(s).

B The mixture of the corresponding carboxylic acids, suitable solvent(s) such as DMF and dichloromethane, suitable organic base(s) such as triethylamine and diisopropylethylamine, corresponding alcohols, HOBt if necessary, and EDC hydrochloride was stirred overnight. After concentration, the mixture was purified with high performance liquid chromatography (water/acetonitrile, each containing 0.1% TFA) to obtain the intended compound(s).

C The mixture of the corresponding carboxylic acids, corresponding alcohols and 4M hydrogen chloride dioxane solution was stirred at 90° C. for several hours. After removing the solvent, the obtained crude material was purified with high performance liquid chromatography (water/acetonitrile, each containing 0.1% TFA) to obtain the intended compound(s).

Examples 82 to 86

Synthesis of the Compounds of the Following Formula (E-26) which has a Substituent(s) of Examples 82 to 86 of Table 16

The intended compounds were obtained by the same procedure as that of either A, B, or C in the above mentioned Examples.

Examples 87 to 88

Synthesis of the Compounds of the Following Formula (E-27) which has a Substituent(s) of Examples 87 to 88 of Table 17

Example 87

The substance obtained in Process 2 of Example 50 was purified with high performance liquid chromatography (water/acetonitrile, each containing 0.1% TFA) to obtain the intended compound.
MS(ESI MH+): 570

Example 88

Methanol (2 mL) and 2M hexane solution (1 mL) of trimethylsilyldiazomethane were added to the substance obtained in Process 2 of Example 50 and stirred for 3 hours. After removing the solvent, the obtained substance was purified with high performance liquid chromatography(water/acetonitrile, each containing 0.1% TFA) to obtain the intended compound.
MS(ESI MH+): 584

Example 89

Synthesis of the Compound of the Following Formula (E-28)

Process 1 N-(2,6-dichlorobenzoyl)-4-[1-methyl-6-(2-hydroxyethylamino)-2,4-quinazoline-dione-3-yl]-L-phenylalanine methylester The mixture of the crude material obtained in Process 3 of Example 43 (100 mg), dimethylacetoamide (2 mL), copper iodide (3 mg), aminoethanol (0.011 mL) and potassium carbonate (41 mg) was stirred at 80° C. overnight. After extracting the mixture with ethyl acetate and removing the solvent, the residue was purified with high performance liquid chromatography (water/acetonitrile, each containing 0.1% TFA) to obtain the intended compound.

Process 2

The mixture of the crude material obtained in Process 2, 4M hydrogen chloride dioxane solution (2 mL) and water (200 µL) was stirred at 90° C. for 4 hours. After removing the solvent, the residue was purified with high performance liquid chromatography (water/acetonitrile, each containing 0.1% TFA) to obtain 1 mg of the intended compound.
MS(ESI MH+): 571

Example 90

Synthesis of the Compound of the Following Formula (E-29)

The mixture of 40 mg of the carboxylic acid obtained in Example 34, 5 mL of ethanol and 5 mL of dioxane solution containing 4M hydrogen chloride was stirred at 90° C. for 2 hours. After removing the solvent, the residue was purified with high performance liquid chromatography (water/acetonitrile, each containing 0.1% TFA) to obtain the intended compound.
MS(ESI MH+): 597 H-NMR(DMSO) δ 1.20 (3H, t), 2.80 (6H, s), 2.95-3.25 (2H, m), 3.55 (3H, s), 4.15 (2H, q), 4.45 (2H, s), 4.80 (1H, m), 7.20 (2H, d), 7.35-7.50 (6H, m), 7.70 (1H, s), 8.15 (1H, d), 9.25 (1H, d).

Example 91

Synthesis of the Compound of the Following Formula (E-30)

The mixture of 50 mg of the carboxylic acid obtained in Example 54, 0.5 mL of benzyl alcohol and 1 mL of dioxane solution containing 4M hydrogen chloride was stirred at 90° C. for 4 hours. After concentrating the reaction solvent, the mixture was purified with high performance liquid chromatography (water/acetonitrile, each containing 0.1% TFA) to obtain the intended compound.
MS(ESI MH+): 659 H-NMR(DMSO) δ 1.20 (3H, s), 2.90-3.40 (4H, m), 3.55 (3H, s), 4.25 (2H, t), 4.90 (1H, m), 5.20 (2H, s), 7.20 (2H, d), 7.30-7.50 (10H, m), 7.60 (1H, d), 7.90 (1H d), 8.25 (1H, d), 8.80 (2H, br), 9.30 (1H, d).

Example 92

Synthesis of the compound of the following formula (E-31)

Process 1 Acylation Reaction

The mixture of 600 mg of N-(2,6-dichlorobenzoyl)-4-amino-L-phenylalanine obtained in Process 4 of Example 1 wherein the carboxyl group bonded with Wang resin, 730 mg of 2-amino-4,5-difluorobenzoic acid, 320 µL of DIC (diisopropylcarbodiimide), 570 mg of HOAt (1-hydroxy-7-azabenzotriazole) and 6 mL of NMP (N-methyl-pyrrolidone) was shaken at room temperature overnight. After removing the solvent, the residue was washed with NMP, methanol, dichloromethane and diethylether, and dried under reduced pressure.

Process 2 Construction of Quinazolinedione Ring with Carbonyldiimidazole

Carbonyldiimidazole (600 mg) and NMP (4.9 mL) were added to the resin obtained in Process 1 and stirred at room temperature for 13 hours. After removing the excess solvent, the resin was washed with NMP, methanol and dichloromethane four times each, and dried under reduced pressure. Carbonyldiimidazole (600 mg) and NMP (4.9 mL) were added again to the resin and stirred at room temperature for 16 hours. After removing the excess solvent, the resin was washed with NMP, methanol and dichloromethane four times each, and dried under reduced pressure.

Process 3 Substitution of Fluoro Group with Amine

Imidazole (600 mg), diisopropylethylamine (600 µL) and NMP (3 mL) were added to 340 mg of the resin obtained in Process 2 and reacted for 14.5 hours. After removing the excess solvent, the resin was washed with NMP, methanol and dichloromethane four times each, and dried under reduced pressure.

Process 4 Alkylation

Triphenylphosphine (780 mg), methanol (120 µL), 40% toluene solution (1.5 mL) of diisopropylazodicarboxylic acid and dichloromethane (3 mL) were added to the resin obtained in Process 3 and stirred for 18.5 hours. After removing the excess solvent, the resin was washed with NMP, methanol and dichloromethane four times each, and dried under reduced pressure.

Process 5 Cleavage from Resin, Purification

The cleavage from resin and purification thereof were conducted to the resin obtained in Process 4 by the same procedure as that of Process 10 in Example 1 to obtain 95 mg of the intended compound.

MS(ESI MH+): 596 ¹H-NMR(DMSO-d$_6$): δ2.94-3.04 (1H, m), 3.20-3.27(1H, m), 4.71-4.80(1H, m), 7.23(2H, d, J=8.4 Hz), 7.39-7.47(5H, m), 7.58(1H, s), 7.87(1H, d, J=6.0 Hz), 8.04-8.10(2H, m), 8.96(1H, s), 9.15(1H, d, J=8.1 Hz), 12.80(1H, brs).

Example 93

Synthesis of the Compound of the Following Formula (E-32)

Process 1 Synthesis of N-(t-butoxycarbonyl)-4-(6-dimethylamino-2,4-quinazoline-dione-3-yl)-L-phenylalanine methylester 3 g of N-(t-butoxycarbonyl)-4-amino-L-phenylalanine methylester, 2.73 g of methyl 2-amino-5-(dimethylamino) benzoate dihydrochloride, 1.65 g of CDI (carbonyldiimidazole) and 50 mL of acetonitrile were stirred at room temperature. Then, 2.8 mL of triethylamine was added thereto and stirred at 60° C. overnight. After removing the solvent, the obtained residue was extracted with ethyl acetate, washed with water and saturated aqueous solution of sodium chloride and dried over magnesium sulfate. After removing the solvent, the obtained residue was purified with silica gel column chromatography to obtain 2 g of the title compound.

Process 2 Synthesis of 4-(6-dimethylamino-1-methyl-2,4-quinazoline-dione-3-yl)-L-phenylalanine methyl ester dihydrochloride The mixture of 500 mg of the quinazolinedione obtained in Process 1, 0.3 mL of methanol, 0.4 g of triphenylphosphine, 0.7 mL of 45% toluene solution of diisopropylazodicarboxylic acid and dichloromethane was stirred overnight. After removing the solvent, the residue was treated in accordance with the ordinary method using dichloromethane as an extracting solvent to obtain a crude material of N-(t-butoxycarbonyl)-4-(6-dimethylamino-1-methyl-2,4-quinazoline-dione-3-yl)-L-phenylalanine methylester. The mixture of the crude material, 5 mL of dioxane solution containing 4M hydrogen chloride and 5 mL of dichloromethane was stirred at room temperature for 5 hours. After removing the solvent, the obtained residue was washed with dichloromethane to obtained a crude material of the title compound.

Process 3 Synthesis of N-(2-chloro-6-fluorobenzoyl)-4-(6-dimethylamino-1-methyl-2,4-quinazoline-dione-3-yl-L-phenylalanine trifluoroacetate methylester The mixture of 100 mg of the amine crude material obtained in Process 2, 80 mg of 2-chloro-6-fluorobenzoyl chloride, 100 μL of triethylamine and 4 mL of DMF (dimethylformamide) was stirred at room temperature and treated in accordance with the ordinary method using ethyl acetate as an extracting solvent to obtain a crude material. The obtained crude material was purified with high performance liquid chromatography (water/acetonitrile, each containing 0.1% TFA) to obtain 51 mg of the intended compound.

MS (ESI MH+): 553

Process 4 Synthesis of N-(2-chloro-6-fluorobenzoyl)-4-(6-dimethylamino-1-methyl-2,4-quinazoline-dione-3-yl-L-phenylalanine trifluoroacetate The mixture of 15 mg of the methylester compound obtained in Process 3 of Example 93, 3 mL of dioxane solution containing 4M hydrogen chloride and 2 mL of water was stirred at 80° C. for 2 hours. After removing the solvent, the residue was purified with high performance liquid chromatography (water/acetonitrile, each containing 0.1% TFA (trifluoroacetic acid)) to obtain the intended compound.

MS (ESI MH+): 539

Example 94

Synthesis of the compound of the following formula (E-33)

Process 1 Acylation Reaction

The mixture of 50 mg of the amine compound obtained in Process 2 of Example 93, 38 mg of 2,4-dichloropyridine-2-carboxylic acid obtained by the same procedure as that of Eur. J. Org. Chem. 2001, 1371-1376, 30 mg of HOAt, 38 mg of EDC/HCl (1-dimethylaminopropyl-3-ethylcarbodiimide hydrochloride), 560 μL of triethylamine and 2 mL of DMF was stirred at 40° C. The reaction solvent was purified with high performance liquid chromatography (water/acetonitrile, each containing 0.1% TFA (trifluoroacetic acid)) to obtain the intended compound.

MS (ESI MH+): 570

Process 2 Hydrolysis of Ester

The intended compound was obtained by the same procedure as that of Process 4 in Example 93 using the ester obtained in Process 1.

MS (ESI MH+): 556

Example 95

Synthesis of the Compound of the Following Formula (E-34)

The intended compound was obtained by the same procedure as that of Process 4 in Example 92 using the resin obtained by the same procedure as that of Process 2 in Example 92.

MS (ESI MH+): 548

Example 96

Synthesis of the Compound of the Following Formula (E-35)

Lithium hydroxide (7 mg), methanol (3.5 mL), tetrahydrofuran (0.5 mL) and acetone (2.0 mL) were added to the compound obtained in Example 88 (60 mg) and stirred at room temperature for 30 minutes. After removing the excess solvent, the residue was purified with high performance liquid chromatography (water/acetonitrile, each containing 0.1% TFA) to obtain 6.3 mg of the intended compound.

MS (ESI MH+): 570

Example 97

Synthesis of the Compound of the Following Formula (E-36)

Process 1 N-(2,6-dichlorobenzoyl)-4-(1-methyl-2,4-dioxo-1,2,3,4-tetrahydro-pyrimido[4,5-d]pyrimidine-3(2H)-yl)-L-phenylalanine The mixture of the compound obtained in Example 131 (15 mg), 4M hydrogen chloride dioxane solution (1 mL) and water (200 μL) was stirred at 90° C. for 2 hours. After removing the solvent, the residue was purified with high performance liquid chromatography (water/acetonitrile, each containing 0.1% TFA) to obtain 12 mg of the intended compound.

MS(ESI MH+): 514

Examples 98 to 99

Synthesis of the Compounds of the Following Formula (E-37) which has a Substituent(s) of Examples 98 to 99 of Table 18

The compounds were synthesized by the same procedure as that of Process 3 in Example 53 except that corresponding amines were used instead of morpholine.

MS (ESI MH+) data of the compound of Example 99: 555
NMR data of the compound of Example 99: $^1$H-NMR (DMSO-$d_6$): δ2.58(3H, t, J=5.1 Hz), 2.98(1H, dd, J=14.1, 10.5 Hz), 3.24(1H, dd, J=14.1, 4.5 Hz), 3.55(3H, s), 4.22-4.28(1H, m), 4.61-4.80(1H, m), 7.20(2H, d, J=8.4 Hz), 7.39-7.46(5H, m), 7.60(1H, d, J=9.0 Hz), 7.88(1H, d, J=6.9 Hz), 8.24(1H, d, J=1.5 Hz), 8.80(2H, brs), 9.15(1H, d, J=8.7 Hz), 12.90(1H, brs)

Example 100

Synthesis of the Compound of the following formula (E-38)

Process 1 Alkylation

Methyl iodide (200 μL), potassium carbonate (200 mg) and NMP (4 mL) were added to the resin obtained in Process 2 of Example 19 (400 mg) and stirred at 60° C. for 9 hours. After removing the solvent, the resin was washed with NMP, methanol and dichloromethane three times each, and dried under reduced pressure.

Process 2 Cleavage from Resin, Purification

The cleavage from resin and purification thereof were conducted to the resin obtained in Process 1 by the same procedure as that of Process 10 in Example 1 to obtain 31 mg of the intended compound.

MS(ESI MH+): 555

Examples 101 to 121

Synthesis of the Compounds of the Following Formula (E-39) which has a Substituent(s) of Examples 101 to 121 of Tables 19-1, 19-2 and 19-3

The intended compounds were obtained by the following methods, A to

A (Methylesterification)

The corresponding carboxylic acids were added to the mixture of methanol and thionyl chloride and stirred overnight. After removing the solvent, the residue was purified with high performance liquid chromatography (water/acetonitrile, each containing 0.1% TFA) to obtain the intended compound(s).

B The mixture of the corresponding carboxylic acids, suitable solvent(s) such as DMF and dichloromethane, suitable organic base(s) such as triethylamine and diisopropylethylamine, corresponding alcohols, HOBt if necessary, and EDC hydrochloride was stirred overnight. After concentration, the mixture was purified with high performance liquid chromatography (water/acetonitrile, each containing 0.1% TFA) to obtain the intended compound(s).

C The mixture of the corresponding carboxylic acids, corresponding alcohols and 4M hydrogen chloride dioxane solution was stirred at 90° C. for several hours. After removing the solvent, the obtained crude material was purified with high performance liquid chromatography (water/acetonitrile, each containing 0.1% TFA) to obtain the intended compound(s).

D The mixture of the corresponding carboxylic acids, methylalcohol and 2.0M hexane solution of trimethylsilyldiazomethane was stirred at room temperature for a few minutes. After removing the solvent, the obtained crude material was purified with high performance liquid chromatography (water/acetonitrile, each containing 0.1% TFA) to obtain the intended compound(s).

E The mixture of the corresponding carboxylic acids, ethylene glycol, EDC/HCl, HOAt and dichloromethane was stirred. After removing the solvent, the obtained crude material was purified with high performance liquid chromatography (water/acetonitrile, each containing 0.1% TFA) to obtain the intended compound(s).

NMR data of the compound of Example 111: $^1$H-NMR (DMSO-$d_6$): δ9.23 (d, 1H, J=8.1 Hz), 8.64-8.79(br, 2H), 8.23 (d, 1H, J=2.2 Hz), 7.86 (dd, 1H, J=2.1 Hz, J=8.7 Hz), 7.57 (d, 1H, J=8.7 Hz) 7.35-7.45 (m, 6H), 7.19 (d, 2H, J=8.3 Hz), 4.93 (sep, 1H, J=6.3 Hz), 4.75 (m, 1H), 4.24 (m, 2H), 3.53(s, 3H), 3.17 (dd, 1H, J=5.0 Hz, J=14.5 Hz), 2.94-3.00 (m, 3H), 1.21 (d, 3H, J=6.2 Hz), 1.19 (t, 3H, J=7.3 Hz), 1.17 (d, 3H, J=6.2 Hz). Corresponding carboxylic acid which is a synthetic raw material of the compound of Example 111 is the compound of Example 54. Further, the compound of Example 111 was obtained by the same procedure as that of Process 3 in Example 53 except that the compound of Process 1 in Example 174 was used as a raw material and ethylamine was used instead of morpholine.

Examples 122 to 123

Synthesis of the Compounds of the Following Formula (E-40) which has a Substituent(s) of Examples 122 to 123 of Table 20

The intended compounds were obtained by the same procedure as that of either C or D in the above mentioned Examples.

Example 124

Synthesis of the compounds of the following formula (E-41)

The intended compound was obtained by the same procedure as that of D in the above Examples 101 to 121.

MS(ESI MH+): 610

Example 125

Synthesis of the Compounds of the Following Formula (E-42)

The intended compound was obtained by the same procedure as that of D in the above Examples 101 to 121.

MS(ESI MH+): 530

Examples 126 to 127

Synthesis of the Compounds of the Following Formula (E-43) which has a Substituent(s) of Examples 126 to 127 of Table 21

Example 126

The crude material obtained in Process 2 of Example 47 was treated in accordance with the ordinary method to obtain the title compound.

Example 127

Isopropanol (2 mL) and the concentrated sulfuric acid (0.1 mL) were added to the substance obtained in Example 47 (50 mg) and heated and refluxed for 2 hours. After removing the solvent, the reaction mixture was treated in accordance with the ordinary method to obtain the title compound.

Example 128

Synthesis of the Compounds of the Following Formula (E-44)

The intended compound was obtained by the same procedure as that of D in the above Examples 101 to 121.
MS(ESI MH+): 527

Example 129

Synthesis of the Compounds of the Following Formula (E-45)

Process 1 4-[(4-aminopyrimidine-5-yl) carbonyl]amino-N-(2,6-dichlorobenzoyl)-L-phenylalanine methylester The mixture of N-(2,6-dichlorobenzoyl)-4-amino-L-phenylalanine methylester (1.0 g), EDC/HCl (783 mg), HOAt (555 mg), triethylamine (747 µL), 4-aminopyrimidine-5-carboxylic acid (417 mg) and dichloromethane (15 mL) was stirred overnight. After diluting the mixture with dichloromethane and washing with saturated sodium bicarbonate water, the organic layer thereof was dried over sodium sulfate and concentrated. The residue was washed with dichloromethane to obtain 145 mg of a crude material of the title compound.

Process 2 N-(2,6-dichlorobenzoyl)-4-(2,4-dioxo-1,2,3,4-tetrahydropyrimido[4,5-d]pyrimidine-3(2H)-yl)-L-phenylalanine methylester The mixture of the crude material obtained in Process 1 (145 mg), DMF (10 mL) and carbonyldiimidazole (482 mg) was stirred at 110° C. for 24 hours. The mixture was extracted with ethyl acetate and treated in accordance with the ordinary method to obtain a crude material of the title compound.

Process 3 N-(2,6-dichlorobenzoyl)-4-(1-methyl-2,4-dioxo-1,2,3,4-tetrahydropyrimido[4,5-d]pyrimidine-3(2H)-yl)-L-phenylalanine methylester DMF (2 mL), potassium carbonate (62 mg) and methyl iodide (40 µL) were added to the crude material obtained in Process 2 and stirred at room temperature for 3 hours. The mixture was extracted with ethyl acetate and purified with high performance liquid chromatography (water/acetonitrile, each containing 0.1% TFA) to obtain 61 mg of the intended compound(s).
MS(ESI MH+): 528

Example 131

Synthesis of the Compounds of the Following Formula (E-46)

The intended compound was obtained by the same procedure as that of D in the above Examples 101 to 121.
MS(ESI MH+): 583

Example 132

Synthesis of the Compounds of the Following Formula (E-47)

The intended compound was obtained by the same procedure as that of C in the above Examples 101 to 121.
MS(ESI M+): 624

Examples 133 to 134

Synthesis of the Compounds of the Following Formula (E-48) which has a Substituent(s) of Examples 133 to 134 of Table 22

Example 133

The mixture of the compound of Example 54 (19 mg), acetonitrile (3 mL), triethylamine (18 µL) and methyl chloroformate (5 µL) was stirred at room temperature for 5 minutes. After removing the solvent, the residue was purified with high performance liquid chromatography (water/acetonitrile, each containing 0.1% TFA) to obtain 17 mg of the intended compound(s).
MS(ESI MH+): 641

Example 134

The mixture of the compound of Example 54 (26 mg), acetonitrile (3 mL), triethylamine (20 µL) and acetyl chloride (6 µL) was stirred at room temperature for 10 minutes. After removing the solvent, the residue was purified with high performance liquid chromatography (water/acetonitrile, each containing 0.1% TFA) to obtain 22 mg of the intended compound(s).
MS(ESI MH+): 625

Reference Example 1

Synthesis of 3-methoxymethyl-2-nitrobenzoic Acid

Process 1 Methoxylation

Methanol solution (4.7 mL) of sodium methoxide (197 mg) was added dropwise into the mixture of methyl 3-bromomethyl-2-nitrobenzoate (1 g) and methanol (7 mL) under heating and refluxing. Two minutes later, the mixture was cooled down with ice and 1.82 mL of 4M hydrogen chloride dioxane solution was added dropwise thereto. After removing the solvent, diethylether and water were added and the organic layer thereof was dried over sodium sulfate. After removing the solvent, the obtained residue was purified with silica gel column chromatography to obtain 621 mg of methyl 3-methoxymethyl-2-nitrobenzoate.

Process 2 Hydrolysis of Methylester

The mixture of 582 mg of the substance obtained in Process 1, 10 mL of 1,4-dioxane and 10 mL of 6M hydrochloric acid was stirred at 80° C. for two nights. After adding ethyl acetate and 1N hydrochloric acid to the reaction mixture and extracting it, the organic layer was washed with sodium hydroxide aqueous solution. Further, the aqueous layer was acidified with hydrochloric acid and extracted with ethyl acetate. After removing the solvent, the residue was dried under reduced pressure to obtain 288 mg of the title compound.

Reference Example 2

Synthesis of 4-methoxymethyl-2-nitrobenzoic Acid

Process 1 Reduction of Carboxylic Acid

Tetrahydrofuran solution of 1.0M borane-tetrahydrofuran complex was added dropwise to tetrahydrofuran solution (45 mL) of 2.25 g of 4-methoxycarbonyl-3-nitrobenzoic acid and stirred at room temperature for 48 hours. Methylalcohol (2 ml) and 1N hydrochloric acid (10 ml) were added thereto and concentrated. After ethyl acetate and water were added, liquid separation was conducted. The organic layer was washed with saturated sodium hydrogen carbonate and dried over sodium sulfate. After removing the solvent, the obtained crude material was purified with silica gel column chromatography to obtain 1.33 g of methyl 4-hydroxymethyl-2-nitrobenzoate.

Process 2 Chlorination

The mixture of 1.33 g of benzylalcohol obtained in Process 1, 18 mL of tetrahydrofuran, 60 mL of diethylether, 1.8 mL of thionyl chloride and 91 µL of pyridine was stirred at room temperature overnight. After ethyl acetate and 10 mL of 1N hydrochloric acid were added, liquid separation was conducted. The organic layer was washed with saturated aqueous solution of sodium hydrogen carbonate and saturated aqueous solution of sodium chloride. After removing the solvent, the mixture was dried under reduced pressure to obtain 1.29 g of methyl 4-chloromethyl-2-nitrobenzoate.

Process 3 Methoxidation, Hydrolysis of Methylester 40 mL of Methylalcohol and 1.22 g of sodium methoxide were added to 1.29 g of the benzyl chloride obtained in Process 2 and stirred at 80° C. for 1.5 hours. After cooling the reaction solution to room temperature, 10 mL of water was added thereto and stirred overnight. Ethyl acetate and water, an aqueous solution of 0.1N sodium hydroxide and a saturated aqueous solution of sodium chloride were added thereto and liquid separation was conducted. The water layer was made acidic by hydrochloric acid and extracted with ethyl acetate. After removing the solvent, the obtained crude material was purified with high performance liquid chromatography (water/acetonitrile, each containing 0.1% TFA) to obtain 450 mg of the title compound.

Reference Example 3

Synthesis of Methyl 2-amino-5-(dimethylamino) benzoate/dihydrochloride

Process 1:

30.0 g (148 mmol) of 5-chloro-2-nitrobenzoic acid was dissolved in 78 mL (744 mmol) of an aqueous solution of 50% dimethylamine under cooling in the ice bath. The solution was heated at 60° C. in a sealed tube for 23 hours. The reaction solution was fully cooled down and the inner pressure thereof was released. After checking the completion of the reaction by HPLC analysis, the reaction solution was put into another container (using about 50 mL of water), and 49.6 mL of concentrated hydrochloric acid was added thereto and then 200 mL of water was added thereto.

The yellow crystals precipitated by adding the hydrochloric acid. The crystalline solution was ripened at 10° C. overnight, filtered out and dried under reduced pressure to obtain 30.95 g of 5-dimethylamino-2-nitrobenzoic acid. (Yield 99%)

$^1$H NMR (400 MHz, DMSO-$d_6$): 8.88 (bs, 1H), 7.97 (d, 1H, J=9.4 Hz, aryl coupling=1.76 Hz), 6.78 (d, 1H, J=9.4 Hz, aryl coupling=2.84 and 1.92 Hz), 6.71 (s, 1H, aryl coupling=2.88 and 1.60 Hz), 3.08 (s, 6H). $^{13}$C NMR (100 MHz, DMSO-$d_6$): 168.58, 153.86, 133.94, 132.85, 127.03, 111.44, 109.69, 40.24. MS (ESI): m/z 211.17 (M+H)$^+$, 209.27 (M−H)$^−$ Process 2:

40.0 g (190.30 mmol) of 5-dimethylamino-2-nitrobenzoic acid was suspended in 160 mL of methanol at 25° C. The suspension was cooled down in the ice bath and 53.6 mL of concentrated sulfuric acid was added thereto. After adding the concentrated sulfuric acid, the temperature of the solution increased up to about 30° C. The solution in that condition was put into a bath at 60° C. and stirred under heating for 20 hours. After checking the progress of the reaction by HPLC and confirming disappearance of the starting material, 400 mL of toluene was added thereto and diluted. 200 mL of water and sodium hydroxide aqueous solution (wherein 38.06 g of sodium hydroxide was dissolved in 200 mL of water) were further added thereto. Further, the water layer was extracted with 200 mL of toluene and toluene solution was combined thereto. The toluene layer was washed with 300 mL of saturated sodium bicarbonate water. Then, the toluene layer was concentrated under reduced pressure (wherein temperature in the bath was 50° C.) so that the intended compound became about 20 wt %. After removing the solvent under reduced pressure, the crystals of the intended compound were precipitated and ripened at room temperature for 1 hour. 220 mL of n-heptane was added thereto and further stirred at 5° C. overnight. The crystals were separated by suction filtration and washed with 100 mL of n-heptane. The wet crystals were dried under reduced pressure at 60° C. for 3 hours to obtain 34.82 g of yellow crystalline powder of methyl 5-dimethylamino-2-nitrobenzoate. (Yield 82%)

$^1$H NMR (400 MHz, DMSO-$d_6$): 8.02 (d, 1H, J=9.4 Hz), 6.82 (d, 1H, J=9.36 Hz, aryl coupling=2.56 Hz), 6.78 (s, 1H, aryl coupling=2.4 Hz), 3.83 (s, 3H), 3.10 (s, 6H). $^{13}$C NMR (100 MHz, DMSO-$d_6$): 167.70, 153.92, 132.71, 132.34, 127.24, 111.87, 110.07, 53.21, 40.28. MS (FAB): m/z 224.24 (M)$^+$ HR MS (FAB): m/z 224.0830 (M)$^+$ Process 3:

10.06 g (44.9 mmol) of methyl 5-dimethylamino-2-nitrobenzoate was added to 50 mL of methanol and suspended, and 9.0 mL of 10M hydrochloric acid and 1.96 g (wet, 1 mol % per substrate) of 5% palladium charcoal were added thereto. The reaction vessel was substituted with hydrogen gas and stirred at room temperature overnight. After filtering out the palladium catalyst by Celite filtration, the filtrate was concentrated under reduced pressure to become about the half amount thereof. 80 mL of acetone was added to the solution and concentrated under reduced pressure three times to precipitate the compound of the formula (12). After ripening the compound below 10° C., the compound was dried under reduced pressure to obtain 11.16 g of methyl 2-amino-5-(dimethylamino)benzoate/dihydrochloride. (Yield 93%)

$^1$H NMR (400 MHz, DMSO-$d_6$): 8.09 (s, 1H), 7.72 (d, 1H, J=9.0 Hz), 6.96 (d, 1H, 9.08 Hz), 5.50 (bs), 3.83 (s, 3H), 3.04 (s, 6H). $^{13}$C NMR (100 MHz, DMSO-$d_6$): 167.12, 131.64, 126.66, 123.29, 118.7, 108.88, 52.18, 45.84. MS (FAB): m/z 195.3 (M+H)$^+$ HR MS (FAB): m/z 195.1122 (M+H)$^+$

Example 135

Synthesis of the compound of the Following Formula (E-49) which has a Substituent(s) of Example 135 of Table 23

Process 1 N-(t-butoxycarbonyl)-4-(6-iodo-1-methyl-2,4-quinazoline-dione-3-yl)-L-phenylalanine methylester The mixture of N-(t-butoxycarbonyl)-4-amino-L-phenylalanine methylester(10.25 g), 2-amino-5-iodobenzoic acid (9.18 g), EDC/HCl (6.8 g), HOBT (4.8 g), triethylamine (6.6 mL) and tetrahydrofuran (300 mL) was stirred at 40° C. overnight. The solution wherein about a half amount of the solvent was removed was diluted with water and ethyl acetate and liquid separation was conducted. The organic layer was washed with water, saturated aqueous solution of ammonium chloride, saturated aqueous solution of sodium hydrogen carbonate and saturated aqueous solution of sodium chloride and dried over anhydrous sodium sulfate. The solvent was removed to obtain 22 g of the crude material. The crude material (22 g), CDI (carbonyldiimidazole) (17 g) and DMF (200 mL) were stirred at 80° C. overnight. The reaction solution was diluted with water and ethyl acetate, and liquid separation was conducted. The organic layer was washed with water and dried over anhydrous sodium sulfate. The solvent was removed to obtain 23.4 g of the crude material. The crude material (23.4 g), methyl iodide (3 mL), potassium carbonate (10.0 g) and DMF (100 mL) were stirred at room temperature overnight. The reaction solution was diluted with water and ethyl acetate, and liquid separation was conducted. The organic layer was washed with water and dried over anhydrous sodium sulfate. The solvent was removed to obtain 15 g of the intended compound.

Process 2 N-(2-chloro-6-fluorobenzoyl)-4-(6-iodo-1-methyl-2,4-quinazoline-dione-3-yl)-L-phenylalanine methylester The substance obtained in Process 1 (5 g), trifluoroacetic acid (3 mL) and dichloromethane (100 mL) were stirred at room temperature for 3 hours. Trifluoroacetic acid (10 mL) was further added thereto and stirred at room temperature for 2 hours. After removing the solvent, 4N hydrogen chloride dioxane solution was added thereto and concentrated. The residue was diluted with dichloromethane, washed with saturated aqueous solution of sodium hydrogen carbonate and dried over anhydrous sodium sulfate. The solvent was removed to obtain a crude material. The crude material, 2-chloro-6-fluorobenzoyl chloride (2.5 g), triethylamine (5 mL) and dichloromethane (100 mL) were stirred at room temperature overnight. The reaction solution was diluted with water and dichloromethane, and liquid separation was conducted. The organic layer was washed with diluted hydrochloric acid, sodium hydroxide aqueous solution and dried over anhydrous sodium sulfate. The solvent was removed to obtain a crude material. The crude material was purified with silica gel column chromatography (hexane/ethyl acetate) to obtain 2.7 g of the intended compound.

Process 3 N-(2-chloro-6-fluorobenzoyl)-4-(1-methyl-6-chloromethyl-2,4-quinazoline-dione-3-yl)-L-phenylalanine methylester The substance obtained in Process 2 was treated by the same procedures as those of Process 1 and 2 in Example 50, and Process 1 and 2 in Example 53 respectively to obtain the title compound.

Process 4

The mixture of the substance obtained in Process 3 (300 mg), tetrahydrofuran (20 mL) and 2M ethylamine-tetrahydrofuran solution (14 mL) was stirred at room temperature overnight. After removing the solvent, the residue was purified with high performance liquid chromatography (water/acetonitrile, each containing 0.1% TFA) to obtain 70 mg of the intended compound.

MS(ESI MH+): 553

Example 136

Synthesis of the Compound of the Following Formula (E-49) which has a Substituent(s) of Example 136 of Table 23

The substance obtained in Process 3 in Example 135 was reacted by the same procedure as that of Process 4 in Example 135 using 2M methylamine-tetrahydrofuran solution to obtain the intended compound.

MS(ESI MH+): 539

Example 137

Synthesis of the Compound of the Following Formula (E-49) which has a Substituent(s) of Example 137 of Table 23

Process 1 N-(2-chloro-6-methylbenzoyl)-4-(6-iodo-1-methyl-2,4-quinazoline-dione-3-yl)-L-phenylalanine methylester The substance obtained in Process 1 of Example 135 (5 g), trifluoroacetic acid (10 mL) and dichloromethane (100 mL) were stirred at room temperature for 2 hours. After removing the solvent, the residue was diluted with dichloromethane, washed with saturated aqueous solution of sodium hydrogen carbonate and dried over anhydrous sodium sulfate. The solvent was removed to obtain a crude material. The mixture of the crude material, 2-chloro-6-methylbenzoic acid (2.2 g), EDC/HCl (2.7 g), HOBT (2.1 g) and DMF (20 mL) was stirred at room temperature overnight. Water was added to the reaction solution and extracted with ethyl acetate. The organic layer was washed with saturated aqueous solution of sodium chloride and dried over anhydrous sodium sulfate. The solvent was removed to obtain a crude material. The crude material was purified with silica gel column chromatography (hexane/ethyl acetate) to obtain 1.1 g of the intended compound.

Process 2

The substance obtained in Process 1 was reacted by the same procedures as those of Process 3 and 4 in Example 135 to obtain 90 mg of the intended compound.

MS(ESI MH+): 549.

Example 138

Synthesis of the Compound of the Following Formula (E-51) which has a Substituent(s) of Example 138 of Table 25: N-(2,6-dichlorobenzoyl)-4-[6-ethylmethylamino-1-methyl-2,4-quinazoline-dione-3-yl]-L-phenylalanine isopropylester The mixture of the substance obtained in Process 2 of Example 53 (250 mg), isopropanol (6 mL) and 4N hydrogen chloride dioxane solution (6 mL) was stirred at 70° C. for 3 hours. After removing the solvent, isopropanol (5 mL), acetonitrile (2 mL) and methylethylamine (0.4 mL) were added thereto and stirred at room temperature for two days. After removing the solvent, the residue was purified with high performance liquid chromatography (water/acetonitrile, each containing 0.1% TFA) to obtain 138 mg of the intended compound.

MS(ESI MH+): 625

Example 139

Synthesis of the Compound of the Following Formula (E-49) which has a Substituent(s) of Example 139 of Table 23: N-(2,6-dichlorobenzoyl)-4-[6-ethylmethylamino-1-methyl-2,4-quinazoline-dione-3-yl]-L-phenylalanine 4N hydrogen chloride dioxane solution (2 mL) and water (200 μL) were added to the compound of Example 138 (30 mg) and stirred at 80° C. for 2 hours. After removing the solvent, the residue was purified with high performance liquid chromatography (water/acetonitrile, each containing 0.1% TFA) to obtain 15 mg of the intended compound.
MS(ESI MH+): 583

Example 140

Synthesis of the compound of the following formula (E-49) which has a Substituent(s) of Example 140 of Table 23: N-(2,6-dichlorobenzoyl)-4-[6-hydroxy-1-methyl-2,4-quinazoline-dione-3-yl]-L-phenylalanine The mixture of 2-nitro-5-methoxybenzoic acid (4 g), tetrahydrofuran (200 mL), N-(2,6-dichlorobenzoyl)-4-amino-L-phenylalanine methylester(6 g), EDC/HCl (3.6 g), HOBT (3.0 g) and triethylamine (4.4 mL) was added and stirred at 40° C. overnight. The mixture was extracted with ethyl acetate and treated in accordance with the ordinary method. The obtained crude material was dissolved in ethyl acetate (20 mL) and 1 g of 10% palladium charcoal was added thereto and stirred under hydrogen atomospher at room temperature overnight. After Celite filtration, the residue was treated in accordance with the ordinary method. DMF (200 mL) and carbonyldiimidazole (5.2 g) were added to the obtained crude material and stirred at 80° C. for 4 hours. The mixture was extracted with ethyl acetate and treated in accordance with the ordinary method. DMF (200 mL), potassium carbonate (4.4 g) and methyl iodide (1.2 mL) were added to the obtained crude material and stirred at room temperature overnight. The mixture was extracted with ethyl acetate and treated in accordance with the ordinary method. 1M boron tribromide-dichloromethane solution (50 mL) was added to the obtained crude material and stirred at room temperature for 3 days. The mixture was extracted with dichloromethane and treated in accordance with the ordinary method. Water/acetonitrile (1:1) was added to the obtained crude material and the precipitants were filtered out to obtain 2.2 g of a crude material of the intended compound. The filtrate was concentrated and purified with high performance liquid chromatography (water/acetonitrile, each containing 0.1% TFA) to obtain 510 mg of the intended compound.
MS(ESI MH+): 528

Example 141

Synthesis of the Compound of the Following Formula (E-49) which has a Substituent(s) of Example 141 of Table 23: N-(2,6-dichlorobenzoyl)-4-[6-((2S)-2-aminopropoxy)-1-methyl-2,4-quinazoline-dione-3-yl]-L-phenylalanine isopropylester Process 1 t-Butyl (1S)-2-hydroxy-1-methylethylcarbamate Di-t-butyldicarbonate (17 g), triethylamine (9 mL) and dichloromethane (100 mL) were added to L-alaninol (5 g) and stirred at room temperature for 2 hours. The mixture was diluted with dichloromethane and washed with water, and the organic layer was dried over anhydrous magnesium sulfate. After removing the solvent, the obtained crude material was purified with silica gel column chromatography (ethyl acetate-hexane) to obtain 5.9 g of the title compound.

Process 2 t-Butyl (1S)-2-chloro-1-methylethylcarbamate

Methanesulfonyl chloride (3.1 mL), triethylamine (9.0 mL) and dichloromethane (150 mL) were added to the compound obtained in Process 1 (5.9 g) and stirred at 0° C. for 2 hours. The mixture was diluted with dichloromethane and washed with water, and the organic layer was dried over anhydrous magnesium sulfate. After removing the solvent, lithium chloride (2.8 g) and DMF (100 mL) were added to the obtained crude material and stirred at 40° C. overnight. The mixture was diluted with ethyl acetate and washed with water, and the organic layer was dried over anhydrous magnesium sulfate. After removing the solvent, the obtained crude material was purified with silica gel column chromatography (ethyl acetate-hexane) to obtain 3.6 g of the title compound.

Process 3

The compound obtained in Process 2 (15 mg), DMF (2 mL) and potassium carbonate (14 mg) were added to the compound of Example 154 (30 mg) and stirred at 90° C. overnight. The mixture was extracted with ethyl acetate and treated in accordance with the ordinary method. The obtained crude material was dissolved in 4N hydrogen chloride dioxane solution (2 mL) and stirred at room temperature for 2 hours. Water (200 μL) was added thereto and stirred at 80° C. for 2 hours. After removing the solvent, the residue was purified with high performance liquid chromatography (water/acetonitrile, each containing 0.1% TFA) to obtain 10 mg of the intended compound.
MS(ESI MH+): 528

Example 142

Synthesis of the compound of the following formula (E-51) which has a Substituent(s) of Example 142 of Table 23: N-(2,6-dichlorobenzoyl)-4-[6-(2-dimethylaminoethoxy)-1-methyl-2,4-quinazoline-dione-3-yl]-L-phenylalanine t-Butyl 2-chloroethylcarbamate (157 mg), DMF (3 mL) and potassium carbonate (1384 mg) were added to the compound of Example 154 (450 mg) and stirred at 90° C. overnight. The mixture was extracted with ethyl acetate and treated in accordance with the ordinary method. The obtained crude material was dissolved in 4N hydrogen chloride dioxane solution (2 mL) and stirred at room temperature for 2 hours. After removing the solvent, the residue was purified with high performance liquid chromatography (water/acetonitrile, each containing 0.1% TFA) to obtain 350 mg of a purified material. Acetonitrile (5 mL), formalin (37 μL), acetic acid (26 μL) and triacetoxy sodium boron (98 mg) were added to the obtained purified material (170 mg) and stirred at room temperature for 2 hours. After removing the solvent, the residue was purified with high performance liquid chromatography (water/acetonitrile, each containing 0.1% TFA) to obtain 150 mg of a purified material. 4N hydrogen chloride dioxane solution (1 mL) and water (200 μL) were added to the obtained purified material (20 mg) and stirred at 90° C. for 2 hours. After removing the solvent, the residue was purified with high performance liquid chromatography (water/acetonitrile, each containing 0.1% TFA) to obtain 11 mg of a purified material.
MS(ESI MH+): 599

Example 143

Synthesis of the Compound of the Following Formula (E-50) which has a Substituent(s) of Example 143 of Table 24: N-(2,6-dichlorobenzoyl)-4-[7-ethylaminomethyl-1-methyl-2,4-quinazoline-dione-3-yl]-L-phenylalanine Process 1 Methyl 4-[(t-butoxycarbonylethylamino) methyl]-2-nitrobenzoate Triethylamine (1.9 mL) and ethyl chloroformate (11.0 mL) were added to the mixture of 1-methyl 2-nitroterephthalate (2.0 g) and tetrahydrofuran (120 mL) under cooling with ice and stirred for 30 minutes. Sodium borohydride (500 mL) and then 3 pieces of ice were added to the reaction solution and stirred at room temperature for 2 hours. The mixture was extracted with ethyl acetate and treated in accordance with the ordinary method. The obtained crude material (565 mg) was dissolved in dichloromethane (10 mL). Triethylamine (0.74 mL) and methanesulfonyl chloride (0.25 mL) were added thereto under cooling with ice and stirred for 2 hours. The mixture was extracted with dichloromethane and treated in accordance with the ordinary method. The obtained crude material was dissolved in acetonitrile (20 mL) and monoethylamine 2.0M tetrahydrofuran solution (2.68 mL) was added thereto and stirred at room temperature overnight. The mixture was extracted with ethyl acetate and treated in accordance with the ordinary method. The obtained crude material was dissolved in dichloromethane (10 mL). Triethylamine (0.74 mL) and di-t-butyldicarbonate (700 mg) were added thereto under cooling with ice and stirred for 2 hours. The mixture was extracted with dichloromethane and treated in accordance with the ordinary method to obtain 520 mg of the title compound.

Process 2

The substance obtained in Process 1 (520 mg) was dissolved in tetrahydrofuran (20 mL), 1M sodium hydroxide aqueous solution (5 mL) and methanol (10 mL) and stirred at room temperature for 2 hours and then at 40° C. for 2 hours. The mixture was extracted with ethyl acetate and treated in accordance with the ordinary method. Tetrahydrofurn (20 mL), N-(2,6-dichlorobenzoyl)-4-amino-L-phenylalanine methylester(563 mg), EDC/HCl (352 mg), HOBT (248 mg) and triethylamine (425 µL) were added thereto and stirred at 40° C. overnight. The mixture was extracted with ethyl acetate and treated in accordance with the ordinary method. The obtained crude material was dissolved in ethyl acetate (20 mL) and 20 mg of 10% palladium charcoal was added thereto and stirred under the existence of hydrogen at room temperature overnight. After Celite filtration, the residue was treated in accordance with the ordinary method. DMF (10 mL) and carbonyldiimidazole (374 mg) were added to the obtained crude material and stirred at 80° C. for 4 hours. The mixture was extracted with ethyl acetate and treated in accordance with the ordinary method. DMF (10 mL), potassium carbonate (212 mg) and methyl iodide (58 µL) were added to the obtained crude material and stirred at room temperature overnight. The mixture was extracted with ethyl acetate and treated in accordance with the ordinary method. The obtained crude material was dissolved in 4N hydrogen chloride dioxane solution (2 mL) and stirred at room temperature for 4 hours. After concentrating the solvent, 4N hydrogen chloride dioxane solution (2 mL) and water (200 µL) were added thereto and stirred at 80° C. for 2 hours. After removing the solvent, the residue was purified with high performance liquid chromatography (water/acetonitrile, each containing 0.1% TFA) to obtain 40 mg of the intended compound.

MS(ESI MH+): 569

Example 144

Synthesis of the Compound of the Following Formula (E-50) which has a Substituent(s) of Example 144 of Table 24: N-(2,6-dichlorobenzoyl)-4-[7-methylaminomethyl-1-methyl-2,4-quinazoline-dione-3-yl]-L-phenylalanine The intended compound was obtained by the same procedures as those of Process 1 and 2 in Example 143 except that monomethylamine 2.0M tetrahydrofuran solution was used instead of monoethylamine 2.0M tetrahydrofuran solution.

MS(ESI MH+): 555

Example 145

Synthesis of the Compound of the Following Formula (E-50) which has a Substituent(s) of Example 145 of Table 24: N-(2,6-dichlorobenzoyl)-4-[1-methyl-7-propylaminomethyl-2,4-quinazoline-dione-3-yl]-L-phenylalanine The intended compound was obtained by the same procedures as those of Process 1 and 2 in Example 143 except that propylamine was used instead of monoethylamine 2.0M tetrahydrofuran solution.

MS(ESI MH+): 583

Example 146

Synthesis of the Compound of the Following Formula (E-50) which has a Substituent(s) of Example 146 of Table 24: N-(2,6-dichlorobenzoyl)-4-[1-methyl-7-diethylaminomethyl-2,4-quinazoline-dione-3-yl]-L-phenylalanine The intended compound was obtained by the same procedures as those of Process 1 and 2 in Example 143 except that diethylamine was used instead of monoethylamine 2.0M tetrahydrofuran solution.

MS(ESI MH+): 597

Example 147

Synthesis of the Compound of the Following Formula (E-51) which has a Substituent(s) of Example 147 of Table 25

The intended compound was obtained by the same procedure as that of C in the above Examples 101 to 121 using the compound of Example 54.

MS(ESI MH+): 625

Example 148

Synthesis of the Compound of the Following Formula (E-51) which has a Substituent(s) of Example 148 of Table 25

The intended compound was obtained by the same procedure as that of C in the above Examples 101 to 121 using the compound of Example 54. MS(ESI MH+): 625

Example 149

Synthesis of the Compound of the Following Formula (E-51) which has a Substituent(s) of Example 149 of Table 25

The intended compound was obtained by the same procedure as that of C in the above Examples 101 to 121 using the compound of Example 54.

MS(ESI MH+): 597

Example 150

Synthesis of the Compound of the Following Formula (E-51) which has a Substituent(s) of Example 150 of Table 25

The intended compound was obtained by the same procedure as that of C in the above Examples 101 to 121 using the compound of Example 99.

MS(ESI MH+): 583

Example 151

Synthesis of the Compound of the Following Formula (E-51) which has a Substituent(s) of Example 151 of Table 25

The intended compound was obtained by the same procedure as that of C in the above Examples 101 to 121 using the compound of Example 99.

MS(ESI MH+): 597 $^1$H-NMR(DMSO-d$_6$): δ1.19(3H, d, J=6.3 Hz), 1.23(3H, d, J=6.3 Hz), 2.57(3H, t, J=5.1 Hz), 3.01(1H, dd, J=14.1, 9.9 Hz), 3.19(1H, dd, J=14.1, 5.1 Hz), 3.55(3H, s), 4.24(2H, t, J=5.4 Hz), 4.72-4.82(1H, m), 4.95 (1H, sep, J=6.3 Hz), 7.21(2H, d, J=8.4 Hz), 7.37-7.48(5H, m), 7.59(1H, d, J=8.7 Hz), 7.88(1H, dd, J=8.7, 2.1 Hz), 8.24(1H, d, J=2.1 Hz), 8.58(2H, brs), 9.25(1H, d, J=8.1 Hz).

Further, the compound of Example 151 was obtained by the same procedure as that of Process 3 in Example 53 except that the compound of Process 1 in Example 174 was used as a raw material and methylamine was used instead of morpholine.

Example 152

Synthesis of the Compound of the Following Formula (E-51) which has a Substituent(s) of Example 152 of Table 25

The intended compound was obtained by the same procedure as that of C in the above Examples 101 to 121 using the compound of Example 99.

MS(ESI MH+): 611

Example 153

Synthesis of the Compound of the Following Formula (E-51) which has a Substituent(s) of Example 153 of Table 25

The intended compound was obtained by the same procedure as that of C in the above Examples 101 to 121 using the compound of Example 140.

MS(ESI MH+): 556

Example 154

Synthesis of the Compound of the Following Formula (E-51) which has a Substituent(s) of Example 154 of Table 25

The intended compound was obtained by the same procedure as that of C in the above Examples 101 to 121 using the compound of Example 140.

MS(ESI MH+): 570

Example 155

Synthesis of the Compound of the Following Formula (E-51) which has a Substituent(s) of Example 155 of Table 25: N-(2,6-dichlorobenzoyl)-4-[6-(2-dimethylaminoethoxy)-1-methyl-2,4-quinazoline-dione-3-yl]-L-phenylalanine isopropylester t-Butyl 2-chloroethylcarbamate (157 mg), DMF (3 mL) and potassium carbonate (1384 mg) were added to the compound of Example 154 (450 mg) and stirred at 90° C. overnight. The mixture was extracted with ethyl acetate and treated in accordance with the ordinary method. The obtained crude material was dissolved in 4N hydrogen chloride dioxane solution (2 mL) and stirred at room temperature for 2 hours. After removing the solvent, the residue was purified with high performance liquid chromatography (water/acetonitrile, each containing 0.1% TFA) to obtain 350 mg of a purified material. Acetonitrile (5 mL), formalin (37 μL), acetic acid (26 μL) and triacetoxy sodium boron (98 mg) were added to the obtained purified material (170 mg) and stirred at room temperature for 2 hours. After removing the solvent, the residue was purified with high performance liquid chromatography (water/acetonitrile, each containing 0.1% TFA) to obtain 150 mg of the intended compound.

MS(ESI MH+): 641

Example 156

Synthesis of the Compound of the Following Formula (E-52) which has a Substituent(s) of Example 156 of Table 26: N-(2,6-dichlorobenzoyl)-4-[7-ethylaminomethyl-1-methyl-2,4-quinazoline-dione-3-yl]-L-phenylalanine isopropylester 4N hydrogen chloride dioxane solution (2 mL) and isopropanol (2 mL) were added to the compound of Example 143 (20 mg) and stirred at 80° C. for 2 hours. After removing the solvent, the residue was purified with high performance liquid chromatography (water/acetonitrile, each containing 0.1% TFA) to obtain 10 mg of the intended compound.

MS(ESI MH+): 611

Example 157

Synthesis of the Compound of the Following Formula (E-52) which has a Substituent(s) of Example 157 of Table 26: N-(2,6-dichlorobenzoyl)-4-[7-methylaminomethyl-1-methyl-2,4-quinazoline-dione-3-yl]-L-phenylalanine cyclopentylester 4N hydrogen chloride dioxane solution (2 mL) and cyclopentanol (2 mL) were added to the compound of Example 144 (20 mg) and stirred at 80° C. for 2 hours. After removing the solvent, the residue was purified with high performance liquid chromatography (water/acetonitrile, each containing 0.1% TFA) to obtain 15 mg of the intended compound.
MS(ESI MH+): 623

Example 158

Synthesis of the Compound of the Following Formula (E-52) which has a Substituent(s) of Example 158 of Table 26: N-(2,6-dichlorobenzoyl)-4-[7-methylaminomethyl-1-methyl-2,4-quinazoline-dione-3-yl]-L-phenylalanine isobutylester 4N hydrogen chloride dioxane solution (2 mL) and isobutanol (2 mL) were added to the compound of Example 144 (20 mg) and stirred at 80° C. for 2 hours. After removing the solvent, the residue was purified with high performance liquid chromatography (water/acetonitrile, each containing 0.1% TFA) to obtain 12 mg of the intended compound.
MS(ESI MH+): 611

Example 159

Synthesis of the Compound of the Following Formula (E-52) which has a Substituent(s) of Example 159 of Table 26: N-(2,6-dichlorobenzoyl)-4-[1-methyl-7-propylaminomethyl-2,4-quinazoline-dione-3-yl]-L-phenylalanine isopropylester 4N hydrogen chloride dioxane solution (2 mL) and isopropanol (2 mL) were added to the compound of Example 145 (50 mg) and stirred at 80° C. for 3 hours. After removing the solvent, the residue was purified with high performance liquid chromatography (water/acetonitrile, each containing 0.1% TFA) to obtain 25 mg of the intended compound.
MS(ESI MH+): 625

Example 160

Synthesis of the Compound of the Following Formula (E-53) which has a Substituent(s) of Example 160 of Table 27

The intended compound was obtained by the same procedure as that of Example 92 except that 2-methylimidazole was used instead of imidazole.
MS(ESI MH+): 610

Example 161

Synthesis of the Compound of the Following Formula (E-53) which has a Substituent(s) of Example 161 of Table 27

The intended compound was obtained by the same procedure as that of Example 92 except that 2-ethylimidazole was used instead of imidazole. MS(ESI MH+): 624

Example 162

Synthesis of the Compound of the Following Formula (E-53) which has a Substituent(s) of Example 162 of Table 27

The intended compound was obtained by the same procedure as that of C in the above Examples 101 to 121 using the compound of Example 92.

MS(ESI MH+) 638 $^1$H-NMR(DMSO-$d_6$): δ 1.19(3H, d, J=6.3 Hz), 1.23(3H, d, J=6.3 Hz), 3.02(1H, dd, J=14.1, 9.9 Hz), 3.20(1H, dd, J=14.1, 5.4 Hz), 3.59(3H, s), 4.72-4.82 (1H, m), 4.95(1H, sep, J=6.3 Hz), 7.24(2H, d, J=8.1 Hz), 7.38-7.48(5H, m), 7.69(1H, s), 7.91(1H, d, J=6.0 Hz), 8.07-8.14(2H, m), 9.15(1H, s), 9.25(1H, d, J=7.8 Hz).

Examples 163 to 173

Synthesis of the Compounds of the Following Formula (E-54) which have Substituents of Examples 163 to 173 of Table A The compounds obtained in Examples 163 to 173 were synthesized by the same procedure as that of C in Examples 65 to 81.

Example 174

Synthesis of the Compound of the Following Formula (E-55) which has a Substituent(s) of Example 174 of Table B Process 1 Synthesis of 4-[6-(chloromethyl)-1-methyl-2,4-dioxo-1,2,3,4-tetrahydroquinazoline-3(2H)-yl]-N-(2,6-dichlorobenzoyl)-L-phenylalanine isopropylester A mixed solvent of methylene chloride (140 mL) and dimethylformamide (140 mL) was cooled down to 0° C. Phosphorus oxychloride (40.1 mL) was added thereto and stirred for 30 minutes. The compound of Example 234 (25.7 g) was added at 0° C. and stirred at room temperature for 1 hour. Phosphorus oxychloride (0.4 mL) was further added thereto and stirred for 1 hour. Then, ethyl acetate (500 mL) and saturated sodium bicarbonate water (100 mL) were added thereto and stirred strongly. After ethyl acetate (500 mL) and water (200 mL) were added thereto to separate it into layers, the organic layer was washed with saturated sodium bicarbonate water (200 mL), 1N sodium hydroxide aqueous solution (100 mL) and saturated aqueous solution of sodium chloride (200 mL) and dried over anhydrous sodium sulfate. The solvent was removed under reduced pressure to obtain a crude material. The title compound was obtained by crystallization from methylene chloride and hexane.

Yield: 20.32 g MS(ESI MH+): 602

Process 2 Isopropyl (2S)-3-[4-(6-(azidomethyl)-1-methyl-2,4-dioxo-1,2,3,4-tetrahydro-3(2H)-quinazolinyl)phenyl]-2-[(2,6-dichlorobenzoyl)amino]propanoate Sodium azide (56 mg) and dimethylsulfoxide (5 mL) were added to the compound (400 mg) obtained in Process 1 and stirred for 2.5 hours. After diluting with ethyl acetate and washing with water, the organic layer was dried over anhydrous sodium sulfate. The solvent was removed under reduced pressure and the residue was purified with silica gel chromatography (hexane-ethyl acetate) to obtain the title compound (350 mg).

Process 3 Isopropyl (2S)-3-[4-(6-(aminomethyl)-1-methyl-2,4-dioxo-1,2,3,4-tetrahydro-3(2H)-quinazolinyl)phenyl]-2-[(2,6-dichlorobenzoyl)amino]propanoate Triphenylphosphine (52 mg) and tetrahydrofuran (2 mL) were added to the compound (100 mg) obtained in Process 2 and stirred for 30 minutes. Water (200 μL) was added to the reaction solution and further stirred overnight. After the solvent was removed, the residue was purified with high-performance liquid chromatography (water/acetonitrile, each containing 0.1% TFA) to obtain 76 mg of the intended compound.

Examples 175 to 183

Synthesis of the Compounds of the Following Formula (E-55) which have Substituents of Examples 175 to 183 of Table B The compounds were synthesized by the same procedure as that of Process 3 in Example 53 except that the compound of Process 1 in Example 174 was used as a starting material and corresponding amines were used instead of morpholine.

Example 184

Synthesis of the Compound of the Following Formula (E-56) which has a Substituent(s) of Example 184 of Table C Process 1 Isopropyl (2S)-2-[(2,6-dichlorobenzoyl)amino]-3-[4-(7-fluoro-6-iodo-1-methyl-2,4-dioxo-1,2,3,4-tetrahydro-3(2H)-quinazolinyl)phenyl]propanoate The title compound was synthesized by the same procedures as those of Processes 1 to 3 in Example 43 except that N-(2,6-dichlorobenzoyl)-4-[(2-amino-5-iodobenzoyl)amino]-L-phenylalanine ispropylester obtained in Process 1 of Example 234 was used instead of N-(2,6-dichlorobenzoyl)-4-[(2-amino-5-iodobenzoyl)amino]-L-phenylalanine methylester; and 2-amino-4-fluoro-5-iodobenzoic acid was used instead of 2-amino-5-iodobenzoic acid.

Process 2 Isopropyl (2S)-2-[(2,6-dichlorobenzoyl)amino]-3-[4-(7-fluoro-1-methyl-6-[(methylamino)methyl]-2,4-dioxo-1,2,3,4-tetrahydro-3(2H)-quinazolinyl)phenyl]propanoate The compound obtained in Process 1 was treated by the same procedures as those of Processes 4 and 5 in Example 234, Process 1 in Example 174, and Example 175 to obtain the title compound.

Example 185 and 186

Synthesis of the Compounds of the Following Formula (E-56) which have Substituents of Examples 185 and 186 of Table C The compounds were synthesized by the same procedure as that of Example 184 except that corresponding amines were used in Process 2 of Example 184.

Example 187

Synthesis of the Compound of the Following Formula (E-57) which has a Substituent(s) of Example 187 of Table D Process 1 Methyl (2S)-2-amino-3-[4-(6-iodo-1-methyl—2,4-dioxo-1,2,3,4-tetrahydro-3(2H)-quinazolinyl)phenyl]propanoate hydrochloride 4N hydrogen chloride dioxane solution was added to methyl (2S)-2-[(tert-butoxycarbonyl)amino]-3-[4-(6-iodo-1-methyl-2,4-dioxo-1,2,3,4-tetrahydro-3(2H)-quinazolinyl)phenyl]propanoate (5 g) obtained in Process 1 of Example 135 and stirred for 3 hours. The solvent was removed to obtain the title compound (4.2 g).

Process 2 Methyl (2S)-2-[(2-chloro-6-methylbenzoyl)amino]-3-[4-(6-iodo-1-methyl-2,4-dioxo-1,2,3,4-tetrahydro-3(2H)-quinazolinyl)phenyl]propanoate 2-chloro-6-methyl benzoic acid (1.7 g), EDC/HCl (1.9 g), HOAt (1.4 g), triethylamine (2.2 mL) and dichloromethane (42 mL) were added to the compound obtained in Process 1 (2.1 g) and stirred overnight. After the reaction mixture was diluted with ethyl acetate and washed with 1N hydrochloric acid, saturated sodium bicarbonate water and saturated aqueous solution of sodium chloride, the organic layer was dried over anhydrous sodium sulfate. The solvent was removed to obtain a crude material of the title compound.

Process 3 Isopropyl (2S)-2-[(2-chloro-6-methylbenzoyl)amino]-3-[4-(6-iodo-1-methyl-2,4-dioxo-1,2,3,4-tetrahydro-3(2H)-quinazolinyl)phenyl]propanoate 4N hydrogen chloride dioxane solution (30 mL) and water (6 mL) were added to the compound obtained in Process 2 and stirred at 90° C. overnight. After removing the solvent, 4N hydrogen chloride dioxane solution (25 mL) and isopropyl alcohol (25 mL) were added to the residue and stirred at 90° C. for 3.5 hours. After the reaction mixture was diluted with ethyl acetate and washed with 1N hydrochloric acid, saturated sodium bicarbonate water and saturated aqueous solution of sodium chloride, the organic layer was dried over anhydrous sodium sulfate. The solvent was removed to obtain a crude material of the title compound.

Process 4 Isopropyl (2S)-2-[(2-chloro-6-methylbenzoyl)amino]-3-[4-(1-methyl-6-[(methylamino)methyl]-2,4-dioxo-1,2,3,4-tetrahydro-3(2H)-quinazolinyl)phenyl]propanoate The compound obtained in Process 3 was treated by the same procedures as those of Processes 4 and 5 in Example 234, Process 1 in Example 174, and Example 175 to obtain the title compound.

Example 188

Synthesis of the Compound of the Following Formula (E-57) which has a Substituent(s) of Example 188 of Table D The compound was synthesized by the same procedure as that of Example 187 except that a corresponding amine was used in Process 4 of Example 187.

Example 189

Synthesis of the Compound of the Following Formula (E-57) which has a Substituent(s) of Example 189 of Table D The compound obtained in Process 2 of Example 135 was treated by the same procedures as those of Processes 4 and 5 in Example 234, Process 1 in Example 174, and Example 175 to obtain the title compound.

Example 190

Synthesis of the Compound of the Following Formula (E-57) which has a Substituent(s) of Example 190 of Table D The compound was synthesized by the same procedure as that of Example 189 except that a corresponding amine was used in Example 189.

Examples 191 to 206

Synthesis of the Compounds of the Following Formula (E-58) which have Substituents of Examples 191 and 206 of Table E The compounds were synthesized by the same procedure as that of Process 4 in Example 43 except that the compounds of Examples 174 to 188 and 190 were used as starting materials.

Example 207

Synthesis of the Compound of the Following Formula (E-59) which has a Substituent(s) of Example 207 of Table F Methanesulfonyl chloride (30 µL), triethylamine (80 µL) and dichloromethane (3 mL) were added to methyl (2S)-2-[(2,6-dichlorobenzoyl)amino]-3-[4-(6-(3-hydroxypropyl)-1-methyl-2,4-dioxo-1,2,3,4-tetrahydro-3(2H)-quinazolinyl) phenyl]propanoate (150 mg), which is a synthetic intermediate of Example 52, and stirred at 0° C. for 2.5 hours. After the reaction solvent was diluted with ethyl acetate and washed with 1N hydrochloric acid, saturated sodium bicarbonate water and saturated aqueous solution of sodium chloride, the organic layer was dried over anhydrous sodium sulfate and the solvent was removed under reduced pressure. The obtained residue was dissolved in acetonitrile (6 mL), added dropwise to 2M methylamine-tetrahydrofuran solution (9 mL) and stirred at 50° C. overnight. After removing the solvent, 4N hydrogen chloride dioxane solution (6 mL) and water (1.2 mL) were added to the residue and stirred at 90° C. for 2 hours. After removing the solvent, the residue was purified with high-performance liquid chromatography (water/acetonitrile, each containing 0.1% TFA) to obtain 70 mg of the intended compound.

Examples 208 and 209

Synthesis of the Compounds of the Following Formula (E-59) which have Substituents of Examples 208 and 209 of Table F The compounds were synthesized by the same procedure as that of Example 207 except that a tetrahydrofuran solution of each corresponding amines was used instead of 2M methylamine-tetrahydrofuran solution.

Example 210

Synthesis of the Compound of the Following Formula (E-59) which has a Substituent(s) of Example 210 of Table F 4N hydrogen chloride dioxane solution (2 mL) and isopropanol (2 mL) were added to the compound of Example 207 (65 mg) and stirred at 90° C. for 3.5 hours. After removing the solvent, the residue was purified with high-performance liquid chromatography (water/acetonitrile, each containing 0.1% TFA) to obtain 60 mg of the intended compound.

Examples 211 and 212

Synthesis of the Compounds of the Following Formula (E-59) which have Substituents of Examples 211 and 212 of Table F The compounds were synthesized by the same procedure as that of Example 210 using the compounds obtained in Examples 208 and 209.

Examples 213 to 218

Synthesis of the Compounds of the Following Formula (E-60) which have Substituents of Examples 213 to 218 of Table G Process 1 The crude material of the compound of Example 140 (2.49 g), 4N hydrogen chloride dioxane solution (50 mL) and isopropyl alcohol (50 mL) were stirred at 80° C. for 1.5 hours and the solvent was removed therefrom. A mixture of the obtained crude material, 1-bromo-2-chloroethane (3.92 mL), potassium carbonate (6.51 g) and acetone (100 mL) were stirred at 50° C. for 3 days. After removing the solvent, the residue was diluted with water and ethyl acetate, and liquid separation was conducted. After the organic layer was washed with saturated aqueous solution of sodium chloride, the solvent was removed to obtain the crude material (2.85 g).

Process 2 The intended compounds were obtained by the following methods A, B or C.

A. A mixture of alkylhalide in Process 1, a corresponding amine and a suitable solvent(s) such as acetonitrile were stirred at 80° C. for overnight to 3 days. After removing the solvent, the residue was purified with high-performance liquid chromatography (water/acetonitrile, each containing 0.1% TFA) to obtain the intended compound.

B. A mixture of alkylhalide in Process 1, a corresponding amine (or, hydrochloride of the corresponding amine and a base(es) such as triethylamine) and a suitable solvent(s) such as acetonitrile were stirred in a dip pipe at 80° C. for overnight to 3 days. After removing the solvent, the residue was purified with high-performance liquid chromatography (water/acetonitrile, each containing 0.1% TFA) to obtain the intended compound.

C. A mixture of alkylhalide in Process 1, a corresponding amine and a suitable solvent(s) such as acetonitrile were stirred at 50° C. for overnight to 3 days. After removing the solvent, the residue was purified with high-performance liquid chromatography (water/acetonitrile, each containing 0.1% TFA) to obtain the intended compound.

Examples 219 to 224

Synthesis of the Compounds of the Following Formula (E-60) which have Substituents of Examples 219 to 224 of Table G A mixture of a corresponding ester, 4N hydrochloric acid dioxane solution and water were stirred at 80° C. for a few hours to overnight. After removing the solvent, the residue was purified with high-performance liquid chromatography (water/acetonitrile, each containing 0.1% TFA) to obtain the intended compound.

Example 225

Synthesis of the Compound of the Following Formula (E-61) which has a Substituent(s) of Example 225 of Table H The intended compound was obtained by the same procedures as those of Examples 213 to 218 except that 1-bromo-3-chloropropane was used instead of 1-bromo-2-chloroethane

Examples 226 and 227

Synthesis of the Compounds of the Following Formula (E-61) which have Substituents of Examples 226 and 227 of Table H The intended compounds were obtained by the same procedure as that of Examples 219 to 224.

Example 228

Synthesis of the Compound of the Following Formula (E-62)

Process 1 Synthesis of N-(2,6-dichlorobenzoyl)-4-[7-fluoro-6-(2-hydroxyethyl)-1-methyl-2,4-dioxo-1,2,3,4-tetrahydroquinazoline-3(2H)-yl]-L-phenylalanine isopropylester In argon atmosphere, palladium acetate (6.5 mg) and triphenylphosphine (30 mg) were suspended in 5 mL of diethylether and stirred for 10 minutes. After decantation was conducted twice with diethylether, isopropylester of N-(2,6-dichlorobenzoyl)-4-(7-fluoro-1-methyl-2,4-dioxo-6-iodo-1,2,3,4-tetrahydroquinazoline-3(2H)-yl)-L-phenylalanine (374 mg), 2,4,6-trivinylcyclotriboroxane-pyridine complex (138 mg), dimethylformamide (5 mL) and aqueous solution of 2M sodium carbonate (1.15 mL) were added thereto and stirred at 90° C. for 1.5 hours. After removing insoluble materials by Celite filtration, the usual workup was conducted to obtain a crude material (0.36 g). The obtained crude material was dissolved in tetrahydrofuran (3 mL) and cooled down to 0° C. Then, sodium borohydride (35 mg) and trifluoroboran diethylether complex (81 μL) were added thereto and stirred at 0° C. for 1 hour. The reaction mixture was further stirred at room temperature for 1 hour and cooled down again to 0° C. and water (0.26 mL) was slowly added thereto. After the reaction mixture was stirred at room temperature for 1 hour and cooled down again to 0° C., an aqueous solution (5 mL) of Oxone (Registered Trademark) (1.3 g, purchased from Sigma-Aldrich) was added thereto and stirred at room temperature for 3.5 hours. Sodium bisulfite was further added thereto, extracted with ethyl acetate, washed with saturated aqueous solution of sodium chloride, and dried over anhydrous sodium sulfate to obtain a crude material. The obtained crude material was purified with silica gel column chromatography (chloroform:methanol=49:1 to 4:1, gradient) to obtain the title compound.

Yield: 0.197 g (0.32 mmol, 60%) MS(ESI MH+): 616

Process 2 Synthesis of N-(2,6-dichlorobenzoyl)-4-{7-fluoro-1-methyl-6-[2-(methylamino)ethyl]-2,4-dioxo-1,2,3,4-tetrahydroquinazoline-3(2H)-yl}-L-phenylalanine isopropylester The compound obtained in Process 1 (0.197 g) was dissolved in methylene chloride (2 mL), and triethylamine (67 μL) and methanesulfonyl chloride (32 μL) were added at 0° C. After stirring the mixture for 2 hours, the usual workup was conducted to obtain a crude material.

Tetrahydrofuran solution (10 mL) of 2M methylamine and acetonitrile (6 mL) were heated up to 50° C., and acetonitrile solution (6 mL) of the crude material was slowly added dropwise thereto and stirred overnight. After removing the solvent under reduced pressure, the residue was purified with high-performance liquid chromatography (water/acetonitrile, each containing 0.1% TFA) to obtain the title compound.

Yield: 51.7 mg MS(ESI MH+): 629

Example 229

Synthesis of the Compound of the Following Formula (E-63)

Synthesis of N-(2,6-dichlorobenzoyl)-4-{7-fluoro-1-methyl-6-[2-(methylamino) ethyl]-2,4-dioxo-1,2,3,4-tetrahydroquinazoline-3(2H)-yl}-L-phenylalanine 4N hydrogen chloride dioxane solution (4 mL) and water (0.8 mL) were added to the compound of Example 228 (10 mg) and stirred at 90° C. for 2 hours. After removing the solvent under reduced pressure, the residue was purified with high-performance liquid chromatography (water/acetonitrile, each containing 0.1% TFA) to obtain the title compound.

Yield: 5.3 mg MS(ESI MH+): 587

Example 230

Synthesis of the Compound of the Following Formula (E-64)

Synthesis of N-(2,6-dichlorobenzoyl)-4-{1-methyl-6-[2-(methylamino)ethyl]-2,4-dioxo-1,2,3,4-tetrahydroquinazoline-3(2H)-yl}-L-phenylalanine The title compound was obtained by the same procedures as those of Processes 1 and 2 in Example 228, and then Example 229 except that N-(2,6-dichlorobenzoyl)-4-(1-methyl-2,4-dioxo-6-iodo-1,2,3,4-tetrahydroquinazoline-3(2H)-yl)-L-phenylalanine methylester was used as a starting material.

MS(ESI MH+): 569

Example 231

Synthesis of the Compound of the Following Formula (E-65)

The compound of Example 52 (351 mg) was dissolved in dichloromethane (10 mL) and triethylamine (0.167 mL, 1.2 mmol). Methanesulfonyl chloride (0.116 mL, 1.2 mmol) was added dropwise thereto under cooling with ice and stirred for 2 hours. The usual workup was conducted to obtain a crude material. Acetonitrile (5 mL), potassium carbonate (170 mg) and 2M dimethylamine tetrahydrofuran solution (616 μL) were added to the crude material and stirred at room temperature overnight. After removing the solvent, the residue was purified with high-performance liquid chromatography (water/acetonitrile, each containing 0.1% TFA) to obtain 40 mg of the intended compound.

MS (ESI MH+): 611

Example 232

Synthesis of the compound of the following formula (E-66)

4N hydrogen chloride dioxane solution and isopropanol were added to the compound of Example 144 and stirred at 80° C. for 2 hours. After removing the solvent, the residue was purified with high-performance liquid chromatography (water/acetonitrile, each containing 0.1% TFA) to obtain the intended compound.

MS (ESI MH+): 597

Example 233

Synthesis of the Compound of the Following Formula (E-67)

The intended compound was obtained by the same procedure as that of C in the above Examples 101 to 121 using a crude material of the compound of Example 140.

MS (ESI MH+): 542

Example 234

Synthesis of the Compound of the Following Formula (E-68)

Process 1 Synthesis of 4-[(2-amino-5-iodobenzoyl)amino]-N-(2,6-dichlorobenzoyl)-L-phenylalanine isopropylester 4-Amino-N-(2,6-dichlorobenzoyl)-L-phenylalanine Isopropylester, 1-hydroxybenzotriazole monohydrate (11.5 g) and 5-iodoanthranilic acid (17.8 g) were dissolved in dimethylformamide (200 mL) and cooled down to 0° C. 1-ethyl-3-(3-dimethylaminopropyl)carbodiimide hydrochloride (13.7 g) was added thereto and stirred at room temperature for 16 hours. The organic layer wherein ethyl acetate (1 L) was added was washed with 0.1N sodium hydroxide aqueous solution (200 mL, 100 mL), water (100 mL), 0.1N hydrochloric acid (200 mL) and saturated aqueous solution of sodium chloride (200 mL, 100 mL), respectively. After drying the organic layer over anhydrous sodium sulfate and removing the solvent, a solid material obtained from a mixed solvent of methylene chloride and hexane was filtered to obtain the title compound.

Yield: 37.06 g (57.88 mmol) MS(ESI MH+): 640

Process 2 Synthesis of N-(2,6-dichlorobenzoyl)-4-(6-iodo-2,4-dioxo-1,2,3,4-tetrahydroquinazoline-3-(2H)-yl)-L-phenylalanine isopropylester N,N-carbonyldiimidazole (28.16 g) was dissolved in 150 mL of dimethylformamide and heated to 80° C. A dimethylformamide solution (150 mL) of the compound obtained in Process 1 (37.06 g) was added dropwise thereto and stirred overnight. After cooling down the mixture to room temperature, ethyl acetate (1 L) and water (500 mL) were added thereto and extraction was conducted. The obtained organic layer was washed with water (300 mL, 200 mL, 200 mL) and saturated aqueous solution of sodium chloride (100 mL) and dried over anhydrous sodium sulfate. After removing the solvent under reduced pressure, the obtained solid material was suspended in methylene chloride and hexane. The obtained solid material was filtered and dried to obtain the title compound.

Yield: 33.06 g MS(ESI MH+):666

Process 3 Synthesis of N-(2,6-dichlorobenzoyl)-4-(6-iodo-1-methyl-2,4-dioxo-1,2,3,4-tetrahydroquinazoline-3-(2H)-yl)-L-phenylalanine isopropylester The compound obtained in Process 2 (33.06 g) and potassium carbonate (14.5 g) were added to dimethylformamide (200 mL), and then iodomethane (10 mL) was further added thereto and stirred at room temperature for 4 hours. After removing insoluble materials by Celite filtration, ethyl acetate (1 L) and water (300 mL) were added to the filtrate and extraction was conducted. The obtained organic layer was washed with 1N hydrochloric acid (250 mL), saturated sodium bicarbonate water (250 mL) and saturated aqueous solution of sodium chloride (200 mL), respectively. After removing the solvent, the obtained solid material was suspended in methylene chloride and hexane. The obtained solid material was filtered and dried to obtain the title compound.

Yield: 31.85 g MS(ESI MH+): 680

Process 4 Synthesis of N-(2,6-dichlorobenzoyl)-4-(6-carboxy-1-methyl-2,4-dioxo-1,2,3,4-tetrahydroquinazoline-3-(2H)-yl)-L-phenylalanine isopropylester The compound obtained in Process 3 was dissolved in dimethylformamide (140 mL), and triethylamine (130.1 mL) and water (8.5 mL) were added thereto. After bubbling carbon monoxide, palladium acetate (52 mg) was added and stirred under carbon monoxide atmosphere at 70° C. for 11 hours. After removing insoluble materials by Celite filtration, dimethylformamide (about 100 mL) was removed under reduced pressure. Then, ethyl acetate (1 L) and 1N hydrochloric acid (300 mL) were added thereto and extraction was conducted. The obtained organic layer was washed with 1N hydrochloric acid (200 mL) and saturated aqueous solution of sodium chloride (200 mL, 200 mL), and dried over anhydrous sodium sulfate. After removing the solvent under reduced pressure, the obtained solid material was suspended in methylene chloride and hexane. The obtained solid material was filtered and dried to obtain the title compound.

Yield: 27.23 g MS(ESI MH+): 598

Process 5 Synthesis of N-(2,6-dichlorobenzoyl)-4-[6-(hydroxymethyl)-1-methyl-2,4-dioxo-1,2,3,4-tetrahydroquinazoline-3-(2H)-yl]-L-phenylalanine isopropylester The compound obtained in Process 4 was dissolved in tetrahydrofuran (200 mL). Triethylamine (9.51 mL) was added thereto and cooled down to 0° C. Ethyl chloroformate (4.56 mL) was added dropwise and stirred for 30 minutes. After filtering out the insoluble materials, the filtrate was cooled down to 0° C. and sodium borohydride (2.58 g) and ice (5 pieces) were added and stirred for 1 hour. Then, sodium borohydride (0.25 g) was further added thereto and stirred for 20 minutes. 1N hydrochloric acid (74.8 mL), ethyl acetate and water were added respectively and extraction was conducted. The organic layer was washed with 0.3N hydrochloric acid, water, saturated sodium bicarbonate water and saturated aqueous solution of sodium chloride. After removing the solvent, the obtained solid material was suspended in methylene chloride and hexane. The obtained solid material was filtered and dried to obtain the title compound.

Yield: 25.69 g MS(ESI MH+): 584

Example 235

Synthesis of the Compound of the Following Formula (E-69)

The intended compound was obtained as a by-product material of the compound of Example 228.

MS(ESI MH+): 609

Example 236

Synthesis of the Compound of the Following Formula (E-70)

The intended compound was obtained as a by-product material of the compound of Example 229.

MS(ESI MH+): 567

Reference Example 4

Synthesis of 4-amino-N-(2,6-dichlorobenzoyl)-L-phenylalanine isopropylester (Namely, Synthesis of isopropyl (S)-2-(2,6-dichlorobenzoylamino)-3-(4-nitrophenyl)propionate Process 1: Synthesis of 4-nitro-N-(2,6-dichlorobenzoyl)-L-phenylalanine isopropylester Isopropanol (130 mL), tetrahydrofuran (50 mL) and sulfuric acid (0.44 mL) were added to 4-nitro-N-(2,6-dichlorobenzoyl)-L-phenylalanine (2.95 g, 7.70 mmol) and stirred at 50° C. for 5 days. After removing the solvent under reduced pressure, the obtained solid material was washed with water and dried to obtain 3.28 g of a white solid material.

MS(ESI) m/z 425(MH+)

Process 2: Synthesis of 4-amino-N-(2,6-dichlorobenzoyl)-L-phenylalanine isopropylester (Namely, Synthesis of isopropyl (S)-2-(2,6-dichlorobenzoylamino)-3-(4-aminophenyl) propionate Isopropanol (6 mL), tetrahydrofuran (3 mL) and 3% Pt-S/C (20 mg) were added to the solid material obtained in Process 1 (98 mg) and stirred under hydrogen atmosphere at room temperature overnight. After filtering the reaction solution, the filtrate was washed with isopropanol and removed under reduced pressure to obtain 92 mg of the title compound.

MS(ESI) m/z 395(MH+)

Shown below are structural formulae of the compounds in Examples.

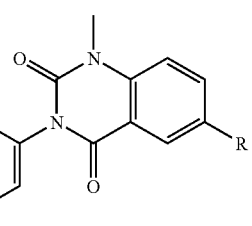

TABLE 2-continued
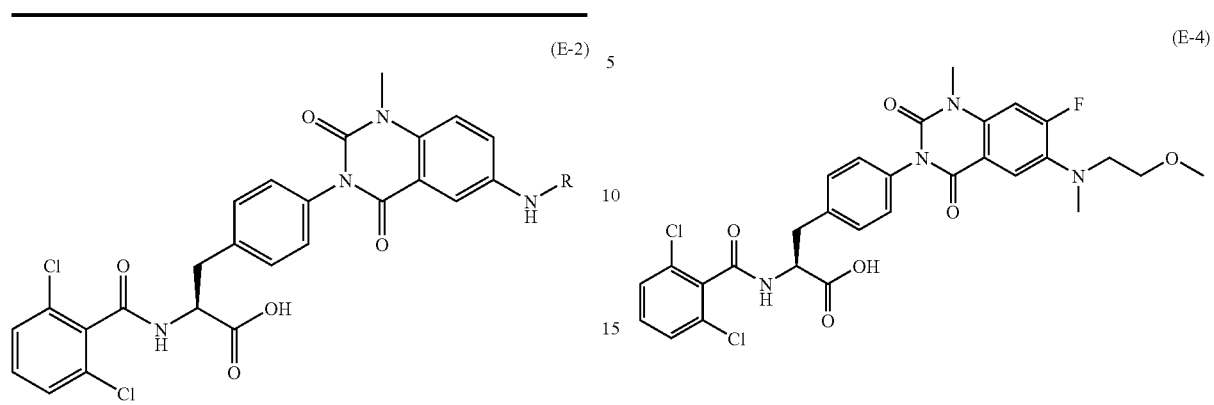
(E-2)
| Example | R— | MS Found (MH+) |
|---------|----|----|
| 11 | ~~O~~Me (propoxyethyl) | 599 |
| 12 | ethylcyclopropyl | 581 |
TABLE 3
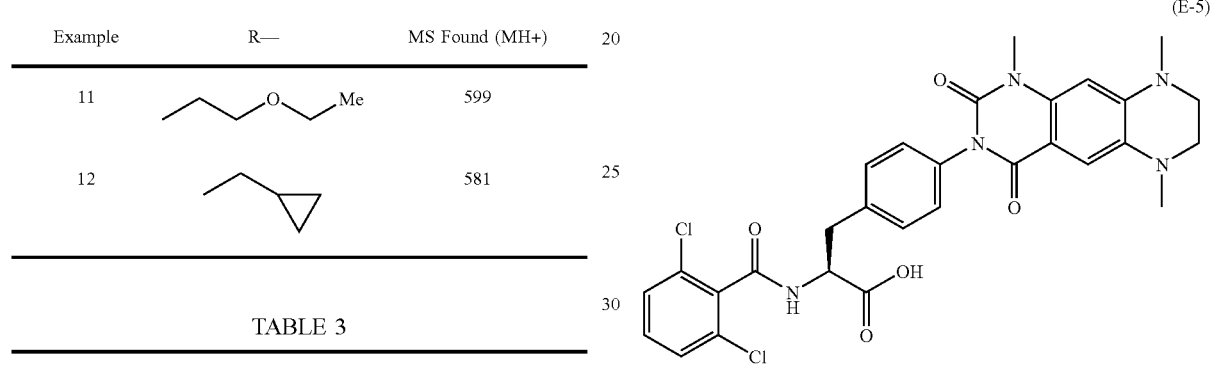
(E-3)
| Example | R— | MS Found (MH+) |
|---------|----|----|
| 13 | Me-N(Me)-CH2CH2-N(Me)Me | 630 |
| 14 | Me-N(Me)-CH2CH2-N(Et)Et | 658 |
| 15 | Me-N(Me)-CH2CH2-OMe | 617 |
The compounds of Examples 16 to 20
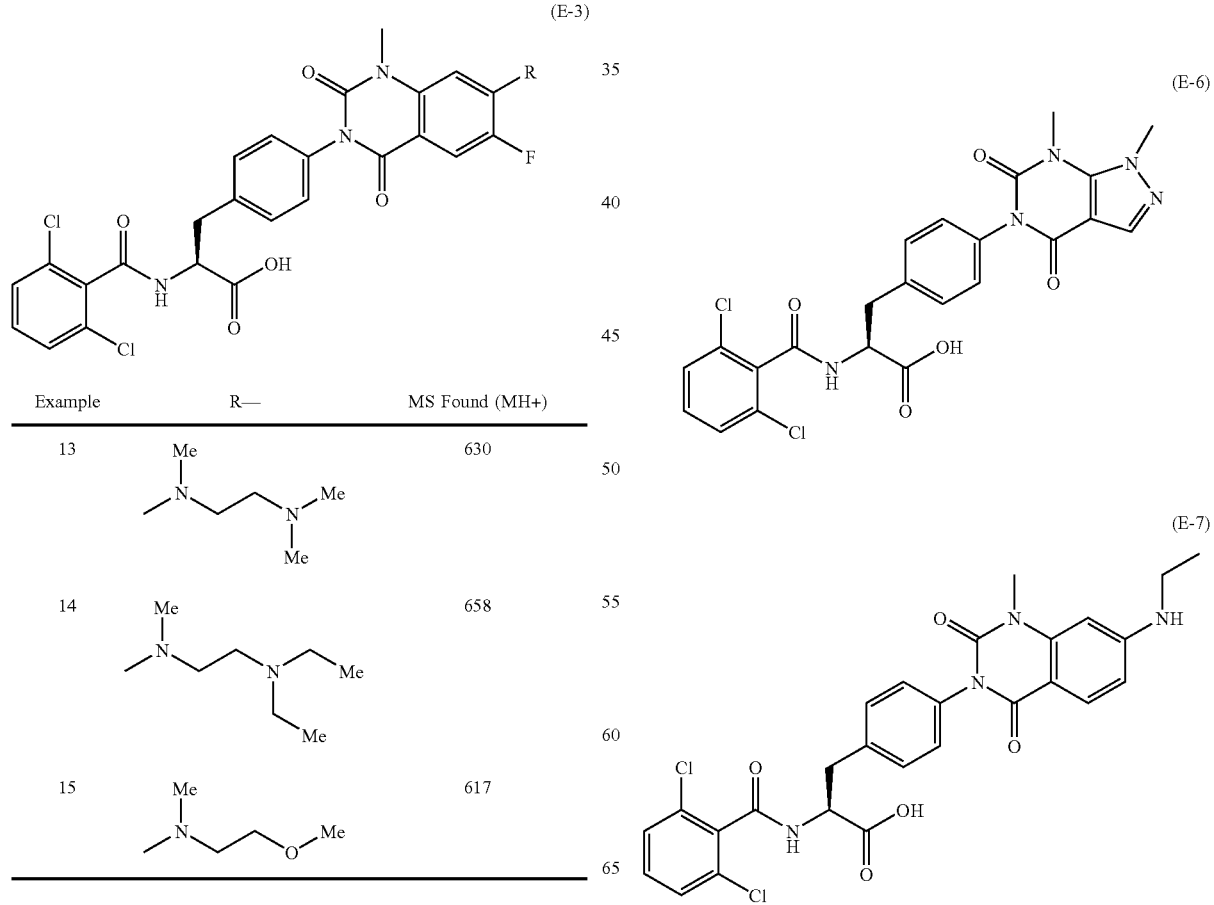

(E-8)
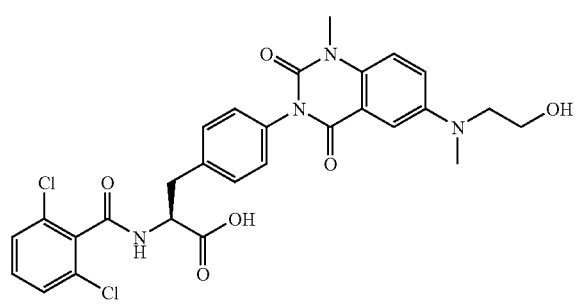
TABLE 4
(E-9)
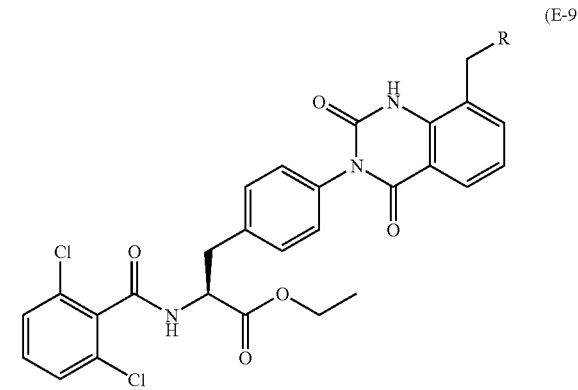
| Example | —R | —R' | MS Found (MH+) |
|---|---|---|---|
| 21 | Me—N⁺(Me)(Me)Me | —H | 569 |
| 22 | Me—N⁺(pyrrolidine) | —H | 595 |
| 23 | Me—N⁺(Me)(Me)Me | —Et | 597 |
| 24 | Me—N⁺(Me)(Me)Me | —CH(Me)Me (iPr) | 611 |
| 25 | Me—N⁺(Me)(Me)Me | —(CH₂)₃Me | 625 |
| 26 | Me—N⁺(Me)(Me)Me | —(CH₂)₄Me | 639 |
TABLE 4-continued
(E-9)
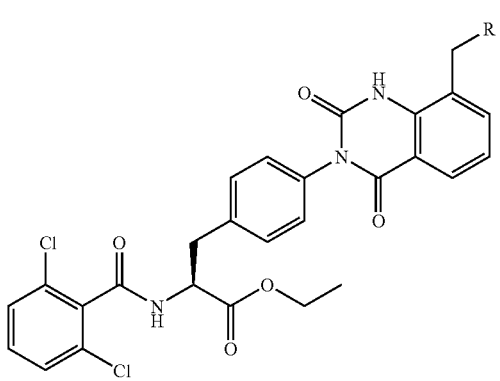
| Example | —R | —R' | MS Found (MH+) |
|---|---|---|---|
| 27 | Me—N⁺(Me)(Me)Me | —CH₂Ph | 659 |
TABLE 5
(E-10)
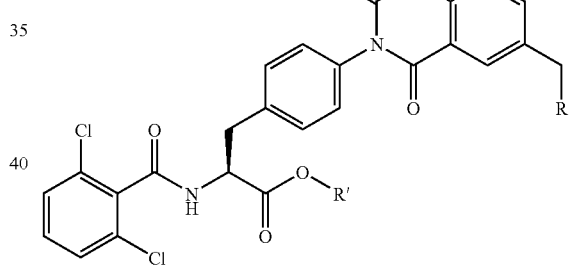
| Example | —R | —R' | MS Found (MH+) |
|---|---|---|---|
| 28 | Me—N(Me)Me | —H | 569 |
| 29 | Me—N(Me)Me | —Et | 597 |
| 30 | Me—N(Me)Me | —CH(Me)Me | 611 |
| 31 | Me—N(Me)Me | —(CH₂)₃Me | 625 |

TABLE 5-continued
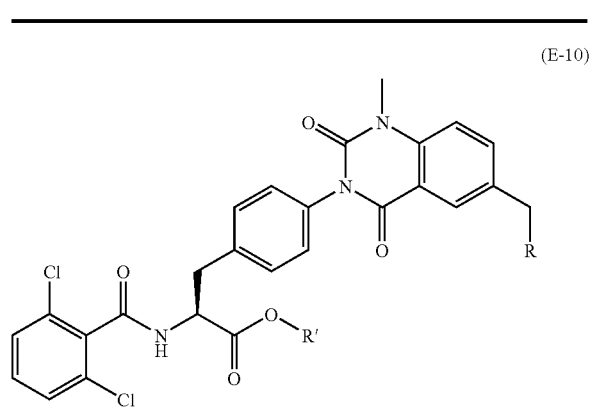
(E-10)
| Example | —R | —R' | MS Found (MH+) |
|---|---|---|---|
| 32 | —N(Me)Me, Me | pentyl | 639 |
| 33 | —N(Me)Me, Me | benzyl | 659 |
TABLE 6
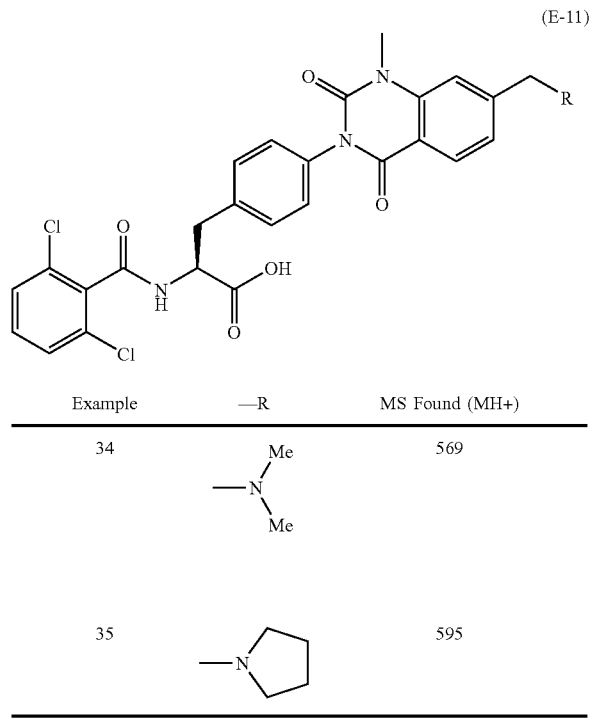
(E-11)
| Example | —R | MS Found (MH+) |
|---|---|---|
| 34 | —N(Me)Me | 569 |
| 35 | pyrrolidinyl | 595 |
The compound of Example 36
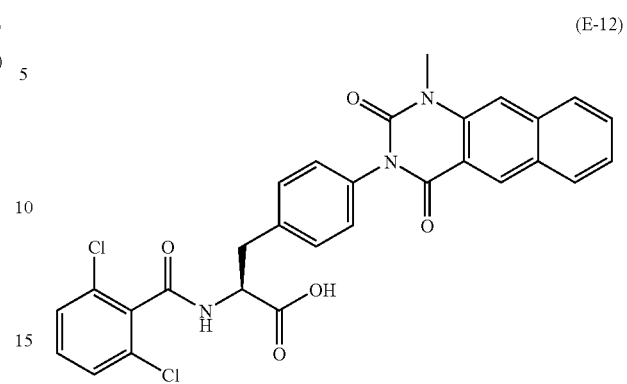
(E-12)
TABLE 7
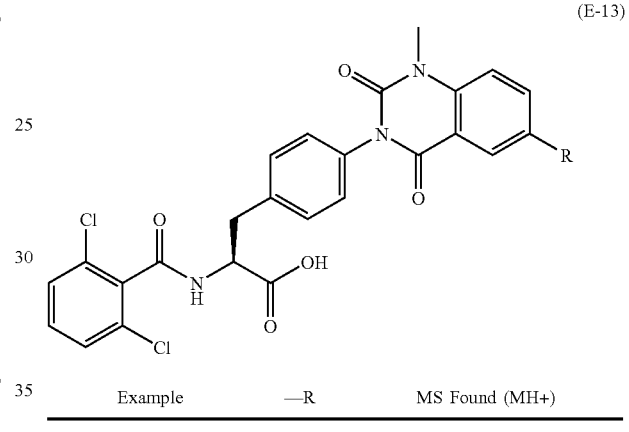
(E-13)
| Example | —R | MS Found (MH+) |
|---|---|---|
| 37 | —SMe | 558 |
| 38 | —SO₂Me | 590 |
TABLE 8
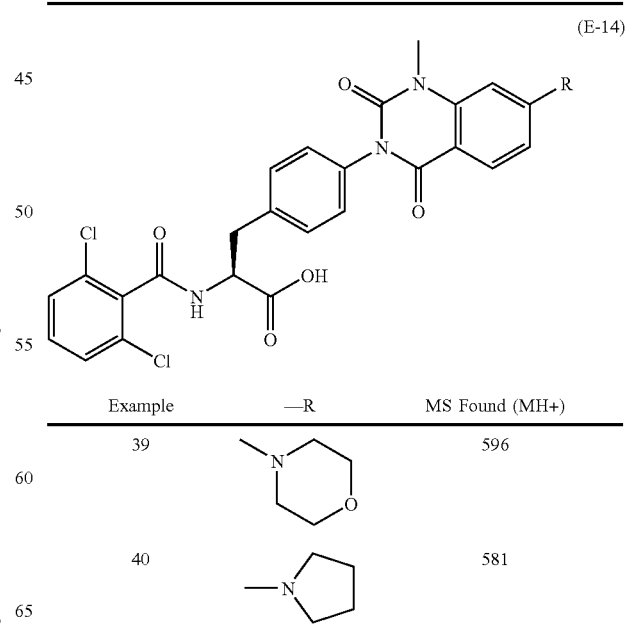
(E-14)
| Example | —R | MS Found (MH+) |
|---|---|---|
| 39 | morpholinyl | 596 |
| 40 | pyrrolidinyl | 581 |

TABLE 9

(E-15)

| Example | —R | MS Found (MH+) |
|---|---|---|
| 41 | N-methylimidazol-yl | 578 |
| 42 | 2-methyl-1-methylimidazol-yl | 592 |

TABLE 10

(E-16)

| Example | —R | MS Found (MH+) |
|---|---|---|
| 43 | —I | 638 |
| 44 | —CN | 537 |
| 45 | —COOCH$_2$Ph | 646 |
| 46 | —COOH | 556 |

The compounds of Examples 47 and 48

(E-17)

(E-18)

TABLE 11

(E-19)

| Example | —R | MS Found (MH+) |
|---|---|---|
| 49 | CH=CH–COOH (trans) | 582 |
| 50 | CH$_2$C(O)NH$_2$ | 555 |
| 51 | CH$_2$CH$_2$COOH | 584 |

TABLE 11-continued
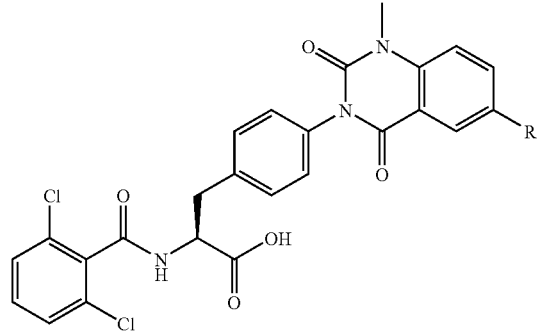
(E-19)
| Example | —R | MS Found (MH+) |
|---|---|---|
| 52 | 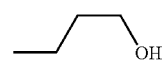 | 570 |
TABLE 12
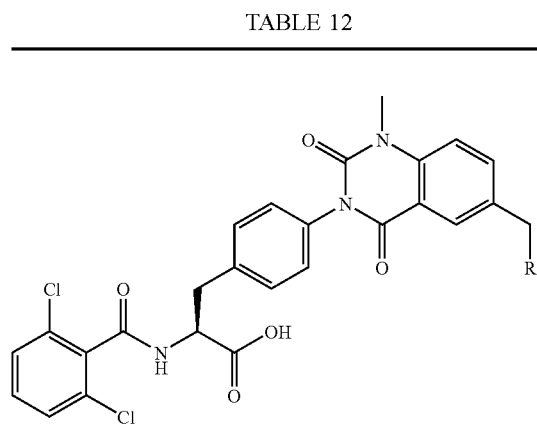
(E-20)
| Example | —R | MS Found (MH+) |
|---|---|---|
| 53 | 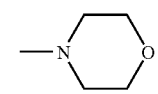 | 611 |
| 54 | —NHEt | 569 |
| 55 | —NEt$_2$ | 597 |
| 56 | 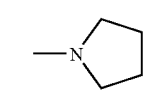 | 595 |
| 57 | 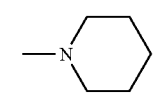 | 609 |
| 58 | 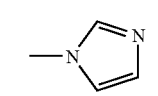 | 592 |
The compound of Example 59
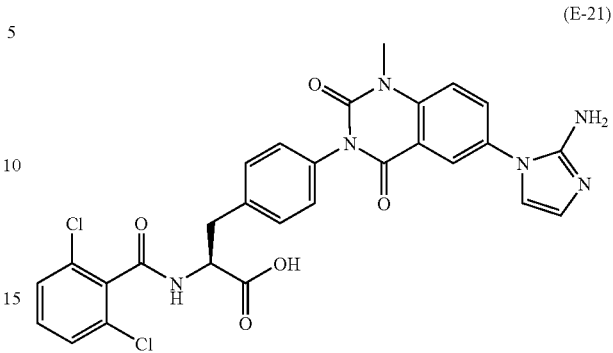
(E-21)
TABLE 13
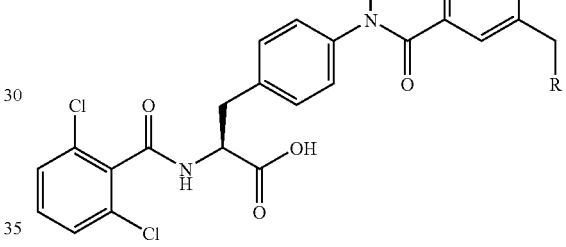
(E-22)
| Example | —R | MS Found (MH+) |
|---|---|---|
| 60 | —OH | 542 |
| 61 | —OMe | 556 |
TABLE 14
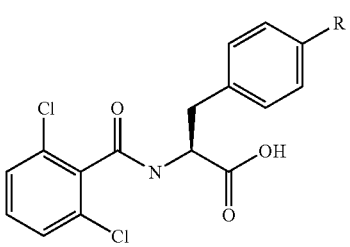
(E-23)
| Example | —R | MS Found (MH+) |
|---|---|---|
| 62 | 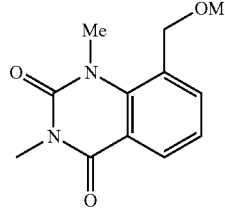 | 556 |

TABLE 14-continued
(E-23)
Example | —R | MS Found (MH+)
--- | --- | ---
63 | Me, OMe quinazolinedione | 556
The compound of Example 64
(E-24)
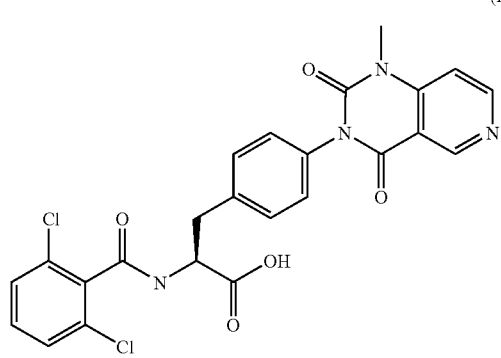
TABLE 15-1
(E-25)
Example | —R | —R' | MS Found (MH+)
--- | --- | --- | ---
65 | pyrrolidinyl | —Me | 595
66 | pyrrolidinyl | —Et | 609
TABLE 15-1-continued
(E-25)
Example | —R | —R' | MS Found (MH+)
--- | --- | --- | ---
67 | —NH-CH2-Me | —Et | 583
68 | —NH-CH2-Me | -propyl-Me | 597
69 | —NH-CH2-Me | -propyl-morpholine | 668
70 | —NH-CH2-Me | -CH2-CH(Me)Me | 597
71 | —NH-CH2-Me | -butyl-Me | 611
72 | —NH-CH(Me)Me | —Me | 583
TABLE 15-2
(E-25)
Example | —R | —R' | MS Found (MH+)
--- | --- | --- | ---
73 | —NH-CH2CH2-Me | —Et | 597

TABLE 15-2-continued (E-25)

| Example | —R | —R' | MS Found (MH+) |
|---|---|---|---|
| 74 | —NH-CH2CH2-Me | -CH(Me)2 | 611 |
| 75 | —NH-CH2CH2-Me | -CH2CH2CH2-Me | 625 |
| 76 | —NH-CH2CH2-Me | -CH2CH2CH2-morpholine | 682 |
| 77 | —NH-CH2-C≡CH | —Me | 579 |
| 78 | —NH-CH2-C≡CH | —Et | 593 |
| 79 | —NH-CH2-C≡CH | -CH(Me)2 | 607 |
| 80 | —NH-CH2-C≡CH | -CH2CH2CH2-Me | 621 |
| 81 | —NH-CH2-C≡CH | -CH2CH2CH2-morpholine | 678 |

TABLE 16

(E-26)

| Example | —R | —R' | MS Found (MH+) |
|---|---|---|---|
| 82 | -CH2CH2-N(Me)2 | -CH2-Ph | 659 |
| 83 | -CH2CH2-N(Me)2 | -CH2CH2CH2CH2-Me | 639 |
| 84 | -CH2CH2-N(Me)2 | -CH2CH2CH2CH2CH2CH2-Me | 661 |
| 85 | -CH2CH2-N(Me)2 | -CH(Me)2 | 611 |
| 86 | -CH2CH2-N(Me)2 | -CH2CH2CH2-Me | 625 |

TABLE 17

(E-27)

| Example | —R |
|---|---|
| 87 | —CO2H |
| 88 | —CO2Me |

The compounds of Examples 89 to 97
(E-28)
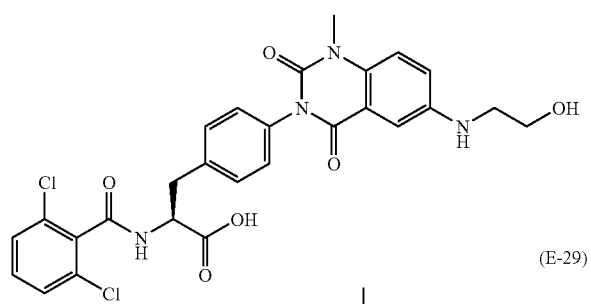
(E-29)
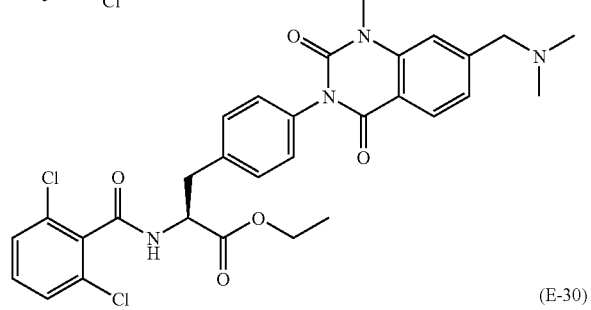
(E-30)
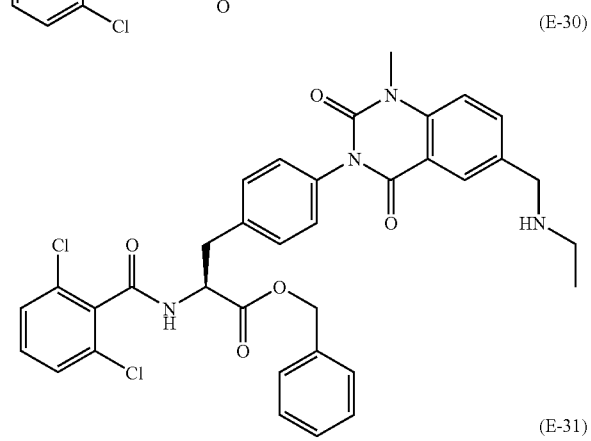
(E-31)
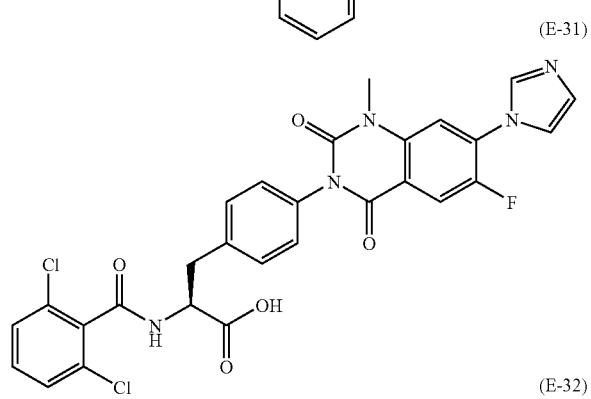
(E-32)
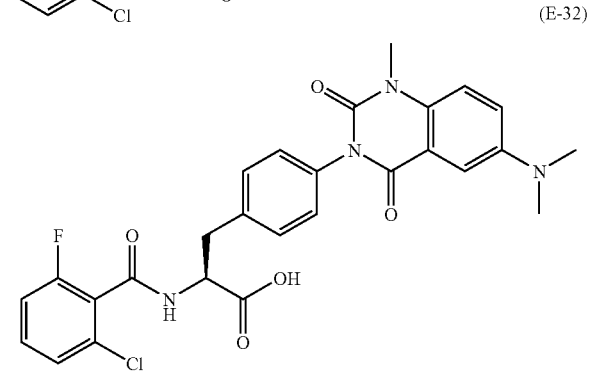
(E-33)
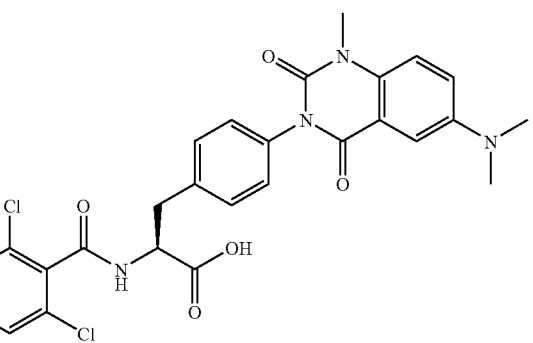
(E-34)
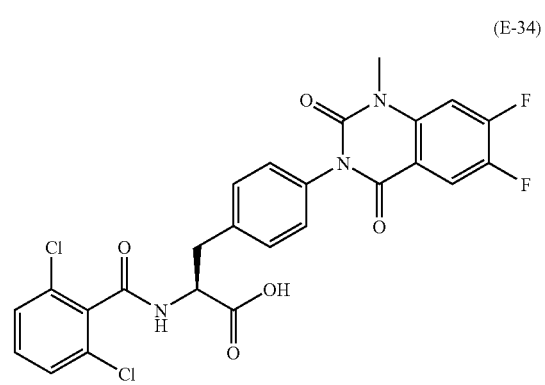
(E-35)
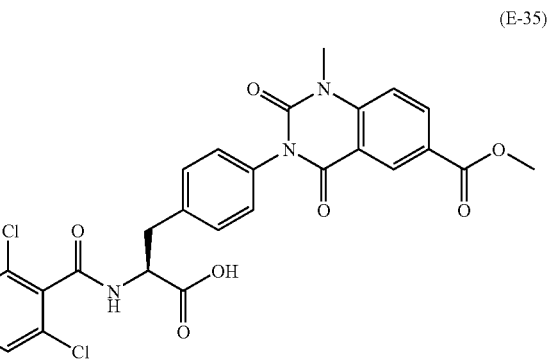
(E-36)
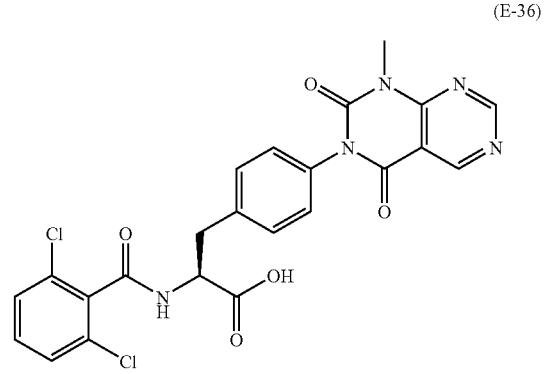

TABLE 18
(E-37)
| Examples | —R | MS Found (MH+) |
|---|---|---|
| 98 |  | 583 |
| 99 |  | 555 |
The compound of Example 100
(E-38)
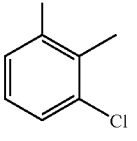
TABLE 19-1
(E-39)
| Example | Method | —R$_1$ | —R$_2$ | —R$_3$ | MS Found (MH+) |
|---|---|---|---|---|---|
| 101 | C |  | 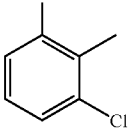 | 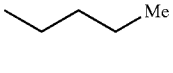 | 569 |
| 102 | C |  | 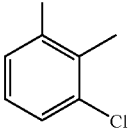 |  | 597 |
| 103 | D |  | 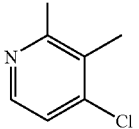 | Me | 553 |
| 104 | D |  | | Me | 570 |

TABLE 19-1-continued
(E-39)
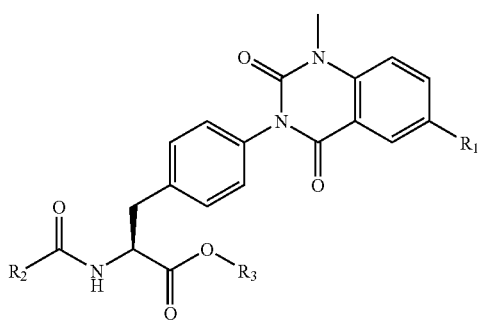
| Example | Method | —R₁ | —R₂ | —R₃ | MS Found (MH+) |
|---------|--------|-----|-----|-----|----------------|
| 105 | C | MeNH-CH(Me)- | 2,6-dichloro-3-methylphenyl | isobutyl | 611 |
| 106 | A | MeNH-CH(Me)- | 2,6-dichloro-3-methylphenyl | Me | 583 |
| 107 | C | MeNH-CH(Me)- | 2,6-dichloro-3-methylphenyl | propylmorpholine | 682 |
Example 19-2
(E-39)
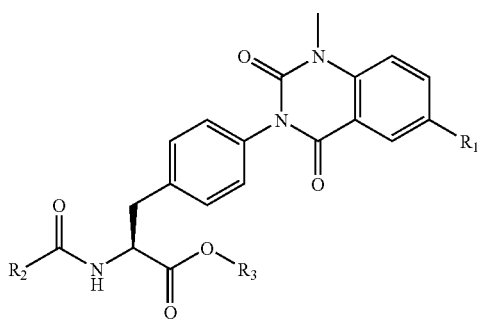
| Example | Method | —R₁ | —R₂ | —R₃ | MS Found (MH+) |
|---------|--------|-----|-----|-----|----------------|
| 108 | C | MeNH-CH(Me)- | 2,6-dichloro-3-methylphenyl | Et | 597 |

-continued
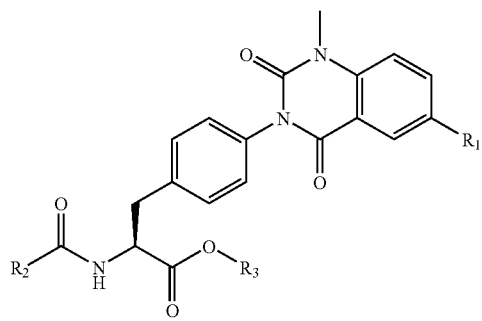
(E-39)
| Example | Method | —R₁ | —R₂ | —R₃ | MS Found (MH+) |
|---|---|---|---|---|---|
| 109 | C | 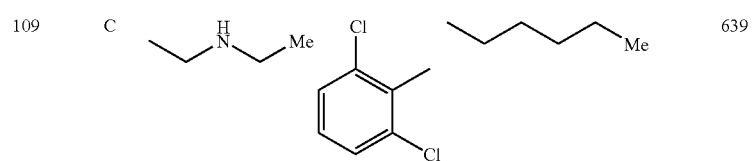 | | | 639 |
| 111 | C | 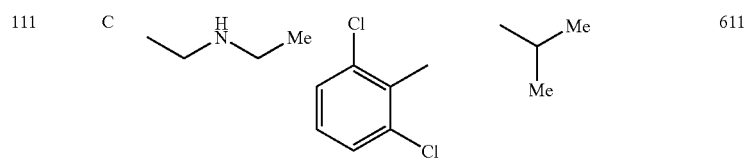 | | | 611 |
| 112 | C | 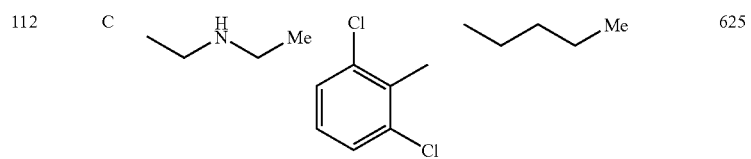 | | | 625 |
| 113 | C | 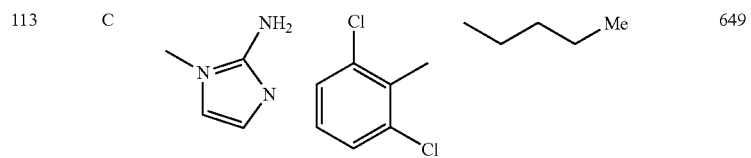 | | | 649 |
| 114 | E | 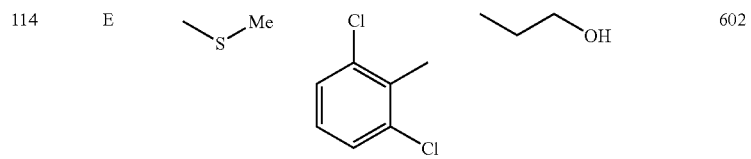 | | | 602 |

Example 19-3
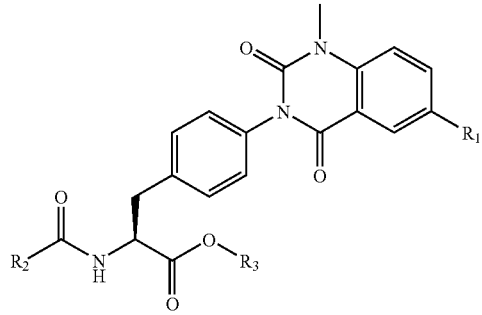
(E-39)
| Example | Method | —R₁ | —R₂ | —R₃ | MS Found (MH+) |
|---|---|---|---|---|---|
| 115 | C | S-Me | 2,6-dichlorophenyl | Et | 586 |
| 116 | D | S-Me | 2,6-dichlorophenyl | Me | 572 |
| 117 | D | CH₂OH | 2,6-dichlorophenyl | Me | 556 |
| 118 | D | S(O)₂Me | 2,6-dichlorophenyl | Me | 604 |
| 119 | C | NHCH₂-cyclopropyl | 2,6-dichlorophenyl | Et | 609 |
| 120 | C | NHCH₂CH₂CH₂Me (Et on N) | 2,6-dichlorophenyl | n-Bu | 639 |
| 121 | C | EtNHMe | 2,6-dichlorophenyl | n-Bu | 611 |

TABLE 20
(E-40)
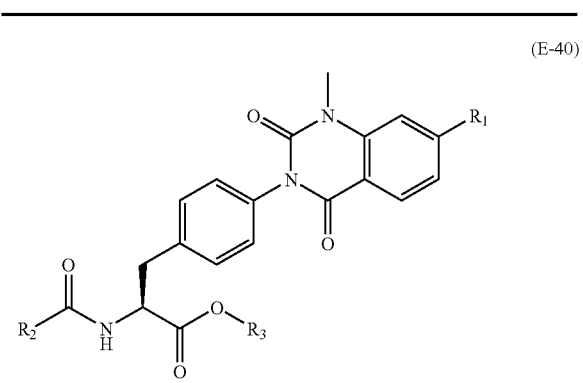
| Example | —R₁ | —R₂ | —R₃ | MS Found (MH+) |
|---|---|---|---|---|
| 122 | D | Me–N(Me)– | 2,6-dichlorophenyl-Me | Me | 569 |
| 123 | C | pyrrolidinyl | 2,6-dichlorophenyl-Me | Me | 639 |
The compounds of Examples 124 and 125
(E-41)
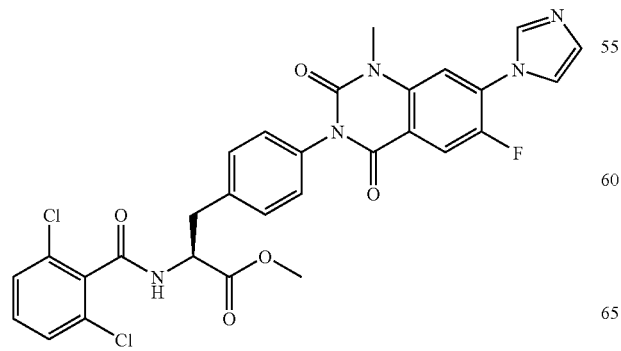
(E-42)
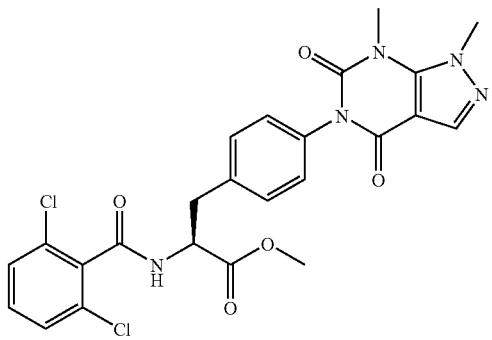
TABLE 21
(E-43)
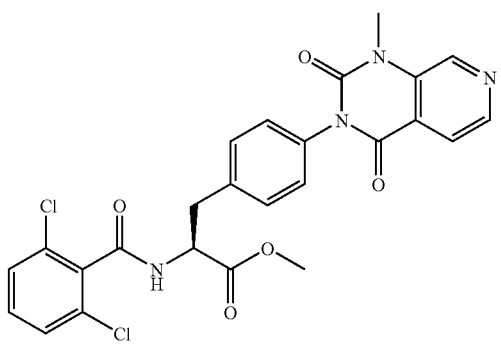
| Example | —R | MS Found (MH+) |
|---|---|---|
| 126 | Me | 527 |
| 127 | CH(Me)Me | 555 |
The compounds of Examples 128 to 132
(E-44)

-continued
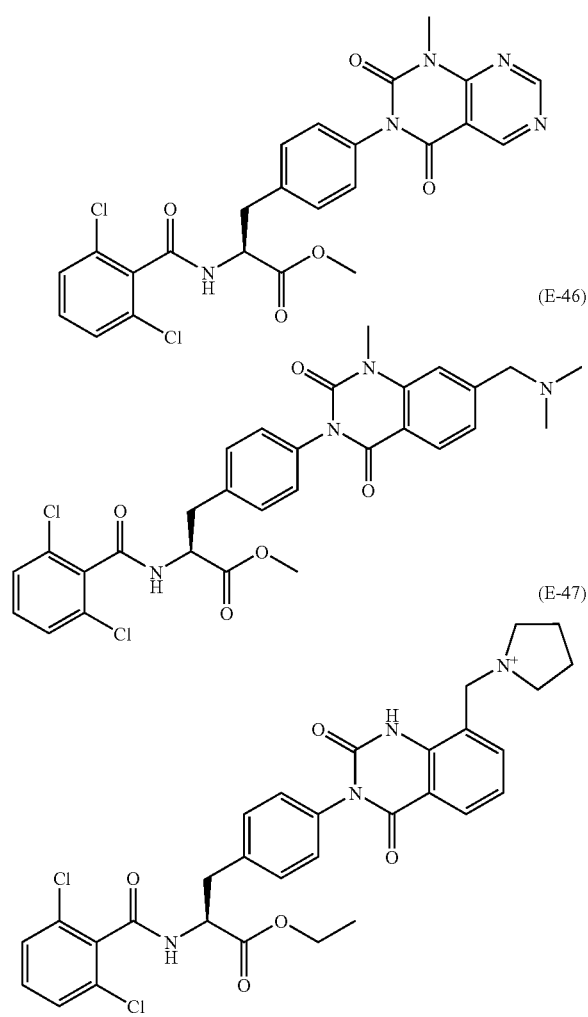
TABLE 22
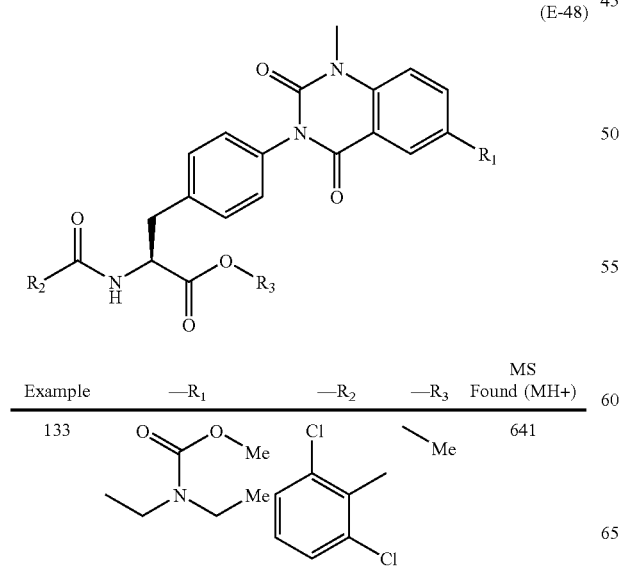
TABLE 22-continued
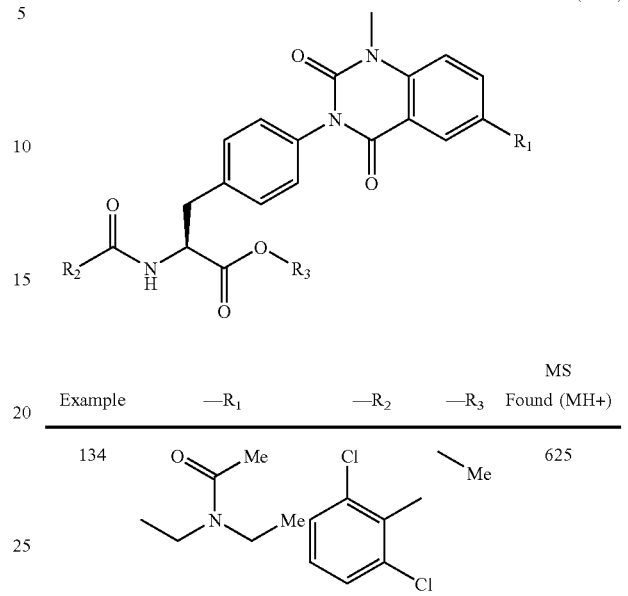
| Example | —R$_1$ | —R$_2$ | —R$_3$ | MS Found (MH+) |
|---|---|---|---|---|
| 134 | (O=C-Me with N-ethyl, N-CH$_2$-) | 2,3-dichloro-methylphenyl | Me | 625 |
TABLE 23
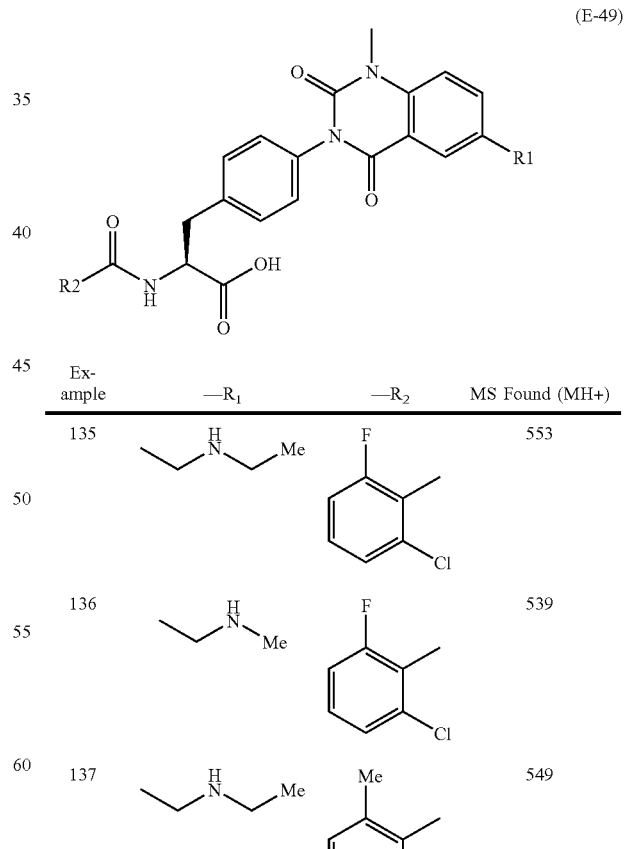
| Example | —R$_1$ | —R$_2$ | MS Found (MH+) |
|---|---|---|---|
| 135 | EtNH-CH(Me)- | 2-F, 3-Cl-methylphenyl | 553 |
| 136 | EtNHMe | 2-F, 3-Cl-methylphenyl | 539 |
| 137 | EtNH-CH(Me)- | 2-Me, 3-Cl-methylphenyl | 549 |

TABLE 23-continued (E-49)

| Example | —R₁ | —R₂ | MS Found (MH+) |
|---|---|---|---|
| 139 | Et-N(Me)-CH₂- (Me) | 2,6-dichloro-3-methylphenyl | 583 |
| 140 | —OH | 2,6-dichloro-3-methylphenyl | 528 |
| 141 | MeO-CH₂-CH(Me)-NH₂ | 2,6-dichloro-3-methylphenyl | 585 |
| 142 | MeO-CH₂CH₂-N(Me)-N(Me)- | 2,6-dichloro-3-methylphenyl | 599 |

TABLE 24

(E-50)

| Example | —R | MS Found (MH+) |
|---|---|---|
| 143 | Et-NH-Me | 569 |
| 144 | Et-NH-Me | 555 |
| 145 | Et-NH-CH₂CH₂-Me | 583 |
| 146 | Et-N(Et)-Me (Et) | 597 |

TABLE 25

(E-51)

| Example | —R₁ | —R₂ | MS Found (MH+) |
|---|---|---|---|
| 147 | Et-NH-CH₂-Me | (S)-CH₂CH(Me)Me | 625 |
| 148 | Et-NH-CH₂-Me | (R)-CH₂CH(Me)Me | 625 |
| 149 | Et-NH-CH₂-Me | Et | 597 |
| 150 | Et-NH-Me | Et | 583 |
| 151 | Et-NH-Me | CH(Me)Me | 597 |

TABLE 25-continued (E-51)

| Example | —R₁ | —R₂ | MS Found (MH+) |
|---|---|---|---|
| 152 | EtNH-Me | sec-Bu (CHMeEt) | 611 |
| 138 | Et₂N-Me | iPr (CHMe₂) | 625 |
| 153 | -OH | Et | 556 |
| 154 | -OH | iPr | 570 |
| 155 | MeOCH₂CH₂-N(Me)- | iPr | 641 |

TABLE 26

(E-52)

| Examples | —R₁ | —R₂ | MS Found (MH+) |
|---|---|---|---|
| 156 | EtNH-Et | iPr | 611 |
| 157 | EtNH-Me | cyclopentyl | 623 |

TABLE 26-continued (E-52)

| Examples | —R₁ | —R₂ | MS Found (MH+) |
|---|---|---|---|
| 158 | EtNH-Me | sec-Bu | 611 |
| 159 | EtNHCH₂CH₂-Me | iPr | 625 |

TABLE 27

(E-53)

| Example | —R₁ | —R₂ | MS Found (MH+) |
|---|---|---|---|
| 160 | 1,2-dimethylimidazol-2-yl (Me, N-Me imidazole) | —H | 610 |
| 161 | 2-ethyl-1-methylimidazolyl | —H | 624 |
| 162 | 1-methylimidazolyl (N-CH₂-) | iPr | 638 |

TABLE A (E-54)

Structure: 1-methyl-3-(4-substituted-phenyl)quinazoline-2,4-dione core with 2,6-dichlorobenzamide and ester linkage, R1 at 6-position, R2 as ester group.

| Example | —R₁ | —R₂ | MS Found (MH+) |
|---|---|---|---|
| 163 | —CH₂NHMe | cyclopentyl | 623 |
| 164 | —CH₂NHMe | —CH(Me)CH₂Me (S) | 611 |
| 165 | —CH₂NHMe | —CH₂CH(Me)Me | 625 |
| 166 | —CH₂CH₂NHMe | —CH₂CH(Me)Me | 639 |
| 167 | —CH₂CH₂NHMe | —CH(Me)CH₂CH₂Me (S) | 639 |
| 168 | —CH₂CH₂NHMe | —CH(Me)CH₂CH₂Me (R) | 639 |
| 169 | —CH₂CH₂NHMe | —CH(Me)CH(Me)Me | 625 |
| 170 | —CH₂CH₂NHMe | cyclohexyl | 651 |
| 171 | —CH₂CH₂NHMe | —CH(Me)CH₂OMe | 641 |
| 172 | —CH₂CH₂NHMe | —CH(Me)CH₂OMe (S) | 641 |
| 173 | —CH₂CH₂NHMe | —CH(Me)CH₂OMe (R) | 641 |

TABLE B (E-55)

Structure: 1-methyl-3-(4-substituted-phenyl)quinazoline-2,4-dione core with 2,6-dichlorobenzamide and isopropyl ester, —CH₂R at 6-position.

| Example | —R | MS Found (MH+) |
|---|---|---|
| 174 | —NHMe | 583 |
| 175 | —NH-cyclopropyl | 623 |
| 176 | —NH-cyclobutyl | 637 |
| 177 | —NHCH(Me)Me | 625 |
| 178 | —NHCH₂CH(Me)Me | 639 |
| 179 | —NHCH₂CH(Me)CH₂Me | 653 |
| 180 | —NHCH₂-cyclopropyl | 637 |
| 181 | —NHCH(Me)CH(Me)Me | 639 |
| 182 | —N(Me)CH(Me)Me with extra Me | 639 |
| 183 | —N(Me)CH₂CH(Me)Me | 653 |

TABLE C
(E-56)
| Example | —R | MS Found (MH+) |
|---|---|---|
| 184 | 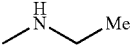 | 615 |
| 185 |  | 629 |
| 186 | 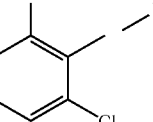 | 643 |
TABLE D
(E-57)
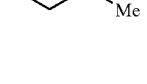
| Example | —R1 | —R2 | MS Found (MH+) |
|---|---|---|---|
| 187 | 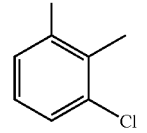 |  | 577 |
| 188 | 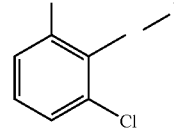 | 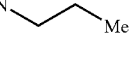 | 605 |
| 189 | 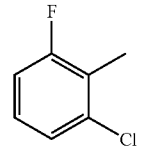 |  | 581 |
TABLE D-continued
(E-57)
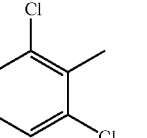
| Example | —R1 | —R2 | MS Found (MH+) |
|---|---|---|---|
| 190 |  |  | 609 |
TABLE E-1
(E-58)
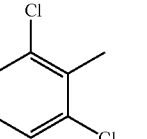
| Example | —R1 | —R2 | —R3 | MS Found (MH+) |
|---|---|---|---|---|
| 191 |  |  | —H | 541 |
| 192 | 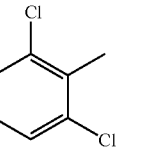 |  | —H | 581 |
| 193 |  | (see R2) | —H | 595 |

TABLE E-1-continued
(E-58)
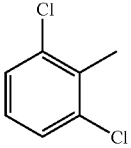
| Example | —R₁ | —R₂ | —R₃ | MS Found (MH+) |
|---|---|---|---|---|
| 194 | 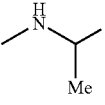 | 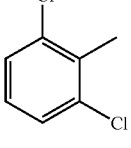 | —H | 583 |
| 195 | 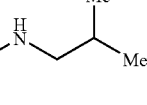 | 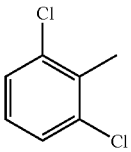 | —H | 597 |
| 196 | 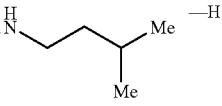 | 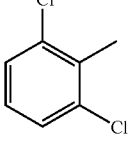 | —H | 611 |
| 197 | 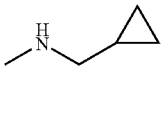 | 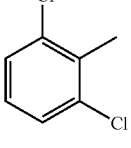 | —H | 595 |
| 198 | 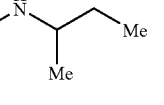 | 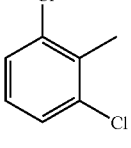 | —H | 597 |
| 199 | 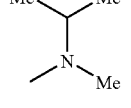 | 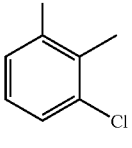 | —H | 597 |
| 200 | 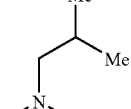 | 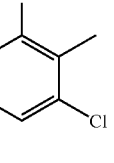 | —H | 611 |
TABLE E-1-continued
(E-58)
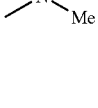
| Example | —R₁ | —R₂ | —R₃ | MS Found (MH+) |
|---|---|---|---|---|
| 201 | 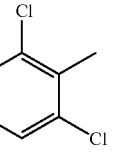 | 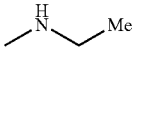 | —F | 573 |
| 202 | 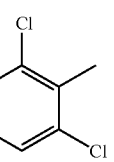 | 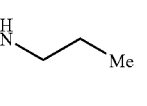 | —F | 587 |
| 203 | 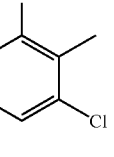 | 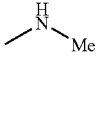 | —F | 601 |
| 204 | 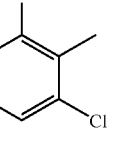 | 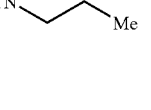 | —H | 577 |
| 205 | 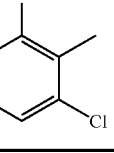 | 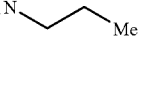 | —H | 605 |
| 206 |  |  | —H | 609 |

TABLE F (E-59)

[Structure: N-methyl quinazoline-2,4-dione with 2,6-dichlorobenzamide phenylalanine ester, 6-position bearing propyl-NR2 chain, ester OR1]

| Example | —R₁ | —R₂ | MS Found (MH+) |
|---|---|---|---|
| 207 | —H | Me | 583 |
| 208 | —H | Et | 597 |
| 209 | —H | n-Pr | 611 |
| 210 | iPr | Me | 625 |
| 211 | iPr | Et | 639 |
| 212 | iPr | n-Pr | 653 |

TABLE G (E-60)

[Structure: N-methyl quinazoline-2,4-dione with 2,6-dichlorobenzamide phenylalanine ester, 6-position bearing O-propyl-R1 chain, ester OR2]

| Example | Method | —R₁ | —R₂ | MS Found (MH+) |
|---|---|---|---|---|
| 213 | A | NHMe(ethyl) | iPr | 641 |
| 214 | A | NHMe(propyl) | iPr | 655 |
| 215 | B | N(Et)Me(ethyl) | iPr | 669 |
| 216 | B | NMe₂(ethyl) | iPr | 655 |
| 217 | C | pyrrolidinyl | iPr | 667 |
| 218 | B | NHMe | iPr | 627 |
| 219 | — | NHMe(ethyl) | —H | 599 |
| 220 | — | NHMe(propyl) | —H | 613 |
| 221 | — | N(Et)Me(ethyl) | —H | 627 |
| 222 | — | NMe₂(ethyl) | —H | 613 |
| 223 | — | pyrrolidinyl | —H | 625 |
| 224 | — | NHMe | —H | 585 |

TABLE H
(E-61)
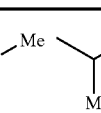
| Example | Method | —R₁ | —R₂ | MS Found (MH+) |
|---|---|---|---|---|
| 225 | B | NHMe (NMe) | iPr (Me, Me) | 641 |
| 226 | — | NHMe | — | 599 |
| 227 | — | NMe₂ (NMe, Me) | — | 613 |
The compounds of Examples 228 to 236
(E-62)
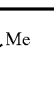
(E-63)
(E-64)
(E-65)
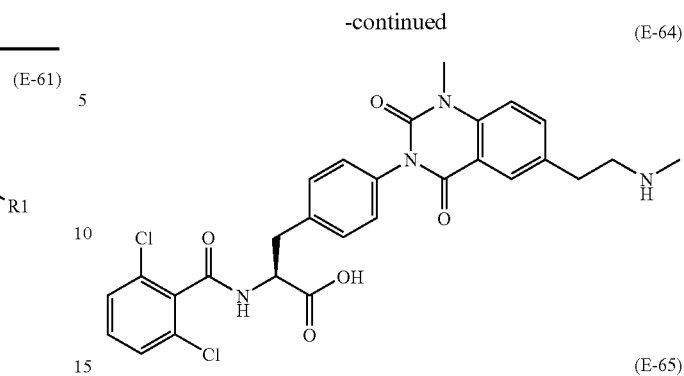
(E-66)
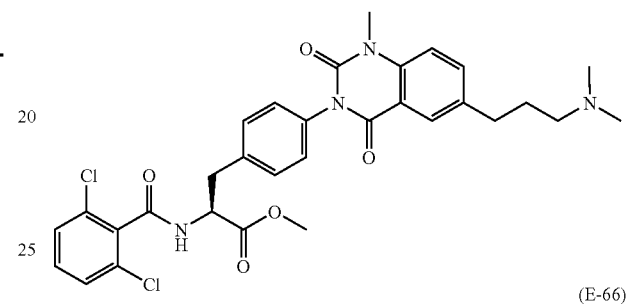
(E-67)
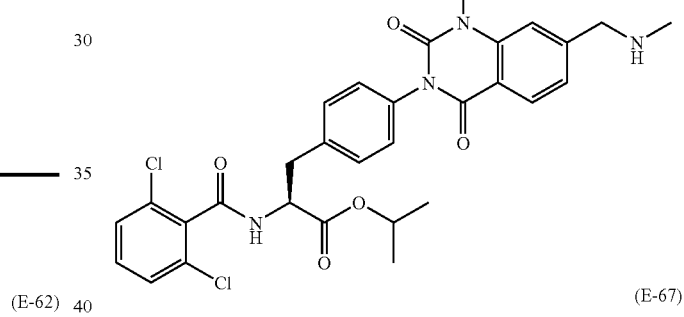
(E-68)
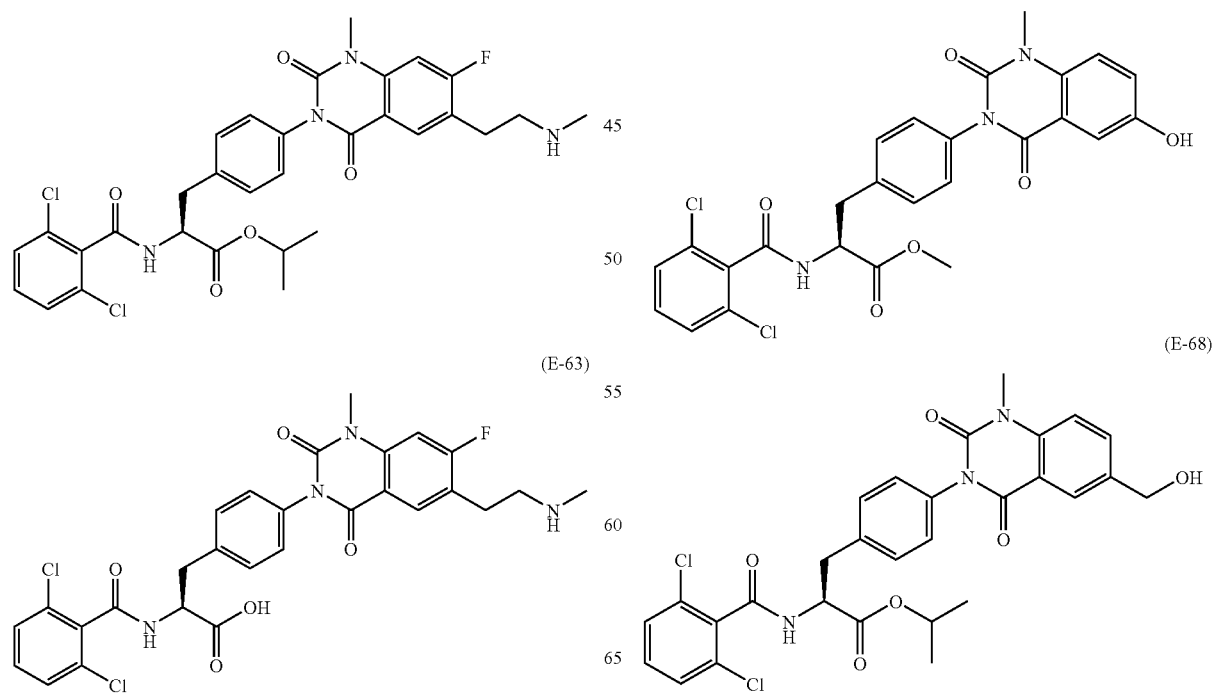

Further, the compounds indicating the following chemical structural formulae are easily produced by the same methods as those of above Examples or the synthesizing methods, or by applying some modifications which are self-explanatory to one skilled in the art to those methods.

TABLE 28-continued
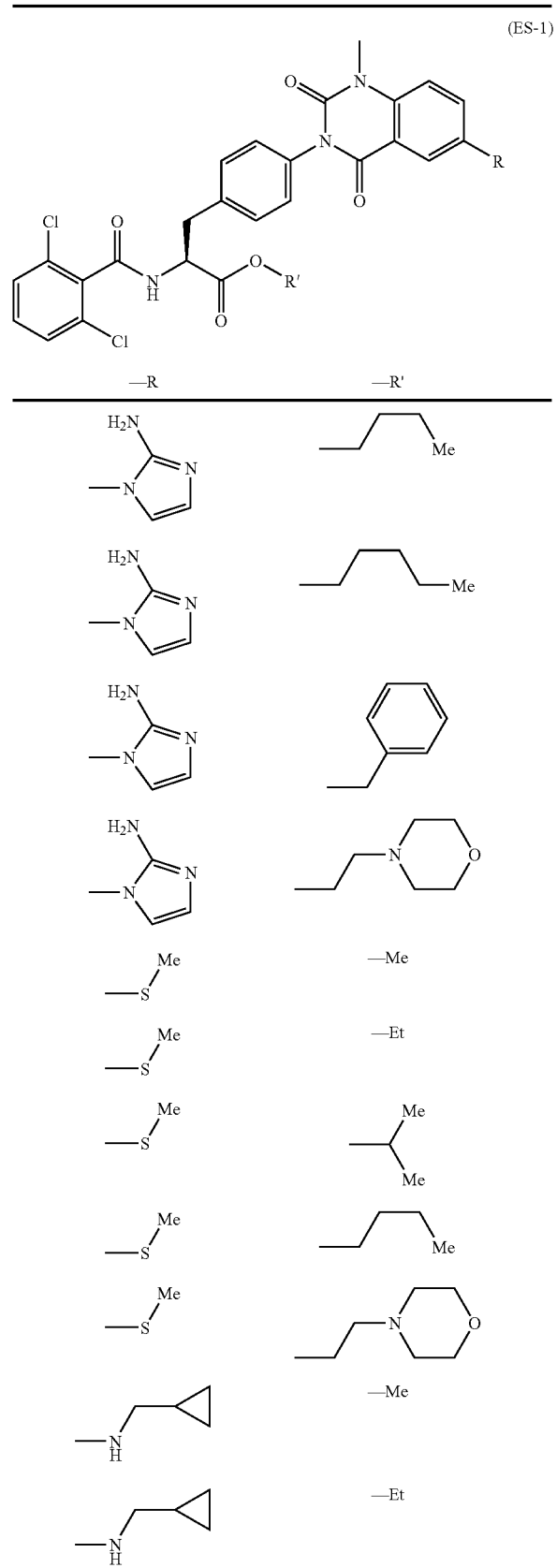
TABLE 28-continued
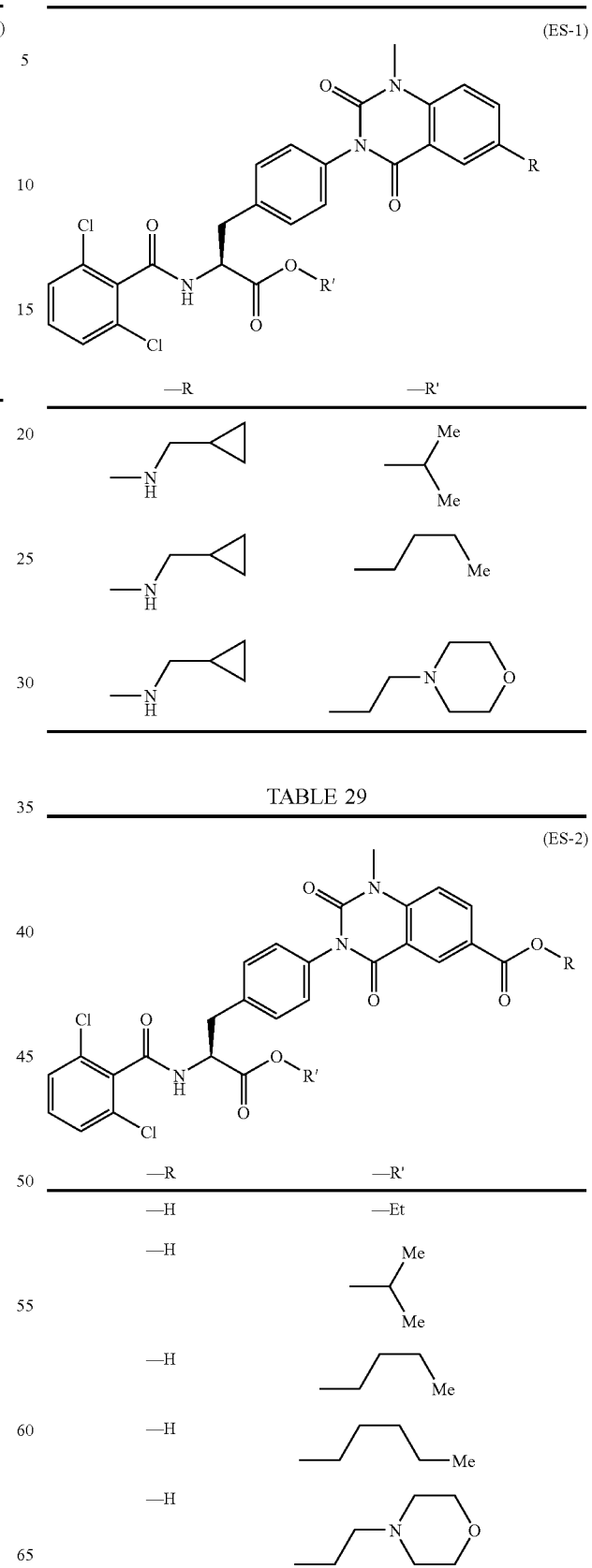

TABLE 29-continued (ES-2)

| —R | —R' |
|---|---|
| —Me | —Et |
| —Me | isopropyl (CH(Me)Me) |
| —Me | n-butyl (CH2CH2CH2Me) |
| —Me | 3-morpholinopropyl |
| —Et | —Me |
| —Et | —Et |
| —Et | isopropyl (CH(Me)Me) |
| —Et | n-butyl (CH2CH2CH2Me) |
| —Et | 3-morpholinopropyl |
| —H | benzyl (CH2Ph) |

TABLE 30

(ES-3)

—R

—Me
—Et isopropyl (CH(Me)Me)

n-butyl (CH2CH2CH2Me)

3-morpholinopropyl

TABLE 31

(ES-4)

—R

—Me
—Et isopropyl (CH(Me)Me)

n-butyl (CH2CH2CH2Me)

3-morpholinopropyl

TABLE 32

TABLE 32-continued
(ES-5)
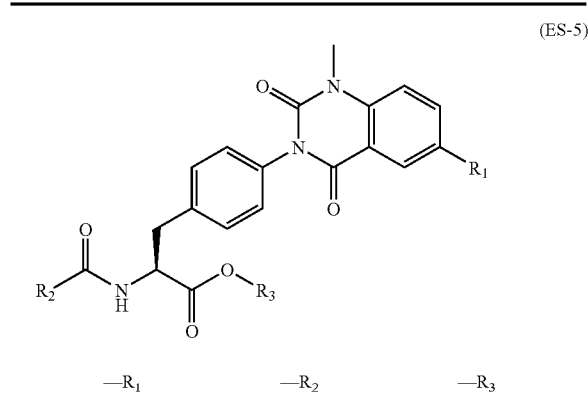
| —R₁ | —R₂ | —R₃ |
|---|---|---|
| 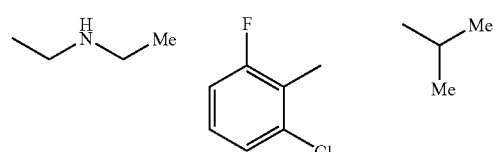 | | |
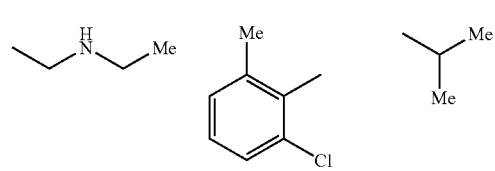
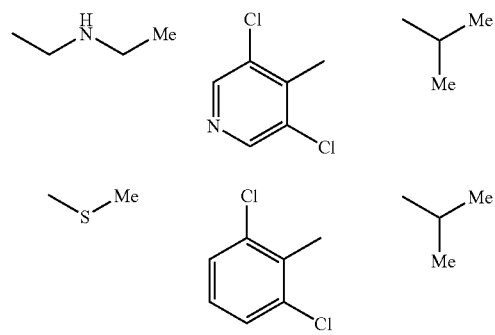
TABLE 33
(ES-6)
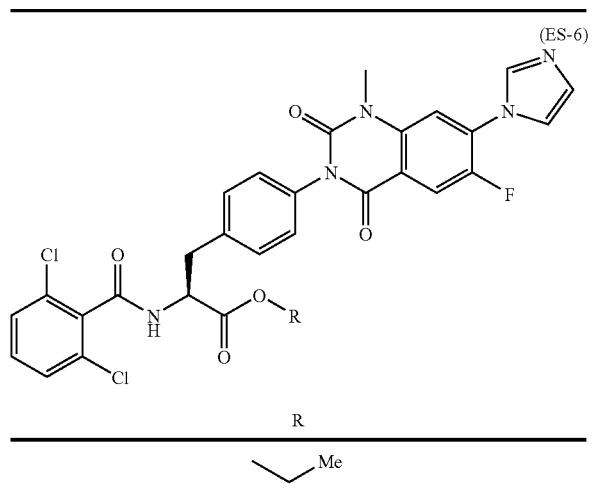
| R |
|---|
| 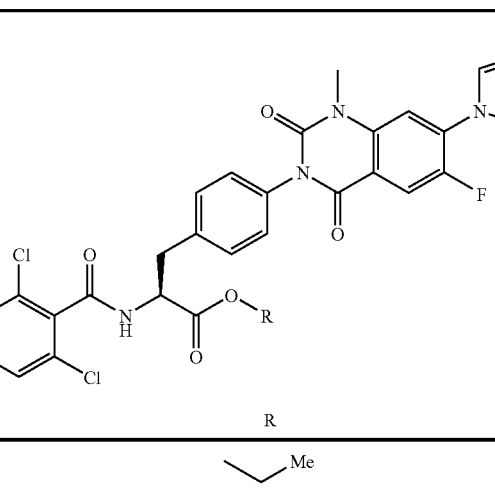 |
TABLE 33-continued
(ES-6)
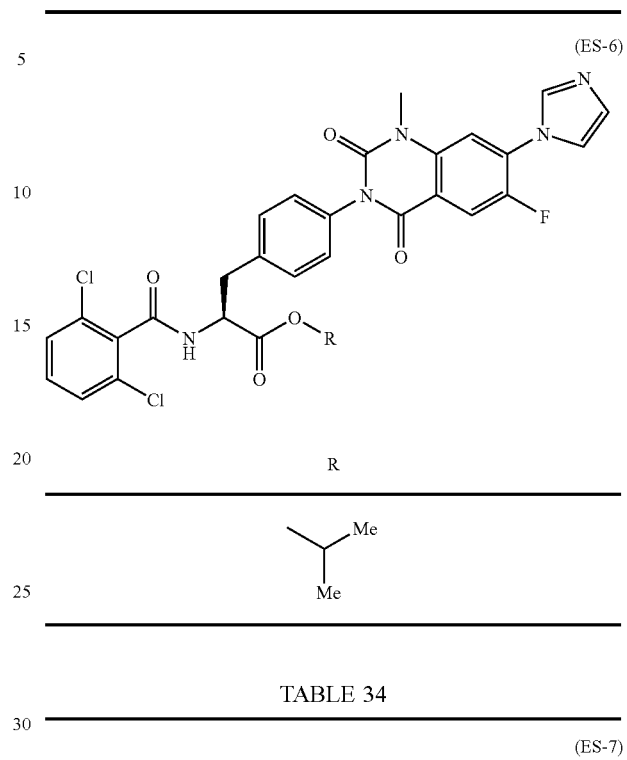
| R |
|---|
TABLE 34
(ES-7)
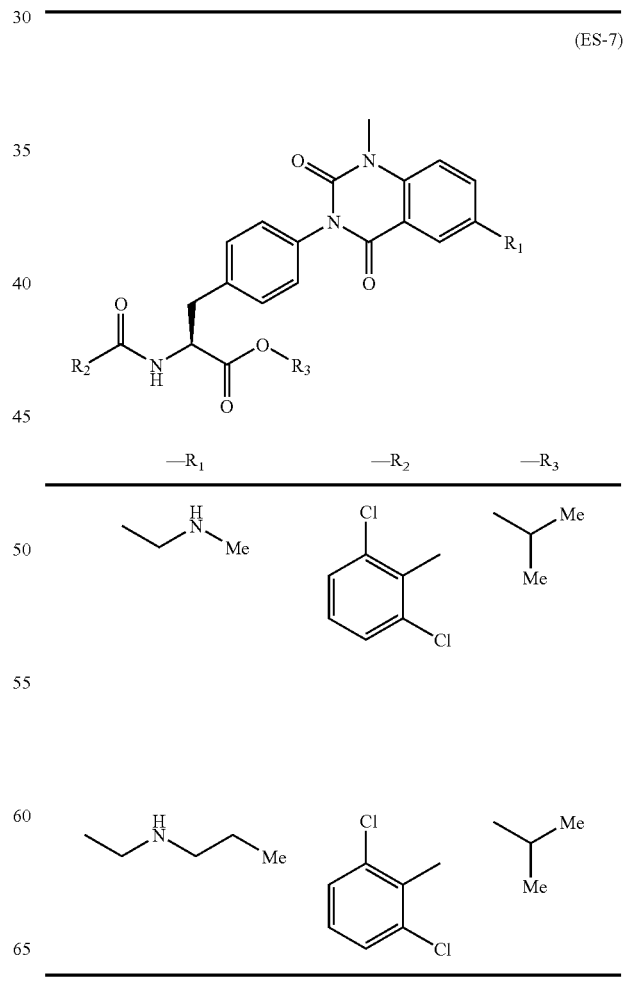
| —R₁ | —R₂ | —R₃ |
|---|---|---|
| 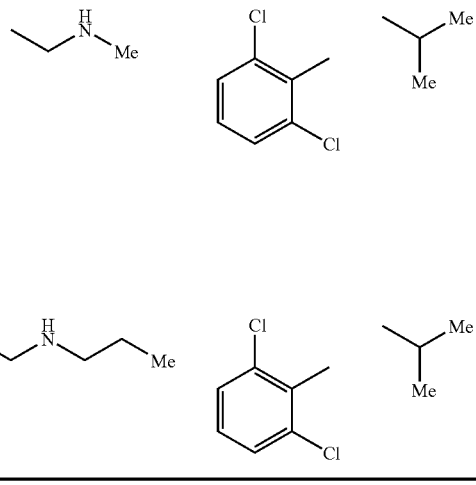 | | |

TABLE 35
(ES-8)
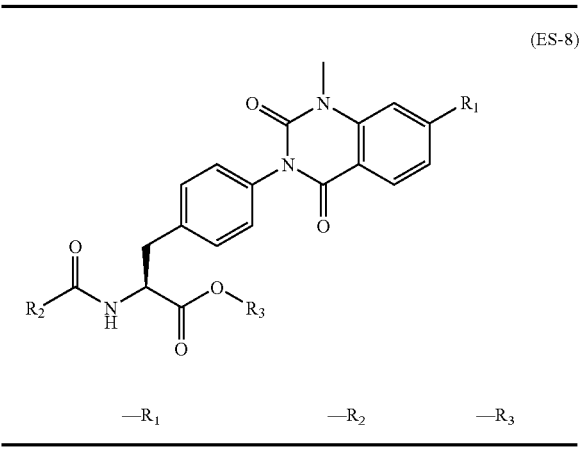
| —R₁ | —R₂ | —R₃ |
|---|---|---|
| 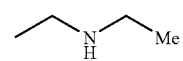 | 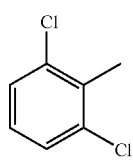 |  |
| 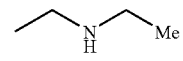 | 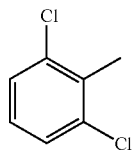 |  |
| 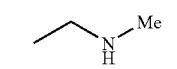 | 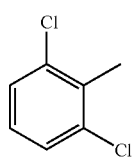 |  |
| 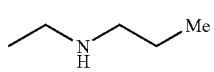 | 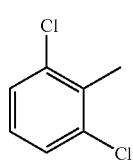 |  |
| 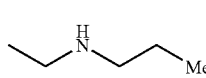 | 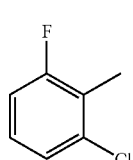 |  |
| 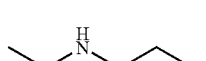 | 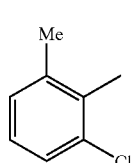 |  |
TABLE 36
(ES-9)
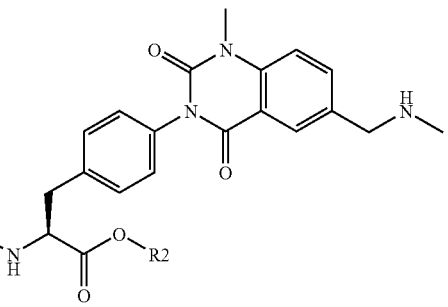
| —R1 | —R2 |
|---|---|
| 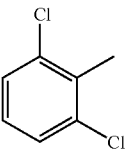 | 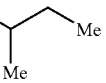 |
| 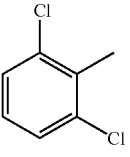 | 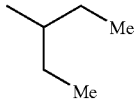 |
| 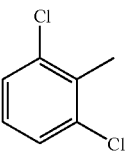 | 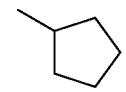 |
| 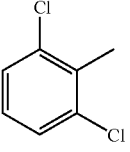 | 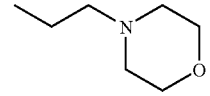 |
| 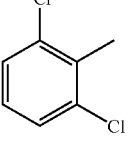 | 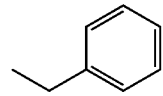 |
| 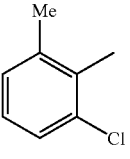 | 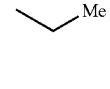 |
| 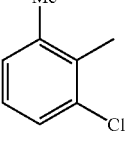 | 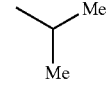 |

TABLE 36-continued
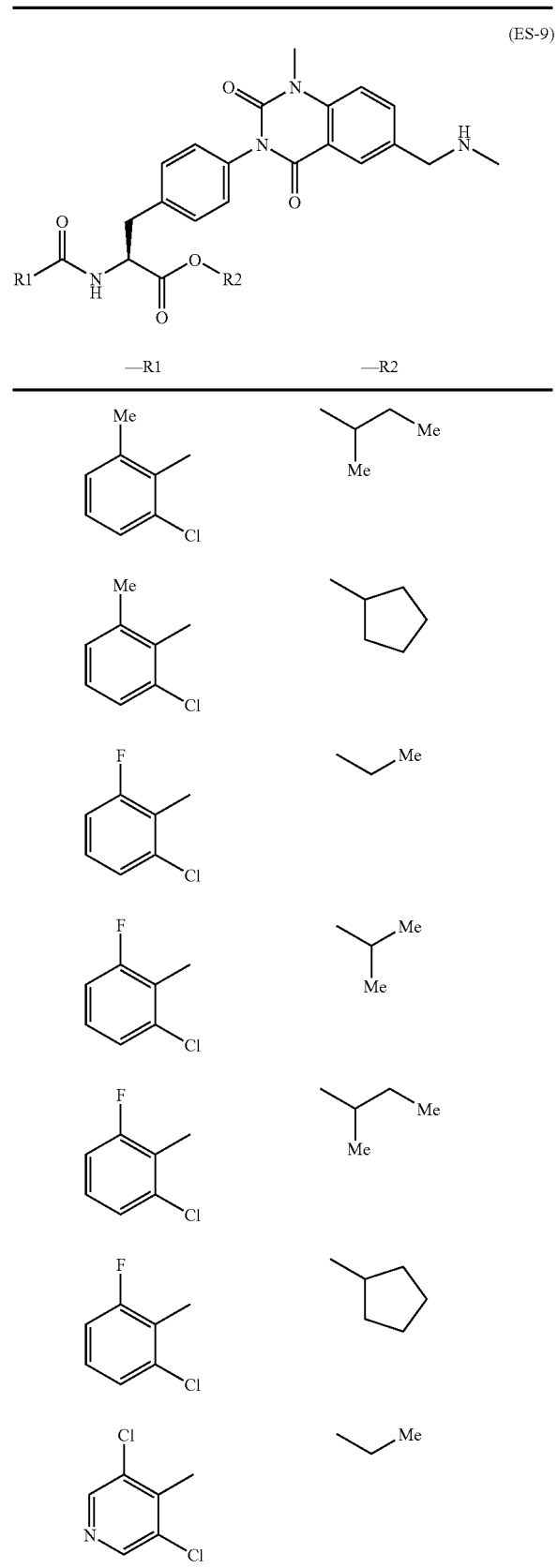
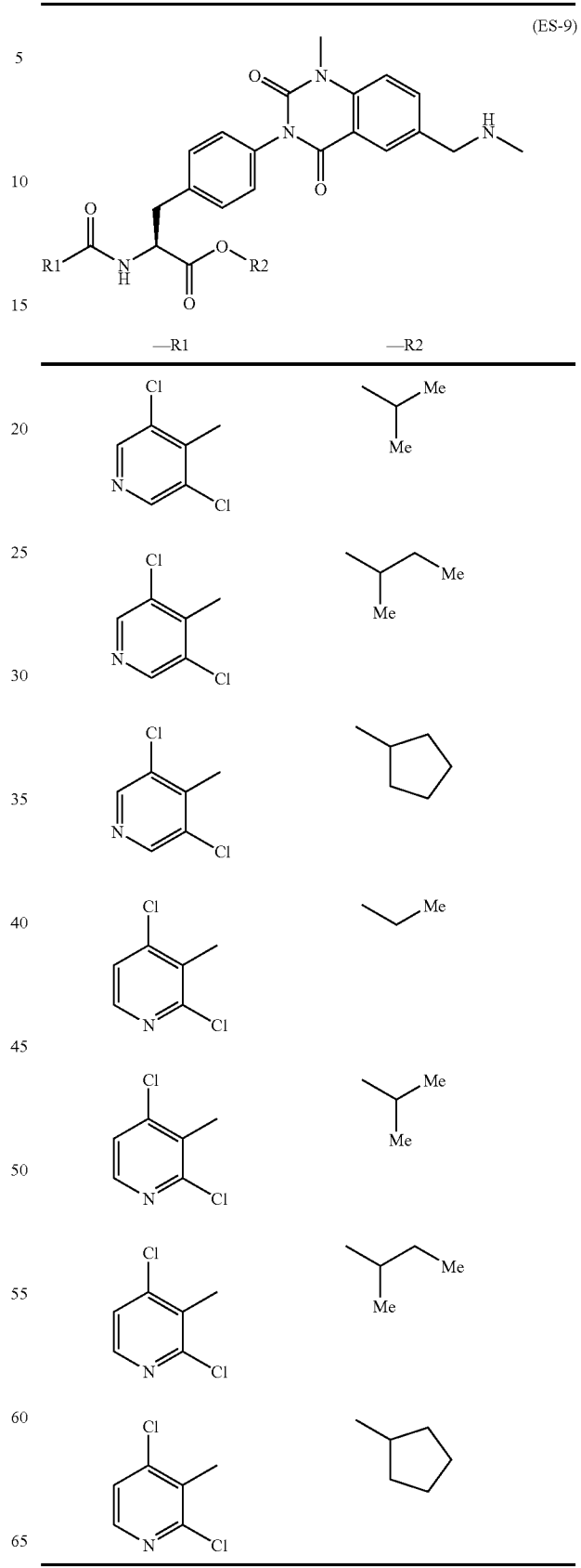

TABLE 37
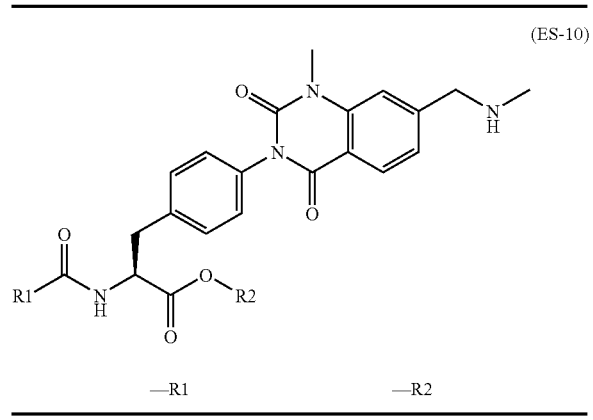
(ES-10)
TABLE 37-continued
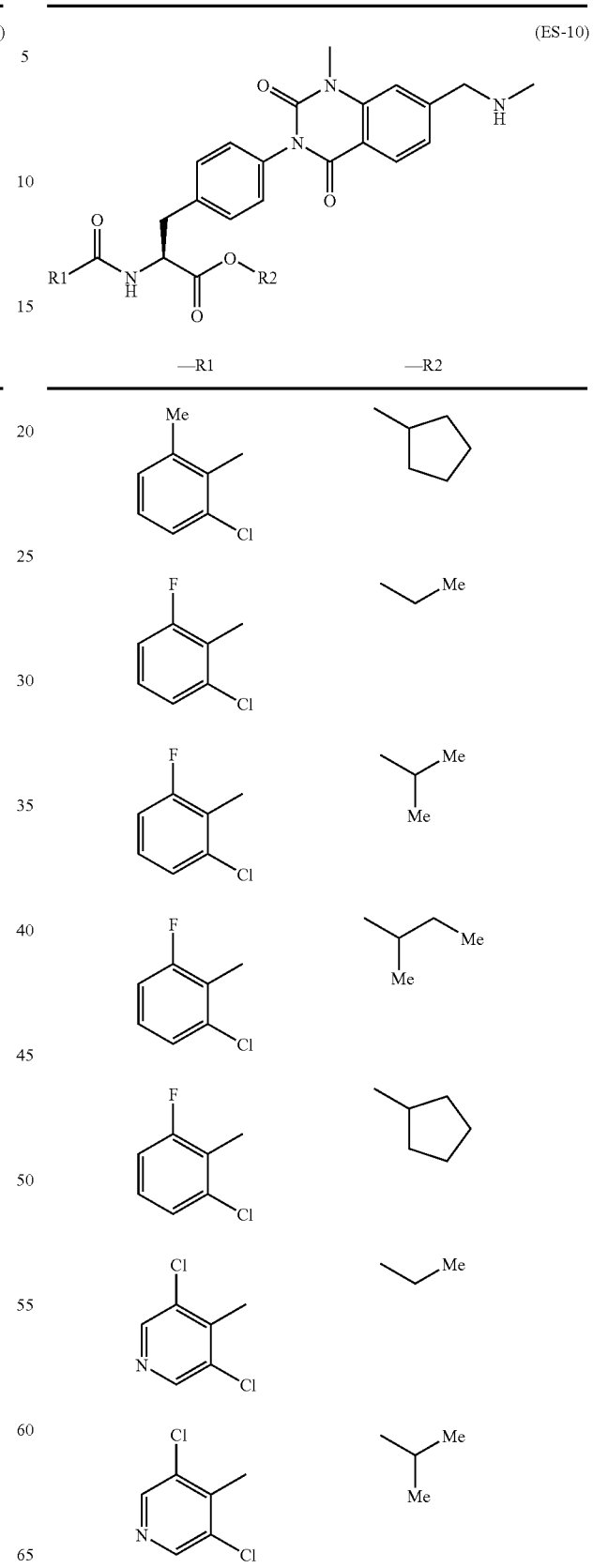

TABLE 37-continued (ES-10)

| —R1 | —R2 |
|---|---|
| 3,5-dichloro-4-methylpyridinyl | isobutyl (CH2CH(Me)Me) |
| 3,5-dichloro-4-methylpyridinyl | cyclopentyl |
| 2,4-dichloro-3-methylpyridinyl | ethyl (CH2Me) |
| 2,4-dichloro-3-methylpyridinyl | isopropyl (CH(Me)Me) |
| 2,4-dichloro-3-methylpyridinyl | isobutyl (CH2CH(Me)Me) |
| 2,4-dichloro-3-methylpyridinyl | cyclopentyl |

TABLE 38

(ES-11)

| —R1 | —R2 |
|---|---|
| —H | —(CH2)3—O—Me |
| —H | —(CH2)3—OH |
| —H | —(CH2)3—N(Me)Me |
| —H | —(CH2)3-morpholinyl |
| —H | —CH2CH(Me)-morpholinyl |
| —H | —Et |
| —Me | —(CH2)3—O—Me |
| —Me | —(CH2)3—OH |
| —Me | —(CH2)3—N(Me)Me |
| —Me | —(CH2)3-morpholinyl |
| —Me | —CH2CH(Me)-morpholinyl |
| —Me | —Et |
| —Me | —CH(Me)Me |
| —Et | —(CH2)3—O—Me |

TABLE 38-continued
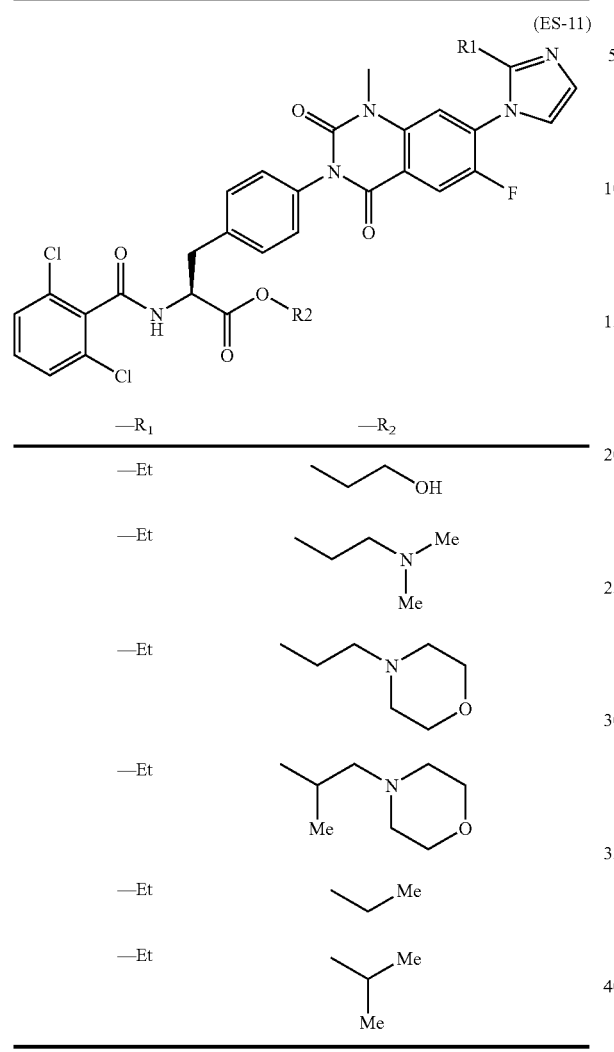
(ES-11)
| —R₁ | —R₂ |
|---|---|
| —Et | propanol (—CH₂CH₂CH₂OH) |
| —Et | —CH₂CH₂CH₂N(Me)Me |
| —Et | —CH₂CH₂CH₂-morpholine |
| —Et | —CH₂CH(Me)-morpholine |
| —Et | —CH₂CH₂Me |
| —Et | —CH(Me)Me |
TABLE 39
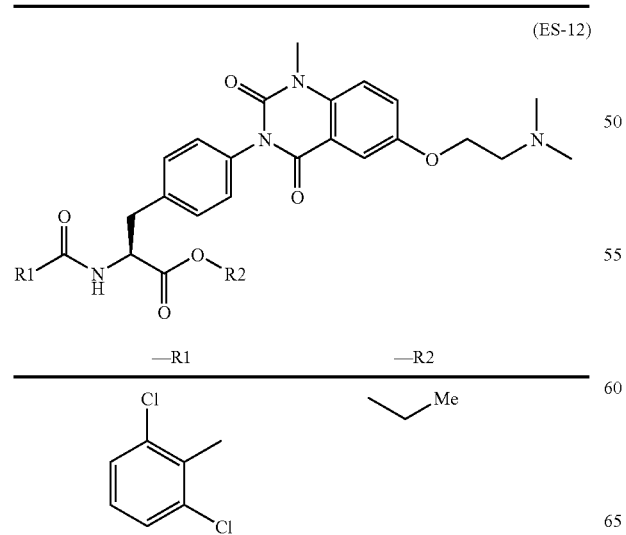
(ES-12)
| —R1 | —R2 |
|---|---|
| 2,6-diCl-phenyl | —CH₂CH₂Me |
TABLE 39-continued
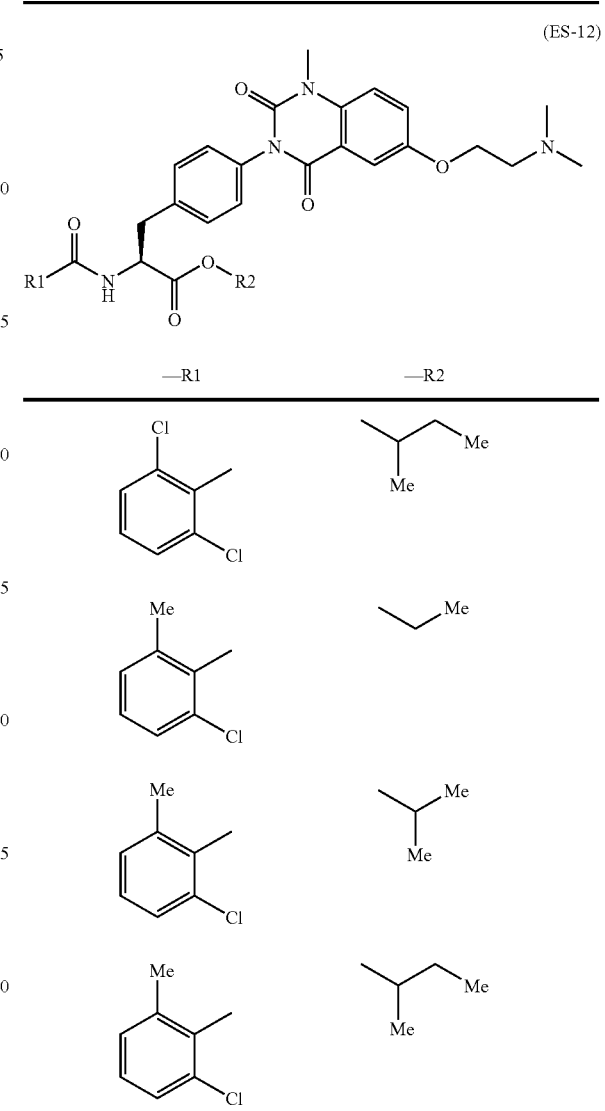
(ES-12)
| —R1 | —R2 |
|---|---|
| 2,6-diCl-phenyl | —CH₂CH(Me)Me |
| 2,6-diCl-phenyl | —CH₂Me |
| 2,6-diCl-phenyl | —CH(Me)Me |
| 2,6-diCl-phenyl | —CH₂CH(Me)Me |
| 2-F-6-Cl-phenyl | —CH₂Me |
| 2-F-6-Cl-phenyl | —CH(Me)Me |
| 2-F-6-Cl-phenyl | —CH₂CH(Me)Me |

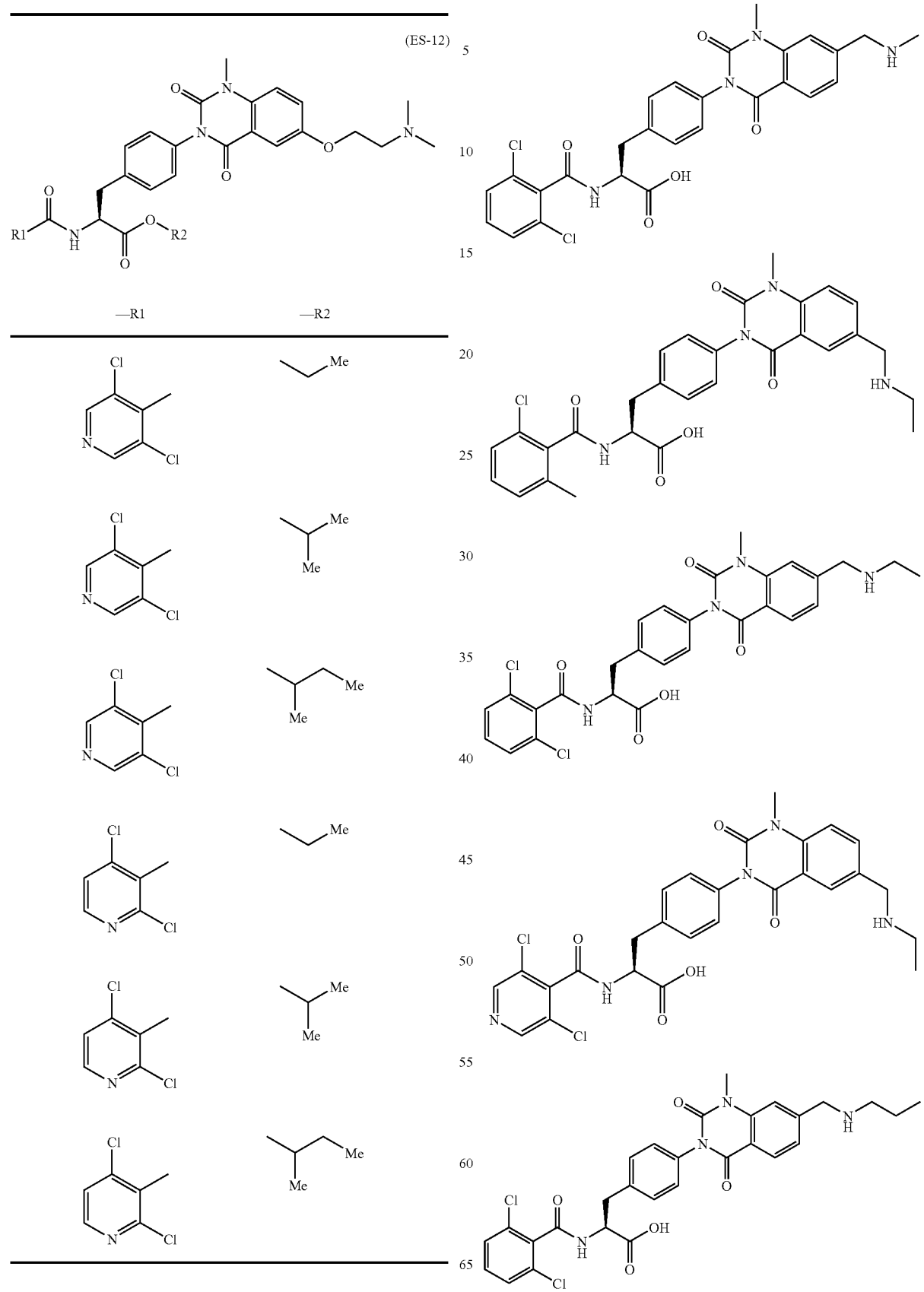

161
-continued
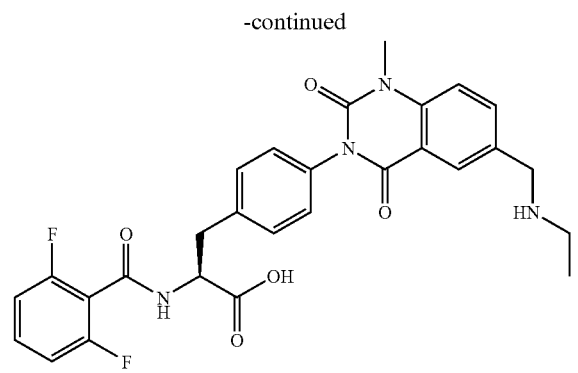
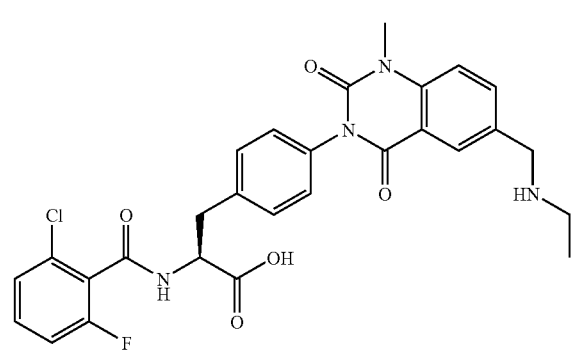
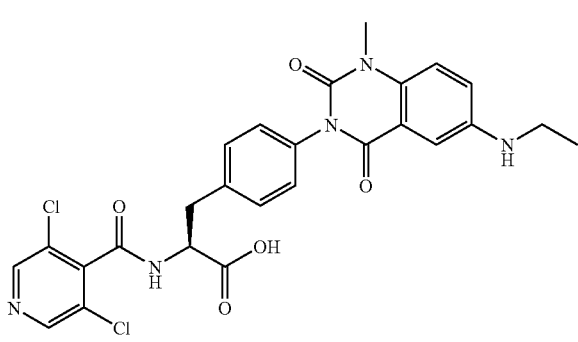
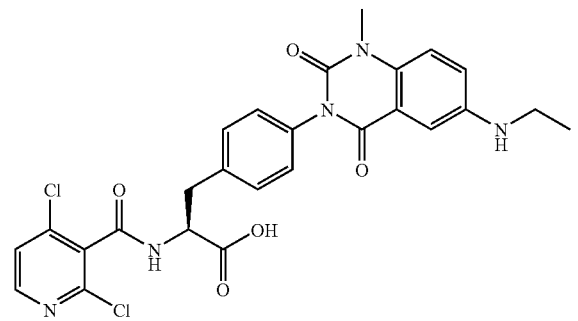
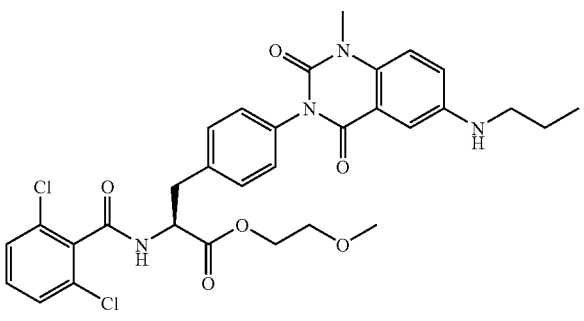
162
-continued
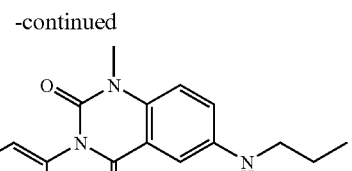
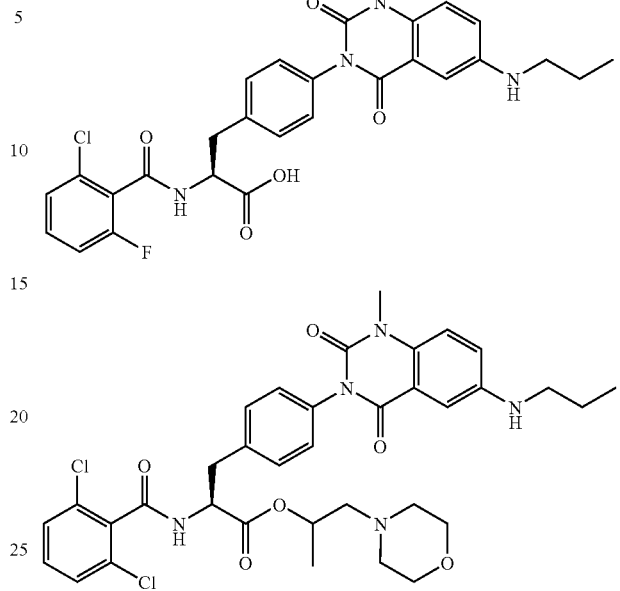
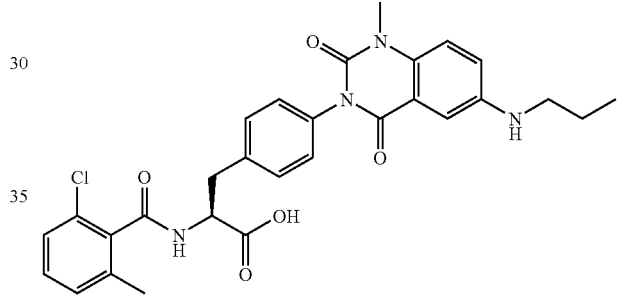
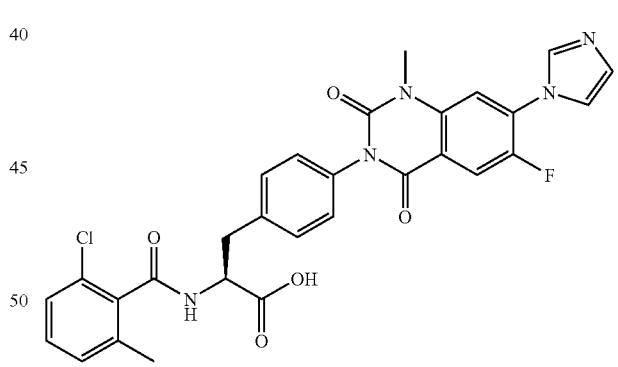
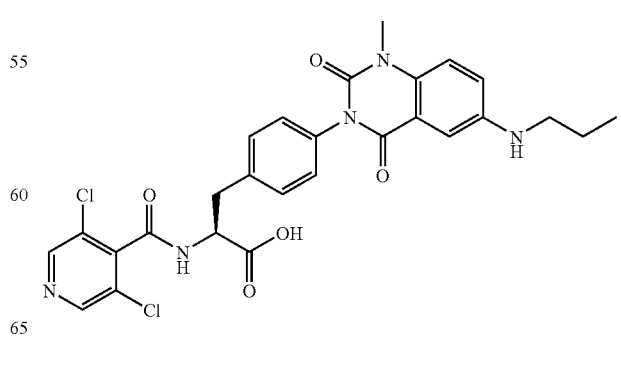

163
-continued
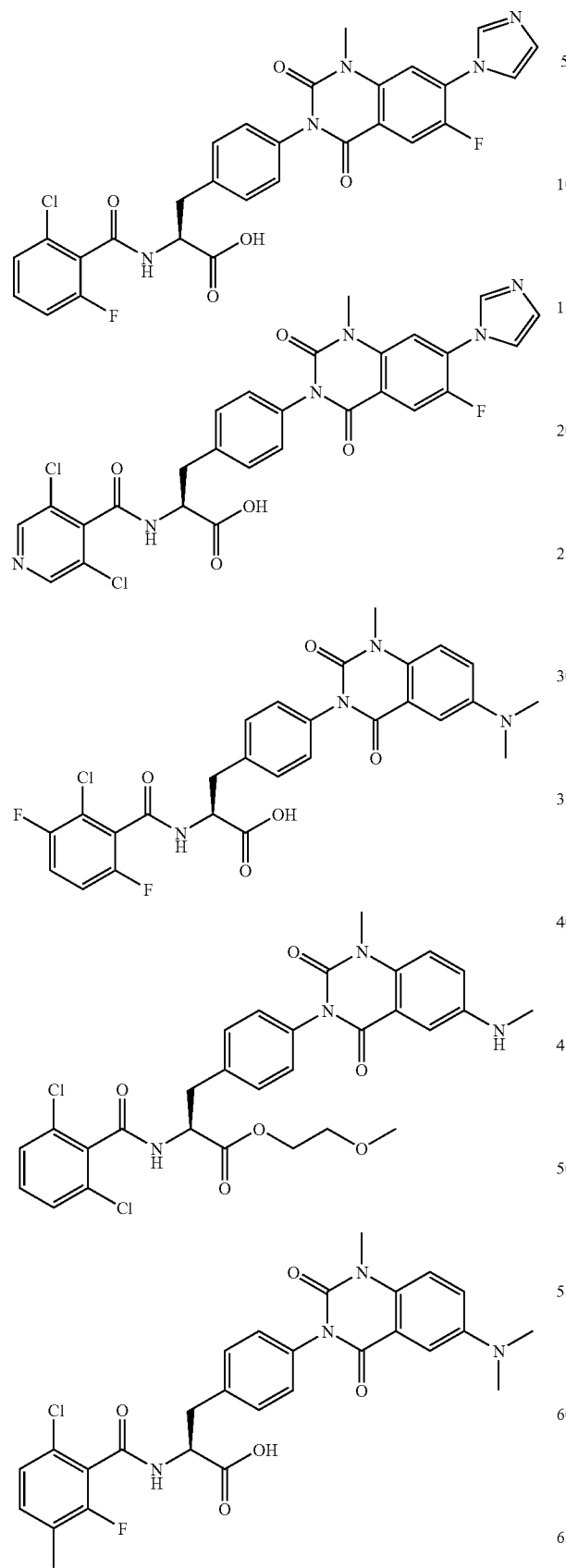
164
-continued
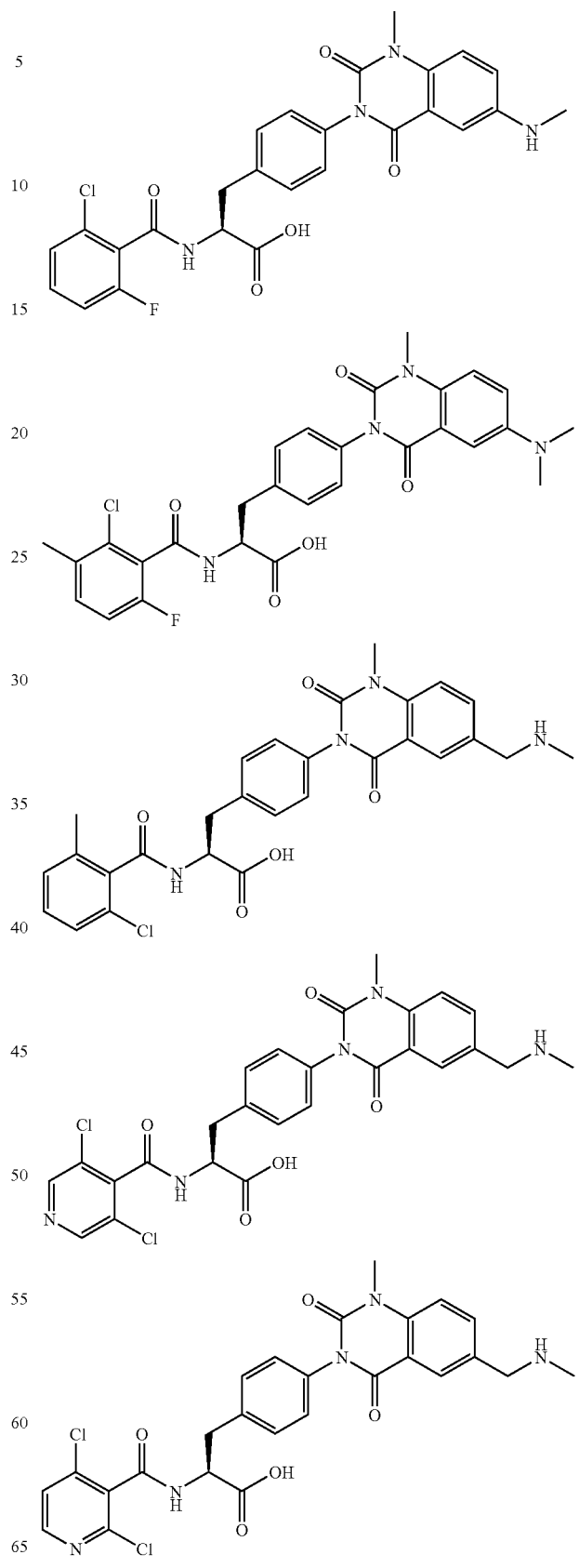

165
-continued
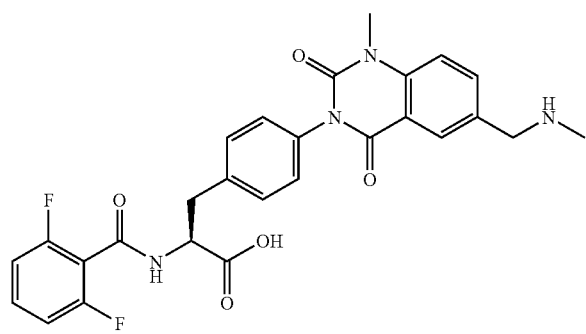
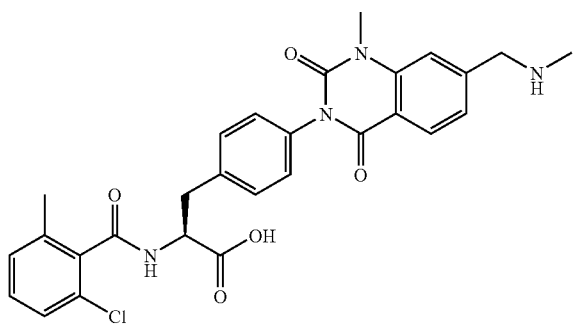
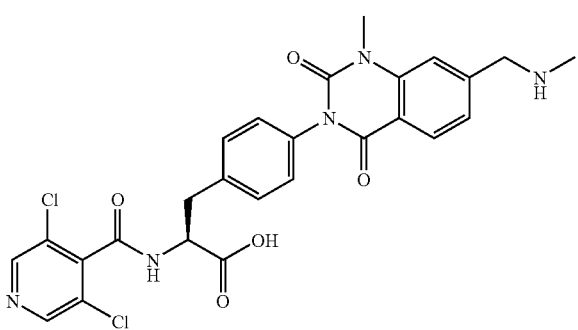
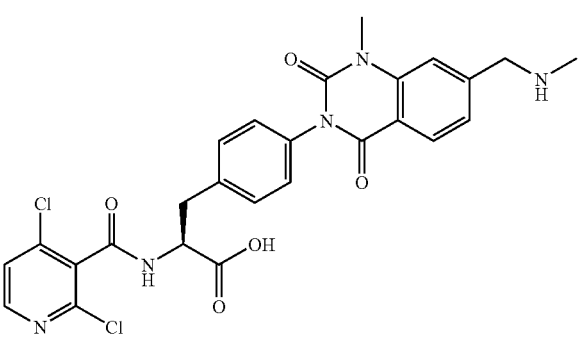
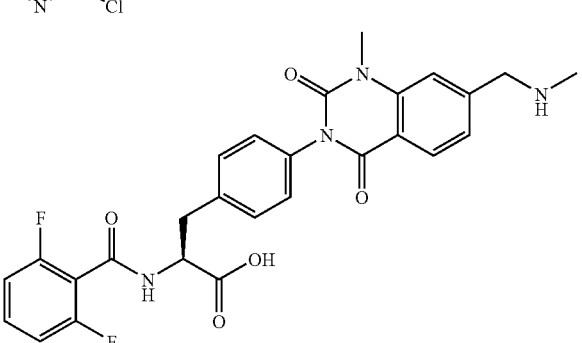
166
-continued
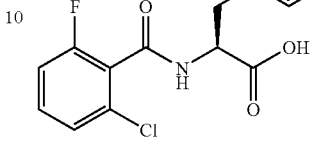
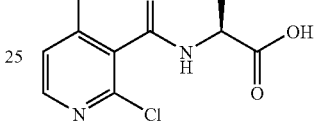
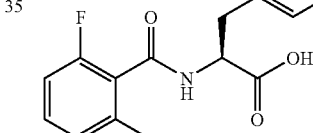
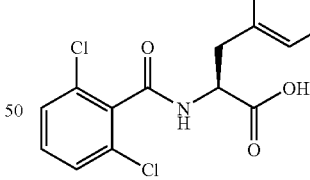
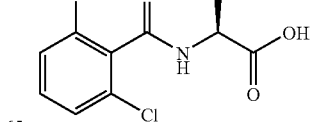

-continued

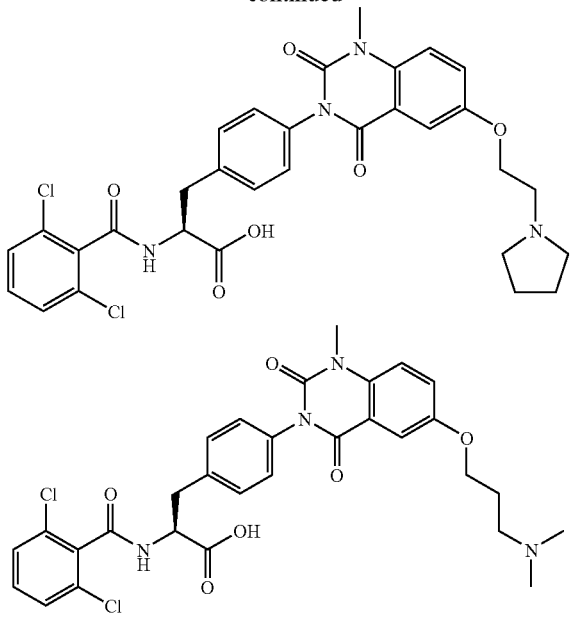

Test Example 1

Assay of Antagonistic Activity to VCAM-1/α4β1 Integrin Binding Under the Existence of Blood Serum The capacity of a test substance antagonistic to the binding of cell strain of human T cells, Jurkat (ATCC TIB-152), known to express integrin α4β1, to VCAM-1 was determined.

Fifty μl/well of a solution (500 ng/ml) of recombinant human VCAM-1/Fc (R & D systems) diluted with buffer A (0.1 M NaHCO$_3$, pH 9.6) was added to a 96-well microtiter plate (Nunc Maxisorp). After the incubation at 4° C. overnight and washing once with PBS, a buffer (buffer B) obtained by diluting Block Ace (Snow Brand Milk Products Co., Ltd.) with PBS to ½ concentration was added in an amount of 150 μl/well. After the incubation at room temperature for 2 hours, buffer B was removed and the plate was washed with PBS once.

Jurkat cells were washed with Dulbecco modified Eagle medium (SIGMA, hereinafter referred to as "DMEM") once. Then, the cells were again suspended in a binding buffer (DMEM containing 20 mM HEPES, 0.1% BSA, 2 mM MnCl$_2$ and 50% human blood serum (Sigma)) to become 1×10$^6$ cells/mL.

Sixty μl of a test substance of various concentrations obtained by the dilution with the binding buffer was added to a round-bottom, 96-well plate (IWAKI). Immediately thereafter, 60 μl of the Jurkat cells (1×10$^6$ cells/ml) were added thereto and shaken on a plate shaker (IKA-Labortechnik, IKA-SCHUTTLER MTS-4) at 1000 rpm for 10 seconds. In 120 μL of the cell suspension to which the test substance was added, each 100 μL thereof was transferred on the VCAM-1/Fc-coated plate and incubated in dark place at room temperature for 60 minutes. After the shaking on the plate shaker at 1000 rpm for 30 seconds, the solution was immediately removed. Then, the unbound cells were removed by washing them with PBS once. A buffer C (PBS containing 0.82% Triton X-100) was added to the plate in an amount of 70 μL/well. After the shaking on the plate shaker at 1000 rpm for 5 minutes, the bound Jurkat cells were lysed. After centrifuging the cells on a plate centrifuge (SIGMA 4-15C) at room temperature at 2500 rpm for 5 minutes, 50 μL of supernatant thereof was transferred to a 96-well microtiter plate (Nunc Maxisorp). Each 50 μL of Substrate Buffer (Promega, CytoTox 96 Non-Radioactive Cytotoxicity Assay) was added thereto, shaken on a plate shaker at 1000 rpm for 10 seconds and reacted in dark place at room temperature for 30 minutes. Then, each 50 μL of Stop Solution (Promega, CytoTox 96 Non-Radioactive Cytotoxicity Assay) was added thereto and shaken on a plate shaker at 1000 rpm for 10 seconds. Its absorbance of 490 nm was determined with a plate reader (Molecular Devices, Vmax). The absorbance thus obtained detects an activity of lactate dehydrogenase (LDH) dissolved in the supernatant of each well. Namely, the absorbance is proportional to the number of remaining Jurkat cells on the plate via the binding to VCAM-1. The test was conducted in duplicate and the binding rate of each test substance in various concentrations was determined while the absorbance of the test substance-free well was determined to be 100% and the absorbance of the Jurkat-cell-free well was determined to be 0%. The concentration for the 50% inhibition of binding, IC$_{50}$, was calculated. The obtained results are shown in Result Table 1.

RESULT TABLE 1

Assay of antagonistic activity to VCAM-1/α 4 β 1 integrin binding (IC$_{50}$, nM)

| Example | IC50[nM] |
|---|---|
| 1 | 1.7 |
| 2 | 22.9 |
| 4 | 14.0 |
| 5 | 10.8 |
| 6 | 8.9 |
| 10 | 15.5 |
| 13 | 5.5 |
| 14 | 5.8 |
| 17 | 22.9 |
| 18 | 11.7 |
| 19 | 23.5 |
| 28 | 13.9 |
| 34 | 10.5 |
| 35 | 7.9 |
| 38 | 12.4 |
| 39 | 6.5 |
| 47 | 15.7 |
| 48 | 3.6 |
| 50 | 15.4 |
| 53 | 23.3 |
| 54 | 14.5 |
| 55 | 14.2 |
| 56 | 13.1 |
| 57 | 16.6 |
| 60 | 25.5 |
| 63 | 10.8 |
| 64 | 12.3 |
| 98 | 18.1 |
| 99 | 11.2 |
| 136 | 10.5 |
| 139 | 8.4 |
| 141 | 12.2 |
| 142 | 14.7 |
| 143 | 7.0 |
| 144 | 4.9 |
| 145 | 3.8 |
| 146 | 7.9 |
| 160 | 9.4 |
| 161 | 16.5 |
| 191 | 12.9 |
| 192 | 17.9 |
| 193 | 8.2 |
| 194 | 6.9 |
| 195 | 6.4 |

RESULT TABLE 1-continued

Assay of antagonistic activity to VCAM-1/α 4 β 1 integrin binding ($IC_{50}$, nM)

| Example | IC50[nM] |
|---|---|
| 196 | 5.3 |
| 197 | 6.3 |
| 198 | 5.7 |
| 199 | 18.0 |
| 208 | 13.4 |
| 209 | 15.2 |
| 219 | 11.9 |
| 220 | 16.9 |
| 221 | 19.7 |
| 222 | 19.5 |
| 223 | 14.6 |
| 224 | 12.4 |
| 226 | 9.2 |
| 229 | 14.7 |
| 230 | 11.7 |
| * | 148.8 |

* is a compound of Example 1 in WO02/16329 (Patent Literature 14).

Test Example 2
Pharmacokinetic Study by Intravenous Administration to a Rat

After the compounds of the present invention wherein R11 to R141 are a hydroxyl group, which were active forms, were weighed by a scale, they were adjusted by dimethylsulfoxide to become 10 mg/mL. Polyethylene glycol 400 and distilled water were added thereto to prepare 1 mg/mL of an administration solution. 1 mg/mL of the administration solution was intravenously administered as a single dose to a Wistar rat in an amount of 1 mL/kg. 1, 5, 10, 30, 60 and 180 minutes later, the drug concentration in the blood plasma obtained by blood drawing from its cervical vein over time under anesthesia was determined with LC/MS. From the obtained results, the area under the plasma concentration time curve from zero to time infinity (AUCinf (iv)) was calculated in accordance with the trapezoidal method of pharmacokinetic analysis. The total body clearance (CLtot, [L/hr/kg]) was calculated as an index of drug disappearance in the blood plasma from a dose [mg/kg] and AUC [μg×hr/mL] in accordance with the formula: CLtot=Dose÷AUCinf(iv). The obtained results are shown in Result Table 2.

RESULT TABLE 2

Total body clearance in intravenous administration to a rat (CLtot, [L/hr/kg])

| Example | CLtot [L/hr/kg]) |
|---|---|
| 7 | 0.1 |
| 8 | 0.22 |
| 12 | 0.21 |
| 28 | 0.1 |
| 34 | 0.31 |
| 37 | 0.33 |
| 40 | 0.19 |
| 46 | 0.33 |
| 54 | 0.27 |
| 59 | 0.32 |
| 99 | 0.23 |
| 135 | 0.17 |
| 137 | 0.24 |
| * | 1.89 |

* is a compound of Example 1 in WO02/16329 (Patient Literature 14).

Test Example 3
Pharmacokinetic Study by Oral Administration to a Rat

After the compounds of the present invention wherein R11 to R141 are other than hydroxyl group, which were prodrug compounds, were weighed by a scale, they were dissolved by dimethylsulfoxide to become 100 mg/mL. The mixed solution of polyethylene glycol 400: propylene glycol=1:1 was added thereto to prepare 2.5 mg/mL of an administration solution. 2.5 mg/mL of the administration solution was orally administered to a male Wistar rat (7 to 9 weeks age) in an amount of 4 mL/kg. 0.25, 0.5, 1, 2, 4, 6 or 8 hours later, the blood was drawn from its cervical vein under anesthesia with a syringe treated with dichlorvos which is an esterase inhibitor. Then, the blood was transferred to a tube treated with heparin and centrifuged, and the blood plasma was obtained. Acetonitrile containing internal standard substance was added in two parts thereof to the obtained blood plasma and the concentration of corresponding active form wherein R11 to R141 are hydroxyl groups was determined by LC/MS/MS. From the obtained results, the area under the plasma concentration time curve from zero to time infinity of the active form, namely, AUCinf (po) was calculated. Bioavailability (BA) was calculated from AUCinf(iv) of the active form in intravenous administration obtained from Test Example 2 by the following formula:

BA(%)=[AUCinf(po)/Dose(po)]/[AUCinf(iv)/Dose(iv)]×100

AUCinf: the area under the plasma concentration time curve from zero to time infinity of the active form in oral or intravenous administration Dose: oral or intravenous dose (as the active form)

The obtained results are shown in Result Table 3.

RESULT TABLE 3

Pharmacokinetic studies in oral administration to a rat

| Example | BA (%) |
|---|---|
| 124 | 30 |
| 103 | 26 |
| 123 | 13 |
| 111 | 13 |
| 108 | 10 |
| 162 | 14 |
| * | 2.7 |

| | AUC0-∞ (umol · h/L) |
|---|---|
| 108 | 14.15 |
| 106 | 12.48 |
| 123 | 10.08 |
| 105 | 8.77 |
| 124 | 7.28 |
| 111 | 6.63 |
| 103 | 5.74 |
| 119 | 5.08 |
| 116 | 4.28 |
| * | 0.27 |

* is a compound of Example 190 in WO02/16329 (Patent Literature 14) and corresponds to a methylester compound of Example 1 in WO02/16329 (Patent Literature 14).

Test Example 4

Activity to Elevate the Number of Lymphocytes in the Peripheral Blood in a Rat

After the substance inhibiting the bond between α4 integrin and VCAM-1 is administered in vivo, in case its inhibitory activity works effectively, it is suggested that the number of lymphocytes in the peripheral blood is increasing by inhibiting adhesion of lymphocytes to the blood vessels or organs (Nonpatent Literatures 45 and 47). The activity of the compounds of the present invention to elevate the number of lymphocytes in the rat was examined.

A dosing solution was prepared by dissolving the compounds of the present invention to dimethylsulfoxide, adding the mixed solution of polyethylene glycol 400: propylene glycol=1:1 and turning it upside and down repeatedly. The final concentration of DMSO was adjusted to become 2.5%.

The dosing solution of a test substance (3 mg/kg, 10 mg/kg or 30 mg/kg) was orally administered to a male Wistar rat (6 to 8 weeks age) in an amount of 4 mL/kg. After the settled time points after the administration, the blood was drawn from its abdominal large vein under anesthesia and stirred in a EDTA-2K coated container for blood collection. Then, the number of lymphocytes in the peripheral blood was determined by an automated comprehensive hematology analyzer (SF-3000, Sysmex). The test was executed in n=5, and the ratio (%) of the number of lymphocytes in the peripheral blood in a test-substance-administered group to that in a vehicle-treated group (a control group) was calculated while the average value of the number of lymphocytes in the peripheral blood in a control group was determined to be 100%.

The obtained results are shown in Result Table 4.

RESULT TABLE 4

Elevation activity assay of lymphocytes in the peripheral blood by an oral administration to a rat

| Example No. | 3 mg/kg 1 hour later | 3 mg/kg 6 hours later | 10 mg/kg 6 hours later | 30 mg/kg 12 hours later |
|---|---|---|---|---|
| WO02/16329 The Compound of Exam. 190 | ○ (195%) | X (≦100%) | X (131%) | X (120%) |
| 71 | ○ | — | — | — |
| 88 | ○ | — | — | — |
| 90 | ○ | ○ | — | — |
| 91 | ○ | — | — | — |
| 102 | ○ | — | — | — |
| 103 | ○ | — | — | — |
| 104 | ○ | — | — | — |
| 106 | ○ | ○ | — | — |
| 107 | ○ | — | — | — |
| 109 | ○ | — | — | — |
| 111 | ○ | ○ | ○ | ○ |
| 112 | ○ | — | — | — |
| 113 | ○ | — | — | — |
| 115 | ○ | ○ | — | — |
| 116 | ○ | ○ | — | — |
| 117 | ○ | — | — | — |
| 118 | ○ | — | — | — |
| 122 | ○ | — | — | — |
| 124 | ○ | — | — | — |
| 125 | ○ | — | — | — |
| 129 | ○ | — | — | — |
| 131 | ○ | ○ | — | — |
| 30 | — | — | ○ | — |
| 85 | — | — | ○ | — |
| 121 | — | — | — | ○ |
| 126 | ○ | — | — | — |
| 127 | ○ | — | — | — |
| 128 | ○ | — | — | — |
| Criterion | 195% or more | 125% or more | 150% or more | 150% or more |
| 138 | — | — | — | ○ |
| 147 | — | — | ○ | ○ |
| 148 | — | — | ○ | — |
| 149 | — | — | ○ | — |
| 150 | — | — | — | ○ |
| 151 | — | — | — | ○ |
| 152 | — | — | — | ○ |
| 153 | — | — | — | ○ |
| 154 | — | — | — | ○ |
| 155 | — | — | — | ○ |
| 156 | — | — | ○ | — |
| 157 | — | — | ○ | — |
| 158 | — | — | ○ | — |
| 159 | — | — | ○ | — |
| 162 | — | — | ○ | ○ |
| 163 | — | — | — | ○ |
| 164 | — | — | — | ○ |
| 165 | — | — | — | ○ |
| 166 | — | — | ○ | — |
| 167 | — | — | ○ | — |
| 168 | — | — | ○ | — |
| 169 | — | — | ○ | — |
| 170 | — | — | ○ | — |
| 171 | — | — | ○ | — |
| 172 | — | — | — | ○ |
| 173 | — | — | — | ○ |
| 174 | — | — | — | ○ |
| 176 | — | — | — | ○ |
| 177 | — | — | — | ○ |
| 178 | — | — | — | ○ |
| 179 | — | — | — | ○ |
| Criterion | 195% or more | 125% or more | 150% or more | 150% or more |
| 180 | — | — | — | ○ |
| 181 | — | — | — | ○ |
| 182 | — | — | — | ○ |
| 183 | — | — | — | ○ |
| 184 | — | — | — | ○ |
| 185 | — | — | — | ○ |
| 186 | — | — | — | ○ |
| 187 | — | — | — | ○ |
| 188 | — | — | — | ○ |
| 189 | — | — | — | ○ |
| 190 | — | — | — | ○ |
| 210 | — | — | — | ○ |
| 211 | — | — | — | ○ |
| 212 | — | — | — | ○ |
| 213 | — | — | — | ○ |
| 214 | — | — | — | ○ |
| 215 | — | — | — | ○ |
| 216 | — | — | — | ○ |
| 217 | — | — | — | ○ |
| 218 | — | — | — | ○ |
| 225 | — | — | — | ○ |
| 228 | — | — | — | ○ |
| 232 | — | — | — | ○ |
| 233 | — | — | — | ○ |
| 234 | — | — | — | ○ |
| 235 | — | — | — | ○ |
| Criterion | 195% or more | 125% or more | 150% or more | 150% or more |

○: pass (criterion measure or more)
X: failure (less than criterion measure)
—: not evaluated

The invention claimed is:

1. A phenylalanine compound of the following formula (1) or pharmaceutically acceptable salts thereof:

(1)

wherein R11 represents a hydroxyl group, an alkoxyl group having 1 to 6 carbon atoms which may have a substituent(s), a morpholinoethyloxy group or a benzyloxy group which may be substituted with one or more methyl groups or one or more methoxy groups,
R12 and R13 each independently represent a hydrogen atom, an alkyl group having 1 to 6 carbon atoms, an acetyl group or methyloxycarbonyl group, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms,
R14 represents a methyl group or an ethyl group,
$R_1'$ represents a hydrogen atom, a fluorine atom or a chlorine atom,
$X_1$ represents —CH(R1a)-, —CH(R1a)CH(R1b)-, —CH(R1a)CH(R1b)CH(R1c)-, —CH(R1a)CH(R1b)CH(R1c)CH(R1d)-, —N(R1a)CH(R1b)CH(R1c)—, —OCH(R1a)CH(R1b)-, —OCH(R1a)CH(R1b)CH(R1c)- or 1,3-pyrrolidinylene, wherein R1a, R1b, R1c and R1d each independently represent a hydrogen atom or a methyl group, and
$Y_{11}$ and $Y_{12}$ represent either one of the combinations, (Cl, Cl), (Cl, Me), (Cl, F), (F, F) and (F, Me).

2. The phenylalanine compound or pharmaceutically acceptable salts thereof according to claim 1, wherein
R11 represents a hydroxyl group, an alkoxyl group having 1 to 6 carbon atoms, a morpholinoethyloxy group or a benzyloxy group which may be substituted with one or more methyl groups or one or more methoxy groups,
when R12 and R13 represents an alkyl group said alkyl group has 1 to 3 carbon atoms, and
$X_1$ represents —CH(R1a)-, —CH(R1a)CH(R1b)-, —N(R1a)CH(R1b)CH(R1c)-, —OCH(R1a)CH(R1b)- or 1,3-pyrrolidinylene.

3. The phenylalanine compound or pharmaceutically acceptable salts thereof according to claim 1, wherein
R11 represents a hydroxyl group, an alkoxyl group having 1 to 6 carbon atoms, a morpholinoethyloxy group or a benzyloxy group which may be substituted with one or more methyl groups or one or more methoxy groups,
when R12 and R13 represents an alkyl group said alkyl group has 1 to 3 carbon atoms, and $X_1$ represents —CH(R1a)-, —CH$_2$CH$_2$—, —N(R1a)CH$_2$CH$_2$—, or 1,3-pyrrolidinylene, wherein R1a represents a hydrogen atom or a methyl group.

4. The phenylalanine compound or pharmaceutically acceptable salts thereof according to claim 1, wherein
R11 represents a hydroxyl group, an alkoxyl group having 1 to 6 carbon atoms, a morpholinoethyloxy group or a benzyloxy group which may be substituted with one or more methyl groups or one or more methoxy groups,
R12 and R13 each independently represent a hydrogen atom or an alkyl group having 1 to 3 carbon atoms, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, and
$X_1$ represents —CH(R1a)-, —CH$_2$CH$_2$—, —N(R1a)CH$_2$CH$_2$—, or 1,3-pyrrolidinylene, wherein R1a represents a hydrogen atom or a methyl group.

5. The phenylalanine compound or pharmaceutically acceptable salts thereof according to claim 1, wherein
R11 represents a hydroxyl group, an alkoxyl group having 1 to 6 carbon atoms, a morpholinoethyloxy group or a benzyloxy group which may be substituted with one or more methyl groups or one or more methoxy groups,
R12 represents a methyl group or an ethyl group,
R13 represents a hydrogen atom, a methyl group or an ethyl group, or
N(R12)R13 represents 1-pyrrolidinyl group, 1-piperidinyl group or 4-morpholinyl group,
R14 represents a methyl group,
$R_1'$ represents a hydrogen atom,
$X_1$ represents —CH$_2$—, which is located on the sixth, seventh or eighth position of quinazolinedione ring, and
$Y_{11}$ and $Y_{12}$ represent either one of the combinations, (Cl, Cl), (Cl, Me), (Cl, F), (F, F) and (F, Me).

6. The phenylalanine compound or pharmaceutically acceptable salts thereof according to claim 1, wherein
when R12 is an alkyl group said alkyl group has 1 to 3 carbon atoms,
R13 represents a hydrogen atom, a methyl group or an ethyl group,
R11 represents a hydroxyl group, an alkoxyl group having 1 to 6 carbon atoms, a morpholinoethyloxy group or a benzyloxy group which may be substituted with one or more methyl groups or one or more methoxy groups,
$X_1$ represents —CH$_2$—, which is located on the sixth, seventh or eighth position of quinazolinedione ring, and
$Y_{11}$ and $Y_{12}$ represent the combination of (Cl, Cl).

7. The phenylalanine compound or pharmaceutically acceptable salts thereof according to claim 6, wherein
R13 represents a hydrogen atom, a methyl group or an ethyl group, and
$X_1$ represents —CH$_2$—, which is located on the sixth position of quinazolinedione ring.

8. The phenylalanine compound or pharmaceutically acceptable salts thereof according to claim 6, wherein
R13 represents a hydrogen atom, a methyl group or an ethyl group, and
$X_1$ represents —CH$_2$—, which is located on the seventh position of quinazolinedione ring.

9. The phenylalanine compound or pharmaceutically acceptable salts thereof according to claim 3, wherein
R12 and R13 each independently represent a methyl group or an ethyl group, R14 represents a methyl group, R$_1$' represents a hydrogen atom or a fluorine atom, which is located on the sixth or seventh position of quinazolinedione ring, X$_1$ represents —N(CH$_3$)CH$_2$CH$_2$— or 1,3-pyrrolidinylene, which is located on the sixth or seventh position of quinazolinedione ring, and Y$_{11}$ and Y$_{12}$ represent the combination of (Cl, Cl).

10. The phenylalanine compound or pharmaceutically acceptable salts thereof according to claim 2, wherein R12 and R13 each independently represent a hydrogen atom, a methyl group or an ethyl group, or N(R12)R13 represents 1-pyrrolidinyl group, 1- piperidinyl group or 4-morpholinyl group, R14 represents a methyl group or an ethyl group, R$_1$' represents a hydrogen atom, X$_1$ represents —OCH(R1a)CH(R1b)-, wherein R1a and R1b each independently represent a hydrogen atom or a methyl group, and Y$_{11}$ and Y$_{12}$ represent either one of the combinations, (Cl, Cl), (Cl, Me), (Cl, F), (F, F) and (F, Me).

11. The phenylalanine compound or pharmaceutically acceptable salts thereof according to claim 10, wherein R12 and R13 each independently represent a hydrogen atom, a methyl group or an ethyl group, R14 represents a methyl group, and Y$_{11}$ and Y$_{12}$ represent the combination of (Cl, Cl).

12. The phenylalanine compound or pharmaceutically acceptable salts thereof according to claim 1, wherein R11 represents a hydroxyl group or an alkoxyl group having 1 to 6 carbon atoms which may have a methoxy group(s) as a substituent(s), R12 represents a hydrogen atom or an alkyl group having 1 to 6 carbon atoms, R13 represents a hydrogen atom, a methyl group or an ethyl group, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, R14 represents a methyl group, R$_1$' represents a hydrogen atom, X$_1$ represents —CH(R1a)-, —CH(R1a)CH(R1b)-, —CH(R1a)CH(R1b)CH(R1c)- or —OCH(R1a)CH(R1b)-, which is located on the sixth position of quinazolinedione ring, wherein each of R1a, R1b and R1c represents a hydrogen atom, and Y$_{11}$ and Y$_{12}$ represent the combination of (Cl, Cl).

13. The phenylalanine compound or pharmaceutically acceptable salts thereof according to claim 1, wherein R11 represents a hydroxyl group or an alkoxyl group having 1 to 6 carbon atoms, R12 represents an alkyl group having 1 to 6 carbon atoms, R13 represents a hydrogen atom, a methyl group or an ethyl group, R14 represents a methyl group, R$_1$' represents a hydrogen atom, X$_1$ represents —CH(R1a)- or —CH(R1a)CH(R1b)-, which is located on the sixth position of quinazolinedione ring, wherein each of R1a and R1b represents a hydrogen atom, and Y$_{11}$ and Y$_{12}$ represent the combination of (Cl, Cl).

14. The phenylalanine compound or pharmaceutically acceptable salts thereof according to claim 1, wherein R11 represents a hydroxyl group or an alkoxyl group having 1 to 6 carbon atoms, R12 represents an alkyl group having 1 to 5 carbon atoms, R13 represents a hydrogen atom, R14 represents a methyl group, R$_1$' represents a hydrogen atom, X$_1$ represents —CH(R1a)-, —CH(R1a)CH(R1b)- or —CH(R1a)CH(R1b)CH(R1c)-, which is located on the sixth position of quinazolinedione ring, wherein each of R1a, R1b and R1c represents a hydrogen atom, and Y$_{11}$ and Y$_{12}$ represent the combination of (Cl, Cl).

15. The phenylalanine compound or pharmaceutically acceptable salts thereof according to claim 1, wherein R11 represents a hydroxyl group or an alkoxyl group having 1 to 6 carbon atoms, R12 represents a methyl group or an ethyl group, R13 represents a hydrogen atom, R14 represents a methyl group, R$_1$' represents a hydrogen atom, X$_1$ represents —CH(R1a)-, —CH(R1a)CH(R1b)- or —CH(R1a)CH(R1b)CH(R1c)-, which is located on the sixth position of quinazolinedione ring, wherein each of R1a, R1b and R1c represents a hydrogen atom, and Y$_{11}$ and Y$_{12}$ represent the combination of (Cl, Cl).

16. The phenylalanine compound or pharmaceutically acceptable salts thereof according to claim 1, wherein R11 represents a hydroxyl group or an alkoxyl group having 1 to 6 carbon atoms, R12 represents a methyl group, an ethyl group, an isobutyl group, a cyclopropylmethyl group, a cyclobutyl group, a sec-butyl group or an isopentyl group, R13 represents a hydrogen atom, R14 represents a methyl group, R$_1$' represents a hydrogen atom, X$_1$ represents —CH(R1a)-, which is located on the sixth position of quinazolinedione ring, wherein R1a represents a hydrogen atom, and Y$_{11}$ and Y$_{12}$ represent the combination of (Cl, Cl).

17. The phenylalanine compound or pharmaceutically acceptable salts thereof according to claim 1, wherein R11 represents a hydroxyl group or an alkoxyl group having 1 to 6 carbon atoms, R12 represents a hydrogen atom or an alkyl group having 1 to 3 carbon atoms, R13 represents a hydrogen atom, a methyl group or an ethyl group, or N(R12)R13 represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, R14 represents a methyl group, R$_1$' represents a hydrogen atom, X$_1$ represents —O—CH(R1a)CH(R1b)- or —O—CH(R1a)CH(R1b)CH(R1c)-, which is located on the sixth position of quinazoline-dione ring, wherein each of R1a, R1b and R1c independently represents a hydrogen atom or a methyl group, and Y$_{11}$ and Y$_{12}$ represent the combination of (Cl, Cl).

18. The phenylalanine compound or pharmaceutically acceptable salts thereof according to claim 1, wherein R11 represents a branched alkoxyl group having 3 to 6 carbon atoms.

19. The phenylalanine compound or pharmaceutically acceptable salts thereof according to claim 1 represented by the following formulae:

177
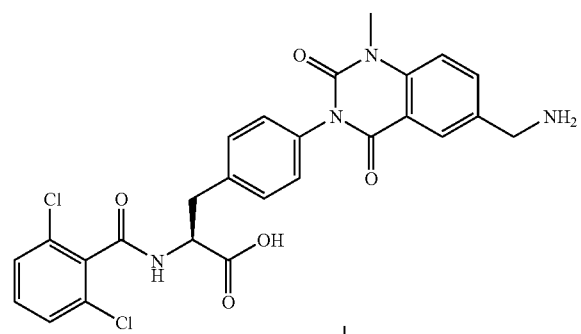
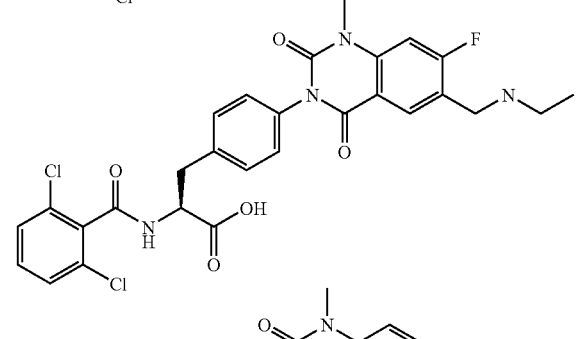
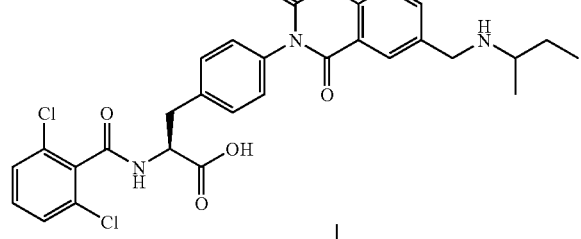
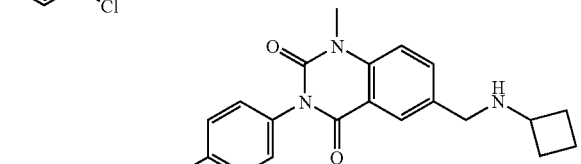
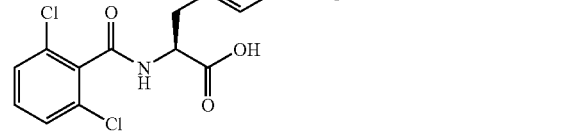
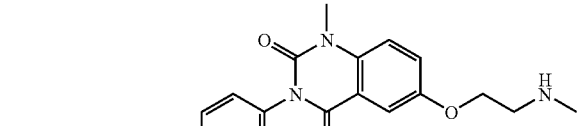
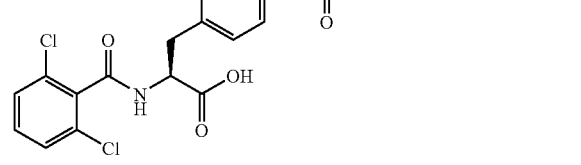
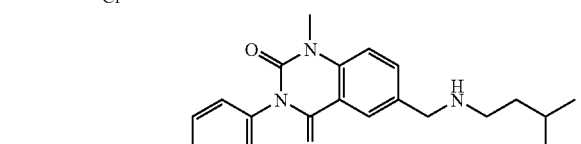
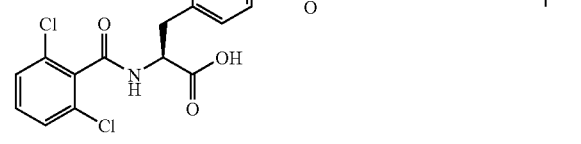
178
-continued
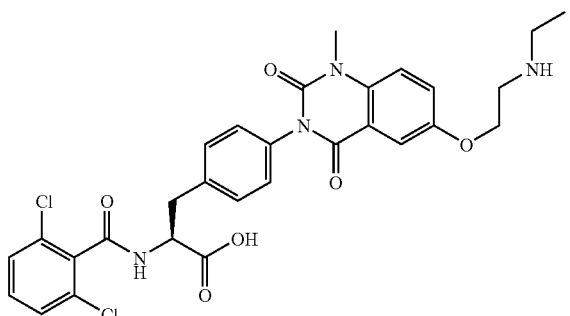
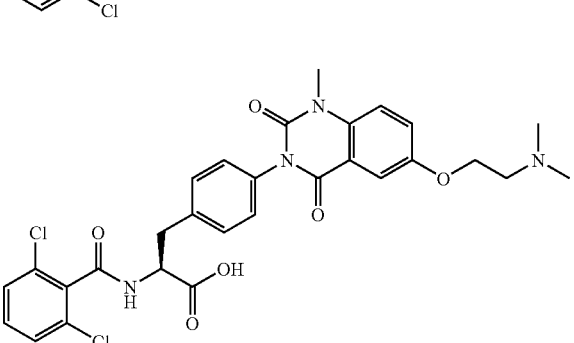
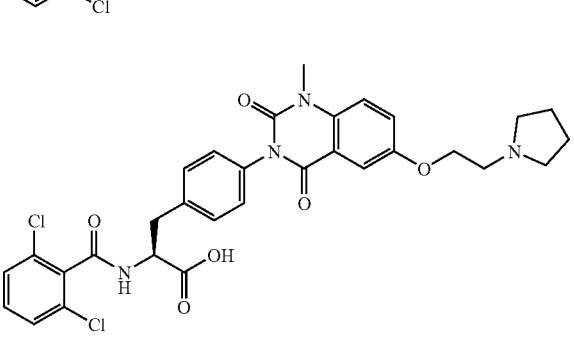
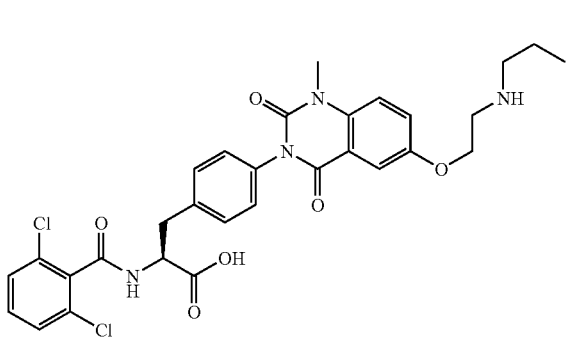
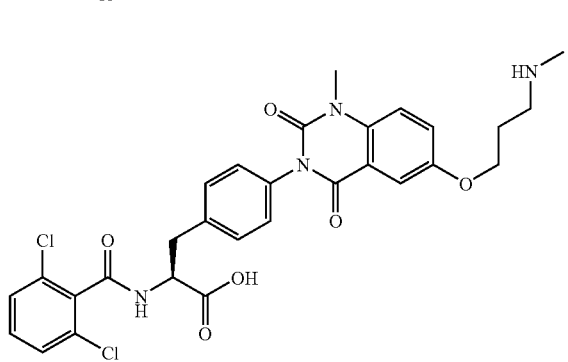

179
-continued
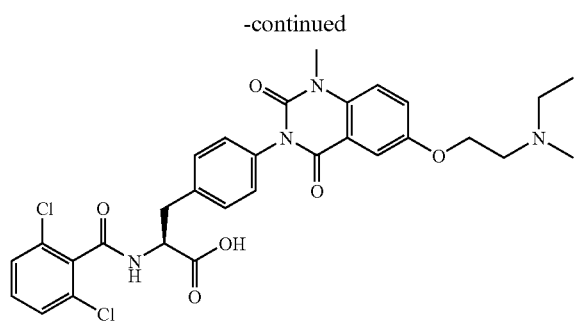
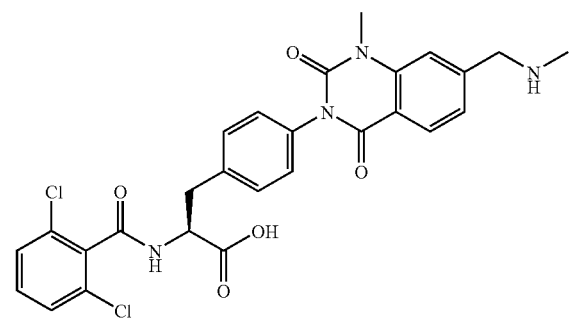
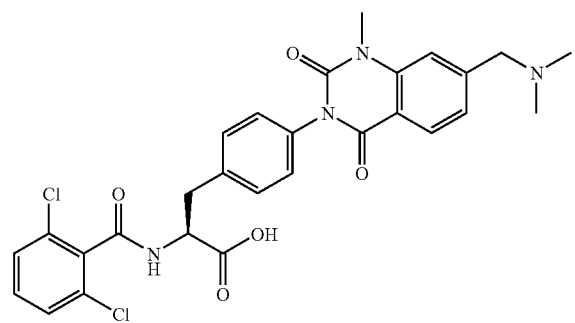
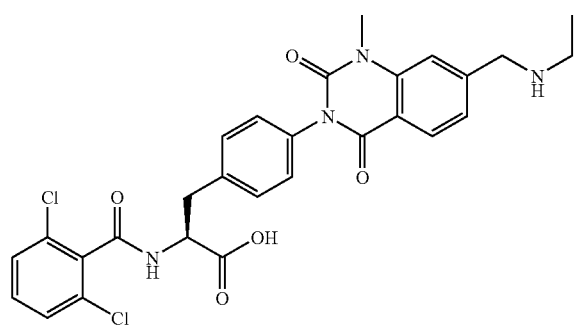
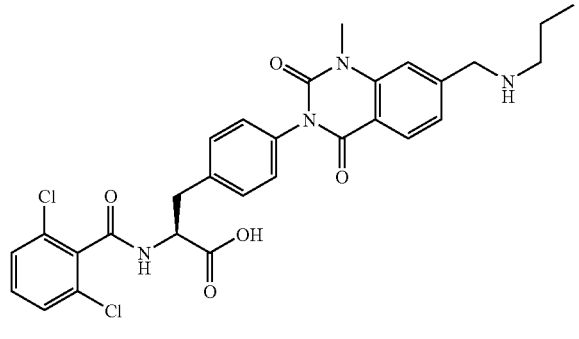
180
-continued
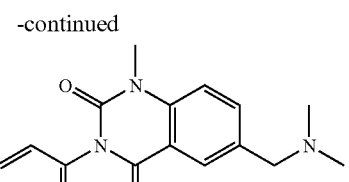
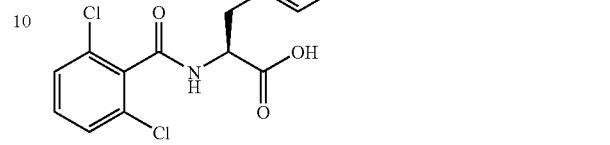
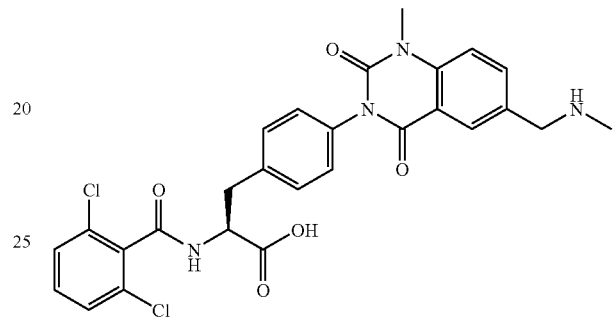
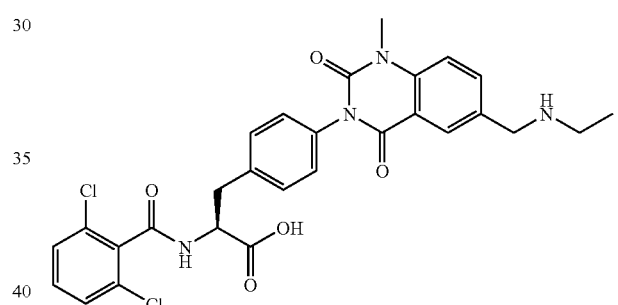
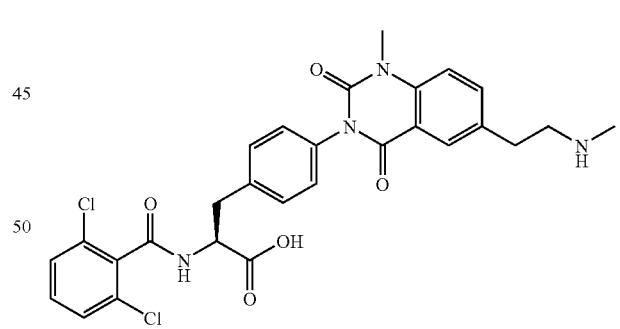
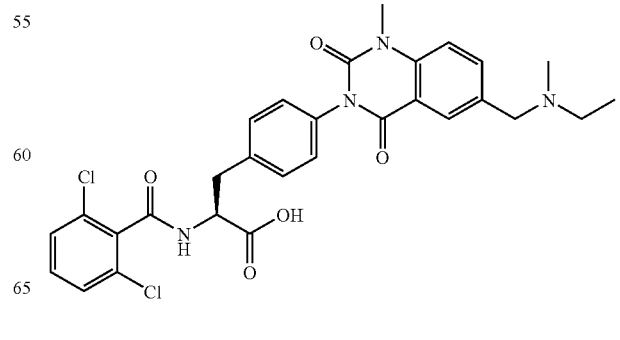

181
-continued
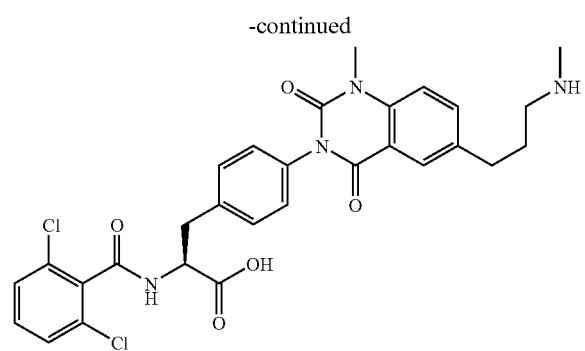
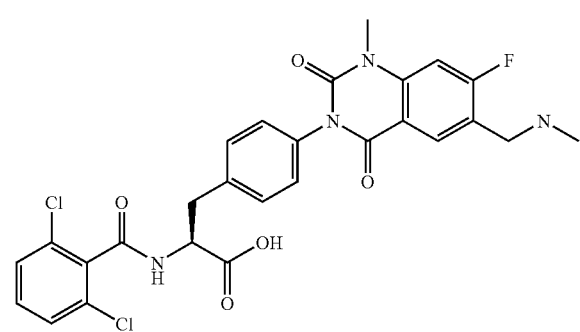
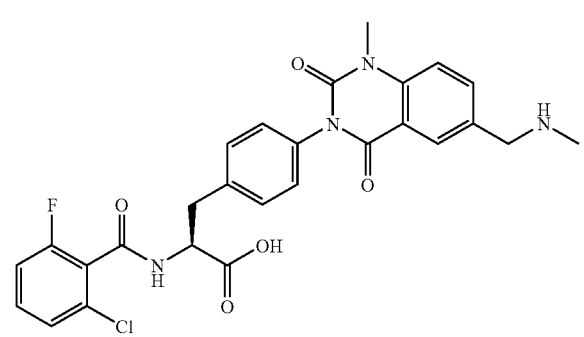
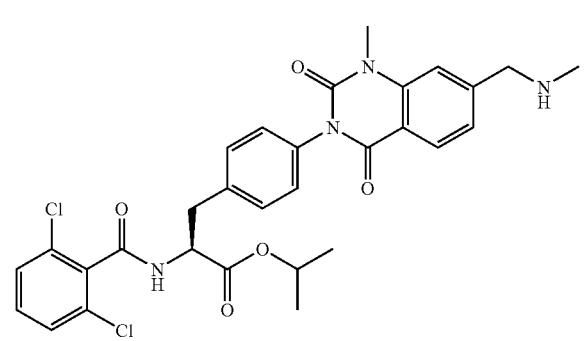
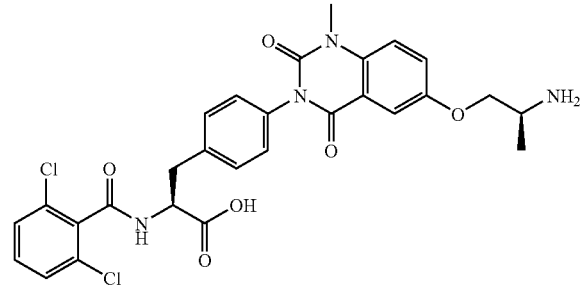
182
-continued
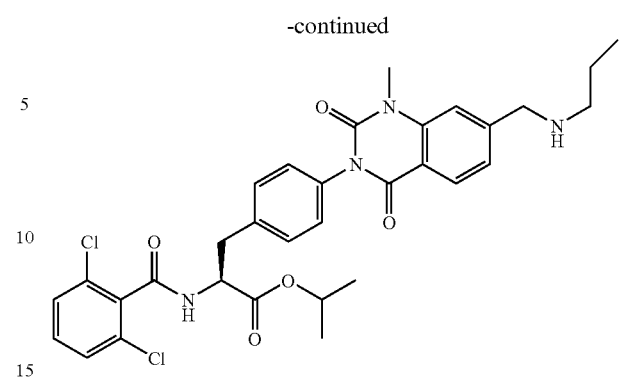
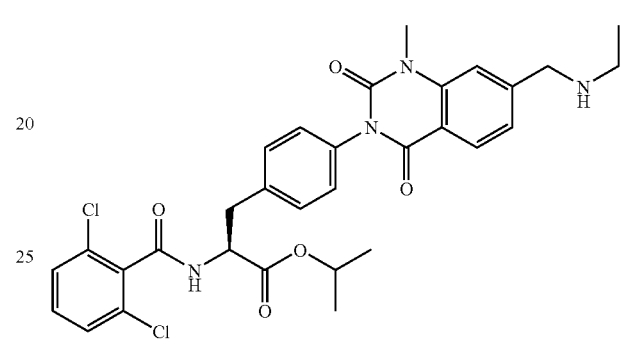
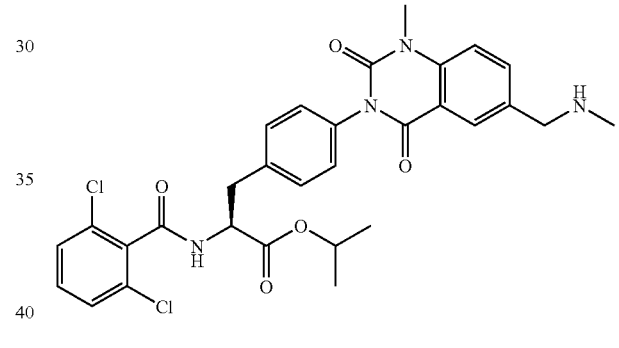
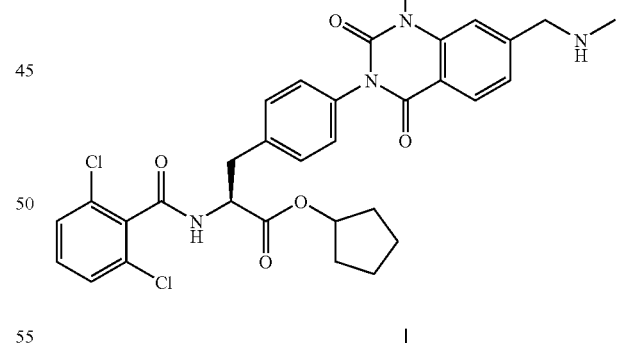
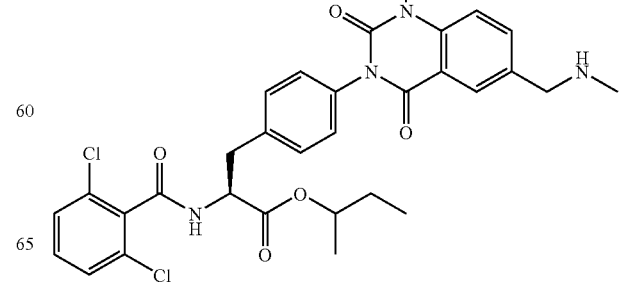

183
-continued
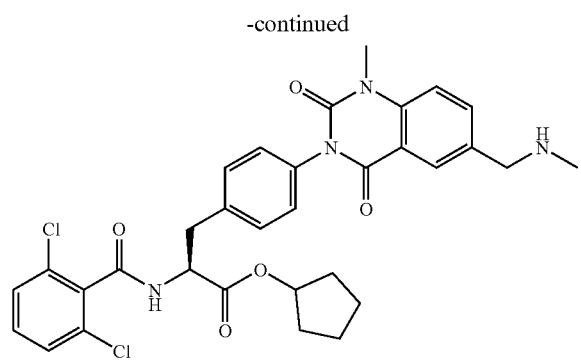
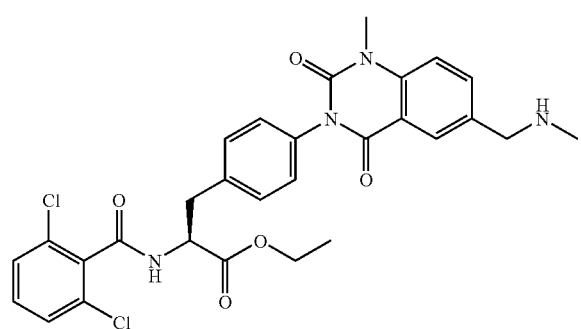
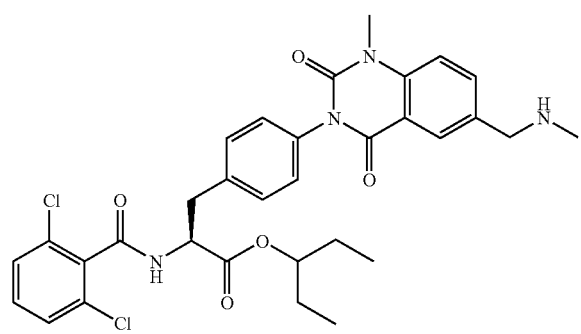
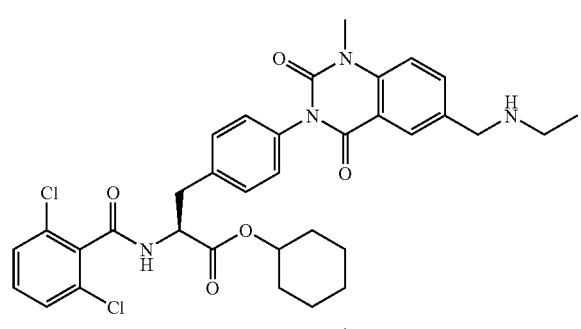
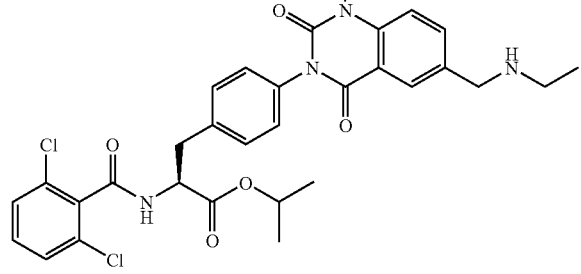
184
-continued
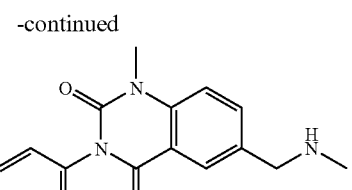
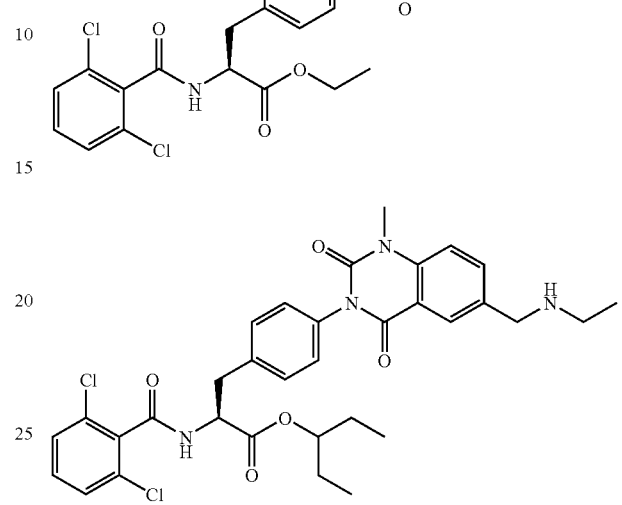
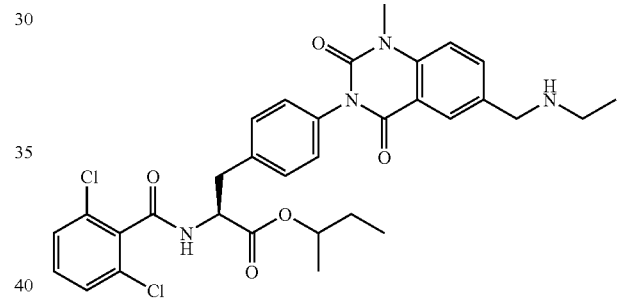
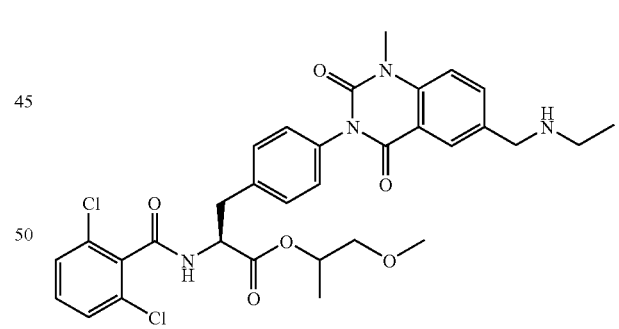
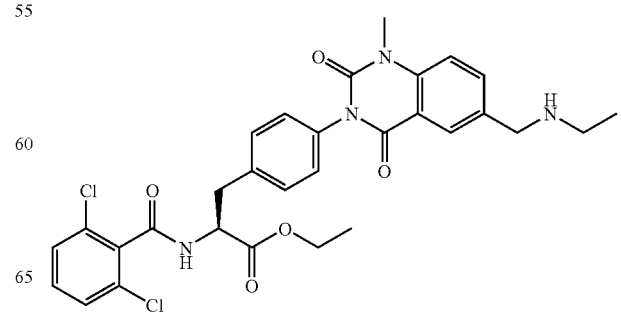

185
-continued
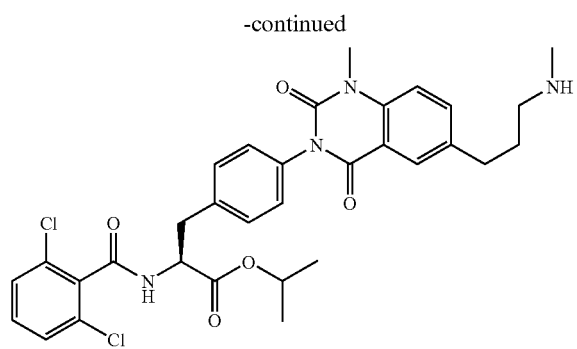
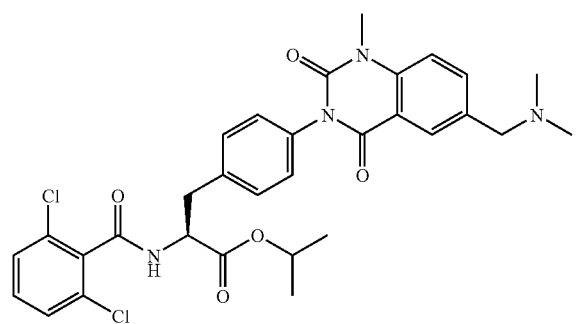
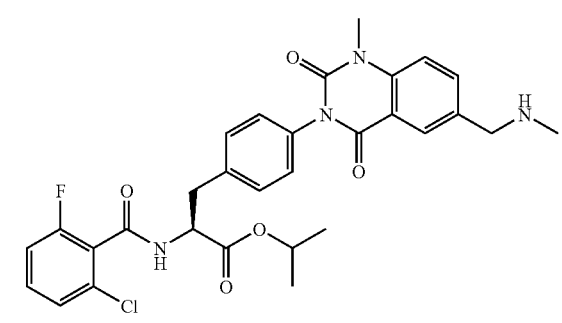
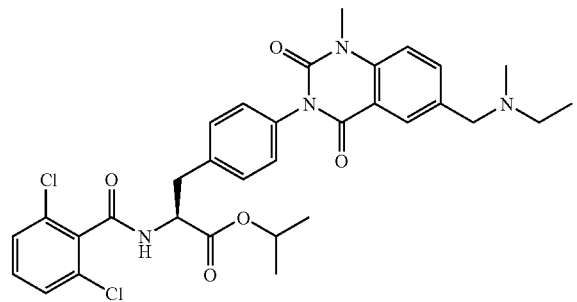
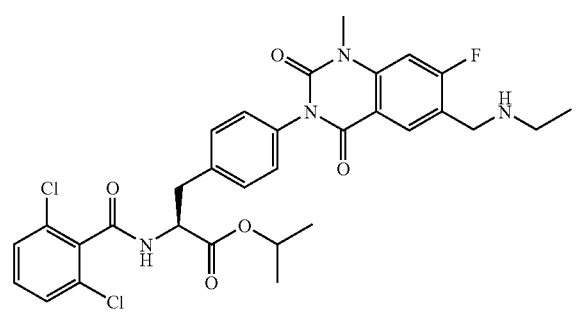
186
-continued
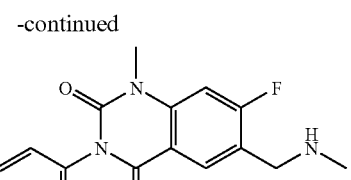
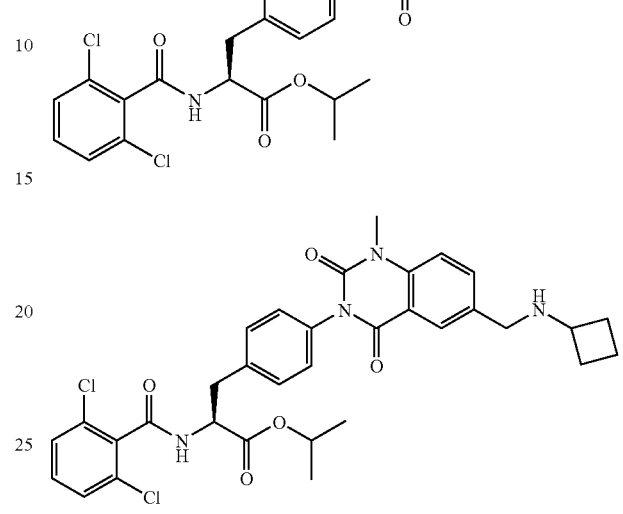
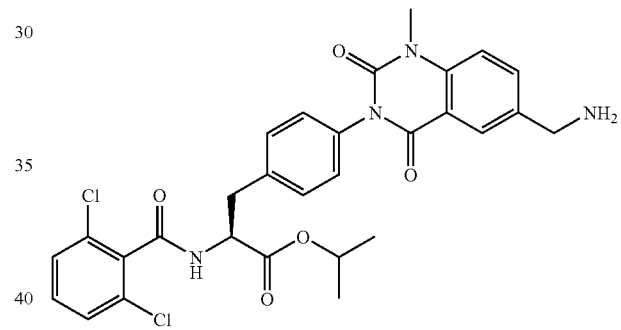
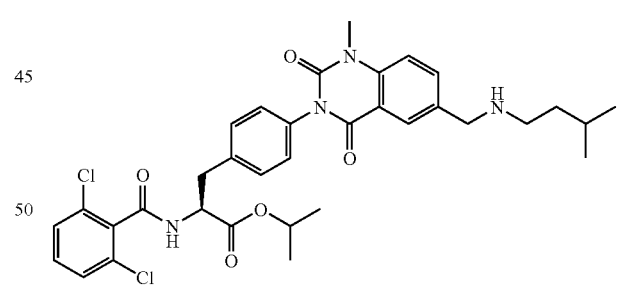
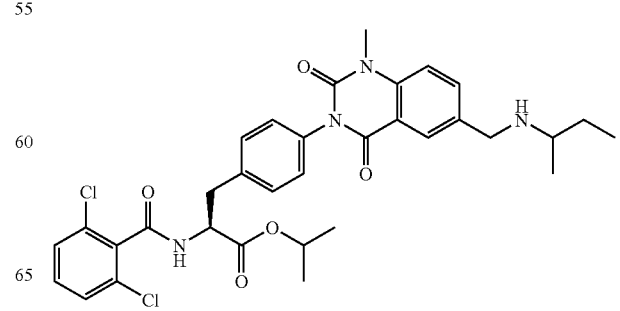

-continued

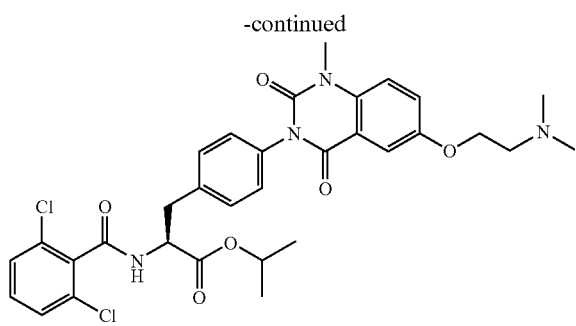

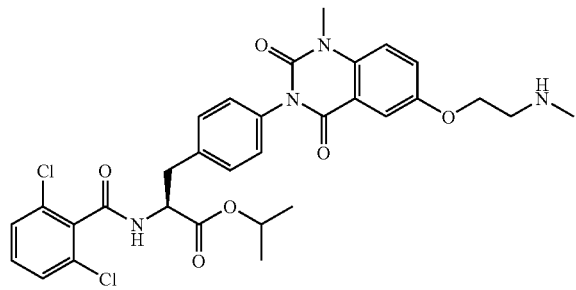

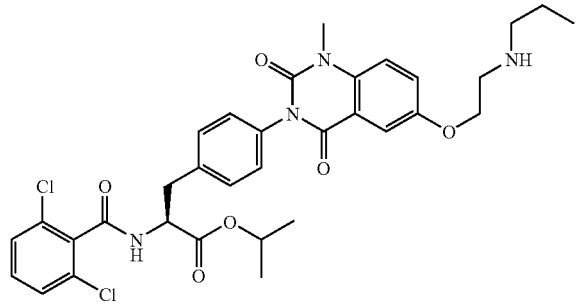

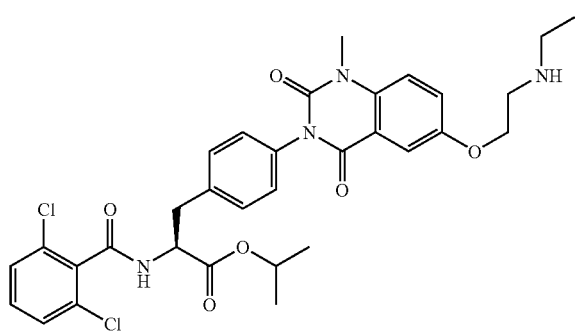

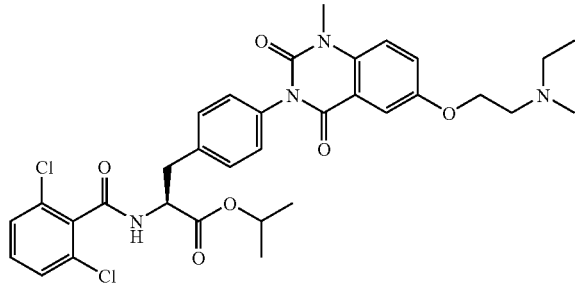

-continued

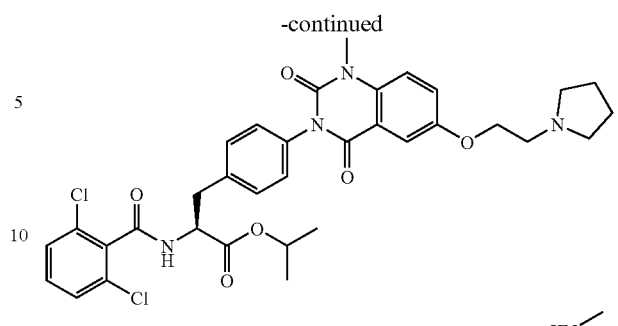

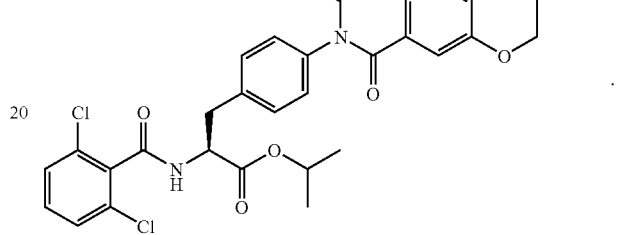

20. A phenylalanine compound of the following formula (2) or pharmaceutically acceptable salts thereof:

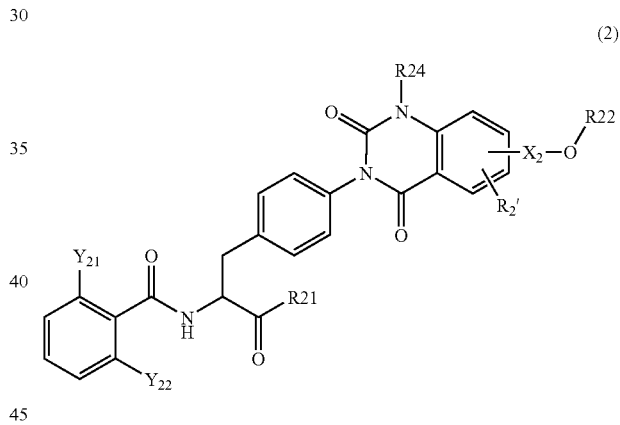

(2)

wherein R21 represents a hydroxyl group, an alkoxyl group having 1 to 6 carbon atoms, a morpholinoethyloxy group or a benzyloxy group which may be substituted with one or more methyl groups or one or more methoxy groups, R22 represents a hydrogen atom or an alkyl group having 1 to 3 carbon atoms, R24 represents a methyl group or an ethyl group, $R_2'$ represents a hydrogen atom, a fluorine atom or a chlorine atom, $X_2$ represents —CH(R2a)-, —CH$_2$CH$_2$— or —N(R2a)CH$_2$CH$_2$—, wherein R2a represents a hydrogen atom or a methyl group, and $Y_{21}$ and $Y_{22}$ represent either one of the combinations, (Cl, Cl), (Cl, Me), (Cl, F), (F, F) and (F, Me).

21. The phenylalanine compound or pharmaceutically acceptable salts thereof according to claim 20, wherein R22 represents a methyl group or an ethyl group, R24 represents a methyl group, $R_2'$ represents a hydrogen atom, $X_2$ represents —$CH_2$—, which is located on the sixth, seventh or eighth position of quinazolinedione ring, and $Y_{21}$ and $Y_{22}$ represent the combination of (Cl, Cl).

22. The phenylalanine compound or pharmaceutically acceptable salts thereof according to claim 20, wherein R22 represents a hydrogen atom, a methyl group or an ethyl group, R24 represents a methyl group, $R_2'$ represents a hydrogen atom or a fluorine atom, which is located on the sixth or seventh position of quinazolinedione ring, $X_2$ represents —$N(CH_3)CH_2CH_2$— or —$NHCH_2CH_2$—, which is located on the sixth or seventh position of quinazolinedione ring, and $Y_{21}$ and $Y_{22}$ represent the combination of (Cl, Cl).

23. A phenylalanine compound of the following formula (3) or pharmaceutically acceptable salts thereof:

(3)

[Chemical structure]

wherein R31 represents a hydroxyl group, an alkoxyl group having 1 to 6 carbon atoms, a morpholinoethyloxy group or a benzyloxy group which may be substituted with one or more methyl groups or one or more methoxy groups, $R_{34}$ represents a methyl group or an ethyl group, R3' represents a hydrogen atom or a fluorine atom, (3-1)

[Chemical structure]

the formula (3-1) represents 4-morpholinyl group, 4-thiomorpholinyl group, 3-tetrahydrothiazolyl group, 1-piperazinyl group of which the fourth position may be substituted with an alkyl group having 1 to 3 carbon atoms, or 1-imidazolyl group which may be substituted with a methyl group, an ethyl group or an amino group, wherein X3 represents an oxygen atom, a nitrogen atom which may be substituted with an alkyl group having 1 to 3 carbon atoms, or a sulfur atom, and $Y_{31}$ and $Y_{32}$ represent either one of the combinations, (Cl, Cl), (Cl, Me), (Cl, F), (F, F) and (F, Me).

24. The phenylalanine compound or pharmaceutically acceptable salts thereof according to claim 23, wherein the formula (3-1) represents 4-morpholinyl group, 4-thiomorpholinyl group, 3-tetrahydrothiazolyl group, 1-piperazinyl group of which the fourth position may be substituted with an alkyl group having 1 to 3 carbon atoms, or 1-imidazolyl group which may be substituted with a methyl group or an amino group, wherein $X_3$ represents an oxygen atom, a nitrogen atom which may be substituted with an alkyl group having 1 to 3 carbon atoms, or a sulfur atom.

25. The phenylalanine compound or pharmaceutically acceptable salts thereof according to claim 24, wherein $R_{34}$ represents a methyl group, $R_3'$ represents a hydrogen atom, the formula (3-1) represents 4-morpholinyl group or 1-piperazinyl group of which the fourth position may be substituted with an alkyl group having 1 to 3 carbon atoms, and $Y_{31}$ and $Y_{32}$ represent the combination of (Cl, Cl).

26. The phenylalanine compound or pharmaceutically acceptable salts thereof according to claim 24, wherein $R_{34}$ represents a methyl group, R3' represents a hydrogen atom, the formula (3-1) represents 2-amino-1-imidazolyl group, and $Y_{31}$ and $Y_{32}$ represent the combination of (Cl, Cl).

27. The phenylalanine compound or pharmaceutically acceptable salts thereof according to claim 23, wherein $R_{34}$ represents a methyl group, R3' represents a hydrogen atom or a fluorine atom, the formula (3-1) represents 1-imidazolyl group of which the second position may be substituted with a methyl group or an ethyl group, and $Y_{31}$ and $Y_{32}$ represent the combination of (Cl, Cl).

28. A phenylalanine compound of the following formula (4) or pharmaceutically acceptable salts thereof:

(4)

[Chemical structure]

wherein $R_{41}$ represents a hydroxyl group, an alkoxyl group having 1 to 6 carbon atoms, a morpholinoethyloxy group or a benzyloxy group which may be substituted with one or more methyl groups or one or more methoxy groups, Ring represents a benzene ring, a pyridine ring, a thiophene ring, a piperidine ring of which the first position may be substituted with an alkyl group having 1 to 3 carbon atoms, a piperazine ring of which the first and/or fourth position may be substituted with an alkyl group having 1 to 3 carbon atoms, , or a pyrrolidine ring of which the first position may be substituted with an alkyl group having 1 to 3 carbon atoms, $R_{44}$ represents a methyl group or an ethyl group, and $Y_{41}$ and $Y_{42}$ represent either one of the combinations, (Cl, Cl), (Cl, Me), (Cl, F), (F, F) and (F, Me).

29. The phenylalanine compound or pharmaceutically acceptable salts thereof according to claim 28, wherein Ring represents a piperazine ring of which the first and/or fourth position may be substituted with a methyl group, R₄₄ represents a methyl group, and Y₄₁ and Y₄₂ represent the combination of (Cl, Cl).

30. A phenylalanine compound of the following formula (5) or pharmaceutically acceptable salts thereof:

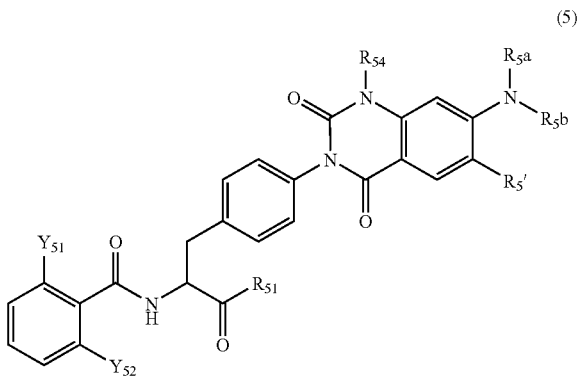

(5)

wherein $R_{51}$ represents a hydroxyl group, an alkoxyl group having 1 to 6 carbon atoms, a morpholinoethyloxy group or a benzyloxy group which may be substituted with one or more methyl groups or one or more methoxy groups, $R_{54}$ represents a methyl group or an ethyl group, $R_5'$ represents a hydrogen atom or a fluorine atom, R5a and R5b each independently represent a hydrogen atom or an alkyl group having 1 to 3 carbon atoms, or N(R5a)R5b represents 1-pyrrolidinyl group or 1-piperidinyl group, and $Y_{51}$ and $Y_{52}$ represent either one of the combinations, (Cl, Cl), (Cl, Me), (Cl, F), (F, F) and (F, Me).

31. The phenylalanine compound or pharmaceutically acceptable salts thereof according to claim 30, wherein $R_{54}$ represents a methyl group, $R_5'$ represents a hydrogen atom, N(R5a)R5b represents an ethylamino group or 1-pyrrolidinyl group, and $Y_{51}$ and $Y_{52}$ represent the combination of (Cl, Cl).

32. A phenylalanine compound of the following formula (8) or pharmaceutically acceptable salts thereof:

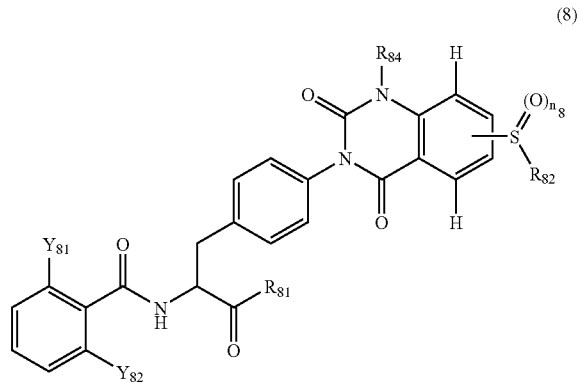

(8)

wherein $R_{81}$ represents a hydroxyl group, an alkoxyl group having 1 to 6 carbon atoms, a morpholinoethyloxy group, a benzyloxy group which may be substituted with one or more methyl groups or one or more methoxy groups, or hydroxyethyl group, $R_{82}$ represents a methyl group or an ethyl group, $R_{84}$ represents a methyl group or an ethyl group, $n_8$ represents an integer from 0 to 2, and $Y_{81}$ and $Y_{82}$ represent either one of the combinations, (Cl, Cl), (Cl, Me), (Cl, F), (F, F) and (F, Me).

33. The phenylalanine compound or pharmaceutically acceptable salts thereof according to claim 32, wherein, in the formula (8), $R_{81}$ represents a hydroxyl group, an alkoxyl group having 1 to 6 carbon atoms, a morpholinoethyloxy group or a benzyloxy group which may be substituted with one or more methyl groups or one or more methoxy groups.

34. The phenylalanine compound or pharmaceutically acceptable salts thereof according to claim 32, wherein $R_{82}$ represents a methyl group, $R_{84}$ represents a methyl group, $n_8$ represents either one of the integers 0 or 2, S is located on the sixth position of quinazolinedione ring, and $Y_{81}$ and $Y_{82}$ represent the combination of (Cl, Cl).

35. A phenylalanine compound of the following formula (9) or pharmaceutically acceptable salts thereof:

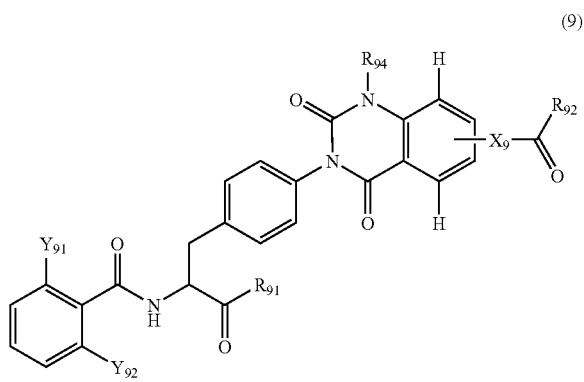

(9)

wherein $R_{91}$ represents a hydroxyl group, an alkoxyl group having 1 to 6 carbon atoms, a morpholinoethyloxy group or a benzyloxy group which may be substituted with one or more methyl groups or one or more methoxy groups, $R_{92}$ represents a hydroxyl group, an alkoxyl group having 1 to 6 carbon atoms, an amino group or a benzyloxy group which may be substituted with one or more methyl groups or one or more methoxy groups, $R_{94}$ represents a methyl group or an ethyl group, $X_9$ represents an atomic bond, —CH₂—, —CH₂CH₂— or —CH=CH—, and $Y_{91}$ and $Y_{92}$ represent either one of the combinations, (Cl, Cl), (Cl, Me), (Cl, F), (F, F) and (F, Me).

36. The phenylalanine compound or pharmaceutically acceptable salts thereof according to claim 35, wherein $X_9$ represents —CH₂CH₂— or —CHCH— and $R_{92}$ represents a hydroxyl group, or $X_9$ represents an atomic bond and $R_{92}$ represents a benzyloxy group, $X_9$ is located on the sixth position of quinazolinedione ring, $R_{94}$ represents a methyl group, and $Y_{91}$ and $Y_{92}$ represent the combination of (Cl, Cl).

37. The phenylalanine compound or pharmaceutically acceptable salts thereof according to claim 35, wherein X9 represents an atomic bond and R92 represents a hydroxyl group, a methoxy group or an amino group, X9 is located on the sixth position of quinazolinedione ring, R94 represents a methyl group, and Y91 and Y92 represent the combination of (Cl, Cl).

38. A phenylalanine compound of the following formula (11) or pharmaceutically acceptable salts thereof:

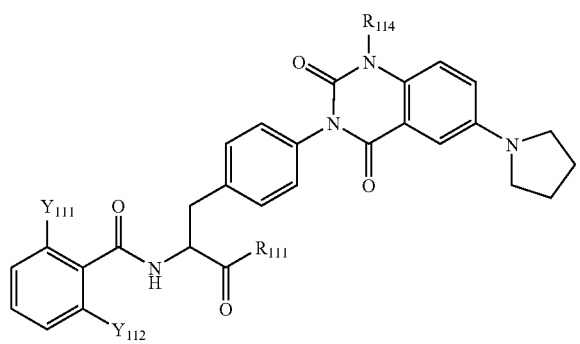

(11)

wherein R111 represents an alkoxyl group having 1 to 6 carbon atoms or a morpholinoethyloxy group, R114 represents a methyl group or an ethyl group, and Y111 and Y112 represent either one of the combinations, (Cl, Cl), (Cl, Me), (Cl, F), (F, F) and (F, Me).

39. A phenylalanine compound of the following formula (13) or pharmaceutically acceptable salts thereof:

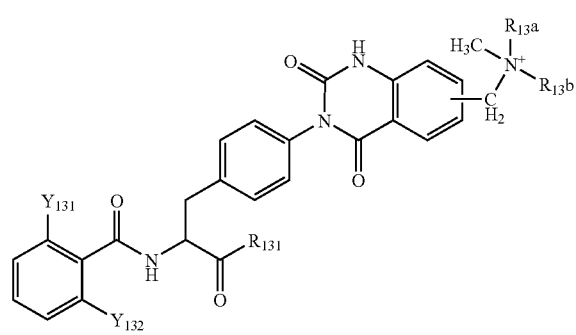

(13)

wherein R131 represents a hydroxyl group, an alkoxyl group having 1 to 6 carbon atoms, a morpholinoethyloxy group or a benzyloxy group which may be substituted with one or more methyl groups or one or more methoxy groups, R13a and R13b each independently represent an alkyl group having 1 to 3 carbon atoms, or N(R13a)R13b represents 1-pyrrolidinyl group, 1-piperidinyl group, 4-morpholinyl group, 4-thiomorpholinyl group, 3-tetrahydrothiazolyl group or 1-piperazinyl group of which the fourth position may be substituted with an alkyl group having 1 to 3 carbon atoms, and Y131 and Y132 represent either one of the combinations, (Cl, Cl), (Cl, Me), (Cl, F), (F, F) and (F, Me).

40. A phenylalanine compound of the following formula (14) or pharmaceutically acceptable salts thereof:

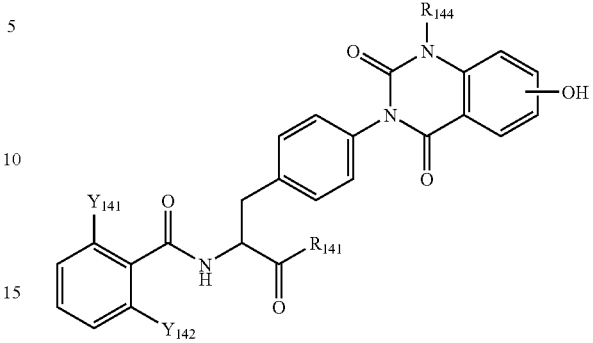

(14)

wherein R141 represents a hydroxyl group, an alkoxyl group having 1 to 6 carbon atoms or a morpholinoethyloxy group, R144 represents a methyl group or an ethyl group, a hydroxyl group on a quinazolinedione ring is located on the sixth or seventh position of the ring, and Y141 and Y142 represent either one of the combinations, (Cl, Cl), (Cl, Me), (Cl, F), (F, F) and (F, Me).

41. The phenylalanine compound or pharmaceutically acceptable salts thereof according to claim 40, wherein R144 represents a methyl group, a hydroxyl group on a quinazolinedione ring is located on the sixth position of the ring, and Y141 and Y142 represent the combination of (Cl, Cl).

42. A pharmaceutical composition comprising a phenylalanine compound or a pharmaceutically acceptable salt thereof according to claim 1 as an active ingredient and a pharmaceutically acceptable carrier thereof.

43. A method of treating or preventing inflammatory diseases in which α4 integrin-depending adhesion process participates in the pathology, which comprises administering to a subject in need thereof an effective amount of a composition comprising a phenylalanine compound or a pharmaceutically acceptable salt thereof according to claim 1 as an active ingredient and a pharmaceutically acceptable carrier thereof.

44. A method of treating a disease selected from the group consisting of rheumatoid arthritis, inflammatory bowel diseases, systemic lupus erythematosus, multiple sclerosis, Sjögren's syndrome, asthma, psoriasis, allergy, diabetes mellitus, cardiovascular diseases, arterial sclerosis, restenosis, tumor proliferation, tumor metastasis and transplant rejection, which comprises administering to a subject in need thereof an effective amount of a composition comprising a phenylalanine compound or a pharmaceutically acceptable salt thereof according to claim 1 as an active ingredient and a pharmaceutically acceptable carrier thereof.

45. The phenylalanine compound or pharmaceutically acceptable salts thereof according to claim 2, wherein R11 represents a branched alkoxyl group having 3 to 6 carbon atoms.

46. The phenylalanine compound or pharmaceutically acceptable salts thereof according to claim 3, wherein R11 represents a branched alkoxyl group having 3 to 6 carbon atoms.

47. The phenylalanine compound or pharmaceutically acceptable salts thereof according to claim 4, wherein R11 represents a branched alkoxyl group having 3 to 6 carbon atoms.

48. The phenylalanine compound or pharmaceutically acceptable salts thereof according to claim 5, wherein R11 represents a branched alkoxyl group having 3 to 6 carbon atoms.

49. The phenylalanine compound or pharmaceutically acceptable salts thereof according to claim 6, wherein R11 represents a branched alkoxyl group having 3 to 6 carbon atoms.

50. The phenylalanine compound or pharmaceutically acceptable salts thereof according to claim 7, wherein R11 represents a branched alkoxyl group having 3 to 6 carbon atoms.

51. The phenylalanine compound or pharmaceutically acceptable salts thereof according to claim 8, wherein R11 represents a branched alkoxyl group having 3 to 6 carbon atoms.

52. The phenylalanine compound or pharmaceutically acceptable salts thereof according to claim 9, wherein R11 represents a branched alkoxyl group having 3 to 6 carbon atoms.

53. The phenylalanine compound or pharmaceutically acceptable salts thereof according to claim 10, wherein R11 represents a branched alkoxyl group having 3 to 6 carbon atoms.

54. The phenylalanine compound or pharmaceutically acceptable salts thereof according to claim 11, wherein R11 represents a branched alkoxyl group having 3 to 6 carbon atoms.

55. The phenylalanine compound or pharmaceutically acceptable salts thereof according to claim 12, wherein R11 represents a branched alkoxyl group having 3 to 6 carbon atoms.

56. The phenylalanine compound or pharmaceutically acceptable salts thereof according to claim 13, wherein R11 represents a branched alkoxyl group having 3 to 6 carbon atoms.

57. The phenylalanine compound or pharmaceutically acceptable salts thereof according to claim 14, wherein R11 represents a branched alkoxyl group having 3 to 6 carbon atoms.

58. The phenylalanine compound or pharmaceutically acceptable salts thereof according to claim 15, wherein R11 represents a branched alkoxyl group having 3 to 6 carbon atoms.

59. The phenylalanine compound or pharmaceutically acceptable salts thereof according to claim 16, wherein R11 represents a branched alkoxyl group having 3 to 6 carbon atoms.

60. The phenylalanine compound or pharmaceutically acceptable salts thereof according to claim 17, wherein R11 represents a branched alkoxyl group having 3 to 6 carbon atoms.

61. The phenylalanine compound or pharmaceutically acceptable salts thereof according to claim 19 represented by the following formula:

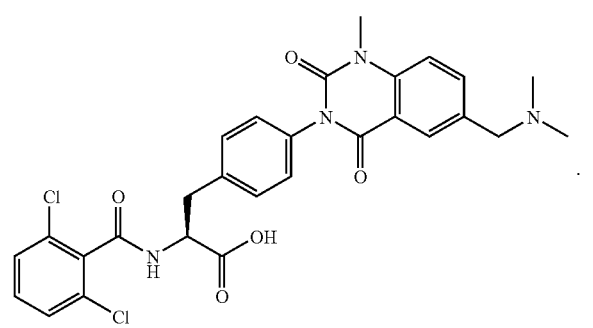

62. The phenylalanine compound or pharmaceutically acceptable salts thereof according to claim 19 represented by the following formula:

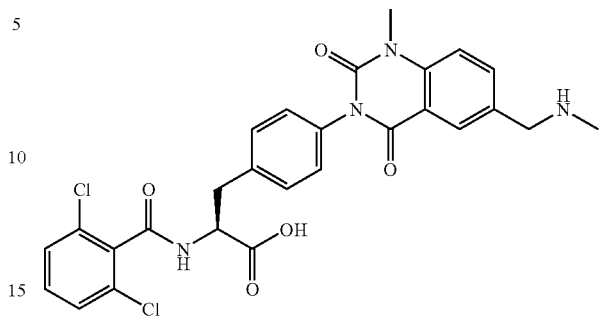

63. The phenylalanine compound or pharmaceutically acceptable salts thereof according to claim 19 represented by the following formula:

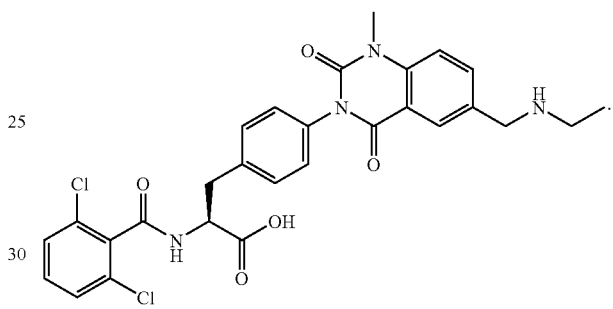

64. The phenylalanine compound or pharmaceutically acceptable salts thereof according to claim 19 represented by the following formula:

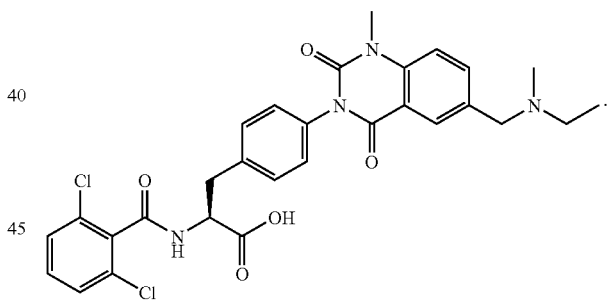

65. The phenylalanine compound or pharmaceutically acceptable salts thereof according to claim 19 represented by the following formula:

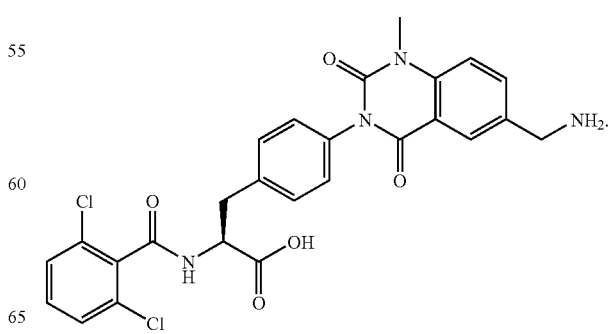

66. The phenylalanine compound or pharmaceutically acceptable salts thereof according to claim 19 represented by the following formula:

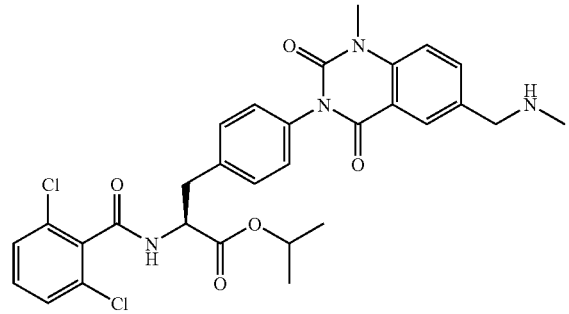

67. The phenylalanine compound or pharmaceutically acceptable salts thereof according to claim 19 represented by the following formula:

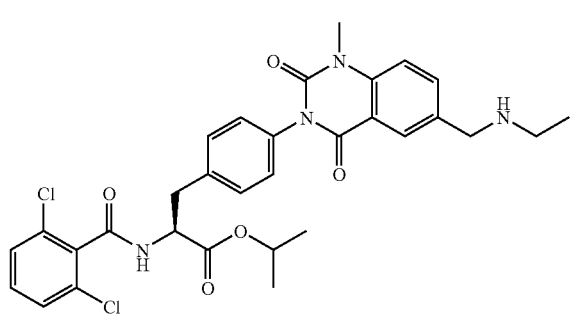

68. The phenylalanine compound or pharmaceutically acceptable salts thereof according to claim 19 represented by the following formula:

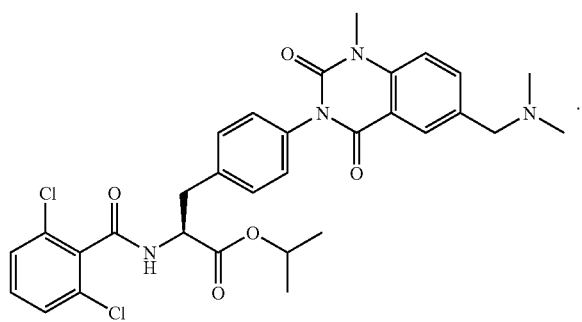

69. The phenylalanine compound or pharmaceutically acceptable salts thereof according to claim 19 represented by the following formula:

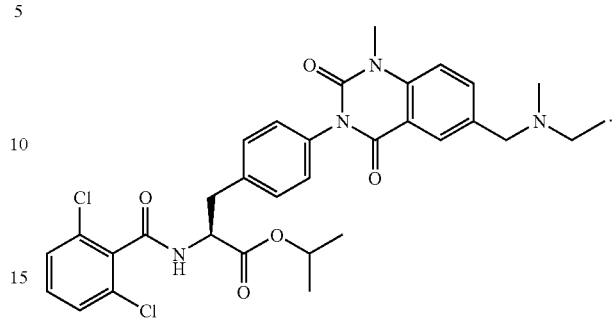

70. The phenylalanine compound or pharmaceutically acceptable salts thereof according to claim 19 represented by the following formula:

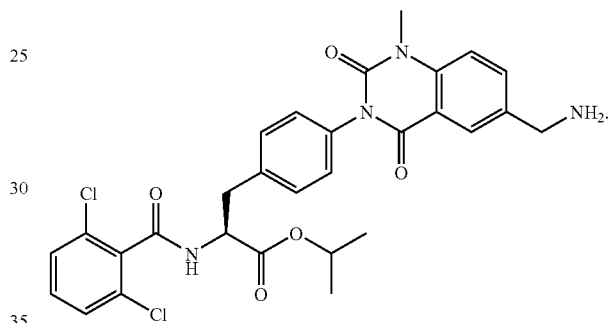

71. The phenylalanine compound or pharmaceutically acceptable salts thereof according to claim 1, wherein R11 represents a hydroxyl group, an alkoxyl group having 1 to 6 carbon atoms, a morpholinoethyloxy group or a benzyloxy group which may be substituted with one or more methyl groups or one or more methoxy groups, R12 represents a methyl group or an ethyl group, R13 represents a hydrogen atom, a methyl group or an ethyl group, or N(R12)R13 represents 1-pyrrolidinyl group, 1-piperidinyl group or 4-morpholinyl group, R14 represents a methyl group, $R_1'$ represents a hydrogen atom, $X_1$ represents —$CH_2$—, which is located on the sixth, seventh or eighth position of quinazolinedione ring, and $Y_{11}$ and $Y_{12}$ represent the combination of (Cl, Cl).

* * * * *

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

It is certified that error appears in the above-identified patent and that said Letters Patent is hereby corrected as shown below:

Column 1, line 42, "the potential to participates in the pathology."
    should read -- the potential to participate in the pathology. --.

Column 3, line 50, "antibody against a 4-integrin in asthma models was reported"
    should read -- antibody against α 4-integrin in asthma models was reported --.

Column 5, lines 14-67, "Ligerature"   should read -- Literature --.

Column 6, lines 1-11, "Ligerature"   should read -- Literature --.
         line 53, "the potential to participates in the pathology."
    should read -- the potential to participate in the pathology. --.

Column 7, line 3, "Namely, the present invention is describes as follows:"
    should read -- Namely, the present invention is described as follows: --.

Column 8, lines 36-37, "4-thiomorpholnyl group,"
    should read -- 4-thiomorpholinyl group, --.

Column 11, line 21, "wherein R7$_1$ represents a hydroxyl group,"
    should read -- wherein R$_{71}$ represents a hydroxyl group, --.

Column 15, line 36, "have the potential to participates in the"
    should read -- have the potential to participate in the --.

Column 17, line 19, "R11"   should read -- R111 --.

Column 18, line 30, "The term "aryr" in an"   should read -- The term "aryl" in an --.

Column 19, line 24, "[4]"   should read -- [3] --.

Column 35, line 62, "Formula (5)< "   should read -- Formula (5)> --.

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

It is certified that error appears in the above-identified patent and that said Letters Patent is hereby corrected as shown below:

Column 37, line 3, "S(=(O)ns)R82" should read -- $S(=(O)ns)R_{82}$ --;
  line 26, "R91 is preferably" should read -- $R_{91}$ is preferably --.

Column 38, line 3, "R10 is preferably" should read -- $R_{10}$ is preferably --;
  line 10, "R10 represents an" should read -- $R_{10}$ represents an --;
  line 39, "R13a and R13b are preferably a methyl group, or N(R13a)"
    should read -- $R_{13a}$ and $R_{13b}$ are preferably a methyl group, or $N(R_{13a})$ --;
  line 40, "R13b is preferably" should read -- $R_{13b}$ is preferably --.
  line 57, "R144 represents a" should read -- $R_{144}$ represents a --.

Column 39, lines 6 and 13, "wherein R11 represents"
  should read -- wherein $R_{11}$ represents --.

Column 47, lines 43 and 46, "α4" should read -- $\alpha$ 4 --.

Column 56, line 22, "mixture of 11.0 g" should read -- mixture of 1.0 g --.

Column 57, line 34, "mixture of 11.0 g" should read -- mixture of 1.0 g --.

Column 62, lines 58-59, "chloroformate (4001μL)"
  should read -- chloroformate (400μL) --.

Column 69, lines 37 and 38, "5 mL" should read -- 5mL --.

Column 71, line 44, "methods, A to" should read -- methods, A to E: --.

Column 81, line 12, "chloroformate (11.0" should read -- chloroformate (1.0 --.

Column 86, line 30, "oxychloride (40.1 mL)" should read -- oxychloride (4.1 mL) --.

Column 94, line 10, "triethylamine (130.1" should read -- triethylamine (13.1 --.

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

Page 3 of 6

It is certified that error appears in the above-identified patent and that said Letters Patent is hereby corrected as shown below:

Column 110, Table 16, line 32, "661" should read -- 681 --.

Column 135, Table G, lines 42-50, and
Column 136, Table G, lines 5-15,

"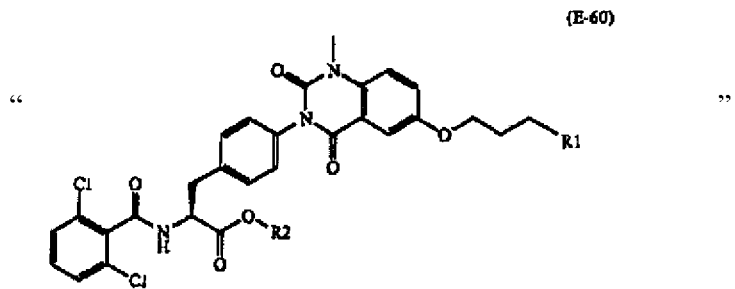"

should read

--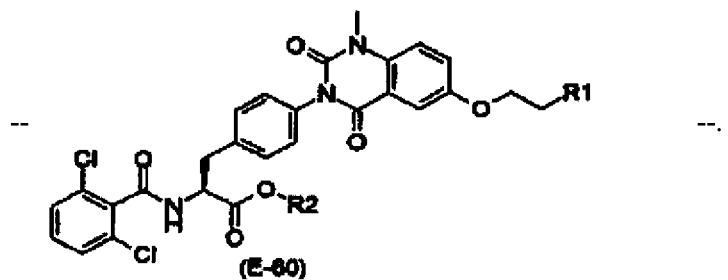--.

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

It is certified that error appears in the above-identified patent and that said Letters Patent is hereby corrected as shown below:

Column 137, Table H, lines 25-34,

"

| 226 | — |  | — | 599 |
| 227 | — | 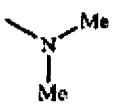 | — | 613 |

"

should read

| 226 | — | 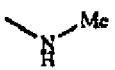 | — | H | 599 |
| 227 | — |  | — | H | 613 |

--.

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

It is certified that error appears in the above-identified patent and that said Letters Patent is hereby corrected as shown below:

Column 149, Table 35, lines 53-65,

"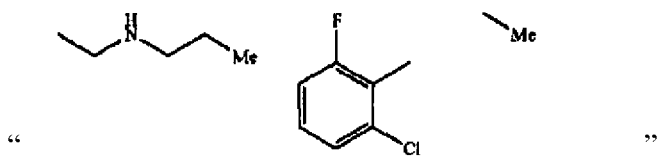

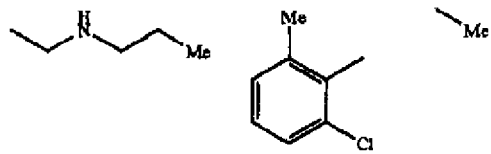"

should read

--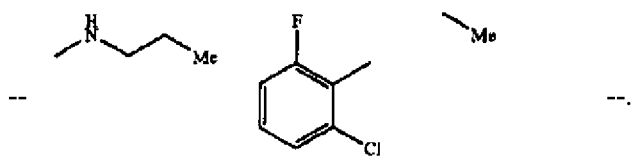

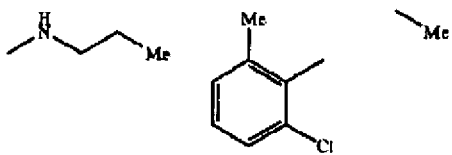--.

UNITED STATES PATENT AND TRADEMARK OFFICE
CERTIFICATE OF CORRECTION

PATENT NO. : 7,345,049 B2
APPLICATION NO. : 11/018226
DATED : March 18, 2008
INVENTOR(S) : Kazuyuki Sagi et al.

It is certified that error appears in the above-identified patent and that said Letters Patent is hereby corrected as shown below:

Column 184, delete lines 5-15, duplicate of previously listed formula.

Column 192, line 58, "–CHCH–" should read -- –CH=CH– --.

Column 194, line 37, "43. A method of treating or preventing inflammatory" should read -- 43. A method of treating inflammatory --.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,345,049 B2 | Page 1 of 6 |
| APPLICATION NO. | : 11/018226 | |
| DATED | : March 18, 2008 | |
| INVENTOR(S) | : Kazuyuki Sagi et al. | |

It is certified that error appears in the above-identified patent and that said Letters Patent is hereby corrected as shown below:

Column 173, line 3 (Claim 1, line 2) "(1) or pharmaceutically acceptable salts thereof:" should read --(1):--

Column 173, line 47 (Claim 1, last line) "(F, Me)." should read --(F, Me), or a pharmaceutically acceptable salt thereof.--

Column 173, line 49 (Claim 2, line 2) "salts" should read --salt--

Column 173, line 60 (Claim 3, line 2) "salts" should read --salt--

Column 174, line 5 (Claim 4, line 2) "salts" should read --salt--

Column 174, line 21 (Claim 5, line 2) "salts" should read --salt--

Column 174, line 39 (Claim 6, line 2) "salts" should read --salt--

Column 174, line 53 (Claim 7, line 2) "salts" should read --salt--

Column 174, line 59 (Claim 8, line 2) "salts" should read --salt--

Column 174, line 65 (Claim 9, line 2) "salts" should read --salt--

Column 175, line 10 (Claim 10, line 2) "salts" should read --salt--

Column 175, line 23 (Claim 11, line 2) "salts" should read --salt--

Column 175, line 29 (Claim 12, line 2) "salts" should read --salt--

Column 175, line 51 (Claim 13, line 2) "salts" should read --salt--

Signed and Sealed this
Thirtieth Day of August, 2011

David J. Kappos
*Director of the United States Patent and Trademark Office*

Column 175, line 65 (Claim 14, line 2) "salts" should read --salt--

Column 176, line 10 (Claim 15, line 2) "salts" should read --salt--

Column 176, line 25 (Claim 16, line 2) "salts" should read --salt--

Column 176, line 40 (Claim 17, line 2) "salts" should read --salt--

Column 176, line 62 (Claim 18, line 2) "salts" should read --salt--

Column 176, line 66 (Claim 19, line 2) "salts thereof according to claim 1 represented" should read --salt thereof according to claim 1, which is a compound represented--

Column 188, line 26 (Claim 19, last line) after formula "." should read --or a pharmaceutically acceptable salt thereof.--

Column 188, line 28 (Claim 20, line 2) "(2) or pharmaceutically acceptable salts thereof:" should read --(2):--

Column 188, line 61 (Claim 20, last line) "(F, Me)." should read --(F, Me), or a pharmaceutically acceptable salt thereof.--

Column 188, line 64 (Claim 21, line 2) "salts" should read --salt--

Column 189, line 6 (Claim 22, line 2) "salts should read --salt--

Column 189, line 18 (Claim 23, line 2) "(3) or pharmaceutically acceptable salts thereof:" should read --(3):--

Column 189, line 62 (Claim 23, last line) "(F, Me)." should read --(F, Me), or a pharmaceutically acceptable salt thereof.--

Column 189, line 64 (Claim 24, line 2) "salts" should read --salt--

Column 190, line 8 (Claim 25, line 2) "salts" should read --salt--

Column 190, line 16 (Claim 26, line 2) "salts" should read --salt--

Column 190, line 23 (Claim 27, line 2) "salts" should read --salt--

Column 190, line 31 (Claim 28, line 2) "(4) or pharmaceutically acceptable salts thereof:" should read --(4):--

CERTIFICATE OF CORRECTION (continued)
U.S. Pat. No. 7,345,049 B2

Column 190, line 65 (Claim 28, last line) "(F, Me)." should read --(F, Me), or a pharmaceutically acceptable salt thereof.--

Column 190, line 67 (Claim 29, line 2) "salts" should read --salt--

Column 191, line 6 (Claim 30, line 2) "(5) or pharmaceutically acceptable salts thereof:" should read --(5):--

Column 191, line 37 (Claim 30, last line) "(F, Me)." should read --(F, Me), or a pharmaceutically acceptable salt thereof.--

Column 191, line 39 (Claim 31, line 2) "salts" should read --salt--

Column 191, line 46 (Claim 32, line 2) "(8) or pharmaceutically acceptable salts thereof:" should read --(8):--

Column 192, line 7 (Claim 32, last line) "(F, Me)." should read --(F, Me), or a pharmaceutically acceptable salt thereof.--

Column 192, line 9 (Claim 33, line 2) "salts" should read --salt--

Column 192, line 15 (Claim 34, line 2) "salts" should read --salt--

Column 192, line 23 (Claim 35, line 2) "(9) or pharmaceutically acceptable salts thereof:" should read --(9):--

Column 192, line 55 (Claim 35, last line) "(F, Me)." should read --(F, Me), or a pharmaceutically acceptable salt thereof.--

Column 192, line 57 (Claim 36, line 2) "salts" should read --salt--

Column 192, line 67 (Claim 37, line 2) "salts" should read --salt--

Column 193, line 9 (Claim 38, line 2) "(11) or pharmaceutically acceptable salts thereof:" should read --(11):--

Column 193, line 32 (Claim 38, last line) "(F, Me)." should read --(F, Me), or a pharmaceutically acceptable salt thereof.--

Column 193, line 34 (Claim 39, line 2) "(13) or pharmaceutically acceptable salts thereof:" should read --(13):--

Column 193, line 65 (Claim 39, last line) "(F, Me)." should read --(F, Me), or a pharmaceutically acceptable salt thereof.--

Column 193, line 67 (Claim 40, line 2) "(14) or pharmaceutically acceptable salts thereof:" should read --(14):--

Column 194, line 26 (Claim 40, last line) "(F, Me)." should read --(F, Me), or a pharmaceutically acceptable salt thereof.--

Column 194, line 28 (Claim 41, line 2) "salts" should read --salt--

Column 194, line 38 (Claim 43, line 2) "diseases" should read --disease--

Column 194, line 57 (Claim 45, line 2) "salts" should read --salt--

Column 194, line 61 (Claim 46, line 2) "salts" should read --salt--

Column 194, line 65 (Claim 47, line 2) "salts" should read --salt--

Column 195, line 2 (Claim 48, line 2) "salts" should read --salt--

Column 195, line 6 (Claim 49, line 2) "salts" should read --salt--

Column 195, line 10 (Claim 50, line 2) "salts" should read --salt--

Column 195, line 14 (Claim 51, line 2) "salts" should read --salt--

Column 195, line 17 (Claim 52, line 2) "salts" should read --salt--

Column 195, line 21 (Claim 53, line 2) "salts" should read --salt--

Column 195, line 25 (Claim 54, line 2) "salts" should read --salt--

Column 195, line 29 (Claim 55, line 2) "salts" should read --salt--

Column 195, line 33 (Claim 56, line 2) "salts" should read --salt--

Column 195, line 37 (Claim 57, line 2) "salts" should read --salt--

Column 195, line 41 (Claim 58, line 2) "salts" should read --salt--

Column 195, line 45 (Claim 59, line 2) "salts" should read --salt--

Column 195, line 49 (Claim 60, line 2) "salts" should read --salt--

Column 195, line 53 (Claim 61, line 2) "salts thereof according to claim 19 represented" should read --salt thereof according to claim 19, which is a compound represented--

Column 195, line 65 (Claim 61, last line) after formula "." should read --or a pharmaceutically acceptable salt thereof.--

Column 196, line 2 (Claim 62, line 2) "salts thereof according to claim 19 represented" should read --salt thereof according to claim 19, which is a compound represented--

Column 196, line 17 (Claim 62, last line) after formula "." should read --or a pharmaceutically acceptable salt thereof.--

Column 196, line 19 (Claim 63, line 2) "salts thereof according to claim 19 represented" should read --salt thereof according to claim 19, which is a compound represented--

Column 196, line 33 (Claim 63, last line) after formula "." should read --or a pharmaceutically acceptable salt thereof.--

Column 196, line 35 (Claim 64, line 2) "salts thereof according to claim 19 represented" should read --salt thereof according to claim 19, which is a compound represented--

Column 196, line 48 (Claim 64, last line) after formula "." should read --or a pharmaceutically acceptable salt thereof.--

Column 196, line 50 (Claim 65, line 2) "salts thereof according to claim 19 represented" should read --salt thereof according to claim 19, which is a compound represented--

Column 196, line 65 (Claim 65, last line) after formula "." should read --or a pharmaceutically acceptable salt thereof.--

Column 197, line 2 (Claim 66, line 2) "salts thereof according to claim 19 represented" should read --salt thereof according to claim 19, which is a compound represented--

Column 197, line 19 (Claim 66, last line) after formula "." should read --or a pharmaceutically acceptable salt thereof.--

Column 197, line 21 (Claim 67, line 2) "salts thereof according to claim 19 represented" should read --salt thereof according to claim 19, which is a compound represented--

Column 197, line 38 (Claim 67, last line) after formula "." should read --or a pharmaceutically acceptable salt thereof.--

CERTIFICATE OF CORRECTION (continued)
U.S. Pat. No. 7,345,049 B2

Column 197, line 40 (Claim 68, line 2) "salts thereof according to claim 19 represented" should read --salt thereof according to claim 19, which is a compound represented--

Column 197, line 55 (Claim 68, last line) after formula "." should read --or a pharmaceutically acceptable salt thereof. --

Column 198, line 2 (Claim 69, line 2) "salts thereof according to claim 19 represented" should read --salt thereof according to claim 19, which is a compound represented--

Column 198, line 18, (Claim 69, last line) after formula "." should read --or a pharmaceutically acceptable salt thereof.--

Column 198, line 20 (Claim 70, line 2) "salts thereof according to claim 19 represented" should read --salt thereof according to claim 19, which is a compound represented--

Column 198, line 37 (Claim 70, last line) after formula "." should read --or a pharmaceutically acceptable salt thereof.--

Column 198, line 39 (Claim 71, line 2) "salts" should read --salt--